United States Patent [19]
Stover

[11] Patent Number: 5,583,038
[45] Date of Patent: Dec. 10, 1996

[54] BACTERIAL EXPRESSION VECTORS CONTAINING DNA ENCODING SECRETION SIGNALS OF LIPOPROTEINS

[75] Inventor: Charles K. Stover, Silver Spring, Md.

[73] Assignee: MedImmune, Inc., Gaithersburg, Md.

[21] Appl. No.: 977,630

[22] Filed: Nov. 17, 1992

Related U.S. Application Data

[63] Continuation-in-part of Ser. No. 780,261, Oct. 21, 1991, abandoned.

[51] Int. Cl.$^6$ .............................. C12N 1/21; A61K 39/04
[52] U.S. Cl. ......................................... 435/252.3; 424/93.2
[58] Field of Search .............................. 424/93 A, 94.4, 424/93.2; 435/252.3, 320.1

[56] References Cited

FOREIGN PATENT DOCUMENTS

WO88/06626  9/1988  WIPO ........................... C12N 15/00

OTHER PUBLICATIONS

Simon et al., J. Infect. Dis., 164:123 (1991).
Fikrig et al., Science (Wash., D.C.), 250:553 (1990).
Fikrig et al., Infect. Immun., 60:657 (1992).
Fikrig et al., Proc. Natl. Acad. Sci. USA, 89:5418 (1992).
Howe, et al., Infect. and Immun. 54:207–212 (1986).
Dunn et al., Protein Exp. and Purif., 1:159–168 (1990).
Schaible et al., Proc. Natl. Aca. Sci., 87:3768–3772 (1990).
Jacobs et al., Curr. Topics in Micro & Imm, 155:155:153–160 (1990).
Woodley et al., Antimicrob., 19:571–574 (1981).
Ray Wu, Recomb DNA, 153:492–517 (1987).
Howe et al., (1985), Science 227:645–646.
Shibui et al. (1989), App.. Microbiol. Biotechnol. 31:253–258.
Andersen et al. (1989), Infect. Immun. 57(8):2481–2488.
Stover et al. (1991), Nature 351:456–460.
Yother et al. (1992), J. Bacteriol. 174(2):601–609.
Wallich et al. (1989), Nucl. Acids Res. 17(21: 8864.
Matsuo et al. (1990), Infect. Immun. 58(12):4049–4054.
Snapper et al. (1988), Proc. Natl. Acad. Sci USA 85:6987–6991.

*Primary Examiner*—Mindy Fleisher
*Assistant Examiner*—Philip W. Carter
*Attorney, Agent, or Firm*—Elliot M. Olstein

[57] ABSTRACT

An expression vector for expressing a protein or polypeptide in a bacterium, which comprises a first DNA sequence encoding at least a secretion signal of a lipoprotein, and a second DNA sequence encoding a protein or fragment thereof, or polypeptide or peptide heterologous to the bacterium which expresses the protein or fragment thereof, or polypeptide or peptide. The bacterium expresses a fusion protein a lipoprotein or lipoprotein segment and the protein or fragment thereof, or polypeptide or peptide heterologous to the bacterium which expresses the protein or fragment thereof, or polypeptide or peptide. Such expression vectors increase the immunogenicity of the protein or fragment thereof, or polypeptide or peptide by enabling the protein or fragment thereof, or polypeptide or peptide to be expressed on the surface of the bacterium. Bacteria which may be transformed with the expression vector include mycobacteria such as BCG. The expression vectors of the present invention may be employed in the formation of live bacterial vaccines against Lyme disease wherein the bacteria express a surface protein of *Borrelia burgdorferi*, the causative agent of Lyme disease.

31 Claims, 64 Drawing Sheets

FIG. 3
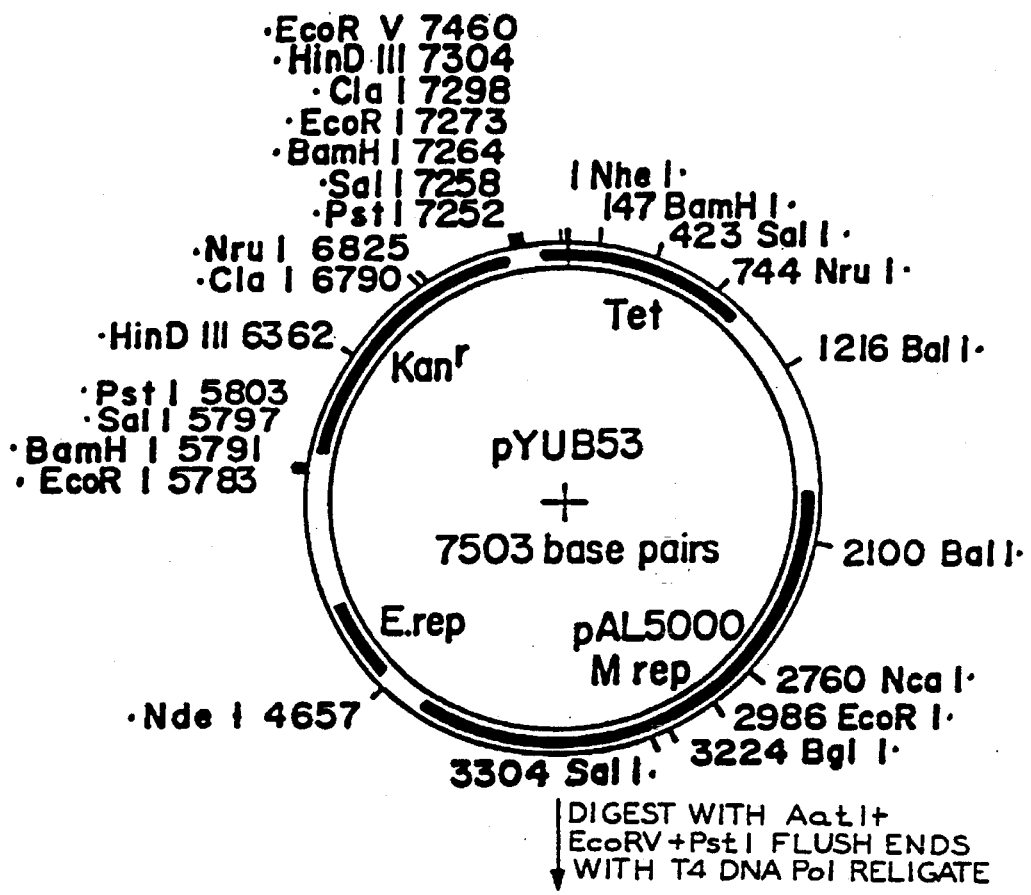
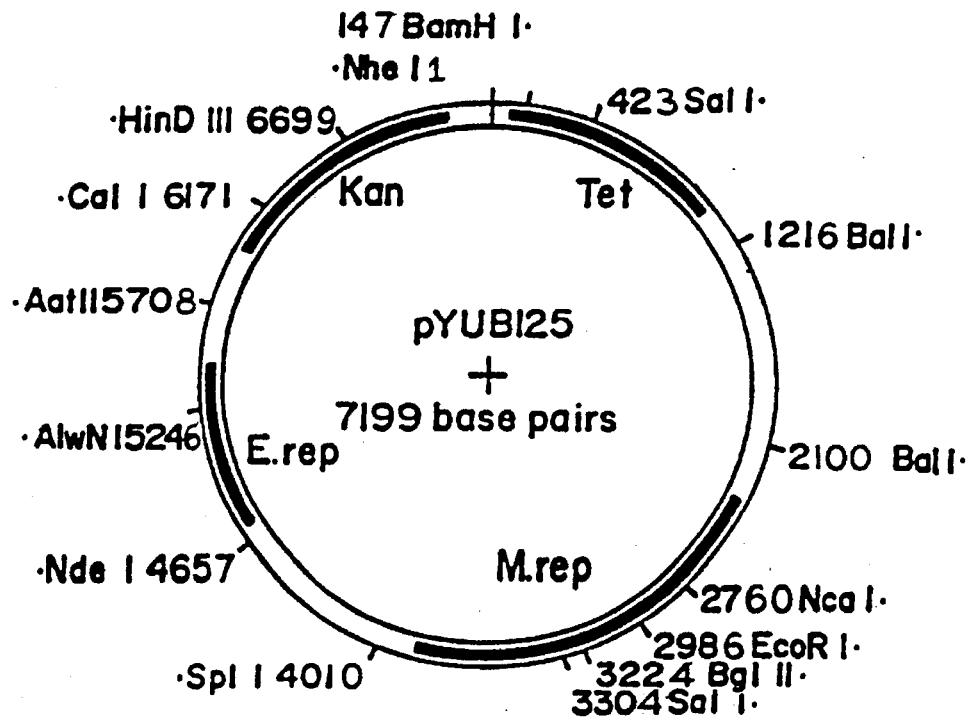

```
N
h
e
I
     GCTAGCTCTATATGCTTTGATGCAAATTTCTATGCGCACCCGTTCTCGGAGC
  1 ----------+----------+----------+----------+----------+--
     CGATCGCGATATACGCAACTACGTTAAAGATACGCGTGGGCAAGAGCCTCGT
                                              Bcm - M. rep      H,m,a,B
                                              ──────────        I ──
     CGAGCCACTATCGACTACGCGATCATGGCGACCACACCCGTCCTGTCGATC
 101 ----------+----------+----------+----------+----------+--
     CCTCGGTGATAGCTGATGCGCTAGTACCGCTGGTGTGGGCAGGACACCTAGG TTGTCTGCCCTCCCCGCGTTGCGTCGCGGTGCATGGAGCCGGGCCACCTCGA
 201 ----------+----------+----------+----------+----------+--
     AACAGACGGAGGGGCGCAACGCAGCGCCACGTACCTCGGCCCCGTGGACCT ATTCGAGCCAATCAATTCTTGCGGAGAACTGTGAATGCGCAAACCAACCCTT
 301 ----------+----------+----------+----------+----------+--
     TAACCTCGGTTAGTTAAGAACGCCTCTTGACACTTACGCGTTTGGTTGGGAAC
                          I,la,S
     GCATCTCGGGCAGCGTTGGTCCTGCCCACGGGTGCGCATGATCGTGCTCCTG
 401 ----------+----------+----------+----------+----------+--
     CGTAGAGCCCGTCGCAACCAGGACCGGTGCCCACGCGTACTACCACGAGG GAATGAATCACCGATACGCCAGCGAACGTGAAGCGACTGCTGCTGCAAAAC
 501 ----------+----------+----------+----------+----------+--
     CTTACTTAGTGCCTATGCGCTCGCTTGCACTTCGCTGACGACGACGTTTTGC TAAAGTCTCGAAACGCGGAAGTCAGCGCCCTGCACCATTATGTTCCGGATCT
 601 ----------+----------+----------+----------+----------+--
     ATTTCAGACCTTTGCGCCTTCAGTCGCGGGACGTGGTAATACAAGGCCTAGA TAACGAAGCGCTGGCATTGACCCTGAGTGATTTTTCTCTGGTCCCGCCGCAT
 701 ----------+----------+----------+----------+----------+--
     ATTGCTTCGCGACCGTAACTGGGACTCACTAAAAAGAGACCAGGGCGGCGTA TTCATCATCAGTAACCCGTATCGTGAGCATCCTCTCTCGTTTCATCGGTATC
 801 ----------+----------+----------+----------+----------+--
     AAGTAGTAGTCATTGGGCATAGCACTCGTAGCAGACACCAAAGTAGCCATA CCAAACAGGAAAAAACCGCCCTTAACATGGCCCGCTTTATCAGAAGCCAGA
 901 ----------+----------+----------+----------+----------+--
     CCTTTGTCCTTTTTTGGCGGGAATTGTACCGGGCGAAAYAGTCTTCGGTCT AGACATCTGTGAATCGCTTCACGACCACGCTGATGAGCTTTACCGCAGAAC
1001 ----------+----------+----------+----------+----------+--
     TCTGTAGACACTTAGCGAAGTGCTGGTGCGACTACTCGAAATGGCGTCTTG CACTCAACCTCGAAGCGTGTGGTTGCGGAGCCATCTAGCAACCACACGAAA
1101 ----------+----------+----------+----------+----------+--
     GTGAGTTGGAACTTCGCACACCAACGCCTCGGTAGATCGTTGGTGTGCTT GAACTGACTGCTATCGTTGGTAAACCTAGTTTGACCAGCATGTTTTAACTA
1201 ----------+----------+----------+----------+----------+--
     CTCGACTGAGCATAGCAACCATTTGGATCAAACTGGTCGTACAAAATTGAT
              ┌──BalI
     ACGAGAGTCGCCACGGATGCCACCACAAGCACTACAACCGAGTTCGCCACG
1301 ----------+----------+----------+----------+----------+--
     TGCTCTCACCGGTGCCTACGGTGCTGTTCGTGATGTTGCCTCAAGCGGTGC CGAAATGCCTTGGTATCGACCAAGATTCGTAGAACCCGTCTCGTCTGGCTG
1401 ----------+----------+----------+----------+----------+--
     CCTTTACCGAACCATAGCTGGTTCTAAGCATCTTGGGGCAGAGCAGACCGA
```

MATCH WITH FIG. 5b

FIG. 5b

```
         ACTGTCCGACCCCTTTGGCCGCCGCCCAGTCCTGCTCGCTTCGCTACTT
         ........+.........+.........+.........+.........+ 100
         GACAGGCTGGCGAAACCGGCGGCGGGTCAGGACGAGCGAAGCGATGAA
                                      N,a,r,I
         CTCTACCCGGACGCATCGTGGCCGGCATCACCGGCGCCGCCCTATACC
         ........+.........+.........+.........+.........+ 200
         AGATGGGCCTGCGTAGCACCGGCCGTAGTGGCCGCGGCGGGATATGG
         CCTGAATGGAAGCCGGCGGCACCTCGCTAACGGATTCACCACTCCAAGA
         ........+.........+.........+.........+.........+ 300
         CGACTTACCTTCGGCCGCCGTGGAGCGATTGCCTAAGTGGTGAGGTTCT
         CGCATAACATATCCATCGCGTCCGCCATCTCCACCAGCCGCACGCGGC
         ........+.........+.........+.........+.........+ 400
         CGTCTTGTATAGGTAGCGCAGGCGGTAGAGGTCGTCGGCGTGCGCCG

TCGTTGAGGACCCGGCTAGGCTGGCGGGGTTGCCTTACTCGTTAAGCA
         ........+.........+.........+.........+.........+ 500
         ACACCAACTCCTGGGCCCATCCGACCGCCCCAACGGAATGACCAATCGT
         GTCTGCGACCTGAGCAACAACATGAATGGTCTTCCGTTTCCGTGTTTCG
         ........+.........+.........+.........+.........+ 600
         AGACGCTGGACTCGTTGTTGTACTTACCAGAAGCCAAAGGCACAAAGC
         GCATCGCAGGATGCTGCTGGCTACCCTGTGGAACACCTACATCTGTAT
         ........+.........+.........+.........+.........+ 700
         CGTAGCHTCCTACCACGACCGATGGGACCAATTGTGGATGTAGACATA
         CCATACCGCCACTTGTTTACCCTCACAACGTTCCAGTAACCGGGCATG
         ........+.........+.........+.........+.........+ 800
         GGTATGGCGGTCAACAAATGGGAGTGTTGCAAGGTCATTGGCCCGTAC
         ATTACCCCCATGAACAGAAATTCCCCCTTACACGGAGGCATCAAGTGA
         ........+.........+.........+.........+.........+ 900
         GTAATGGCGGTACTTGTCTTTAAGGGGGAATGTGCCTCCGTAGTTCACT
         CATTAACGCTTCTGGAGAAACTCAACGAGGTGGACGCGGATGAACAGGC
         ........+.........+.........+.........+.........+ 1000
         GTAATTGCGAAGACCTCTTTGAGTTGCTCGACCTGCGCCTACTTGTCCG
         GAGGACAGTCGCACGACGAAGTTCTTCTGGATCGCGCCGTGTCGGAAG
         ........+.........+.........+.........+.........+ 1100
         CTCCTGTCAGCGTGGTGCTTCAAGAAGACCTAGCGCGGGCACGACCTTC
         CATGCGCAACGAACCGCGCAACGAACAACGCCTAGAACTGGCACTAGAT
         ........+.........+.........+.........+.........+ 1200
         TGTACGCGTTGCTTGGCGCGTTGCTTGTTGCCGATCTTGACCGTGATCTA
         CGTTCGGTGAGCTGTCAACGGGGCCTGTAACGGCACAACGAACCGTGCA
         ........+.........+.........+.........+.........+ 1300
         GCAAGCCACTCGACAGTTGCCCCGGACATTGCCGTGTTGCTTGGCACGT

TACATCACCACAACCACCGATTCTGGCGGTGAGCTCCACGATATTCACC
         ........+.........+.........+.........+.........+ 1400
         ATGTAGTCGTGTTGGTGCTAAGACCGCCACTCGAGGTGCTATAAGTCG
         GTATTCAAAACGGACGCAACGAAACACGCAACGAGACAGGCATGGCCC
         ........+.........+.........+.........+.........+ 1500
         CCATAAGTTTTGCCTGCGTTGCTTTGTGCGTTGCTCTGTCCGTACCGCG
```

MATCH WITH FIG. 5a

DELETED IN pHV111, 113–200s

```
              AAACCAGAAAACTACCCTCTACCAGGACTTTTACCTGTCCGACCCGTTGCAA
1501----------+---------+---------+---------+---------+---
              TTTGGTCTTTTGATCGCAGATCGTCCTGAAAATGGACAGGCTGGGCAACGTT

GAACAGCGGTGGATTGTCGGCTTCGTTGTGGGCCTTTTGACCCGCTTCCTG
1601----------+---------+---------+---------+---------+---
              CTTGTCGCCACCTAACAGCCGAAGCAACACCCCGAAAACTCGGCGAAGCAC
  e           F  L  P  P  N  D  A  E  N  E  A  K  Q  A  A  E  Q

TCCAGATGCAGCCCGAAATGTTTGCCCGTTTGCGGCCAAGAGTGGCCCTCGT
1701----------+---------+---------+---------+---------+---
              AGGTCTACGTCGGGCTTTACAAACCGGCAAACGCCGGTTCTCACCGGGAGCA
  e              L  E  L  G  F  M  K  A  T  Q  P  W  S  E  G  E  D

CCCAACTCGCTGCGTTCCTGCGCCACGAGCCGGACGACGTGGCGTTCGGAT
1801----------+---------+---------+---------+---------+---
              CGGTGAGCGACGCAAGGACGCGGTGCTCGGCCTGCTGCACCGCAAGCCTAT
  e              N  E  S  R  E  Q  A  V  L  R  V  V  H  R  E  S  L

GACAGTCGGCTGCCGGTTGTAGCCGTCGCTGTAGCCGTCGCTGTAGCCGTCG
1901----------+---------+---------+---------+---------+---
              CTGTCAGCCGACGGCCAACATCGGCAGCGACATCGGCAGCGACATCGGCAGC
  d
  e              V  T  P  C  R  W  Y  G  D  S  Y  G  D  S  Y  G  D  S

CTGTGCTCGCCGCCGTGCGCGCTGCTGCGCCCTTCCGCTAGATGGCCGACTG
2001----------+---------+---------+---------+---------+---
              CACACGACCGGCGGCACCCGCGACCACGCCCGAAGGCGCTCTACCGGCTGAC
  d              I  S  A  A  T  R  A  A  A  G  K  R  S  I  A  S  Q
  e              H  E  G  G  W  A  S  S  R  G  E  A  L  H  G  V  P

GCGCGACTTGGTTGTGATCCAACGCCAAATGCTGTTGGCCATGGCCCCGAC
2101----------+---------+---------+---------+---------+---
              CGCGCTGAACCAACACTAGGTTGCGGTTTACGACAACCGCTACCGCGCCTG
  d              R  S  X  T  T  I  W  R  W  I  S  W  A  I  A  R  V
  e              A  V  Q  N  E  D  L  A  L  E  Q  Q  R  E  R  P  G

GCGTTTCGCGCGTGGCACTCGGCATAGATCGCGCGGCCGAGTCCGTCCACG
2201----------+---------+---------+---------+---------+---
              CGCAAAGCGCGCACCGTGAGCCGTATCTAGCGCGCCGGCTCAGGCAGGTG
  d              N  R  A  R  C  E  A  Y  I  A  R  G  L  G  D  V
  e              R  K  A  R  P  V  R  C  L  D  R  P  R  T  R  G  R

ACCTGACGGAATCGAACAGTGCGCAATTCCGCCCTAGCGGCGTCGGAGCCG
2301----------+---------+---------+---------+---------+---
              TGGACTGCCTTAGCTTGTCACGCGTTAAGGCGGGATCGCCGCAGCCTCGGC
  d              R  V  S  D  F  L  A  C  N  R  G  L  P  T  P  A  A
  e              Q  R  P  R  V  T  R  L  E  A  R  A  A  D  S  G  G
                              B,g,1I,r
              CAGCTCCGCCTCGATGTGGCTGAGTGTGTAGAGATCTGAGTGGACCCATTCC
2401----------+---------+---------+---------+---------+---
              CTCGAGGCGGAGCTACACCGACTCACACATCTCTAGACTCACCTCGGTAAGG
  d              L  E  A  E  I  E  S  L  T  Y  L  D  E  H  L  W  E  T
  e              A  R  G  R  E  P  Q  T  E  L  S  R  L  P  A  M  G
              S,a,1,I  C-TPCR MUTAGENOSISPHV 110-300s
              CTGCGGTCGCCGTCGACGCCGCGCCGAAGGCCTTCGGCGCACGCCGCCATGT
2501----------+---------+---------+---------+---------+---
              GACGCCAGCGGCAGCTGCCGCGCGGCTTCCGGAAGCCGCGTGCGCCGGYAC
  d              R  D  G  D  V  A  R  R  L  G  E  A  C  A  A  M  T
  e              Q  P  R  R  R  R  R  A  S  P  R  R  R  V

TGAGTCCCCACACTGCGTGTGCGTCGCCGTTGGCGCGATTGCCCACGATCGC
2601----------+---------+---------+---------+---------+---
              ACTCACGGGTGTGACGCACACGCACCGGCAACCGCGCTAACGGGTGCTAGC
  d              L  A  W  V  A  E  A  N  G  N  A  R  N  G  V  I  A
```

FIG. 5Aa  MATCH WITH FIG. 5Ab

FIG. 5Ab  MATCH WITH FIG. 5Aa

```
         CGGAACCCCCCACGGAACCCCCGCGACACCCGCTCCCCAATTGCGTTA
         ........+.........+.........+.........+.........+ 1600
         GCCTTGCGGGCTGCCTTGGGCGCGCTGTGGGCGAGGGGTTAACGCAAT

TTCTGCCCCACGCTCTTTCCTCGCCCGATAGCCGAGTCGCTTAACGGTG
         ........+.........+.........+.........+.........+ 1700
         AAGACGGCGTGCGAGAAAGGACCCCGCTATCGGCTCAGCGAATTGCCAC
          K  A  A  R  E  K  R  A  R  Y  G  L  R  K  V  T  D

CGTCGTGATAGGCGCGGATGCGTTCGCGGCGTGCACCCTGCTCGGCCA
         ........+.........+.........+.........+.........+ 1800
         GCAGCACTATCCGCGCCTACGCAAGCGCCGCACGTCGGACGAGCCGGT
           D  E  Y  A  R  I  R  E  R  R  A  A  Q  E  A  L

AGTCCGGTGATTCGAGCGCCTTCGGCGGCGGTCACGCGCCGCTTTTTGCG
         ........+.........+.........+.........+.........+ 1900
         CAGGCCACTAAGCTCGCGGAAGCCGCCGCCAGTGCGCGGCGAAAAACGC
           G  T  I  R  A  G  E  A  A  T  V  R  R  K  K  R
                      M,c,a,I  CATG DUPLICATION pHV110-300s
         CTCATAGCAATGCCTCCATGGCTGACGCGGACTTTGCGCGCCGCGCAA
         ........+.........+.........+.........+.........+ 2000
         GAATATCGTTACGGAGGTACCGACTGCGCCTGAAACGCGCGGCGCGTT
           •  L  L  A  S  M  A  S  A  S  K  A  R  R  A  V
              M  A  T  G  G  E  S  V  R  V  K  R  A  A  C  S

GCGCGCACTGAGTGTGGCCTCGTAGACCACGATCCCGTCCGCCCAAAT
         ........+.........+.........+.........+.........+ 2100
         CGCCCGTGACTCACACCGGAGCATCTGGTGCTAGGGCAGGCGGGTTTA
           R  A  S  L  T  A  E  Y  V  V  I  G  D  A  W  I
           A  C  Q  T  E  G  R  L  G  R  D  R  G  G  L  E
         G-APCR MUTAGENOSIS
         ph V110-300s                                IRocE
         CTCGCTGTCCGGTAGCGGTCCGGGACACACGTCGTTGCACGGGAATTCG
         ........+.........+.........+.........+.........+ 2200
         GAGCGACAGGCCATCGCCAGCCCCTGTGTGCAGCAACGTGCCCTTAAGC
           E  S  D  P  L  P  G  P  C  V  D  N  C  P  F  E  A
           R  Q  G  T  A  T  R  S  V  R  R  Q  V  P  I  R

TTCCGGGTCGGCAGGTAGATCCGCATGAGGGCCGGACGATAGGCCCACA
         ........+.........+.........+.........+.........+ 2300
         CAAGGCCCAGCCGTCCATCTAGGCGTACTCCCGCCCTGCTATCCGGGTGT
           X  R  T  P  L  Y  I  R  M  L  A  P  R  Y  A  W  L
           E  P  D  A  P  L  D  A  E  P  R  S  S  L  G  V  V

CTTTGTACTTGGTCTGCTCACGCCAGCGCGGCGGTGGCATGTTCGCCCC
         ........+.........+.........+.........+.........+ 2400
         GAAACATGCACCAGACGACTGCGGTCGCGCCGCCACCGTACAAGCGCGG
           K  Y  T  T  Q  Q  R  W  R  P  P  P  M  W  A  G
           Q  V  E  D  A  S  A  L  A  A  T  A  H  E  R  R

GTTTCCCAGGCGATGTGGCCGGCGTTTTTTGGTCATGAGGCCCTGAGTAA
         ........+.........+.........+.........+.........+ 2500
         CAAAGGGTCCGCTACACCGGCCCCAAAAACCAGTACTCCGGACTCATT
           E  W  A  I  H  G  P  M  K  T  M  L  G  S  Y  S
         N  G  L  R  W  P  R  P  K  Q  D  E  P  R  L  L

ATGCGAGCGGCTTACGCCGCGCGTATTCGGTGCGTGGAACAGGGGCGT
         ........+.........+.........+.........+.........+ 2600
         ATACGCTCGCCGAATGCGGCGCGCATAAGCCACGCACCTTGTCCCCGCA
           A  L  P  K  R  R  A  Y  E  T  R  P  V  P  A  N

GTTGGGCAGCGGATGGGACCCCCCGGCGCTGAGCGCTCGGAGCGCTGC
         ........+.........+.........+.........+.........+ 2700
         GCAACCCGTCGCCCTACCCTGGGGGCCGCGACTCGCGAGCCTCGCGACG
           N  P  L  P  N  S  G  R  A  S  L  A  R  L  A  A
```

FIG. 5Ba

```
       GTCTGGATGGTCTACGTCCACGACCAGCAGGTTTGCCAGCCCTCTTC
2701-..........+..........+..........+..........+........
       CAGACCTACCAGATGCAGGTGCTGGTCGTCCAAACGGTCGCGACAAC
   d    D  P  N  D  V  D  V  V  L  L  N  A  L  A  T  P

ATCCCCTCGAGCAGATCGTCGCTTGCCAGCGCCCAGTACGGCAGCCA
2801-..........+..........+..........+..........+........
       TAGGGGAGCTCGTCTAGCAGCGAACGGTCGCGGGTCATGCCCTCGGT
   d     G  E  L  L  D  D  S  A  L  P  W  Y  P  L  W

TAATCACCGGTGTATGGTCCGACACGACCTCCAAGTCAGATATTTCG
2901-..........+..........+..........+..........+........
   d   ATTAGTGGCCACATACCAGGCTGTGCTCGAGGTTCAGTCTATAAAGC
        T  V  P  T  N  D  S  V  L  E  L  D  S  I  E  S

TGATGAAACACCACCCACAGCCGAGCACCCCCAACCACCTGTACCAAC
3001-..........+..........+..........+..........+........
       ACTACTTTGTGGTCGCTGTCGCCTCGTGCCGGTTGGTGGACATGGTTG
   d   S  S  V  G  A  V  A  S  C  G  W  G  G  T  G

CTGTCCGCCCGTACACGCCGCCTTAGACCCGTTAGACCCCCTGCCGC
3101-..........+..........+..........+..........+........
       GAGACCGCGGCATGTGCGGCGGAATCTGGGCAATCTGGGGGACGGC
          ┌─────────────┐
          │ S,p,l,I │
          └─────────────┘
       CTCACCTGGCTTTATGGCGTACGAATCGGCTGTGTGCGACCTGTTGGGC
3201-..........+..........+..........+..........+........
       CAGTGGACCGAAATACCGCATGCTTAGCCGACACACGCTGGACAACCCG

CGAGCCCGCACGGCCGCGCGCGGTGTCAACAACCGGGTGAGTCGTGCAC
3301-..........+..........+..........+..........+........
       GCTCGGGCGTGCCGGCGCGCGCCACAGTTGTTGGCCCACTCAGCACGTG

CCGCCCGATGAGCCGCGCCTTACGCTGGCTGCCAGCCGTTCGCGGGCTCG
3401-..........+..........+..........+..........+........
       GGCGGGCTACTCGGCGCGGAATGCGACCGACGGTCCGCAAGCGCCCGAC

AGGCCTCGCCCTTTTTAAGGCTGAATTTGCTTGTCTCCGAATCCAACTGG
3501-..........+..........+..........+..........+........
       TCCGGAGCGGGAAAAATTCCGACTTAAACGAACAGAGGCTTAGGTTGAC

ACACATGACCAACTTCGATAACGTTCTCGGCTCGATCTCCCTCGCGCGTT
3601-..........+..........+..........+..........+........
       TGTGTACTGGTTGAAGCTATTGCAAGAGCCGAGCTAGACGGAGCCCGCAA

ACAGCTTGTCTGTAAGCGGATGCCGCGAGCAGACAAGCCCGTCAGGGCGC
3701-..........+..........+..........+..........+........
       TGTCGAACACACATTCGCCTACGGCCCTCGCTGTTCGGGCAGTCCCGCGC

GCGATAGCCGACTGTATACTGGCTTAACTATGCGGCATCAGAGCAGATTGT
3801-..........+..........+..........+..........+........
       CGCTATCGGCTCACATATGACCGAATTGATACGCCGTAGTCTCGTCTAACA

AGAAAATACCGCATCAGGCGCTCTTCCGCTTCCTCGCTCACTGACTCGCTG
3901-..........+..........+..........+..........+........
       TCTTTTATGGCGTAGTCCGCGAGAACCCGAAGGAGCGAGTGACTGAGCGAC

TAATACGGTTATCCACAGAATCAGCGGATAACGCAGGAAAGAACATCTGAG
4001-..........+..........+..........+..........+........
       ATTATGCCAATAGGTCTCTTAGTCCCCTATTGCGTCCTTTCTTGTACACTC

GTTTTTCCATAGGCTCCGCCCCCCGTACGAGCATCACAAAAATCGACGCTC
4101-..........+..........+..........+..........+........
       CAAAAAGGTATCCGAGCCCCGGGGACTGCTCGTACTGTTTTTACCTCCGA

CCCCCTGGAAGCTCCCTCGTGCGCTCTCCTGTTCCGACCCTGCCGCTTAC
4201-..........+..........+..........+..........+........
       GGCCGACCTTCGAGGGAGCACGCGAGAGGACAAGGCTGGGACGGCGAATG
```

MATCH WITH FIG. 5Bb

FIG. 5Bb

```
GGTTCCCCTCGATGTACCGGCGCCCTAGGGCCGACGCGCGGCTTTGGCGTAG
 -+---------+---------+---------+---------+---------+ 2800
CAACCCCAGCTACATGGCCGCCGGATCCCCGCTGCGCGCCGAAACCGCCATC
  M  A  E  I  Y  R  R  G  L  A  S  A  R  S  Q  R  Y  I
GAGCTGCTCAAATTCGTCGGCGACGTGGCTCACGCTTGGTAGTAGACCACGAT
 -+---------+---------+---------+---------+---------+ 2900
CTCGACGAGTTTAAGCAGCCGCTGCACCGAGTGCGAACCATCATCTGGTGCTA
  L  Q  E  F  E  D  A  V  M  S  V  S  P  L  L  G  R  N
TGAGGGGCCACCCCACAACTGCACACTCCCCCGCTCTCCCGTCGAGCCCTGA
 -+---------+---------+---------+---------+---------+ 3000
ACTCCCCGGTGGGGTGTTGACGTGTGAGGGGGCGAGAGGGCAGCTCGGGACT
  L  P  W  G  V  V  A  C  E  G  A  R  G  D  L  G  S
CAGGAGGAACACATGCGTCGTTTCGAGGACGTTTCCGGGCCGCTAAGAGCCG
 -+---------+---------+---------+---------+---------+ 3100
GTCCTCCTTGTGTACGCAGCAAAGCTCCTGCAAAGGCCCGGCGATTCTCGGC
  V  L  L  F  V
CTGAATCCGCCGGTACGAGCCACACAGCACCCGAACTTACGGAGCTGGTGGG
 -+---------+---------+---------+---------+---------+ 3200
GGACTTACGCGCCCATGCTCGGTGTGTCGTGGGCTTGATGCCTCGACCACCC
                                        M. rep - Mlu
                                        ◄───────────
GAGGTGAGATACCGCTACTCACGCTGGCAAGGGCGACACAGCCGCCCCAC
 +---------+---------+---------+---------+---------+ 3300
CTCCACTCTATGCGCGATGAGTGCGACCGTTCCCGCTGTGTCGGCGGGGTG
ACCAGCAGGTGTTCGAGGCTTGGCTCGAAGTGCAGGACATCGTGGCGAACG
 +---------+---------+---------+---------+---------+ 3400
TGGTCGTCCACAAGCTCCGAACCGAGCTTCACGTCCTGTAGCACCGCTTGC
TTGGTCGCAGCGCGTCGAGCGGTTAGAGGCCCTGCGGTGTTCCACCACCGC
 +---------+---------+---------+---------+---------+ 3500
CAACCACGTCGCCCAGCTCGCCAATCTCCGGGACCCCACAAGGTGGTGGCG
CTTGTCCAAGGGTGTATCTACGCTTAGTCCAAAGTTCAAACGAGGGGATT
 +---------+---------+---------+---------+---------+ 3600
CGAACAGGTTCCCACATAGATGCGAATCAGGTTTCAAGTTTGCTCCCCTAA
TCGGTGATGACGGTGAAAACCTCTGACACATGCAGCTCCCGGAGACGGTC
 +---------+---------+---------+---------+---------+ 3700
AGCCACTACTGCCACTTTTCCAGACTGTGTACGTCGAGGCCCTCTGCCAG
GTCAGCGGGTGTTGGCGGGTGTCGGGGCGCAGCCATGACCCAGTCACGTA
 +---------+---------+---------+---------+---------+ 3800
AGTCGCCCACAACCGCCCACAGCCCCGCGTCGGTACTGGGTCAGTGCAT
  M,a,c,I
ACTGAGAGTGCACCATATGCGGTGTGAAATACCGCACAGATGCGTAAGG
 .........+---------+---------+---------+---------+ 3900
TGACTCTCACGTGGTATACGCCACACTTTATGGCGTGTCTACGCATTCC
CGCTCGGTCGTTCGGCTGCGGCGAGCGGTATCAGCTCACTCAAAGGCGG
 .........+---------+---------+---------+---------+ 4000
GCGAGCCAGCAAGCCAGATTATTTTACCATGGTCTAGCGAGTTTCCTGAGT
CAAAAGCCCAGCAAAAGACCAGGAACCGTAAAAGGCCGCGTTGCTGGC
 ....+---------+---------+---------+---------+------+ 4100
GTTTTCCGGTCGTTTTCCGGTCCTTGGCATTTTTCCGGCGCAACGACCG
AAGTCAGAGGTGGCCAAACCCGACAGGACTATAAAGATACCAGGCGTTT
 ....+---------+---------+---------+---------+------+ 4200
GTTCAGTCTGCACCGGCTTTGGGCTGTCCTGATATTTCTATGGTCCGCAAA
CGGATACCTGTCCCCCTTTCTCCCTTCGGGAAGCGTGGCGCTTTCTCAAT
 ....+---------+---------+---------+---------+------+ 4300
GCCTATGGACAGGCGGAAAGAGGGAAGCCCTTCGCACCGCGAAAGAGTTA
```

MATCH WITH FIG. 5Ba

DELETED IN MU112-200s

```
       TTGATGTTGGAGGAGTGGCAATCCCAGGATACCAGGATCTTGAACTCGCCCTGGGTGAGTTTCTCCTTCATTACAGAAACCGCTTT
5501 ----------+---------+---------+---------+---------+---------+---------+---------+ 6000
       AACTACAACCTGCTCAGCCTTAGCGTCTGGGTCTATGGTCCTAGAACCGTAGAACCCACTCAAAAGAGGAAGTAATGTCTTTGCCGAAA
       D  V  G  R  V  G  I  A  D  R  Y  Q  D  L  A  I  L  W  N  C  L  G  E  F  S  P  S  L  G  K  R  L  F

TCAAAATATGGTATTGATAATCCYGATACTCATTTGATGCTGAATAAAATGCAGTTCATTTCAATCAGAATTCTAATCAGAATTCGTGTAACAC
6001 ----------+---------+---------+---------+---------+---------+---------+---------+ 6100
       AGTTTTATACCATAACTATTAGGACTACTGATTAAGCTGTCAAAGTAAACTACGAGCTACTCAAAAGACTAGTCTAACCAATTAACAATTGTG
       Q  K  Y  G  I  D  N  P  D  M  M  K  L  Q  F  E  L  M  L  D  E  F  F

TGGCCAGAGCATTACGCTGACTTACGGGACTGGCCTTTGTTGAATAATCGAACTTTTGCTGAGTTGAAGGATCAGATCAGGCCATCTCCCGACAAGGC
6101 ----------+---------+---------+---------+---------+---------+---------+---------+ 6200
       ACCGGTCTCGTAATGCGACTGAACTGCCCTGCCGCCGAAACAACTTATTAGCTTGAAAAAGGACTCAACTTCCTAGTCGTGCGTAGAAGGGCTGTTGCG

AGACCGGTTCCGTCGTGGCAAAGCAAAGTCAAAATCACCAACTGGTCCACTCACAACAAAGCTCTCATCAACCGCTCCCTCACTTTCTCGGCTGATGAT
6201 ----------+---------+---------+---------+---------+---------+---------+---------+ 6300
       TCTGCCAAGGCACCGTTCGTTTCAAGTTTTAGTTGTTTCGAGATGTTGTGGCACCGAGGTAGTGCACCGAGGAGTGAAAGACCGACCTACTA

GGGGCCGATTCAGCCCTGGTATGAGTCAGCAACACCTTCTTCAGGAGCCAGACCTCAGCGCCCCCATGTCATTCCGACAGCCATGCCAGTCACTATG
6301 ----------+---------+---------+---------+---------+---------+---------+---------+ 6400
       CCCGGGCTAAGTCGGACCATACTCAGTCGTTGTGGAAGAAGTCCCGTCGTTCGGAGTCGCGGGCCGCTAGCAGGTAGCGGTAGCGGTCAGTCAGTGATAC
                                                              ──────────────▶
                                                                  MAB-SPE

GCGTGCT
6401 ------ 6407
       CGCACGA
```

FIG. 9

SYNTHETIC MULTIPLE CLONING SITE (MCS) + STRAND

GAA GGC GCG GCC GCG GTA CCA GAT CTT TAA ATC TAG ATA TCC ATG GAT
CCA GCT GCA GAA TTC GAA GCT TAT CGA TGT CGA CGT AGT TAA CTA GCG
TAC GAT CGA CTG CCA GGC ATC AAA TAA AAC GAA AGG CTC AGT CGA AAG
AGT GGG CCT TTC GTT TTA TCT GTT GTT TGT CCG GCC ATC ATG GCC GCG
GTG ATC AGC TAG TAC G

FIG. 12a

NheI
Begin Kan Cassette                    pMV 206

```
      GCTAGCCAACAAAGCCGACGTTGTGTCTCAAAATCTCTGATGTTACATTGCAC
    1 ----------+----------+----------+----------+----------+---
      CGATCGGTTGTTCGCTGCAACACAGAGTTTTAGAGACTACAATGTAACGTG
                              KAN START CONDON
      ACAGTAATACAAGGGGTGTTATGAGCCATATTCAACCGGGAAACGTCTTGCTC
  101 ----------+----------+----------+----------+----------+---
      TGTCATTATGTTCCCCACAATACTCGGTATAAGTTGCCCTTTGCAGAACGAG
                    NruI
      ATGGGCTCGCGATAATGTCGGGCAATCAGGTGCGACAATCTATCGTTGTAT
  201 ----------+----------+----------+----------+----------+--
      TACCCGAGCGCTATTACAGCCCGTTAGTCCACGCTGTTAGATAGCAACAT
      GTTGCCAATGATGTTACAGATGAGATGGTCAGACTAAACTGGCTGACGGAA
  301 ----------+----------+----------+----------+----------+--
      CAACGGTTACTACAATGTCTACTCTACCAGTCTGATTTGACCGACTGCCTTAA
      CATGGTTACTCACCACTGCGATCCCCGGGAAAACAGCATTCCAGGTATTAGA
  401 ----------+----------+----------+----------+----------+--
      GTACCAATGAGTGGTGACGCTAGGGGCCCTTTTGTCGTAAGGTCCATAATCT
      CCTGCGCCGGTTGCATTCGATTCTGTTTGTAATTGTCCTTTTAACAGCGATC
  501 ----------+----------+----------+----------+----------+--
      GGACGCGGCCAACGTAAGCTAAGGACAAACATTAACAGGAAAATTGTCGCTA
      GTTGATGCGAGTGATTTTGATGACGAGCGTAATGGCTGGCCTGTTGAACAAG
  601 ----------+----------+----------+----------+----------+--
      CAACTACGCTCACTAAAACTACTGCTCGCATACCGACCGGACAACTTGTTCA
      TCACTCATGGTGATTTCTCACTTGATAACCTTATTTTTGACGAGGGGAAATTA
  701 ----------+----------+----------+----------+----------+--
      AGTGAGTACCACTAAAGAGTGAACTATTGGAATAAAAACTGCTCCCCTTTAA
      GGATCTYGCCATCCTATGGAACTGCCTCGGTGAGTTTTCTCCTTCATTACA
  801 ----------+----------+----------+----------+----------+--
      CCTAGAACGGTAGGATACCTTGACGGAGCCACTCAAAAGAGGAAGTAATG
                                              KAN STOP CONDON
      TTGCAGTTTCATTTGATGCTCGATGAGTTTTTCTAATCAGAATTGGTTAATT
  901 ----------+----------+----------+----------+----------+--
      AACGTCAAAGTAAACTACGAGCTACTCAAAAGATTAGTCTTAACCAATTAA
      TTGTTGAATAAATCGAACTTTTGCTGAGTTGAAGGATCAGATCACGCATCTTC
 1001 ----------+----------+----------+----------+----------+---
      AACAACTTATTTAGCTTGAAAACGACTCAACTTCCTAGTCTAGTGCGTAGAAG
      AACTGGTCCACCTACAACAAAGCTCTCATCAACCGTGGCTCCCTCACTTTCTG
 1101 ----------+----------+----------+----------+----------+---
      TTGACCAGGTGGATGTTGTTTCGAGAGTAGTTGGCACCGAGGGAGTGAAAGA
      END KAN CASSETTE I,e,P,S BEGIN E. RAP
      CCTCACGAGGCAGACCTCACTAGTTCCACTGAGCGTCAGACCCCGTAGAAAA
 1201 ----------+----------+----------+----------+----------+---
      GAAGTGCTCCGTCTGGAGTGATCAAGGTGACTCGCAGTCTGGGGCATCTTTT
      CTTGCAAACAAAAAAACCACCGCTACCAGCGGTGGTTTGTTTGCCCGGATCAA
 1301 ----------+----------+----------+----------+----------+---
      GAACGTTTGTTTTTTTGGTGGCGATGGTCGCCACCAAACAAACGGCCTAGTT
      ATACCAAATACTGTCCTTCTAGTGTAGCCGTAGTTAGGCCACCACTTCAAGA
 1401 ----------+----------+----------+----------+----------+---
      TATGGTTTATGACAGGAAGATCACATCGGCATCAATCCGGTGGTGAAGTTCT
```

MATCH WITH FIG. 12b

FIG. 12b

MATCH WITH FIG. 12a

```
AAGATAAAAATATATCATCATGAACAATAAAACTGTCTGCTTACATAA
........+.........+.........+.........+.........+ 100
TTCTATTTTTATATAGTAGTACTTGTTATTTTGACAGACGAATGTATT

GAGGCCGCGATTAAATTCCAACATGGATGCTGATTTATATGGGTATAA
........+.........+.........+.........+.........+ 200
CTCCGGCGCTAATTTAAGGTTGTACCTACGACTAAATATACCCATATT

GGGAAGCCCCATGCGCCAGAGTTGTTTCTGAAACATGGCAAAGGTAGC
........+.........+.........+.........+.........+ 300
ACCCTTCGGGGTACGCGGTCTCAACAAAGACTTTGTACCGTTTCCATCG

TTTATGCCTCTTCCGACCATCAAGCATTTTATCCGTACTCCTGATGATG
........+.........+.........+.........+.........+ 400
ATACGGAGAAGGCTGGTAGTTCGTAAAATAGGCATGAAGGACTACTAC

AGAATATCCTGATTCAGGTGAAAATATTGTTGATGCGCTGGCAGTGTT
........+.........+.........+.........+.........+ 500
TCTTATAGGACTAAGTCCACTTTTATAACAACTACGCGACCGTCACAA

GCGTATTTCGTCTCGCTCAGGCGCAATCACGAATGAATAACGGTTTG
........+.........+.........+.........+.........+ 600
GCGCATAAAGCAGAGCGAGTCCGCGTTAGTGCTTACTTATTGCCAAAC

TCTGGAAAGAAATGCATAATCTTTTGCCATTCTCACCGGATTCAGTCG
........+.........+.........+.........+.........+ 700
GACCCTTTCTTTACGTATTAGAAAACGGTAAGAGTGGCCTAAGTCAGC

ATAGGTTGTATTGATGTTGGACGAGTCGGAATCGCAGACCGATACCA
........+.........+.........+.........+.........+ 800
TTATCCAACATAACTACAACCTGCTCAGCCTTAGCGTCTGGCTATGGT

GAAACGGCTTTTTCAAAAATATGGTATTGATAATCCTGATATGAATAAA
........+.........+.........+.........+.........+ 900
TCTTTGCCGAAAAAGTTTTTATACCATAACTATTAGGACTATACTTATTT

GGTTGTAACACTGGCAGAGCATTACGCTGACTTGACGGGACGGCGGCT
........+.........+.........+.........+.........+ 1000
CCAACATTGTGACCGTCTCGTAATGCGACTGAACTGCCCTGCCGCCGA

CCGACAACGCAGACCGTTCCGTGGCAAAGCAAAAGTTCAAAATCACC
........+.........+.........+.........+.........+ 1100
GGCTGTTGCGTCTGGCAAGGCACCGTTTCGTTTTCAAGTTTTAGTGG

GCTGGATGATGGGCGATTCAGGCCTGGTATGAGTCAGCAACACCTT
........+.........+.........+.........+.........+ 1200
CCGACCTACTACCCCGCTAAGTCCGGACCATACTCAGTCGTTGTGGAA

GATCAAAGGATCTTCTTGAGATCCTTTTTTTCTGCGCGTAATCTGCTG
........+.........+.........+.........+.........+ 1300
CTAGTTTCCTAGAAGAACTCTAGGAAAAAAAGACGCGCATTAGACGAC

GAGCTACCAACTCTTTTTCCGAAGGTAACTGGCTTCAGCAGAGCGCAG
........+.........+.........+.........+.........+ 1400
CTCGATGGTTGAGAAAAAGGCTTCCATTGACCGAAGTCGTCTCGCGTC

ACTCTGTAGCACCGCCTACATACCTCGCTCTGCTAATCCTGTTACCAG
........+.........+.........+.........+.........+ 1500
TGAGACATCGTGGCGGATGTATGGAGCGAGACGATTAGGACAATGGTC
```

```
                TGGCTGCTGCCAGTGGCGATAAGTCGTGTCTTACCGGGTTGGACTCAA GAC
1501- - - - - - - - - +- - - - - - - - - +- - - - - - - - - +- - - - - - - - - +- - - - - - - - - +-
                ACCGACGACGGTCACCGCTATTCAGCACAGAATGGCCCAACCTGAGTTCTG

CACACAGCCCAGCTTGGAGCGAACGACCTACACCGAACTGAGATACCTACA
1601- - - - - - - - - +- - - - - - - - - +- - - - - - - - - +- - - - - - - - - +- - - - - - - - - +
                GTGTGTCGGGTCGAACCTCGCTTGCTGGATGTGGCTTGACTCTATGGATG

AGGTATCCGGTAAGCGGCAGGGTCCGAACAGGAGAGCGCACGAGGGAGCT
1701- - - - - - - - - +- - - - - - - - - +- - - - - - - - - +- - - - - - - - - +- - - - - - - - - +-
                TCCATAGGCCATTCGCCGTCCCAGCCTTGTCCTCTCGCGTGCTCCCTCGAA

TCTGACTTGAGCGTCGATTTTTGTGATGCTCGTCAGGGGGCGGAGCCTA
1801- - - - - - - - - +- - - - - - - - - +- - - - - - - - - +- - - - - - - - - +- - - - - - - - - +-
                AGACTGAACTCGCAGCTAAAAACACTACGAGCAGTCCCCCCGCCTCGGATA

GCCTTTTGCTCACATGTTCTTTCCTGCGTTATCCCCTGATTCTGTGGATAA
1901- - - - - - - - - +- - - - - - - - - +- - - - - - - - - +- - - - - - - - - +- - - - - - - - - +-
                CGGAAAACGAGTGTACAAGAAAGGACGCAATAGGGACTAAGACACCTATT
        END E.rep                    BEGIN M.rep
         I,U,1,  M I,t,o,N I,U,1 M
                ACCGAGCGCAACGCGTGCGGCCGCACGCGTGAGCCCACCAGCTCCGTAAGT
2001- - - - - - - - - +- - - - - - - - - +- - - - - - - - - +- - - - - - - - - +- - - - - - - - - +-
                TGGCTCGCGTTGCGCACGCCGGCGTGCGCACTCGGGTGGTCGAGGCATTCA ACGGGTCTAAGGCGGCGTGTACGGCCGCCACAGCGGCTCTCAGCGGCCCG
2101- - - - - - - - - +- - - - - - - - - +- - - - - - - - - +- - - - - - - - - +- - - - - - - - - +-
                TGCCCAGATTCCGCCGCACATGCCGGCGGTGTCGCCGAGAGTCGCCGGGC TGGGGGTGCTCGGCTGTCGCTGGTGTTCCACCACCAGGGCTCGACGGGAG
2201- - - - - - - - - +- - - - - - - - - +- - - - - - - - - +- - - - - - - - - +- - - - - - - - - +
        ---- ACCCCCACGAGCCGACAGCGACCACAAGGTGGTGGTCCCGAGCTGCCCTC TGGAGCTCGTGTCGGACCATACACCGGTGATTAATCGTGGTCTACTACCAA
2301- - - - - - - - - +- - - - - - - - - +- - - - - - - - - +- - - - - - - - - +- - - - - - - - - +-
                ACCTCGAGCACAGCCTGGTATGTGGCCACTAATTAGCACCAGATGATGGTT GCCGCTGGCAAGCGACGATCTGCTCGAGGGGATCTACCGCCAAAGCCGCG
2401- - - - - - - - - +- - - - - - - - - +- - - - - - - - - +- - - - - - - - - +- - - - - - - - - +-
                CGGCGACCGTTCGCTGCTAGAACGAGCTCCCCTAGATGGCGGTTTCGGCGC AACCTGCTGGTCGTGGACGTAGACCATCCAGACGCAGCGCTCCGAGCGCTC
2501- - - - - - - - - +- - - - - - - - - +- - - - - - - - - +- - - - - - - - - +- - - - - - - - - +
                TTGGACGACCAGCACCTGCATCTGGTAGGTCTGCGTCGCGAGGCTCGCGAG CCAACGGCCACGCACACGCAGTGTGGGCACTCAACGCCCCTGTTCCACGCA
2601- - - - - - - - - +- - - - - - - - - +- - - - - - - - - +- - - - - - - - - +- - - - - - - - - +
                GGTTGCCGGTGCGTGTGCGTCACACCCGTGAGTTGCGGGGACAAGGTGCG AGGCCTTCGGCGCGCCGTCGATGGCGACCGCAGTTACTCAGGCCTCATGA
2701- - - - - - - - - +- - - - - - - - - +- - - - - - - - - +- - - - - - - - - +- - - - - - - - - +
                TCCGGAAGCCGCGCGGCAGCTACCGCTGGCGTCAATGAGTCCGGAGTAC CTCTACACACTCAGCCACATCGAGGCCGAGCTCGGCGCGAACATGCCACC
2801- - - - - - - - - +- - - - - - - - - +- - - - - - - - - +- - - - - - - - - +- - - - - - - - - +-
                GAGATGTGTGAGTCGGTGTAGCTCCGGCTCGAGCCGCGCTTGTACGGTGG GGCGGAATTGCGCACTGTTCATTCCGTCAGGTTGTGGGCCTATCGTCCCG
2901- - - - - - - - - +- - - - - - - - - +- - - - - - - - - +- - - - - - - - - +- - - - - - - - - +-
                CCGCCTTAACGCGTGACAAGCTAAGGCAGTCCAACACCCGGATAGCAGGGC CGCGATCTATGCCGAGTGCCACGCGCGAAACGCCGAATTTCCGTGCAACG
3001- - - - - - - - - +- - - - - - - - - +- - - - - - - - - +- - - - - - - - - +- - - - - - - - - +-
                GCGCTAGATACGGCTCACGGTGCGCGCTTTGCGGCTTAAAGGCACGTTGC AGCATTTGGCGTTGGATCACAACCAAGTCGCGCATTTGGGCGGACGGGAT
3101- - - - - - - - - +- - - - - - - - - +- - - - - - - - - +- - - - - - - - - +- - - - - - - - - +-
                TCGTAAACCGCAACCTAGTGTGGTTCAGCGCGTAAACCCGCCTGCCCTAG
```

FIG. 12Ab   MATCH WITH FIG. 12Aα

FIG. 12Aα

```
                GATAGTTACCGGATAAGGCGCAGCGGTCGGGCTGAACGGCGGGTTCGTG
            ........+........+........+........+........+........+ 1600
                CTATCAATGGCCTATTCCGCGTCGCCAGCCCGACTTGCCCCCCAAGCAC
                GCGTGAGCATTGAGAAAGCGCCACGCTTCCCGAAGGGAGAAAGGCGGAC
            ........+........+........+........+........+........+ 1700
                TCGCACTCGTAACTCTTTCGCGGTGCGAAGGGCTTCCCTCTTTCCGCCTG
                TCCAGGGGGAAACGCCTGGTATCTTTATAGTCCTGTCGGGTTTCGCCACC
            ........+........+........+........+........+........+ 1800
                GGTCCCCCTTTGCGGACCATAGAAATATCAGGACAGCCCAAAGCGGTGG
                TGGAAAAACGCCAGCAACGCGGCCTTTTTACGTTCCTGGCCTTTTGCTG
            ........+........+........+........+........+........+ 1900
                CCTTTTTGCGGTCGTTGCGCCGGAAAAATGCCAAGGACCGGAAAACGAC
                CCGTATTACCGCCTTGAGTGAGCTGATACCGCTCGCCGCAGCCGAACG
            ........+........+........+........+........+........+ 2000
                GGCATAATGGCGGAAACTCACTCGACTATGGCGAGCGGCGTCGGCTTGC

TCGGGCGCTGTGTGGCTCGTACCCGCGCATTCAGGCGGCAGGGGGTCTA
            ........+........+........+........+........+........+ 2100
                AGCCCGCGACACACCGAGCATGGGCGCGTAAGTCCGCCGTCCCCCAGAT
                GAAACGTCCTCGAAACGACGCATGTGTTCCTCCTGGTTGGTACAGGTGGT
            ........+........+........+........+........+........+ 2200
                CTTTGCAGGAGCTTTGCTGCGTACACAAGGAGGACCAACCATGTCCACCA
                AGCGGGGAGTGTGCAGTTGTGGGGTGGCCCCTCAGCGAAATATCTGACT
            ........+........+........+........+........+........+ 2300
                TCGCCCCCTCACACGTCAACACCCCACCGGGGAGTCGCTTTATAGACTGA
                GCGTGAGCCACGTCGCCGACGAATTTGAGCAGCTCTGGCTGCCGTACTG
            ........+........+........+........+........+........+ 2400
                CGCACTCGGTGCAGCGGCTGCTTAAACTCGTCGAGACCGACGGCATGAC
                CGTCGGCCCTAGGCCGCCGGTACATCGAGGCGAACCCAACAGCGCTGGCA
            ........+........+........+........+........+........+ 2500
                GCAGCCGGGATCCGGCGGCCATGTAGCTCCGCTTGGGTTGTCGCGACCGT
                AGCGCCCGGGGGTCCCATCCGCTGCCCAACGCGATCGTGGGCAATCGCG
            ........+........+........+........+........+........+ 2600
                TCGCGGGCCCCAGGGTAGGCGACGGGTTGCGCTAGCACCCGTTAGCGC
                CCGAATACGCGCGGCGTAAGCCGCTCGCATACATGGCGGCGTGCGCCGA
            ........+........+........+........+........+........+ 2700
                TGGCTTATGCGCGCCGCATTCGGCGAGCGTATGTACCGCCGCACGCGGCT
                CCAAAAACCCCGGCCACATCGCCTGGGAAACGGAATGGCTCCACTCAGAT
            ........+........+........+........+........+........+ 2800
                TGTTTTTGGGGCCGGTGTAGCGGACCCTTTGCCTTACCGAGGTGAGTCTA
                GCCGCGCTGGCGTCAGCAGACCACGTACAAAGCGGCTCCGACGCCGCTAG
            ........+........+........+........+........+........+ 2900
                CGGCGCGACCGCAGTCGTCTGGTGCATGTTCGCCGAGGCTGCGGCGATC
                CCCTCATGCGGATCTACCTGCCGACCCGGAACGTGGACGGACTCGGCCG
            ........+........+........+........+........+........+ 3000
                GGGAGTACGCCTAGATGGACGGCTGGGCCTTGCACCTGCCTGGAGCCGGC
                ACGTGTGTCCCGGACCGCTACCGGACAGCGAGGTCCGCGCCATCGCCAAC
            +........+........+........+........+........+........+ 3100
                TGCACACAGGGCCTGGCGATGGCCTGTCGCTCCAGGCGCGGTAGCGGTTG
                CGTGGTCTACGAGGCCACACTCAGTGCGCGCCAGTCGGCCATCTCGCGGA
            ........+........+........+........+........+........+ 3200
                CACCAGATGCTCCGGTGTGAGTCACGCGCGGTCAGCCGGTAGAGCGCCT
```

FIG. 12Ab    MATCH WITH FIG. 12Aa

```
             AGGGCGCAGCAGCGCCCACGGCGGCGAGCACAGTTGCGCGGCGCGCAAAG
3201 ----------+----------+----------+----------+----------+.
             TCCCGCGTCGTCGCGCGTGCCGCCGCTCGTGTCAACGCGCCGCGCGTTTCA

CGGCTACAGCGACGGCTACAACCGGCAGCCGACTGTCCGCAAAAAGCGGCG
3301 ----------+----------+----------+----------+----------+.
             GCCGATGTCGCTGCCGATGTTGGCCGTCGGCTGACAGGCGTTTTTCGCCGC

GTCGTCCGGCTCGTGGCGCAGGAACGCAGCGAGTGGCTCGCCGAGCAGGC
3401 ----------+----------+----------+----------+----------+
             CAGCAGGCCGAGCACCGCGTCCTTGCGTCGCTCACCGAGCGGCTCGTCCG

GGCCGCAAACGGCCAAACATTTCGGGCTGCATCTGGACACCGTTAAGCGA
3501 ----------+----------+----------+----------+----------+
             CCGGCGTTTGCCGGTTTGTAAAGCCCGACGTAGACCTGTGGCAATTCGCT

AAAGGCCCACAACGAAGCCGACAATCCACCGCTGTTCTAACGCAATTGG
3601 ----------+----------+----------+----------+---------.
             TTTCCGGGTGTTGCTTCGGCTGTTAGGTGGCGACAAGATTGCGTTAAC

CAGGTAAAAGTCCTGGTAGACGCTAGTTTTCTGGTTTGGGCCATGCCT
3701 ----------+----------+----------+----------+---------.
             GTCCATTTTCAGGACCATCTGCGATCAAAAGACCAAACCCGGTACGGA

GGGTTCTACGAATCTTGGTCGATACCAAGCCATTTCCGCTGAATATCG
3801 ----------+----------+----------+----------+---------.
             CCCAAGATGCTTAGAACCAGCTATGGTTCGGTAAAGGCGACTTATAGC
```

Multiple Cloning Site
                                         S      B
                                    N         K g
                       End M. rep    o    c    p l
                                     t    I    n I
                                     I    I    I I

```
             TTGTAGTGTTGTGGTGGCATCCGTGGCGCGGCCGCGGTACCAGATCTT
3901 ----------+----------+----------+----------+---------.
             AACATCACAACACCACCGTAGGCACCGCGCCGGCGCCATGGTCTAGAA
                             S
   Stop Codons              p       Begin Transcription Terminator
   3 Frames                 l
                            I
             GACGTAGTTAACTAGCGTACGATCGATCGCCAGGCATCAAATAAAACG.
4001 ----------+----------+----------+----------+---------+
             CTGCATCAATTGATCGCATGCTAGCTGACGGTCCGTAGTTTATTTTGCT
                S
       S       B
       f       c       c
       l       I       l
       I       I       I
             CATCATGGCCGCGGTGATCA
4101 ----------+---------+4120
             GTAGTACCGGCGCCACTAGT
```

MATCH WITH FIG. 12Bb

```
TCCGCGTCAGCCATGCATGGAGGCATTGCTATGAGCGACGGCTACAGCGA
..........+..........+..........+..........+..........+3300
GGCGCAGTCGGTTACGTACCTCCGTAACGATACTCGCTGCCGATGTCGCT

CGTGACCGCCGCCGAAGGCGCTCGAATCACCGGACTATCCGAACGCCAC
..........+..........+..........+..........+..........+3400
GCACTGGCGGCGGCTTCCGCGAGCTTAGTGGCCTGATAGGCTTGCGGTG

TGCACGCCGCGAACGCATCCGCGCCTATCACGACGACGAGGGCCACTCTT
..........+..........+..........+..........+..........+3500
ACGTGCGGCGCTTGCGTAGGCGCGGATAGTGCTGCTGCTCCCGGTGAGAA

CTCGGCTATCGGGCGAGGAAAGAGCGTGCGGCAGAACAGGAAGCGGCTCA
..........+..........+..........+..........+..........+3600
GAGCCGATAGCCCGCTCCTTTCTCGCACGCCGTCTTGTCCTTCGCCGAGT

GGAGCGGGTGTCGCGGGGGTTCCGTGGGGGGTTCCGTTGCAACGGGTCGGA
.+..........+..........+..........+..........+..........+3700
CCCTCGCCCACAGCGCCCCAAGGCACCCCCAAGGCAACGTTGCCCAGCCT

GTCTCGTTGCGTGTTTCGTTGCGCCCGTTTTGAATACCAGCCAGACGAGACG
.+..........+..........+..........+..........+..........+3800
CAGAGCAACGCACAAAGCAACGCGGGCAAAACTTATGGTCGGTCTGCTCTGC

GGGAGCTCACCGCCAGAATCGGTGGTTGTGGTGATGTACGTGGCGAACTCCG
.+..........+..........+..........+..........+..........+3900
CCCTCGAGTGGCGGTCTTAGCCACCAACACCACTACATGCACCGCTTGAGGC
                                        H
                                        i
               E    B      P    E       n
     D   X     c    N      v    Pc      d      C    S
     r   b     o    c      u    so      I      l
               R    o H    I    tR      I
     I   I     V    I I    I    I I     I      I    I
     TAAATCTAGATATCCATGGATCCAGCTGCAGAATTCGAAGCTTATCGATGTC
     .+..........+..........+..........+..........+..........+4000
     ATTTAGATCTATAGGTACCTAGGTCGACGTCTTAAGCTTCGAATAGCTACAG

AAAGGCTCAGTCGAAAGACTGGGCCTTTCGTTTTATCTGTTGTTTGTCCGGC
     .+..........+..........+..........+..........+..........+4100
     TTCCGAGTCAGCTTTCTGACCCGGAAAGCAAAATAGACAACAAACAGGCCG
```

MATCH WITH FIG. 12Ba

FIG. 13

```
      1         10         20         30         40         50         60
      1 TCTAGACAAG GTCGAACGAG GGGCATGACC CGGTGCGGGG CTTCTTGCAC TCGGCATAGG  60
     61 CGAGTGCTAA GAATAACGTT GGCACTCGCG ACCGGTGAGT CGTAGGTCGG GACGGTGAGG 120
    121 CCAGGCCCGT CGTCGCAGCG AGTGGCAGCG AGGACAACTT GAGCCGTCCG TCGGGGCAC  180
    181 TGCCCCCGGC CAGCGGTAAGT AGCGGGGTTG CCGTCACCCG GTGACCCCCG GTTTCATCCC 240
    241 CGATCGGCTAG C                                                       251
```

FIG. 15

```
      1         10         20         30         40         50         60
      1 AGATCTGTCC TCAATGCCGA TGGACCGCTA CGACAGGCAA AGGAGCACAG GGTGAACCGT  60
     61 GGACTGACGG TCGCGGGTAGC CGGAGCCGCC ATTCTGGTCG CAGGTCTTTC CGGATGTTCA 120
    121 AGCAACAAGT CCACGGATCC AGCTGCAGAA TCC                                153
```

FIG. 14
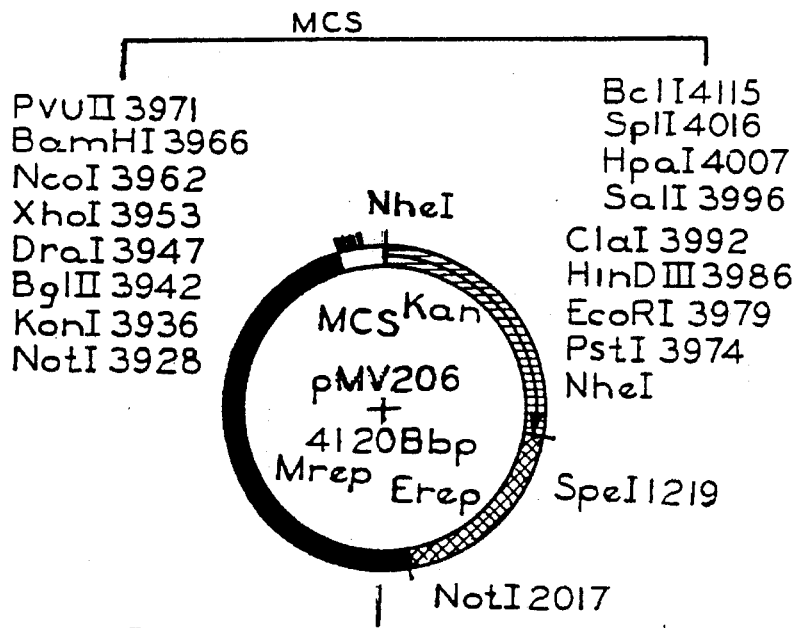
PCR AMPLIFY hsp60 PROMOTER FROM pMV261 PRIMERS INCLUDING ADDED XbaI-NheI SITES. DIGEST PCRhsp60 FRAGMENT WITH XbaI AND NheI. LIGATE INTO XbaI DIGESTED pMV206 AND SCREEN FOR CORRECT ORIENTATION.
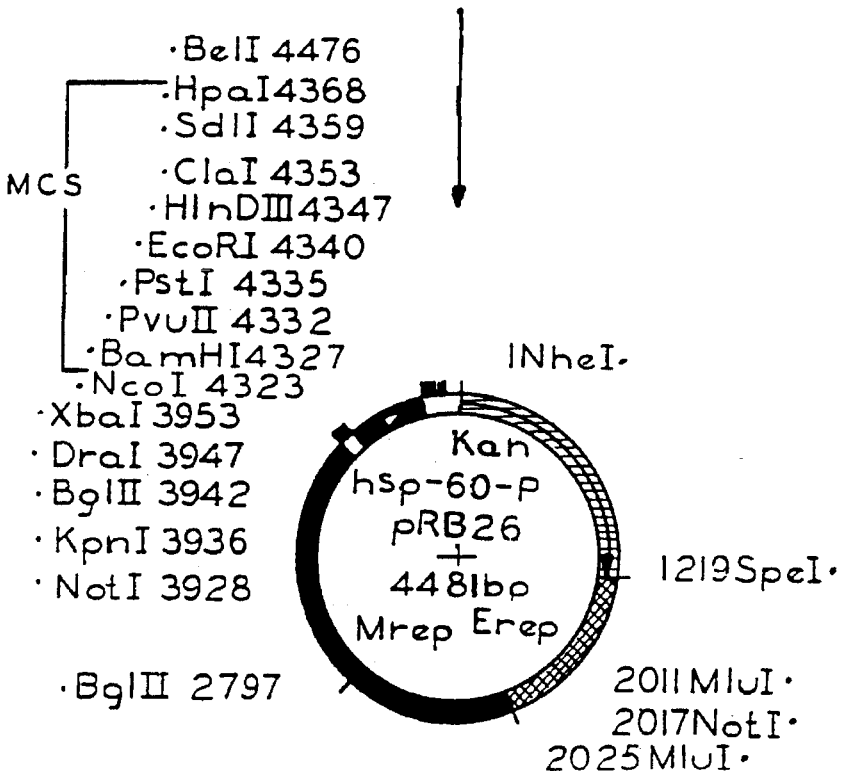

FIG. 16

```
                               • BclI 4476
                               • HpaI 4368
         • HinDIII 4347        • SalI 4359
MCS      • EcoRI 4340          • ClaI 4353
         • PstI 4335
         • PvuII 4332
         • BamHI
         └ NcoI                                    1 NheI •
    • XbaI 3953              ┌─────────┐
    • DraI 3947              │   Kan   │
    • BglII 3942             │ hsp-60-P│
    • KpnI 3936              │  pRB26  │           1219 SpeI •
    • NotI 3928              │  4481bp │           2011 MluI •
                             │ Mrep Erep│          2017 NotI •
         • BglII 2797        └─────────┘           2025 MluI •
```

PCR AMPLIFY SEQUENCES ENCODING THE 19KDa ANTIGEN GENE RBS + START CODON + SIGNAL PEPTIDE FROM M. TUBERCULOSIS CHROMOSOMAL DNA WITH PRIMERS INCLUDING ADDED BglII - BamHI - EcoRI SITES. DIGEST PCR FRAGMENT WITH BglII - EcoRI. LIGATE INTO BamHI - EcoRI DIGESTED pRB26.

```
                  • BclI 4492
                  • HpaI 4394
                  • SalI 4375
MCS               • ClaI 4369
                  • HindIII 4363
         • PstI 4351
         • PvuII 4346                              1 NheI •
         └ BamHI 4343         ┌─────────┐
                              │  19K-S  │
    • XbaI 3953               │ hsp60-P │
    • BglII 3942              │  p2619S │ Kan      1219 SpeI •
    • KpnI 3935               │ 4497bp  │
    • NotI 3928               │ Mrep Erep│         2011 MluI •
                              └─────────┘         2017 NotI •
         • BglII 2797                              2025 MluI •
```

FIG. 18

```
      1          10         20         30         40         50         60
      |          |          |          |          |          |          |
  1   TCTAGACAAG GTCGAACGAG GGGCATGACC CGGTGCGGGG CTTCTTGCAC TCGGCATAGG   60
 61   CGAGTGCTAA GAATAACGTT GGCACTCGCG ACCGGTGAGT CGTAGGTCGG GACGGTGAGG  120
121   CCAGGCCCGT CGTCGCAGCG AGTGCCAGCG AGGACAACTT GAGCCGTCCG TCGCGGCAC   180
181   TGCGCCCGGC CAGCGTAAGT AGCGGGGTTG CCGTCACCCG GTGACCCCCG GTTTCATCCC  240
241   CGATCCGGAG GAATCACTTC GCCATGG                                      267
```

FIG. 26

```
      1          10         20         30         40         50         60
      |          |          |          |          |          |          |
  1   AGATCTGGAC GTCAAGGACG CCAAGCCGCG AAATTGAAGA GCACAGAAAG GTATGGCGTG   60
 61   AAAATTCGTT TGCATACGCT GTTGGCCGTG TTGACCGCTG CGCGGCTGCT GCTAGCAGCG  120
121   GCGGGCTGTG GCTCGAAACC ACCGAGCGGT TCGCCTGAAA CGGGCGCCGG CGCCGGTACT  180
181   GTCGCGACTA CGGATCCAGC TGCAGAATTC                                   210
```

MCS

PvuII 3971
BamHI 3966
NcoI 3962
XhoI 3953
DraI 3947
BglII 3942
KpnI 3936
NotI 3928

BclI 4115
SpII 4016
HpaI 4007
SalI 3996
ClaI 3992
HinDIII 3986
EcoRI 3979
PstI 3974
NheI pMV206
4120Bbp
Mrep Erep
SpeI 1219
NotI 2017

PCR AMPLIFY SEQUENCES ENCODING THE 19KDa ANTIGEN GENE PROMOTER + RBS + START CODON + SIGNAL PEPTIDE FROM M. TUBERCULOSIS CHROMOSOMAL DNA WIT

FIG. 20

```
         1          10         20         30         40         50         60
    1    TCTAGACGGT TTGTGTTCCA TCGGCACTAC ATTGCCACTA CTACGGTGCA CGCCGGTAGA   60
   61    TGCCGGTTGGC GAACCACGCT ACCGACCAGA AAGAGAGAAT TTTCCGCCGC ACCTAGACCT  120
  121    CGGGCCCTGC TAACGCGCAT ACTGCCGAAG CGGTCCTCAA TGCCGATGGA CCGGCTACGAC 180
  181    AGGCAAAGGA GCACAGGGTG AAGGGTGGAC TGACGGTCGC GGTAGCCGGA GCCGCCATTC  240
  241    TGGTCGCAGG TCTTTCCGGA TGTTCAAGCA ACAAGTCCAC GGATCC                 286
```

FIG. 24

```
         1          10         20         30         40         50         60
    1    TCTAGATGTT CTTCGACGGC AGGCTGGTGG AGGAAGGGCC CACCGAACAG CTATTCTCCT   60
   61    CGCCGAAGCA TGCGGAAACC GCCCGATACG TCGCCGGACT GTCGGGGAC  GTCAAGGACG  120
  121    CCAAGCGCGG AAATTGAAGA GCACACAAAG GTATGGCGTG AAAATTCGTT TGCATACGCT  180
  181    GTTGGCCGTG TTGACCGCTG CGCCGCTGCT GCTAGCAGCG GCGGCTGTG  GCTCGAAACC  240
  241    ACCGAGCGGT TCGCCCTGAA ACGGGGCCGG CGGGGCCCGG CGCCGGTACT GTCGCGACTA  CGGATCC 297
```

FIG. 21

MCS

PvuII 3971
BamHI 3966
NcoI 3962
XhoI 3953
DraI 3947
BglII 3942
KpnI 3936
NotI 3928

BclI 4115
SpII 4016
HpaI 4007
NheI

SalI 3996
ClaI 3992
HinDIII 3986
EcoRI 3979
PstI 3974
NheI pMV206
+
4120Bbp
MCS Kan
Mrep  Erep SpeI 1219

NotI 2017

PCR AMPLIFY SEQUENCES ENCODING THE 38kDa ANTIGEN GENE PROMOTER + RBS + START CODON + SIGNAL PEPTIDE FROM M. TUBERCULOSIS CHROMOSOMAL DNA WITH PRIMERS INCLUDING ADDED XbaI-BamHI SITES. DIGEST PCR FRAGMENT WITH XbaI-BamHI. LIGATE INTO XbaI-BamHI DIGESTED pMV206.

MCS:
BclI 4393
HpaI 4386
SalI 4376
ClaI 4370
HinDIII 4364
EcoRI 4357
PstI 4352
PvuII 4349
BamHI 4344
NcoI 4168

·XbaI 3953
·BglII 3942
·KpnI 3936
·NotI 3928

INheI· p38PS
+
4398bp
38K-PS Kan
oriM  oriE

1219 SpeI·

·BglII 2797

2011 MluI·
2017 NotI·
2025 MluI·

FIG. 22

HSP 61 Cassette

```
    TCTAGAGGTGACCACAACGACGAGGCGCCCCCTTTGATCGGGAGTCGTGCGGGCGAGGTCTGCGGGAGTCGTCGTGCGGTCTTGTGTCGTCGGTGCGGTCATGGGCCGAACATAC
1   ---------+---------+---------+---------+---------+---------+---------+---------+---------+---------+ +100
    CGATCCCCACTGGTTGTTGCTGCGCCGGACGAAACTAGCCCTCGACGCCTGCAGAGCCCTTGACTTGGAAATGCCAGAACAACAGCAACCCGCCAGTACCCGGCTTGTATG

TCACCCGGATCGGAGGCGGAAGGACAAGGTCGAAACGAGGGGGCATGACCCGGTGCGGAGGCTTCTTGCACTCGGCATAGGCGAGTGCTAAGATAACGTTGG
101 ---------+---------+---------+---------+---------+---------+---------+---------+---------+---------+ +200
    AGTGGGCCTAGCCTCCGCCTTCCAGCTTGCTCCCGTGTTCCAGCTTGCTCCCGTACTGGGCACGCCCGTGTCCCGGTCGGCCGAAGAACGTGAGCCGTATCCGCTCACGATTCTTATTGCAACC

CACTCGCGACCCGGTGAGTCGTAGGTCGGACCGTGAGCGAGCCCAGGCCCTTCGTGCGAGCGAGGAGGACAACTTGAGCCGTCCGTGCGGGCACTG-
201 ---------+---------+---------+---------+---------+---------+---------+---------+---------+---------+ +300
    GTGAGCGCTGCTGGCCACTCAGCATCCAGCCCTGGCCAGCCCCGTCCCGGACTGGCCAGCAGGCCCTTGCCTCCTGAACTCGGCAGGCAGCCCGTGAC

404
    CGCCCGGCCAGGGTAAGTAGGCGGGGTGCCGTCACCCGGTGACCCGGTTCATCCCGATCGGAGGAATCACTTCGCAATGGCCAAGACAATTGC GGATCC
301 ---------+---------+---------+---------+---------+---------+---------+---------+---------+---------+ +
    GGGGCCGGTCCGATTCATCGCCCCAACGGCAGTGGCGCCACTGGGCAATAGGGCGCCTAGCCGGCCAAAGTAGGGGCCTCCTTAGTGAAGCGTTACCGGTTACGGTTAAGGCCTAGG
                                                                                        M A K T I A D P
```

FIG. 29

|  | DOMAIN 1 | DOMAIN 2 |
|---|---|---|
| INT (λ) | RLAMELAVVTGQRVGDLCEMKWSDIVDG | HELRSLSA-RLYEKQ-ISDKFAQHLLGHKS-DTMASQYR- |
| INT (HK22) | RLAMDLAVVTGQRVGDLCRMKWSDIVDG | HELRSLSA-RLYRNQ-IGDKFAQRLLGHKS-DSMAARYRD |
| INT (φ80) | VFLVKFIMLTGCRTAEIRLSERSWFRLD | HDMRRTIATNLSELG-CPPHVIEKLLGHQM-VGVMAHYN- |
| INT (P2) | KKIAILCLSTGARWGEAARLKAENIIHN | HALRHSFATHFMING-GSIITLQRILGHTR-IEQTMVYAH |
| INT (P4) | MIAVKLSLLTFVRSSELRFARMDEFDFD | HGFRTMARGALGESGLWSDDAIERQSLHSERNNVRAAYIH |
| INT (P22) | KSVVEFALSTGLRRSNINLEWQQIDMQ | HDLRHTWASWLVQAG-VPISVLQEMGGWES-IEMVRRYAH |
| INT (186) | ETVVRICLATGARWSEAESLRKSQLAKY | HVLRHTFASHFMMNG-GNILVLQRVLGHTD-IKMTMRYAH |
| INT (HP1) | GLIVRICLATGARWSEAETLTQSQVMPY | HVLRHTFASHFMMNG-GNILVLKEILGHST-IEMTMRYAH |
| INT (L54a) | AGAVEVQALTGMRIGELLALQVKDVDLK | HTLRHTHISLLAEMN-ISLKAIMKRVGHRDEKTTIKVYTH |
| Cre (P1) | TAGVEKALSLGVTKLVERWISVSGVADD | HSARVGAARDMARAG-VSIPEIMQAGGWTN-VNIVMNYIR |
| D Prot. (F) | KMLLATLWNTGARINEALALTRGDFSLA | HTFRHSYAMHMLYAG-IPLKVLQSLMGHKS-ISSTEVYTK |
| Fim B | YCLTLLCFIHGFRASEICRLRISDIDLK | HMLRHSCGFALANMG-IDTRLIQDYLGHRN-IRHTVRYTA |
| Fim E | YCLILLAYRHGMRISELLDLHYQDLDLN | HMLRHACGYELAERG-ADTRLIQDYLGHRN-IRHTVRYTA |
| Tn2603 ORF3 | RLFAQLLYGTCMRISEGLQLRVKDLDFD | HTLRHSFATALLRSG-YDIRTVQDLLGHSD-VSTTMIYTH |
| Tn554 TnpA | KLILMLMYEGGLRIGEVLSLRLEDIVTW | HMLRHTHATQLIREG-VDVAFVQKRLGHAHVQTTLNTYVH |
| Tn554 TnpB | ATMTMIVQECGMRISELCTLKKGCLLED | HAFRHTVGTRMINNG-MPQHIVQKFLGHES-PEMTSRYAH |
| Tn4430 Tnpl | YAIATLLAYTGVRISEALSIKMNDFNLQ | HQLRHFFCTNAIEKG-FSIHEVANQAGHSN-IHTTLLYT- |
| Rci | YVIFHLALETAMRQQEILALRWEHIDLR | HDLRHEAISRFFELGSLNVMEIAAISGHRS-MNMLKRYTH |
| Tn1545 ORF2 | YDEILILLKTGLRISEFGGLTLPDLDFE | HIGRHLMTSFLSMKGLTELTNVVGNWSDKRASAVATTYTH |
| Flp | ---------------------------- | HIGRHLMTSFLSMKGLTELTNVVGNWSDKRASAVATTYTH |
| CONSENSUS | --lv-L-l-TGmR-SEl--Lr--di--- | H-LRHt-At-L---G---i---iQ-ILgh---i--T--Y-H |
| L5 | RIAAYILAWTSLRFGELIELRRKDIVDD | HDLRAVGATFAAQAG-ATTKELMARLGHTT-PRMAMKYQM |

FIG. 31a

```
      I,1,a,S
   1  GTCGACCACCAAGGGCACCATCTCTGCTTGGGCCACCCCGTTGGCCGCAGC
      ..........+..........+..........+..........+..........+
      CAGCTGGTGGTTCCCGTGGTAGAGACGAACCCGGTGGGGCAACCGGCGTC

101 GCGAGGGTTCCGACCGCTGCAACTCCCGGTGCAACCTTGTCCCGGTCTAT
      ..........+..........+..........+..........+..........+
      CGCTCCCAAGGCTGGCGACGTTGAGGGCCACGTTGGAACAGGGCCAGATAA

GCGCAGGCGGGGGGCTCTATTCGTTTGTCAGCATCGAAAGTAGCCAGATCA
  201 ..........+..........+..........+..........+..........+
      CGCCGTCCGCCCCCCGAGATAAGCAAACAGTCGTAGCTTTCATCGGTCTAG

301 TTGCAGACCCCTGGAAAGAAAAATGGCCAGAGCGCGAAAACACCCTCTGA
      ..........+..........+..........+..........+..........+
      AACGTCTGGGGACCTTTCTTTTTACCGGTCTCCCGCTTTTGTGGGAGACT
                         Nde I
                           I
  401 TGGGTGTCTGCCGACCACATATGGGCCGGTCAAGATAGGTTTTTACCCCCT
      ..........+..........+..........+..........+..........+
      ACCACAGACGGCTGGTGTATACCCGGCCAGTTCTATCCAAAAAATGGGGG

501 TTGAAGCCTGAGAGTTGCACAGGAGTTGCAACCCGGTAGCCTTGTTCACGAC
      ..........+..........+..........+..........+..........+
      AACTTCGGACTCTCAACGTGTCCTCAACGTTGGGCCATCGGAAACAAGTGCT
                     BamHI
                       I
      AGCGCAGCGGGAGGATCCAAGCCTCATACGTCAACCCGCAGGACGGTGTGA
  601 ..........+..........+..........+..........+..........+
      TCGCGTCGCCCTCCTAGGTTCGGAGTATGCAGTTGGGCGTCCTGCCACACT
  Int                                              V  R
                                               Int start?
      CGCGGGCGAGAAGCGGCTCATCGAGATGGAGACCTGGACCCCTCCACAGG
  701 ..........+..........+..........+..........+..........+
      GCGCCCGCTCTTCGCCGAGTAGCTCTACCTCTGGACCTGGGGAGGTGT
  Int L  A  G  E  K  R  L  I  E  M  E  T  W  T  P  P  Q ACCCGGAAGTGGCTCGTGGAGCGCGACCTCGCAGACGGCACCAGGGATCTG
  801 ..........+..........+..........+..........+..........+
      TGGGCCTTCACCGAGCACCTCGCGCTGGAGCGTCTGCCGTGGTCCCTAGAC
  Int T  R  K  W  L  V  E  R  D  L  A  D  G  T  R  D  L CGGTCACAGAGATGACGCCAGCTCTGGTGCGTGCGTGGTGGGCCGGGATGG
  901 ..........+..........+..........+..........+..........+
      GCCAGTGTCTCTACTGCGGTCGAGACCACGCACGCACCACCCGGCCCTACC
  Int V  T  E  M  T  P  A  L  V  R  A  W  W  A  G  M  G GGTGATGAACACAGCGGTCGAGGACAAGCTGATCGCAGAGAACCCGTGCCGG
 1001 ..........+..........+..........+..........+..........+
      CCACTACTTGTGTCGCCAGCTCCTGTTCGACTAGCGTCTCTTGGGCACGGCC
  Int V  M  N  T  A  V  E  D  K  L  I  A  E  N  P  C  R
                                  Bg III
                                     I
      GAGGAGCTGGACATCGTCGCCGCTGAGATCTTCGAGCACTACCGGATCGCGG
 1101 ..........+..........+..........+..........+..........+
      CTCCTCGACCTGTAGCAGCGGCGACTCTAGAAGCTCGTGATGGCCTAGCGCC
  Int E  E  L  D  I  V  A  A  E  I  F  E  H  Y  R  I  A  A TTCGCCGCAAGGACATCGTGGACGACGGCATGACGATGAAGCTCCGGGTGC
 1201 ..........+..........+..........+..........+..........+
      AAGCGGCGTTCCTGTAGCACCTGCTGCCGTACTGCTACTTCGAGGCCCACG
  Int R  R  K  D  I  V  D  D  G  M  T  M  K  L  R  V  R
```

MATCH WITH FIG. 31b

FIG. 31b

```
CAGCTCGCTGAGAGCCGTGAACGACAGGGCGAACGCCAGCCCGCCGACG
----------+---------+---------+---------+---------+ 100
GGTCGAGCGACTCTCGGCACTTGCTGTCCCGCTTGCGGTCGGGCGCTGC
TCTCTTCACTGCACCAGCTCCAATCTGGTGTGAATGCCCCTCGTCTGTTC
----------+---------+---------+---------+---------+ 200
GAGAAGTGACGTGGTCGAGGTTAGACCACACTTACGGGGAGCAGACAAG
GGGATGCGTTGCAACCGCGTATGCCCAGGTCAGAAGAGTCGCACAAGAG
----------+---------+---------+---------+---------+ 300
TCCCTACGCAACGTTGGCGCATACGGGTCCAGTCTTCTCAGCGTGTTCTC
CCAGCG GAGCGGGCGACGGGAATCGAACCCGCGTAGCTAGTTTCGAAGAA
----------+---------+---------+---------+---------+ 400
GGTCGC TCGCCCGCTGCCCTTAGCTTGGGCGCATCGATCAAACCTTGTT
        att P core
CTCGGCTGCATCCTCTAAGTGGAAAGAAATTGCAGGTCGTAGAAGCGCG
----------+---------+---------+---------+---------+ 500
AGAGCCGACGTAGGAGATTCACCTTTCTTTAACGTCCAGCATCTTCGCGC
GAGAGGAGACCTAGTTGGCAACGTCGCGGATGGGGATCGCTGAAGACTC
----------+---------+---------+---------+---------+ 600
GCTCTCCTCTGGATCAACCGTGCAGCGCCTACCCCTAGCGACTTCTGAG
                            PstI
                             I
GGTACTACGCGCTGCAGACCTACGACAACAAG ATGGACGCCGAA GCCTG
----------+---------+---------+---------+---------+ 700
CCATGATGCGCGACGTCTGGATGCTGTTGTTCTACCTGCGGCTTCGGAC
                                 Y Y A L Q T Y D N K M D A E A W
                                              Int start?
ACCGGGCGAAGAAGGCAGCCGCCAGCGCCATCACGCTGGAGGAGTAC
----------+---------+---------+---------+---------+ 800
CCTGGCCCGCTTCTTCCGTCGGCGGTCGCGGTAGTGCGACCTCCTCATG
 D R A K K A A A S A I T L E E Y
TACAGCGGGCACGCGGAGCGCCGCATCTACCCGGTGCTAGGTGAAGTGG
----------+---------+---------+---------+---------+ 900
ATGTCGCCCGTGCGCCTCGCGGCGTAGATGGGCCACGATCCACTTCACC
 Y S G H A E R R I Y P V L G E V A
GTAGGAAGCACCCGACTGCCGCCGGCATGCCTACAACGTCCTCCGGGC
----------+---------+---------+---------+---------+ 1000
ATCCTTCGTGGGCTGACGGCGGCCGTACGGATGTTGCAGGAGGCCCG
  R K H P T A R R H A Y N V L R A
ATCGAGCAGAAGGCAGCCGATGAGCGCGACGTAGAGGCGCTGACGCCT
----------+---------+---------+---------+---------+ 1100
TAGCTCGTCTTCCGTCGGCTACTCGCGCTGCATCTCCGCGACTGCGGA
  I E Q K A A D E R D V E A L T P CATACATCCTGGCGTGGACGAGCCTCCGGTTCGGAGAGCTGATCGAGC
----------+---------+---------+---------+---------+ 1200
GTATGTAGGACCGCACCTGCTCGGAGGCCAAGCCTCTCGACTAGCTCG
   Y I L A W T S L R F G E L I E L
GCCGTGGCGCTTCCCGCGTGGGGAACAAGATCGTCGTTGGCAACGCCAA
----------+---------+---------+---------+---------+ 1300
CGGCACCGCGAAGGGCGCACCCCTTGTTCTAGCAGCAACCGTTGCGGTT
  R G A S R V G N K I V V G N A K
```

MATCH WITH 31a

FIG. 31Aa

```
       GACCGTCCGGTCGAAGCGTCCTGTGACGGTTCCGCCTCACGTCGCGGAG
1301 ---------+---------+---------+---------+---------
       CTGGCAGGCCAGCTTCGCAGGACACTGCCAAGGCGGAGTGCAGCGCCT
Int    T  V  R  S  K  R  P  V  T  V  P  P  H  V  A  E

GCATTCCCTGGTGACCACGACGCAGGGCAACCGGCTGTCGAAGTCCG
1401 ---------+---------+---------+---------+---------
       CGTAAGGACCACTGGTGCTGCGTCCCGTTGGCCGACAGCTTCAGGC
Int    A  F  L  V  T  T  T  Q  G  N  R  L  S  K  S  A

GCATCCACGACCTCCGCGCTGTCGGCGCTACGTTCGCCGCTCAGGCA
1501 ---------+---------+---------+---------+---------
       CGTAGGTGCTGGAGGCGCGACAGCCGCGATGCAAGCGGCGAGTCCGT
Int    I  H  D  L  R  A  V  G  A  T  F  A  A  Q  A

GGCGATGAAGTACCAGATGGCGTCTGAGGCCCGCGACGAGGCTATCGC
1601 ---------+---------+---------+---------+---------+---
       CCGCTACTTCATGGTCTACCGCAGACTCCGGGCGCTGCTCCGATAGCG
Int    A  M  K  Y  Q  M  A  S  E  A  R  D  E  A  I  A

CCCAAGGACACTGAGTCCTAAAGAGGGGGGTTTCTTGTCAGTACGCGAA
1701 ---------+---------+---------+---------+---------+----
       GGGTTCCTGTGACTCAGGATTTCTCCCCCCAAAGAACAGTCATGCGCTT

PvuII
                                              I
       GGCACCAGCCCCGCCGCCGCCAGGAGCATTGCCGTTCCCGCCAGCTGA
1801 ---------+---------+---------+---------+---------+----
       CCGTGGTCGGGGCGGCGGCGGTCCTCGTAACGGCAAGGGCGGTCGACTCAA

GGCGACTTTCCGGCGACGCTGAGGATGTCGATCACAGAGCCTCCGGGAC
1901 ---------+---------+---------+---------+---------+----
       CCGCTGAAAGGCCGCTGCGACTCCTACAGCTAGTGTCTCGGAGGCCCTG

CTCCAGGGCCTCCGGCCTTGCCTGAGAATACAGAGCCAGCTCCCGCTGCGCCT
2001 ---------+---------+---------+---------+---------+---------
       GAGGTCCCGGAGGCCGGAACGGACTCTTATGTCTCGGTCGAGGGCGACGCGG
```

MATCH WITH FIG. 31Ab

FIG. 31Ab

```
ATGATCCGAGCGCACATGAAGGACCGTACGAAGATGAACAAGGGCCCCGAG
+---------+---------+---------+---------+---------+1400
CTACTAGGCTCGCGTGTACTTCCTGGCCTGCTTCTACTTGTTCCCGGGGCTC
 M  I  R  A  H  M  K  D  R  T  K  M  N  K  G  P  E

CGTTCACCAAGTCGCTGAAGCGTGGCTACGCCAAGATCGGTCGGCCGGAACTCC
-+---------+---------+---------+---------+---------+1500
CAAGTGGTTCAGCGACTTCGCACCGATGCGGTTCTAGCCAGCCGGCCTTGAGG
 F  T  K  S  L  K  R  G  Y  A  K  I  G  R  P  E  L  R

GGTGCGACGACCAAGGAGCTGATGGCCCGTCTCGGTCACACGACTCCTAGGAT
...+---------+---------+---------+---------+---------+1600
CCACGCTGCTGGTTCCTCGACTACCGGGCAGAGCCAGTGTGCTGAGGATCCTA
 G  A  T  T  K  E  L  M  A  R  L  G  H  T  T  P  R  M

TGAGGCGATGTCCAAGCTGGCCAAGACCTCCTGAAACGCAAAAAGCCCCCCT
.....+---------+---------+---------+---------+---------+1700
ACTCCGCTACAGGTTCGACCGGTTCTGGAGGACTTTGCGTTTTTCGGGGGGA
 E  A  M  S  K  L  A  K  T  S
                          Int stop GAACCACGCCTGGCCGCGAGCGCCAGCACCGCCGCTCTGTGCGGAGACCTG
......+---------+---------+---------+---------+---------+1800
CTTGGTGCGGACCGGCGCTCGCGGTCGTGGCGGCGAGACACGCCTCTGGAC GTTCTGTTGTGCGCCGCCTATGTAGAGCTGGTCGTTGTAGGTCCGATCTCCA
......+---------+---------+---------+---------+---------+1900
CAAGACAACACGCGGCGGATACATCTCGACCAGCAACATCCAGGCTAGAGGTPvuII CGCCGGTTGCGGTCAAACCTGACCATCCGACAGCGGACGCCGTGGTGTTTC
......+---------+---------+---------+---------+---------+2000
GCGGCCAACGCCAGTTTGGACTGGTAGGCTGTCGCCTGCGGCACCACAAAG SalI
                          I
CCAGCTCCGACGAGCCCGGTGATCGTCTTGGTCGAC
.+---------+---------+---------+---------2089
GGTCGAGGCTGCTCGGGCCACTAGCAGAACCAGCTG
```

MATCH WITH FIG. 31Aa

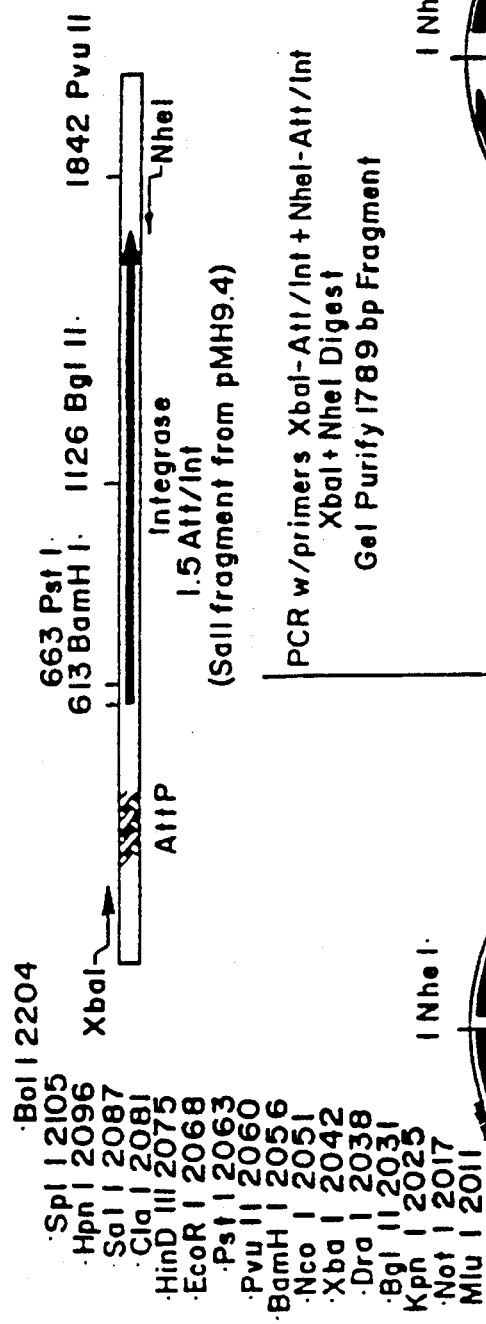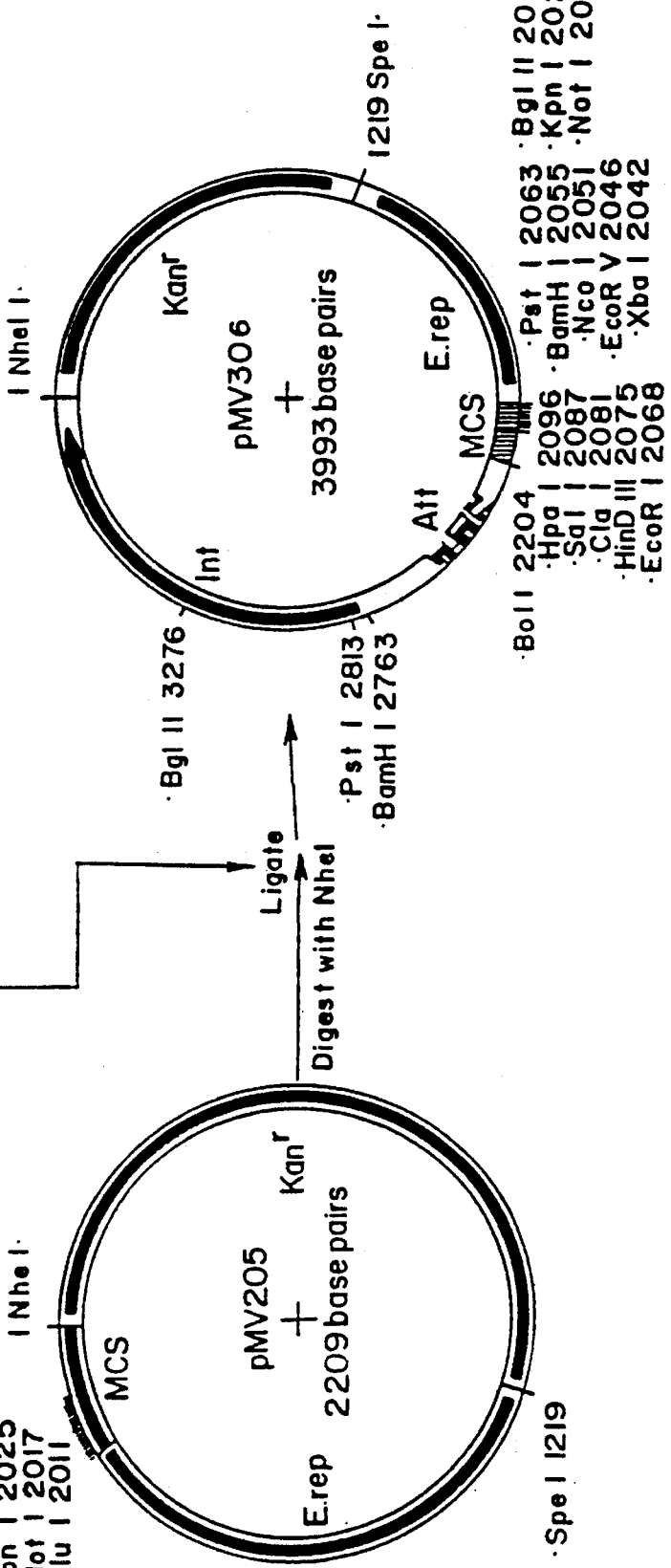
FIG. 47

FIG. 48

```
      1          10         20         30         40         50         60
  1  AGATCTGAGC ACACGACGAC ATACAGGACA AAGGGGCACA GGTATGACAG ACGTGAGCCG   60
 61  AAAGATTCGA GCTTGGGGAC GCCGATTGAT GATCGGCACG GCAGCGGCTG TAGTCCTTCC  120
121  GGGCCTGGTG GGGCTTGCCG GCGGAGCGGC AACCGCGGGC GCGTTCTCCC GGCCGGGGCT  180
181  GCCGGTCGAG TACCTGCAGG TGCCGTCGCC GTCGATGGGC CGGGACATCA AGGTTCAGTT  240
241  CCAGAGCGGT GGGAACAACT CACCTGCGGT TTATCTGCTC GACGGCCTGC GCGCCCAAGA  300
301  CGACTACAAC GGCTGGGATA TCAACACCCC GGGGTTCGAG AGTCGGGACT  360
361  GTCGATAGTC ATGCCGGTCG GCGGGCAGTC CAGCTTCTAC AGCGACTGGT ACAGCCCGGC  420
```

FIG. 50

```
      1          10         20         30         40         50         60
  1  TCTAGACCCG CACGACCAGC GTTAGCATGC TCAGTAAGTT GAGTGCATCA GGCTCAGCTC   60
 61  TCAATTGACA GCACACCGCC GTCGAGGCAA GCTTGAGCGG GGTGCACTCA TCATAGCTAG  120
121  C                                                                   121
```

FIG. 49

- BclI 4476
- HpaI 4368
- HinDIII 4347
- SalI 4359
- EcoRI 4340
- ClaI 4353
- PstI 4335
- PvuII 4332

NheI·

- XbaI 3953
- DraI 3947
- BglII 3942
- KpnI 3936
- NotI 3928

Kan hsp-60-P pRB26 4481bp Mrep Erep

- 1219 SpeI·
- 2011 MluI·
- 2017 NotI·
- 2025 MluI·

· BglII 2797

PCR AMPLIFY DNA SEQUENCES ENCODING THE α-ag ANTIGEN GENE RBS + START CODON + GENE FROM BCG CHROMOSOMAL DNA WITH PRIMERS INCLUDING ADDED BglII - BamHI - EcoRI SITES. DIGEST PCR FRAGMENT WITH BglII - EcoRI. LIGATE INTO BamHI - EcoRI DIGESTED pRB26.

↓

MCS:
- BclI 5362
- HpaI 5254
- SalI 5245
- ClaI 5239
- HinDIII 5233
- EcoRI 5226
- BamHI 5219

NheI·

- NcoI 4297
- XbaI 3953
- DraI 3947
- BglII 3942
- KpnI 3936
- NotI 3928

α-ag Kan hsp-60-PR pAB261 5367bp Mrep Erep

- 1219 SpeI·
- 2011 MluI·
- 2017 NotI·
- 2025 MluI·

BglII 2797

FIG. 51
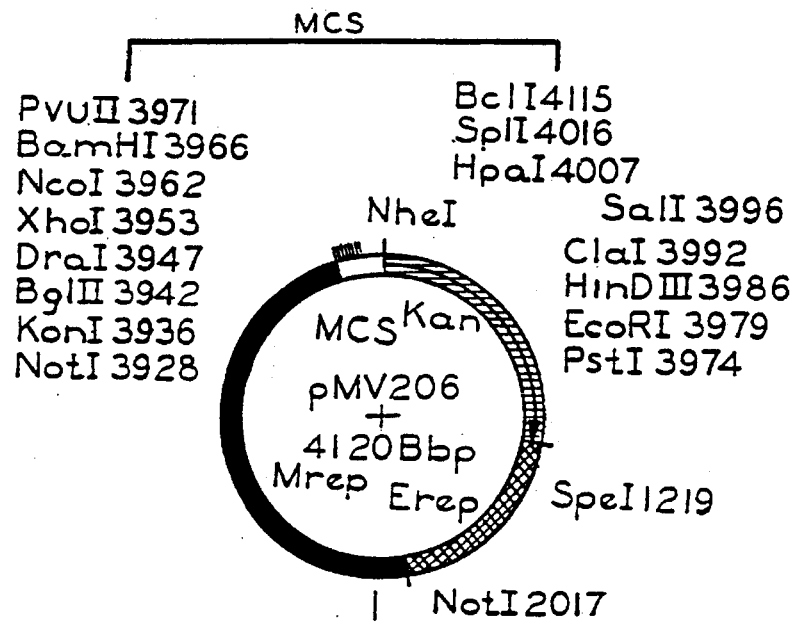
PCR AMPLIFY hsp70 PROMOTER FROM pMV271 PRIMERS INCLUDING ADDED XbaI-NheI SITES. DIGEST PCRhsp70 FRAGMENT WITH XbaI AND NheI. LIGATE INTO XbaI DIGESTED pMV206 AND SCREEN FOR CORRECT ORIENTATION.
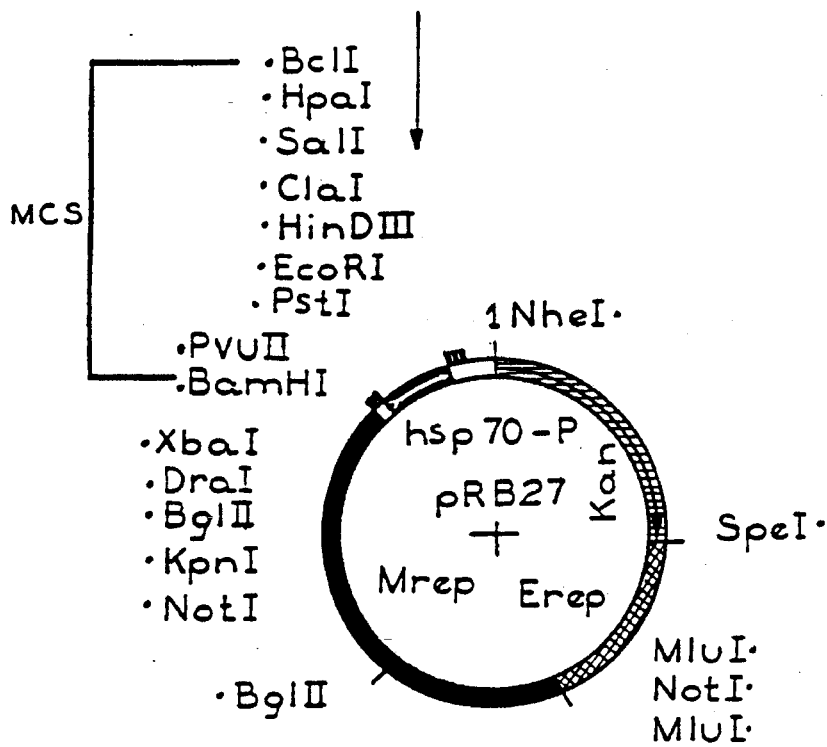

FIG. 52
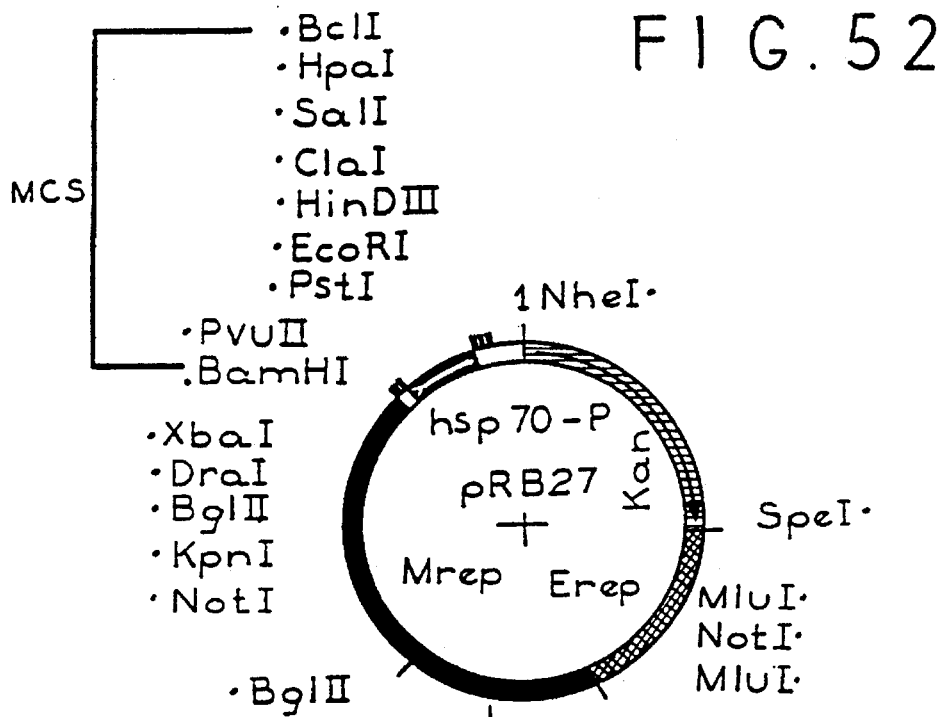
PCR AMPLIFY DNA SEQUENCES ENCODING THE α-ag ANTIGEN GENE RBS + START CODON + GENE FROM BCG CHROMOSOMAL DNA WITH PRIMERS INCLUDING ADDED BgIII – BamHI – EcoRI SITES. DIGEST PCR FRAGMENT WITH BgIII – EcoRI. LIGATE INTO BamHI – EcoRI DIGESTED P RB 27
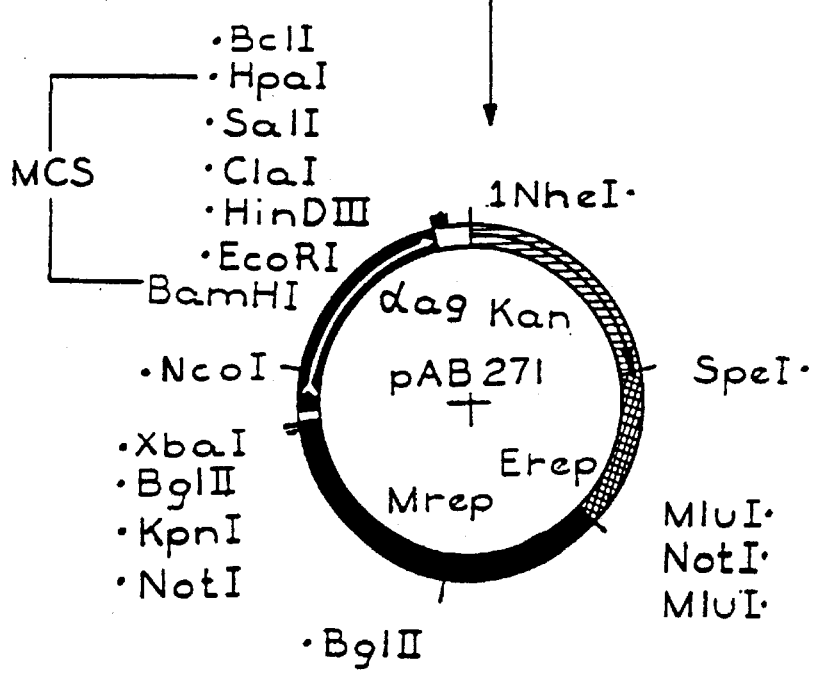

Triton X-114 Fractionation
SDS-PAGE/Western Blot

BACTERIAL EXPRESSION VECTORS CONTAINING DNA ENCODING SECRETION SIGNALS OF LIPOPROTEINS

This application is a continuation-in-part of application Ser. No. 780,261, filed Oct. 21, 1991 now abandoned.

This invention relates to expression vectors for expressing a protein in a bacterium, such as for example, a mycobacterium. More particularly, this invention relates to expression vectors for expressing and secreting proteins which are heterologous to the bacterium which expresses such proteins wherein such vectors further include DNA encoding at least the secretion signals of lipoproteins designed to achieve lipid acylation and surface expression of heterologous proteins.

Certain mycobacteria represent major pathogens of man and animals. For example, tuberculosis is generally caused in humans by *Mycobacterium tuberculosis,* and in cattle by *Mycrobacterium bovis,* which may also be transmitted to humans and other animals. *Mycobacteria leprae* is the causative agent of leprosy. *M. tuberculosis* and mycobacteria of the avium-intracellulare-scrofulaceum group (MAIS group) represent major opportunistic pathogens of patients with acquired immune deficiency syndrome (AIDS). *M. pseudotuberculosis* is a major pathogen of cattle.

On the other hand, Bacille Calmette-Guerin, or BCG, an avirulent strain of *M. bovis,* is widely used in human vaccines, and in particular is used as a live vaccine, which is protective against tuberculosis. BCG is the only childhood vaccine which is currently given at birth, has a very low incidence of adverse effects, and can be used repeatedly in an individual. (eg., in multiple forms). In addition, BCG and other mycobacteria (eg., *M. smegmatis*), employed in vaccines, have adjuvant properties among the best currently known and, therefore, stimulate a recipient's immune system to respond to antigens with great effectiveness.

It has been suggested by Jacobs, et. al, Nature, Vol. 327, No. 6122, pgs. 532–535 (Jun. 11, 1987), that BCG could be used as a host for the construction of recombinant vaccines. In other words, it was suggested to take an existing vaccine (in this case against tuberculosis ) and expand its protective repertoire through the introduction of one or more genes from other pathogens.

Transformation, the process whereby naked DNA is introduced into bacterial cells, has been carried out successfully in mycobacteria. Jacobs, et al (1987), as hereinabove cited, have described transformation of mycobacteria by electroporation. Electroportation can give from $10^5$ to $10^6$ transformants per µg of plasmid DNA and such plasmid DNA's may carry genes for resistance to antibiotic markers such as kanamycin, Snapper, et al, PNAS, Vol. 85, pgs. 6987–6991 (September, 1988); to allow for selection of transformed cells from non-transformed cells.

Jacobs, et al (1987) and Snapper, et al (1988) have also described the use of cloning vehicles such as plasmids and bacteriophages, for carrying genes of interest into mycobacteria.

Lee, et al., PNAS, Vol. 88, pgs. 3111–3115 (April 1991), describe vectors which employ DNA encoding a mycobacterial phage integrase and phage attachment site to effect site-specific integration into a mycobacterial chromosome. Such vectors permit stable integration of vectorss encoding foreign antigen genes into a mycobacterial chromosome.

Stover, et al. , (*Nature,* Vol. 351, pgs. 456–460 (Jun. 6, 1991) ) describe integrative and extrachromosomal vectors employing mycobacterial HSP60 and HSP70 promoters to express foreign antigens cytoplasmically in recombinant BCG. Stover, et al. demonstrated that recombinant BCG expressing foreign antigens with these vectors could be used as immunogens to generate humoral and cellular immune responses to the foreign antigens.

Combination of the above-mentioned techniques, along with standard tools of molecular cloning (e.g., use of restriction enzymes, etc.) allows the cloning of genes of interest into vectors and introduction of such genes into mycobacteria.

In accordance with an aspect of the present invention, there is provided an expression vector for expressing a protein or polypeptide or peptide in a bacterium. The expression vector comprises a first DNA sequence encoding at least a secretion signal of a lipoprotein; and preferably further comprises a second DNA sequence encoding a protein or fragment thereof or polypeptide or peptide heterologous to the bacterium which expresses the protein or fragment thereof, or polypeptide or peptide, whereby the bacterium expresses a fusion protein of a lipoprotein or lipoprotein segment (which may include the secretion signal), and the protein or fragment thereof, or polypeptide or peptide heterologous to the bacterium which expresses the protein or polypeptide or peptide.

Such an expression vector may be employed in any of a variety of bacteria which may be employed in vaccines, including live vaccines. In particular, in one embodiment, the bacterium is a mycobactrium such as, but not limited to, *Mycobacterium bovis*-BCG, *M. smegmatis, M. avium, M. phlei, M. fortuitium, M.lufu, M. paratuberculosis, M. habana, M-scrofalaceum, M. intracellulare,* and *M. vaccae.*

In one embodiment, the mycobacterium is *M. bovis*-BCG.

Although the scope of the present invention is not to be limited to any theoretical reasoning, it is believed that the signal sequence of the lipoprotein enables the expressed recombinant fusion protein to be modified such that the protein is expressed at the surface of the bacterium as a chimetic lipoprotein. For example, the fusion protein may include processing or recognition site(s) for signal peptidase II in the signal sequence portion, which enables lipid acylation of the fusion protein. Such lipid acylation of the fusion protein may enhance the immunogenicity of the heterologous protein or fragment thereof, or polypeptide or peptide portion of the fusion protein. Also, the signal sequence enables the fusion protein to be expressed at and anchored to the surface of the bacterium, thus making the heterologous protein or polypeptide more accessible, which also may increase the immunogenicity of the protein or fragment thereof, or polypeptide or peptide. Also, because such fusion proteins may be expressed on the surface of the bacterium, such expression or secretion of the fusion protein will permit the expression of antigens which may be lethal if expressed or maintained cytoplasmically in the bacterium. It is to be understood that the heterologous protein or fragment thereof, or polypeptide or peptide may itself be a lipoprotein, such as the OspA antigen of *Borrelia burgdorferi,* which is hereinafter discussed, or a non-lipoprotein, such as, for example, HIV antigens, tetanus toxoids, diphtheria toxoids, cholera toxoids, pertussis toxoids, and malarial antigens. Thus, the expression vectors of the present invention enable the genetic engineering of a non-lipoprotein moiety which may become anchored to the surface of a bacterium.

Thus, the expression vectors enable the expression of heterologous genes or gene segments (which originally encoded non-lipoproteins) as chimeric surface lipoproteins. This is accomplished by gene fusion of the foreign genes or gene segments to vector encoded genes or gene segments encoding lipoproteins or lipoprotein signal peptides, respectively.

In one embodiment, the first DNA sequence encodes at least a secretion signal of a mycobacterial lipoprotein. The mycobacterial lipoprotein may, in one embodiment, be an *M. tuberculosis* lipoprotein. The *M. tuberculosis* lipoprotein may be selected from the group consisting of the *M. tuberculosis* 19 kda antigen and the *M. tuberculosis* 38 kda antigen.

Other lipoproteins, of which at least the secretion signal may be encoded by the first DNA sequence include, but are not limited to, Braun's lipoprotein of *E. coli, S. marcescens, E. amylosora, M. morganii,* and *P. mirabilis,* the TraT protein of *E. coli* and Salmonella; the penicillinase (PenP) protein of *B. licheniformis* and *B. cereus* and *S. aureus;* pullulanase proteins of *Klebsiella pneumoniae* and *Klebsiella aerogenese; E. coli* lipoproteins 1pp-28, Pal, Rp1A, Rp1B, OsmB, NlpB, and Orl17; chitobiase protein of *V. harseyi;* the β-1,4-endoglucanase protein of *Pseudomonas solanacearum,* the Pal and Pcp proteins of *H. influenzae;* the OprI protein of *P. aeruginosa;* the MalX and AmiA proteins of *S. pneumoniae;* the 34 kda antigen and TpmA protein of *Treponema pallidum;* the P37 protein of *Mycoplasma hyorhinis;* and the 17 kda antigen of *Rickettsia rickettsii.* It is to be understood, however, that the scope of the present invention is not to be limited to secretion signals of any particular lipoprotein or lipoproteins.

In one embodiment, the first DNA sequence may further include DNA which encodes all or a portion of the lipoprotein. Thus, in such an embodiment, the fusion protein which is expressed by the bacterium is a fusion protein of the secretion signal of the lipoprotein, all or a portion of the lipoprotein, and the heterologous protein or polypeptide or peptide.

The first and second DNA sequences are under the control of a suitable promoter. In one embodiment, the promoter may be the 19 kda antigen promoter or the 38 kda antigen promoter of *M. tuberculosis* if DNA encoding the secretion signal of one of these antigens is employed. Alternatively, the promoter may be a mycobacterial promoter other than the 19 kda and 38 kda *M. tuberculosus* antigen promoters, or a mycobacteriophage promoter.

Mycobacterial and mycobacteriophage promoters which may be employed include, but are not limited to, mycobacterial promoters such as the BCG HSP60 and HSP70 promoters; the mycobactin promoter from *M. tuberculosis* or BCG; the mycobacterial 14 kda and 12 kda antigen promoters; the mycobacterial α-antigen promoter from *M. tuberculosis* or BCG; the MBP-70 promoter, the mycobacterial 45 kda antigen promoter from *M. tuberculosis* or BCG; the superoxide dismutase promoter; the mycobacterial asd promoter, and mycobacteriophage promoters such as the Bxb1, Bxb2, Bxb3, L1, L5, D29 and TM4 promoters. In one embodiment, the promoter is a mycobacterial heat shock protein promoter such as HSP60 or HSP70.

Example of expression vectors including the mycobacterial promoters and mycobacteriophage promoters hereinabove described are further described in application Ser. No. 642,017, filed Jan. 16, 1991, which is a continuation of application Ser. No. 552,828, filed Jul. 16, 1990, now abandoned. The contents of application Ser. No. 642,017 are hereby incorporated by reference.

In a preferred embodiment, the transcription initiation site, the ribosomal binding site, and the start codon, which provides for the initiation of the translation of mRNA, are each of mycobacterial origin. The stop codon, which stops translation of mRNA, thereby terminating synthesis of the heterologous protein, and the transcription termination site, may be of mycobacterial origin, or of other bacterial origin, or may be synthetic in nature, or such stop codon and transcription termination site may be those of the DNA encoding the heterologous protein or polypeptide.

Preferably, the mycobacterial promoter is a BCG promoter, and the mycobacterium is BCG.

Heterologous proteins or polypeptides which may be encoded by the second DNA sequence include, but are not limited to, antigens, anti-tumor agents, enzymes, lymphokines, pharmacologic agents, immunopotentiators, and reporter molecules of interest in a diagnostic context.

Antigens which may be encoded include, but are not limited to, *Mycobacterium leprae* antigens; *Mycobacterium tuberculosis* antigens; Rickettsia antigens; Chlamydia antigens; Coxiella antigens; malaria sporozoite and merozoite proteins, such as the circumsporozoite protein from *Plasmodium berghei* sporozoites; diphtheria toxoids; tetanus toxoids; Clostridium antigens; Leishmania antigens; Salmonella antigens; *E. coli* antigens; Listeria antigens; Borrelia antigens, including the OspA and OspB antigens of *Borrelia burgdorferi;* Franciscella antigens; Yersinia antigens; *Mycobacterium africanum* antigens; *Mycobacterium intracellulare* antigens; *Mycrobacterium avium* antigens; Treponema antigens; Schistosome antigens; Filaria antigens; Pertussis antigens; Staphylococcus antigens; Herpes virus antigens; antigens, and parainfluenza virus antigens; measles virus antigens; Bordatella antigens; Hemophilus antigens; Streptococcus antigens, including the M protein of *S. pyogenes* and pneumococcus antigens such as *Streptococcus pneumoniae* antigens; mumps virus antigens; hepatitis virus antigens; Shigella antigens; Neisseria antigens; rabies antigens; polio virus antigens; Rift Valley Fever virus antigens; dengue virus antigens; measles virus antigens; rotavirus antigens; Human Immunodeficiency Virus (HIV) antigens, including the gag, pol, and env proteins; respiratory syncytial virus (RSV) antigens; snake venom antigens; human tumor antigens; and *Vibrio cholera* antigens. Enzymes which may be encoded include, but are not limited to, steroid enzymes.

In one embodiment, the second DNA sequence encodes at least one protein or polypeptide or fragment or derivative thereof which includes an epitope which is recognized by cytotoxic T lymphocytes induced by an HIV protein or fragment or derivative thereof. The at least one DNA sequence may encode an HIV protein or fragment or derivative thereof. HIV proteins or polypeptides which may be encoded by the at least one DNA sequence includes but are not limited to, HIV-I-gp 120; HIV-I-gp 41; HIV-I-gp 160; HIV-I-pol; HIV-I-nef; HIV-I-tat; HIV-I-rev; HIV-I-vif; HIV-I-vpr; HIV-I-vpu; HIV-I-gag; HIV-2gp 120; HIV-2-gp 160; HIV-2-gp 41; HIV-2-gag; HIV-2-pol; HIV-2-nef; HIV-2-tat; HIV-2-rev; HIV-2-vif; HIV-2-vpr; HIV-2-vpu; and HIV-2-vpx.

Anti-tumor agents which may be encoded include, but are not limited to, interferon-α, interferon-β, or interferon-δ, and tumor necrosis factor, or TNF. Lymphokines which may be encoded include, but are not limited to, interleukins 1 through 8.

It is also contemplated that the heterologous protein or polypeptide may be a reporter molecule or selectable marker.

Reporter molecules which may be encoded include, but are not limited to, luciferase, B-galactosidase, B-glucuronidase, and catechol dehydrogenase.

Other peptides or proteins which may be encoded include, but are not limited to, those which encode for stress proteins, which can be administered to evoke an immune response or to induce tolerance in an autoimmune disease (e.g., rheumatoid arthritis).

Selectable markers which may be encoded include, but are not limited to, the β-galactosidase marker, the kanamycin resistance marker, the chloroamphenicol resistance marker, the neomycin resistance marker, and the hygromycin resistance marker, bacteriophage resistance markers, or genes encoding enzymes involved in the synthesis of nutritional elements, such as amino acids.

In accordance with one embodiment, the vector further includes a mycobacterial origin of replication.

In accordance with another embodiment, the vector may be a plasmid. The plasmid may be a non-shuttle plasmid, or may be a shuttle plasmid which further includes a bacterial origin of replication such as an *E. Coli* origin of replication, a Bacillus origin of replication, a Staphylococcus origin of replication, a Streptomyces origin of replication, or a streptococcal origin of replication. In one embodiment, the shuttle plasmid includes an *E. coli* origin of replication.

In accordance with yet another embodiment, the vector may further include a multiple cloning site, and the second DNA sequence encoding for the heterologous protein is inserted in the multiple cloning site.

In another embodiment, the expression vector may be, for example, a temperate shuttle phasmid or a bacterial-mycobacterial shuttle plasmid. Each of these vectors may be used to introduce the first DNA sequence encoding at least the secretion signal of a lipoprotein and a second DNA sequence encoding a protein or fragment thereof, or polypeptide or peptide heterologous to the mycobacterium which expresses the protein or fragment thereof, or polypeptide or peptide stably into mycobacteria, in which the DNA sequences may be expressed. When a shuttle phasmid, which replicates as a plasmid in bacteria and a phage in mycobacteria, is employed, integration of the phasmid, which includes the first DNA sequence encoding at least the secretion signal of a lipoprotein, and a second DNA sequence encoding a protein or fragment thereof, or polypeptide or peptide heterologous to the mycobacterium which expresses the protein or fragment thereof, or polypeptide or peptide, into the mycobacterial chromosome, occurs through site-specific integration. The DNA sequences are replicated as part of the chromosomal DNA. When a bacterial-mycobacterial shuttle plasmid is employed, the DNA sequences are stably maintained extrachormosomally in a plasmid. Expression of the DNA sequences occur extrachromosomally (e.g., episomally). For example, the DNA sequences are cloned into a shuttle plasmid and the plasmid is introduced into a mycobacterium such as those hereinabove described, wherein the plasmid replicates episomally. Examples of such shuttle phasmids and bacterial-mycobacterial shuttle plasmids are further described in application Ser. No. 361,944, filed Jun. 5, 1989, which is hereby incorporated by reference.

In addition to the first DNA sequence encoding at least the secretion signal of a lipoprotein and the second DNA sequence encoding a heterlogous protein or fragment thereof, or polypeptide or peptide, and the mycobacterial promoter for controlling expression of the DNA encoding the heterologous protein or polypeptide, the expression vector may, in one embodiment, further include a DNA sequence encoding bacteriophage integration into a mycobacterium chromosome. Bacteriophages from which the DNA sequence encoding bacteriophage integration into a mycobacterium chromosome may be derived include, but are not limited to, mycobacteriophages such as but not limited to, the L5, L1, Bxb1, and TM4 mycobacteriophages; the lambda phage of *E. coli*; the toxin phages of Corynebacteria; phages of Actinomycetes and Norcardia; the ΦC31 phage of Streptomyces; and the P22 phage of Salmonella. Preferably, the DNA sequence encodes mycobacteriophage integration into a mycobacterium chromosome. The DNA sequence which encodes bacteriophage integration into a mycobacterium chromosome may include DNA which encodes integrase, which is a protein that provides for integration of the vector into the mycobacterial chromosome. Preferably, the DNA sequence encoding mycobacterial phage integration also includes DNA which encodes an attP site.

The DNA encoding the attP site and the integrase provides for an integration event which is referred to as site-specific integration. DNA containing the attP site and the integrase gene is capable of integrating into a corresponding attB site of a mycobacterium chromosome.

It is to be understood that the exact DNA sequence encoding the attP site may vary among different phages, and that the exact DNA sequence encoding the attB site may vary among different mycobacteria.

Examples of DNA which is a phage DNA portion encoding bacteriophage integration into a mycobacterium chromosome are further described in application Ser. No. 869,330, filed Apr. 15, 1992, which is a continuation-in-part of application Ser. No. 553,907, filed Jul. 16, 1990, now abandoned. The contents of application Ser. No. 869,330 are incorporated by reference.

The vectors of the present invention may be employed to transform bacteria, and in particular, mycobacteria which include, but are not limited to, *Mycobacterium bovis*—BCG, *M. smegmatis, M. avium, M. phlei, M. fortuitum, M. lufu, M. paratuberculosis, M. habana, M. scrofalaceum, M. intracellulare* and *M. vaccae*; in particular, such vectors may be employed to transform BCG. The transformed mycobacteria thus express the heterologous protein, which, as hereinabove stated, may be an antigen, which induces an immune response, or a therapeutic agent. Thus, the transformed mycobacteria may be employed as part of a pharmaceutical composition, such as a vaccine and/or therapeutic agent, which includes the transformed mycobacteria, and an acceptable pharmaceutical carrier. Acceptable pharmaceutical carriers include, but are not limited, to mineral oil, alum, synthetic polymers, etc. Vehicles for vaccines and therapeutic agents are well known in the art and the selection of a suitable vehicle is deemed to be within the scope of those skilled in the art from the teachings contained herein. The selection of a suitable vehicle is also dependent upon the manner in which the vaccine or therapeutic agent is to be administered. The vaccine or therapeutic agent may be in the form of an injectable dose and may be administered intramuscularly, intravenously, orally, intradermally, or by subcutaneous administration.

The mycobacteria are administered in an effective amount. In general, the mycobacteria are administered in an amount of from about $1\times10^5$ to about $1\times10^{10}$ colony forming units (CFU's) per dose.

Other means for administering the vaccine or therapeutic agent should be apparent to those skilled in the art from the teachings herein; accordingly, the scope of the invention is not to be limited to a particular delivery form.

As hereinabove noted, the expression vectors of the present invention may contain DNA which encodes Borrelia antigen(s), including but not limited to surface proteins or antigens of *Borrelia burgdorferi*, the causative agent of Lyme disease. Thus, in accordance with an aspect of the present invention, there is provided a method of protecting an animal against Lyme disease which comprises administering to an animal mycobacteria transformed with DNA which includes at least one DNA sequence which encodes a protein or polypeptide which elicits antibodies against *Borrelia burgdorferi.* The mycobacteria are administered in an amount effective to protect an animal against Lyme disease. Such amounts may be those hereinabove described. In one embodiment, the at least one DNA sequence encodes a surface protein of *Borrelia burgdorferi* or a fragment or derivative thereof. Surface proteins of *Borrelia burgedorferi* which may be encoded by the at least one DNA sequence, include but are not limited to, Outer Surface Protein A and Outer Surface Protein B, sometimes hereafter referred to as OspA and OspB, respectively.

The transformed mycobacteria include those hereinabove described. In one embodiment, the mycobacteria are of the species *M. bovis*-BCG.

The at least one DNA sequence which encodes a protein or polypeptide which elicits antibodies against *Borrelia burgdorferi,* in a preferred embodiment, is contained in a mycobacterial expression vector. In one embodiment, the mycobacterial expression vector may include a DNA sequence encoding at least a secretion signal of a lipoprotein, such as those hereinabove described, and wherein the mycobacterium expresses a chimeric fusion protein of the lipoprotein or lipoprotein segment (which may include the secretion signal) and the protein or polypeptide which elicits antibodies against *Borrelia burgdorferi.* Such an expression vector enables the protein or polypeptide which elicits antibodies against *Borrelia burgdorferi,* to be expressed on the surface of the mycobacterium, whereby the protein or polypeptide becomes more accessible.

It is also contemplated that, in another embodiment, the mycobacterial expression vector may contain DNA which encodes all or a portion of a mycobacterial excretion protein, as well as the DNA which encodes a protein or polypeptide which elicits antibodies against *Borrelia burgdorferi.* The mycobacterium expresses a fusion protein of the mycobacterial excretion protein or a portion thereof, and the protein or polypeptide which elicits antibodies against *Borrelia burgdorferi.* Such an expression vector enables the protein or polypeptide to be excreted from the mycobacterium. Examples of mycobacterial excretion proteins which may be encoded, include, but are not limited to, the α-antigen of *M. tuberculosis* and BCG.

The mycobacterial expression vector, in one embodiment, may include a promoter selected from the group consisting of mycobacterial promoters and mycobacteriophage promoters, such as those hereinabove described, and/or may include a DNA sequence encoding bacteriophage integration into a mycobacterium chromosome, also as hereinabove described.

In another embodiment, the mycobacterial expression vector may be a plasmid, such as a non-shuttle plasmid or a shuttle plasmid which further includes a bacterial origin of replication, also as hereinabove described.

It is also contemplated that the mycobacterial expression vector may be a temperate shuttle phasmid or a bacterial-mycobacterial shuttle plasmid as hereinabove described.

The transformed mycobacteria are employed as part of a composition for protecting an animal against Lyme disease. Such a composition includes the transformed mycobacteria, and an acceptable pharamaceutical carrier such as those hereinabove described.

The invention now will be described with respect to the drawings, wherein:

FIG. 1 is a schematic of the construction of pYUB 12;
FIG. 2 is a schematic of the construction of pYUB53;
FIG. 3 is a schematic of the construction of pYUB125;
FIG. 4 is a schematic of the construction of pMV 110;
FIG. 5 is the DNA sequence of pMV101 ((SEQ ID NO:1) and (SEQ ID NO:2));
FIG. 6 is a schematic of the construction of pMV 113;
FIG. 7 is a schematic of the construction of pMV 123;
FIG. 8 is a schematic of the construction of pMV201;
FIG. 9 is a multiple cloning site (SEQ ID NO:19) having 16 restriction sites unique to pMV201;
FIG. 10 is a schematic of the construction of pMV204;
FIG. 11 is a schematic of the construction of pMV206;
FIG. 12 is the DNA sequence of pMV206 ((SEQ ID NO:20) and (SEQ ID NO:21));
FIG. 13 is an HSP60 promoter fragment (SEQ ID NO:22);
FIG. 14 is a map of pRB26;
FIG. 15 is a PCR amplified fragment (SEQ ID NO:23) including the 19 kda *M. tuberculosis* antigen gene ribosomal binding site, start codon, and signal sequence from *M. tuberculosis* chromosomal DNA;
FIG. 16 is a schematic of the construction of p2619S;
FIG. 17 is a map of p2619::OspA;
FIG. 18 is a PCR fragment (SEQ ID NO:24) including the 5' region of the 19 kda *M. tuberculosis* gene up to the 27th codon;
FIG. 19 is a schematic of the construction of p19PS;
FIG. 20 is a PCR fragment (SEQ ID NO:25) including the 5' region of the 38 kda *M. tuberculosis* antigen up to the 45th codon;
FIG. 21 is a schematic of the construction of p38PS;
FIG. 22 is the BCG HSP61 cassette ((SEQ ID NO:26) and (SEQ ID NO:27)) containing 375 bases 5' to the BCG HSP60 start codon, and 15 bases 3' to the start codon;
FIG. 23 is a schematic of the construction of pMV261;
FIG. 24 is a cassette (SEQ ID NO:31) including the promoters, transcription start sites, ribosome binding site, and start codon of the BCG HSP60 gene;
FIG. 25 is a map of pMV251;
FIG. 26 is a PCR fragment (SEQ ID NO:32) including the 38 kda *M. tuberculosis* antigen gene ribosomal binding site, start codon, and secretion signal sequence;
FIG. 27 is a map of p2638S;
FIG. 28 shows fragments from the attP (SEQ ID NO:33), attL (SEQ ID NO:34), and attB (SEQ ID NO:35) sites of *M. smegmatis,* each of which includes a 43bp core sequence;
FIG. 29 depicts two domains of good conservation ((SEQ ID NO:36) to (SEQ ID NO:54), (SEQ ID NO:56) to (SEQ ID NO:76) and (SEQ ID NO:79)) among integrases;
FIG. 30 is a schematic or the organization of the attP-int region of mycobacteriophage L5;
FIG. 31 shows the amino acid sequence (SEQ ID NO:80) and gene sequence ((SEQ ID NO:81) and (SEQ ID NO:82)) for the attP-int region of mycobacteriophage L5;
FIG. 32 is a map of pUC119;
FIG. 33 is a map of pJR-1;
FIG. 34 is a map of pMH-1;
FIG. 35 is a map of pMH-2;
FIG. 36 is a map of pMH-4;
FIG. 37 is a map of pMH-5;
FIG. 38 is a map of pMD-01;
FIG. 39 is a Southern blot of DNA from six independent pMH-5 *M. smegmatis* transformants which was probed with a 1.9 kb attB probe;
FIG. 40 is a map of pMH-8;
FIG. 41 is a map of pMH9.2;
FIG. 42 is a map of pMH9.4;
FIG. 43 is a map of pMH-12;
FIG. 44 is a Southern blot of BamHI digested mycobacterial DNA's probed with a SalI 1.9 kb *M. smegmatis* fragment containing attB;

FIG. 47 is a schematic of the construction of pMV306;

FIG. 48 is a PCR fragment (SEQ ID NO:83) employed in cloning the 32 kda α-antigen gene of M. tuberculosis or BCG;

FIG. 49 is a schematic of the construction of pAB261.

FIG. 50 is a PCR fragment (SEQ ID NO:84) including the BCG HSP70 promoter;

FIG. 51 is a schematic of the construction of pRB27;

FIG. 52 is a schematic of the construction of pAB271;

Figure 59:
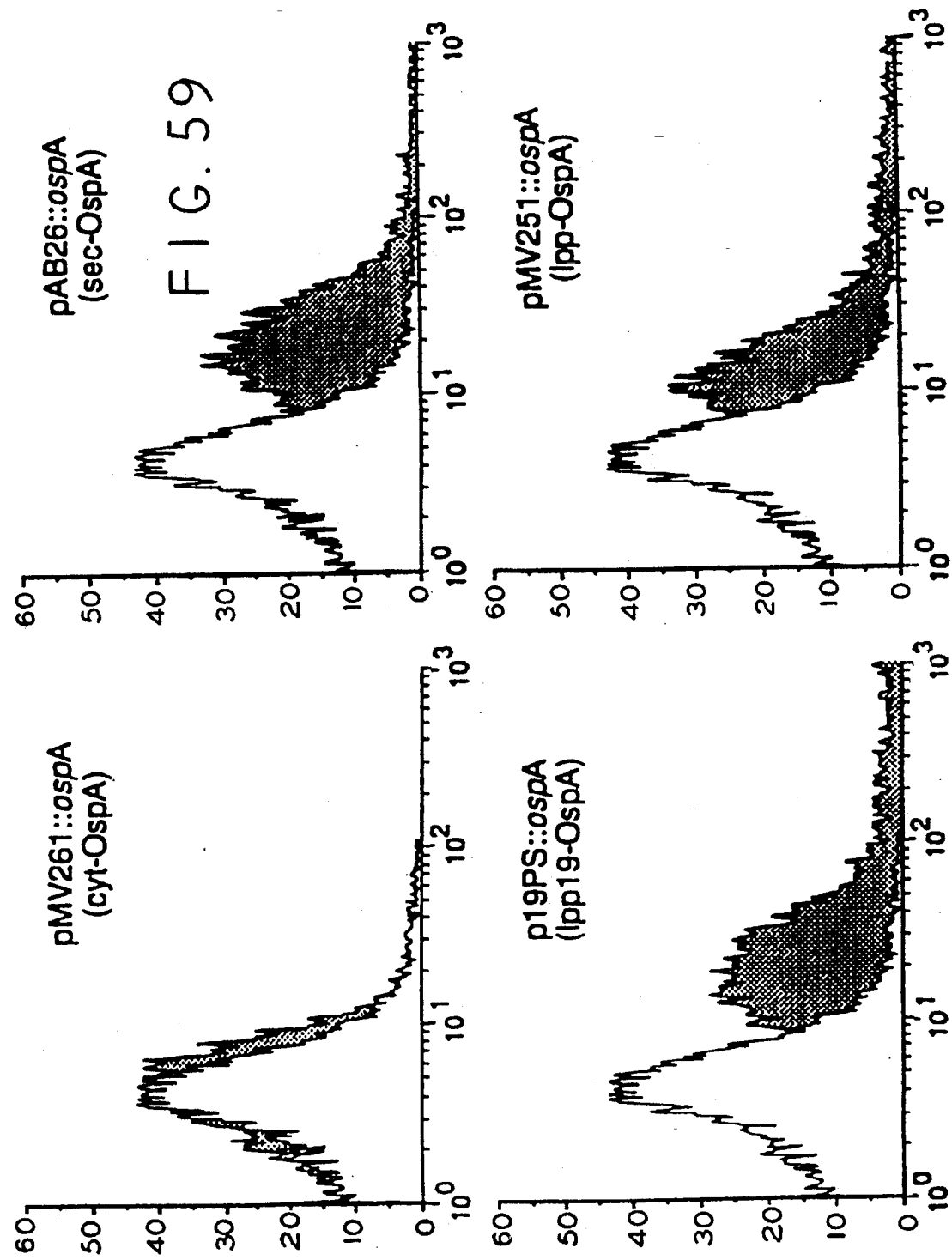
Figure 60:
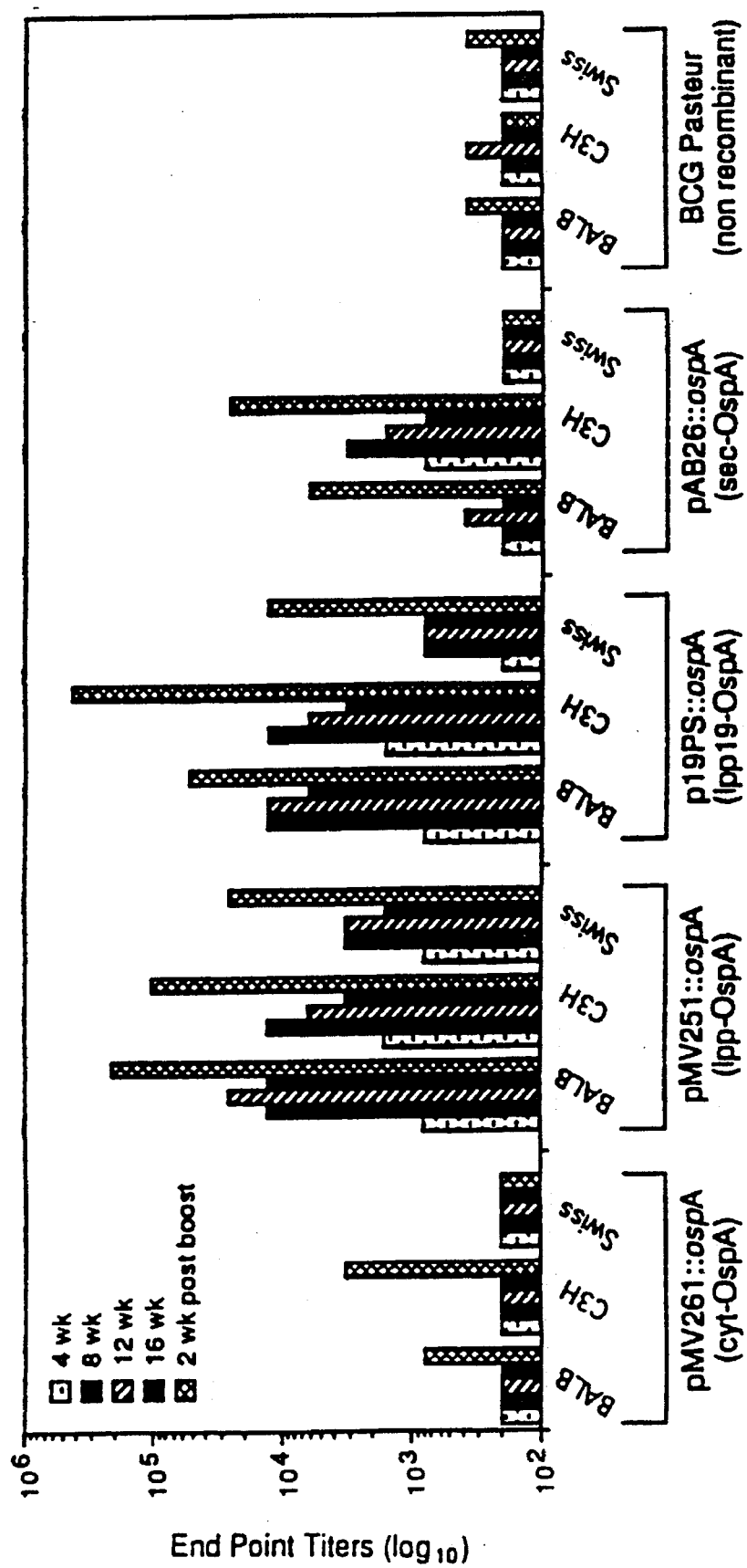

FIG. 59 depicts the flow cytometry results of analysis for expression of chimeric OspA gene products in BCG organisms transformed with pMV261::OspA, pAB26::OspA, p19PS::OspA, and pMV251::OspA; and FIG. 60 shows OspA-specific antibody responses in mice immunized with 10⁶ BCG organisms transformed with pMV261::OspA, pMV251::OspA, p19PS::OspA, or pAB261::OspA, followed by an identical booster dose at 16 weeks.

The invention will now be further described with respect to the following examples; however, the scope of the present invention is not intended to be limited thereby.

EXAMPLE 1

A. Construction of plasmids including mycobacterial promoter expression cassette 1. Construction of pYUB125

Figure 1:
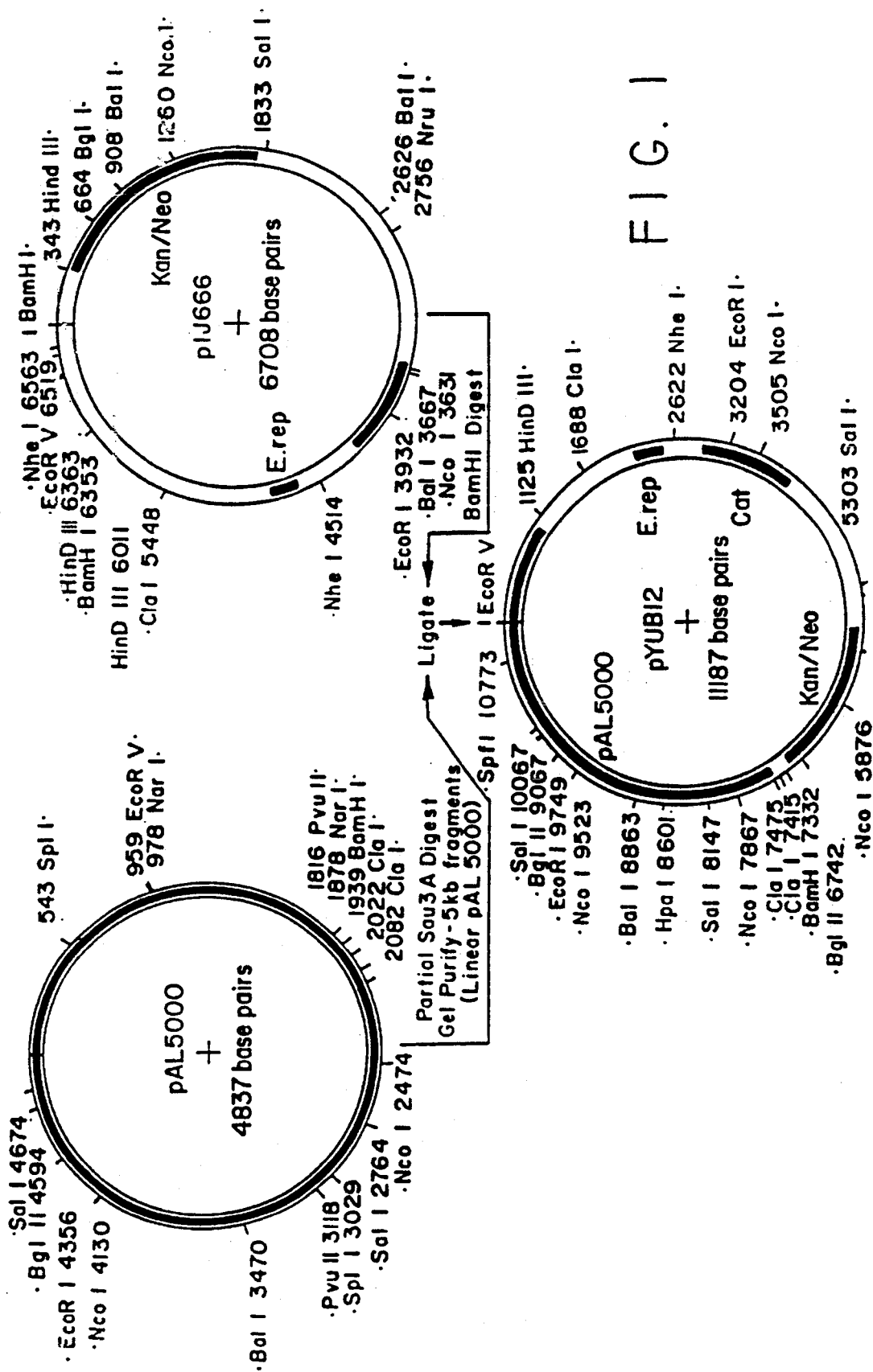

Plasmid pAL5000, a plasmid which contains an origin of replication of M. fortuitum, and described in Labidi, et al., FEMS Microbiol. Lett., Vol. 30, pgs. 221–225 (1985) and in Gene, Vol. 71, pgs. 315–321 (1988), is subjected to a partial Sau 3A digest, and 5kb fragments are gel purified. A 5kb fragment is then ligated to Bam HI digested pIJ666 (an. E. coli vector containing an E. coli origin of replication and also carries neomycin-kanamycin resistance, as described in Kieser, et al., Gene, Vol. 65, pgs. 83–91 (1988) to form plasmid pYUB12. A schematic of the formation of plasmid pYUB12. A schematic of the Formation of plasmid pYUB12 is shown in FIG. 1. pYUB12 and pIJ666 were then transformed into M. smegmatis and BCG. Neomycin-resistant transformants that were only obtained by pYUB12 transformation confirmed that pAL5000 conferred autonomous replication to pIJ666 in M. smegmatis and BCG.

Figure 2:
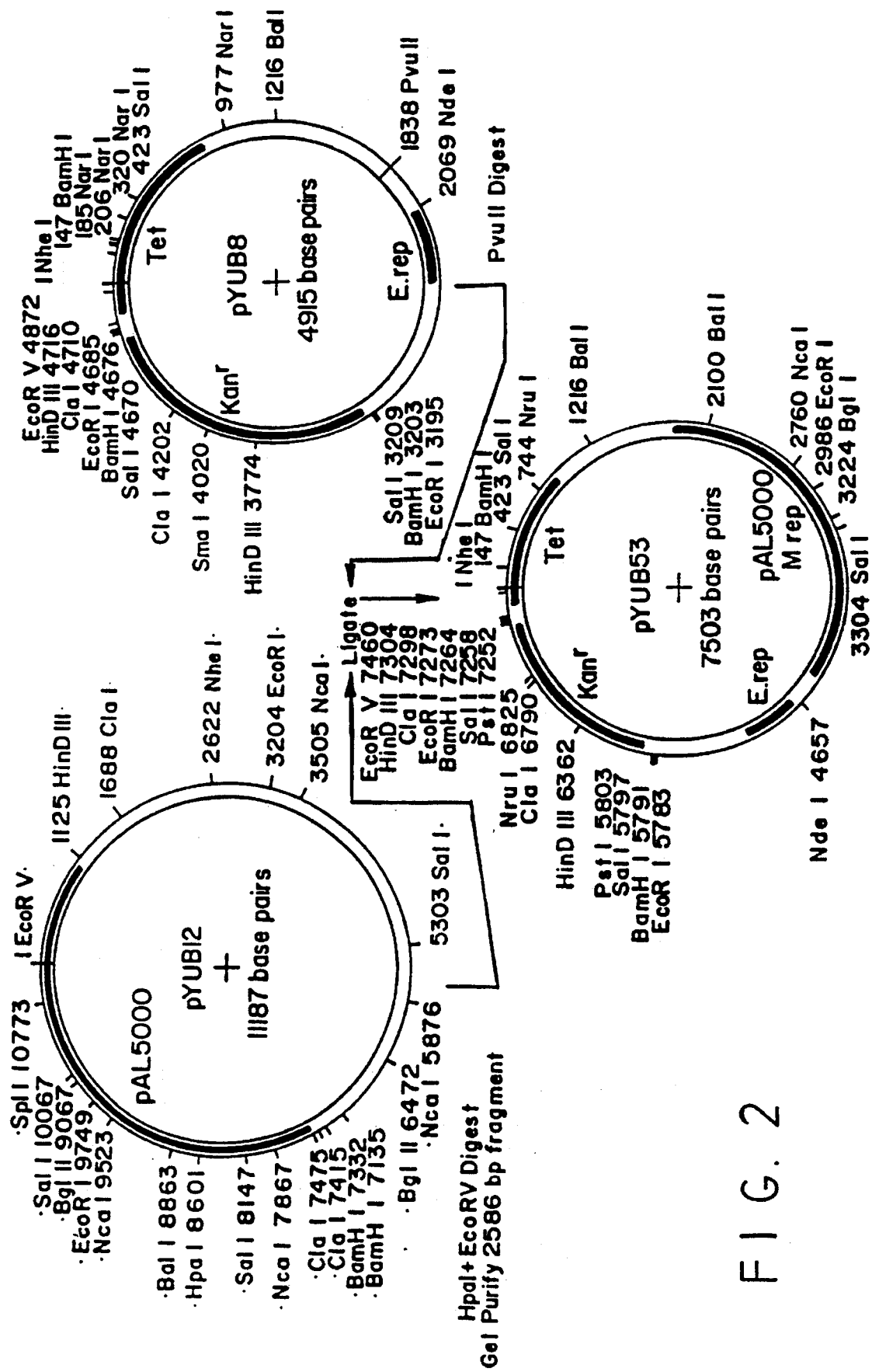

Shotgun mutagenesis by Snapper, et al (1988, hereinabove cited) indicated that no more than half of the pAL5000 plasmid was necessary to support plasmid replication in BCG. This segment presumably carried open reading frames ORF1 and ORF2, identified by Rauzier, et al., Gene, Vol. 71, pgs. 315–321 (1988), and also presumably carried a mycobacterial origin of replication. pYUB12 is then digested with HpaI and EcoRV, a 2586 bp carrying this region or segment pAL5000 is removed and ligated to PvuII digested pYUB8. Plasmid pYUB8 (a pBR322 derivative) includes an E. coli replicon and a kan$^R$ (aph) gene. Ligation of the 2586 bp pYUB12 fragment to PvuII digested pYUB8 results in the formation of pYUB53, as depicted in FIG. 2. Transformation of pYUB53 confirmed that the EcoRV-HpaI fragment, designated M.rep, was capable of supporting autonomous replication in BCG.

Plasmid pYUB53 was then digested with AatI, EcoRV, and PstI in order to remove the following restriction sites:

AatI 5707

EcoRI 5783

BamHI 5791

SalI 5797

PstI 5803

PstI 7252

SalI 7258

BamHI 7264

EcoRI 7273

ClaI 7298

HindIII 7304; and

EcoRV 7460

Fragment ends are then flushed with T4 DNA polymerase and religated to form plasmid pYUB125, construction of which is shown in FIG. 3.

2. Elimination of superfluous vector DNA from pYUB125

Figure 4:
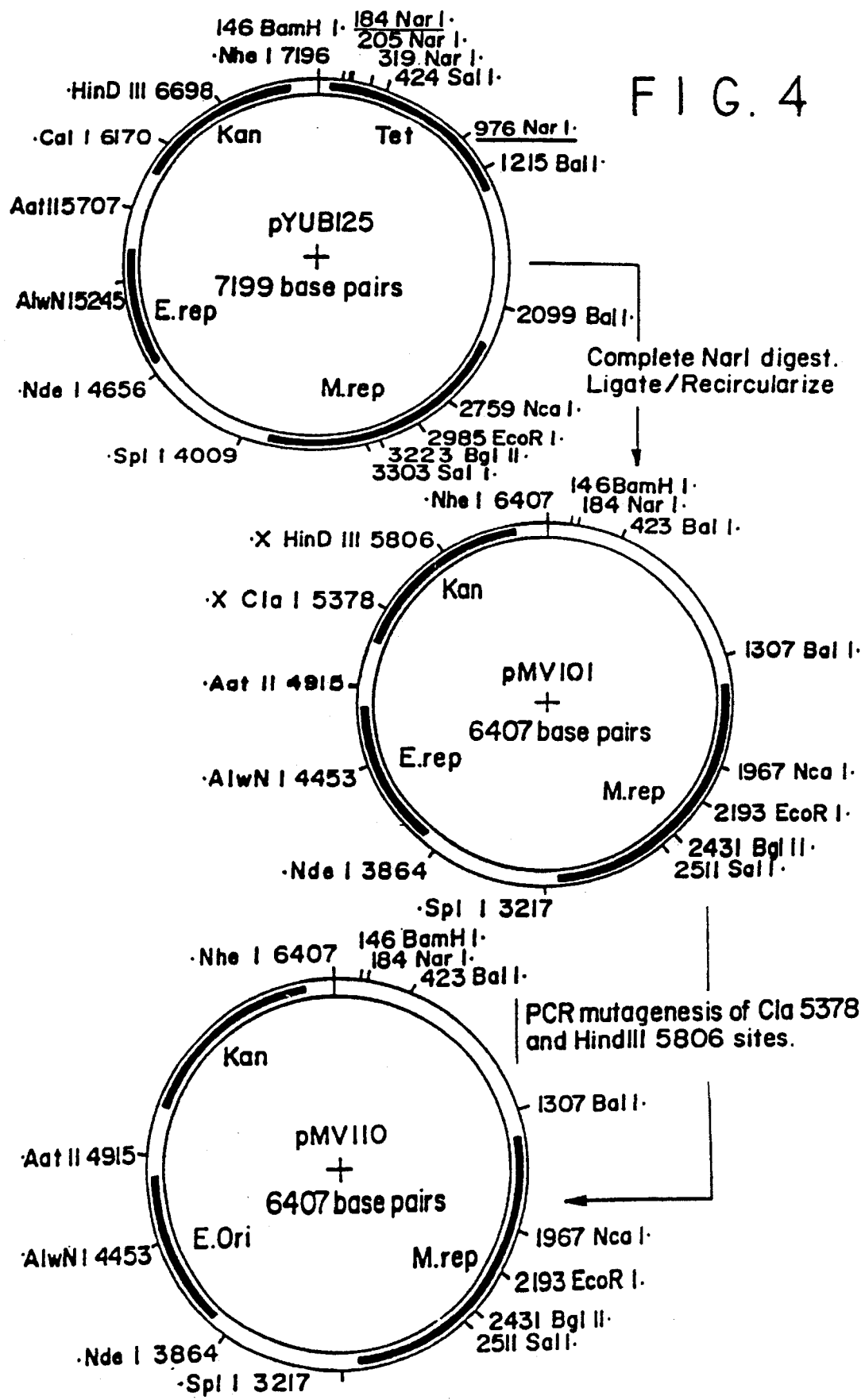

792 bases of the tet gene, which had been inactivated by prior manipulations, was eliminated by a complete NarI digest, gel purification of the 6407 bp fragment, and ligation/recirculation, transformation of E. coli strain HB101, and selection of Kan$^R$ transformants. The construction of resulting plasmid, pMV101, is schematically indicated in FIG. 4, and the DNA sequence of pMV101 (SEQ ID NOS:1 and 2) which includes markings of regions which will be deleted, and of mutations, as hereinafter described, is shown in FIG. 5.

3. Elimination of undesirable restriction sites in aph (kan$^R$) gene

To facilitate future manipulations, the HindIII and ClaI restriction sites in the aph gene were mutagenized simultaneously by polymerase chain reaction (PCR) mutagenesis according to the procedure described in Gene, Vol. 77 pgs. 57–59 (1989). The bases changed in the aph gene were at the third position of codons (wobble bases) within each restriction site and the base substitutions made were designed not to change the amino acid sequence of the encoded protein.

Separate PCR reactions of plasmid pMV101 with primers ClaMut-Kan+HindRMut-Kan and HindFMut-Kan+Bam-Kan were performed at 94° C. (1 min.), 50° C. (1 min.), and 72° C. (1 min.) for 25 cycles. The PCR primers had the following base sequences:

ClaMut-Kan

CTT GTA TGG GAA GCC CC (SEQ ID NO:6)

HindRMut-Kan

GTG AGA ATG GCA AAA GAT TAT GCA TTT CTT TCC AG (SEQ ID NO:7)

HindFMut-Kan

GTC TGG AAA GAA ATG CAT AAT CTT TTG CCA TTC TCA CCG G (SEQ ID NO:8)

Bam-Kan

CGT AGA GGA TCC ACA GGA CG (SEQ ID NO:9)

The resulting PCR products were gel purified and mixed and a single PCR reaction without primers was performed at 94° C. (1 min.), 72° C. (1 min.) for 10 cycles. Primers ClaMut-Kan and Bam-Kan were added and PCR was resumed at 94° C. (1 min.), 50° C. (1 min.), and 72° C. (2 min.) for 20 cylces. The resulting PCR product (Kan. mut) was digested with BamHI and gel purified. Plasmid pMV101 was digested with ClaI and cohesive ends were filled in by Klenow+dCTP+dGTP. Klenow was heat inactivated and the digest was further digested with BamHI. The 5232 base pair fragment was gel purified and mixed with fragment Kan.mut and ligated. The ligation was transformed into E. coli strain HB101 and Kan$^R$ colonies were screened for plasmids resistant to ClaI and HindIII digestion. Such plasmids were designated as pMV110, which is depicted in FIG. 4.

Figure 6:
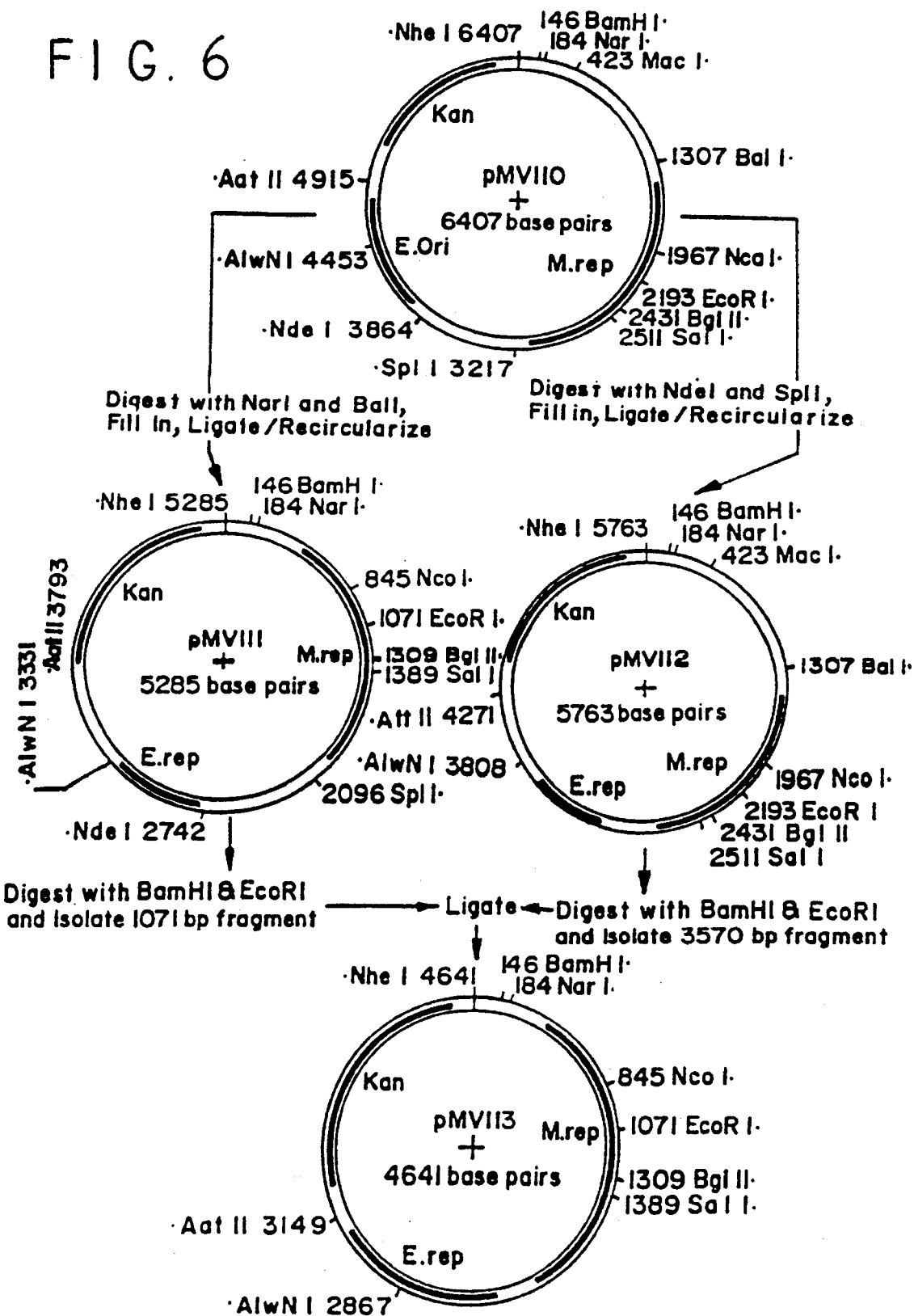

4. Elimination of sequences not necessary for plasmid replication in mycobacteria Plasmid pMV110 was resected in separate constructions to yield plasmids pMV111 and pMV112. In one construction, pMV110 was digested with NarI and BalI, the ends were filled in, and a 5296 base pair fragment was ligated and recircularized to form pMV111. In another construct, pMV110 was digested with NdeI and SpII, the ends were filled in, and a 5763 base pair fragment was ligated and recircularized to form pMV112. Schematics of the constructions of pMV111 and pMV112 are shown in FIG. 6. These constructions further eliminated superfluous E. coli vector sequences derived from pAL5000 not necessary for mycobacterial replication. Cloning was performed in E. coli. Plasmids pMV111 and pMV112 were tested for the ability to replicate in M. smegmatis. Because both plasmids replicated in M. segmatis the deletions of each plasmid were combined to construct pMV113. (FIG. 6).

To construct pMV113, pMV111 was digested with BamHI and EcoRI, and a 1071 bp fragment was isolated. pMV112 was digested with BamHI and EcoRI, and a 3570 bp fragment was isolated, and then ligated to the 1071 bp fragment obtained from pMV111 to form pMV113. These constructions thus defined the region of pal, 5000 necessary for autonomous replication in mycobacteria as no larger than 1910 base paris.

5. Mutagenesis of restriction sites in mycobacterial replicon

To facilitate further manipulations of the mycobacterial replicon, PCR mutagenesis was performed as above to eliminate the Sal I, EcoRI, and BglII sites located in the open reading frame known as ORF1 of pAL5000. PCR mutagenesis was performed at wobble bases within each restriction site and the base substitutions were designed not to change the amino acid sequence of the putative encoded ORF1 protein. The restriction sites were eliminated one at a time for testing in mycobacteria. It was possible to eliminate the SalI and EcoRI without altering replication in M. smegmatis. In one construction PCR mutagenesis was performed at EcoRI1071 of pMV113 with primers Eco Mut-M.rep and Bam-M.rep to form pMV117, which lacks the EcoRI1071 site. Primer Eco Mut-M.rep has the following sequence:

TCC GTG CAA CGA GTG TCC CGG A (SEQ ID NO:10);

and Bam-M.rep has the following sequence:

CAC CCG TCC TGT GGA TCC TCT AC (SEQ ID NO:11).

Figure 7:
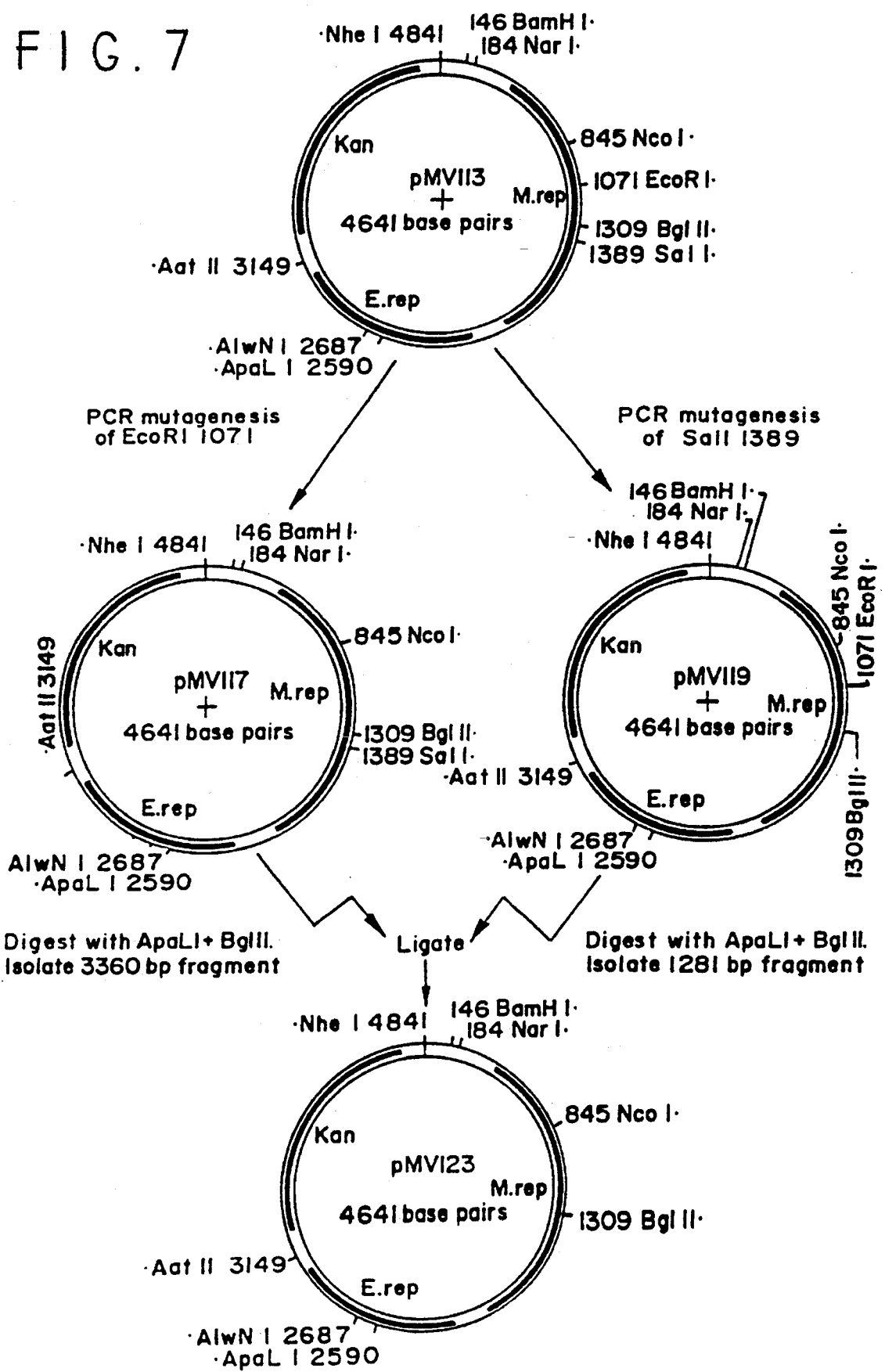

In another construction, PCR mutagenesis was performed at the SalI 1389 site with primer Sal Mut-M. rep and Bam-M.rep to form pMV119, which lacks the SalI 1389 site. Primer Sal Mut-M.rep has the following sequence:

TGG CGA CCG CAG TTA CTC AGG CCT (SEQ ID NO:12).

pMV117 was then digested with ApaLI and BglII, and a 3360 bp fragment was isolated. pMV119 was digested with ApaLI and BglII, and a 1281 bp fragment was isolated and ligated to the 3360 bp fragment isolated from pMV117 to form pMV123. A schematic of the constructions of plasmids pMV117, pMV119, and pMV123 is shown in FIG. 7. Elimination of the BglII site, however, either by PCR mutagenesis or Klenow fill in, eliminated plasmid replication in mycobacteria, thus suggesting that the BglII site is in proximity to, or within a sequence necessary for mycobacteria plasmid replication.

6. Construction of pMV200 series vectors

To facilitate manipulations of all the components necessary for plasmid replication in E. coli and mycobacteria, (E. rep. and M. rep.) and selection of recombinants (Kan$^R$), cassettes of each component were constructed for simplified assembly in future vectrs and to include a multiple cloning site (MCS) containing unique restriction sites and transcription and translation terminators. The cassettes were constructed to allow directional cloning and assembly into a plasmid where all transcription is unidirectional.

Kan$^R$ Cassette

A DNA cassette containing the aph (Kan$^R$) gene was constructed by PCR with primers Kan$^{5'}$ and Kan$^{3'}$. An SpeI site was added to the 5' end of the PCR primer Kan3', resulting in the formation of a PCR primer having the following sequence:

CTC GAC TAG TGA GGT CTG CCT CGT GAA G (SEQ ID NO:13).

Bam HI+NheI sites were added to the 5' end of the primer Kan5', resulting in the formation of a PCR primer having the following sequence:

CAG AGG ATC CTT AGC TAG CCA CT GAC GTC GGG G (SEQ ID NO:14).

PCR was performed at bases 3375 and 4585 of pMV123, and BamHI and NheI sites were added at base 3159, and an SpeI site was added at base 4585. Digestion with BamHI and SpeI, followed by purification resulted in a 1228/2443 Kan$^R$ cassette bounded by BamHI and SpeI cohesive ends with the direction of transcription for the aph gene proceeding from BamHI to Spe I.

E. rep. cassette

A DNA cassette containing the ColEI replicon of pUC19 was constructed by PCR with primers E.rep/Spe and E.rep/Mlu. An SpeI site was added to the 5' end of PCR primer E.rep/Spe and an MluI site was added to the 5' end of PCR primer E.rep./Mlu. The resulting primers had the following sequences:

E.rep./Spe

CCA CTA GTT CCA CTG AGC GTC AGA CCC (SEQ ID NO:15).

E.rep./Mlu

GAG AAC GCG TTG CGC TCG GTC GTT CGG CTG (SEQ ID NO:16).

PCR was performed at bases 713 and 1500 of pUG19, and an MluI site was added to base 713, and a SpeI site was added to base 1500. Digestion with MluI and SpeI, followed by purification resulted in an E.rep. cassette bounded by SpeI and MluI cohesive ends with the direction of transcription for RNA I and RNA II replication primers proceeding from SpeI to MluI.

M.rep. cassette

A DNA cassette containing sequences necessary for plasmid replication in mycobacteria was constructed by PCR of pMV123 with primers M.rep/Mlu and M.rep/Bam. An MluI site was added to the 5' end of PCR primer M.rep/Mlu. A BamHI site was added to the 5' end of PCR primer M/rep/Bam. The resulting PCR primers had the following base sequences:

M.rep./Mlu

CCA TAC GCG TGA GCC CAC CAG CTC CG (SEQ ID NO:17)

M.rep./Bam

CAC CCG TCC TGT GGA TCC TCT AC (SEQ ID NO:18)

PCR was performed at bases 134 and 2082 of pMV123. An MluI sited was added to base 2082. Digestion with BamHI and MluI, followed by gel purification resulted in a 1935 base pair DNA cassette bounded by MluI and BamHI cohesive ends with the direction of transcription for the pAL5000 ORF1 and ORF2 genes proceeding from MluI to Bam HI.

Figure 8:
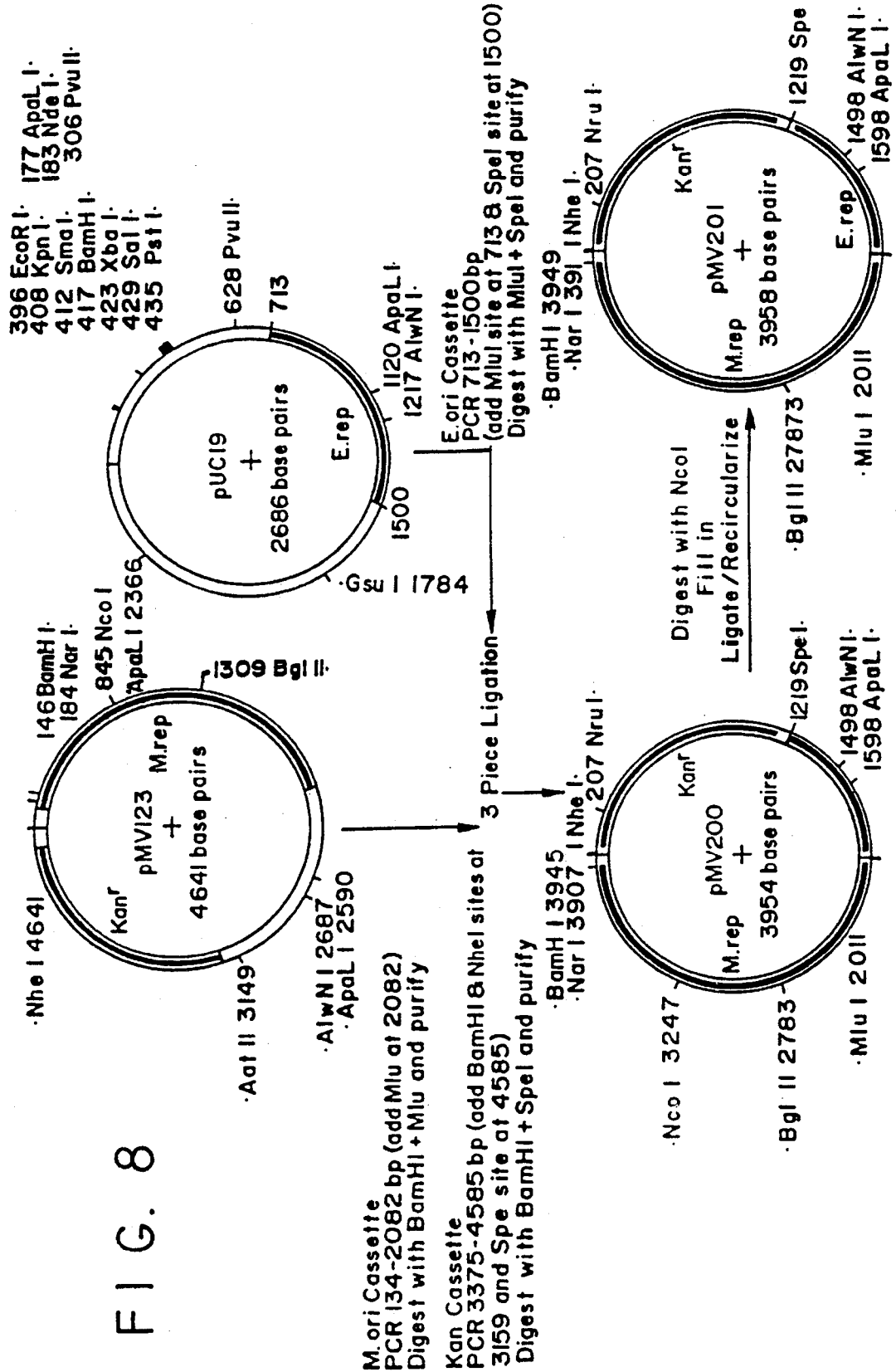

The Kan$^R$, E.rep, and M.rep PCR cassettes were then mixed in equimolar concentrations and ligated, and then transformed in *E. coli* strain HB101 for selection of Kan$^R$ transformants. Colonies were screened for the presence of plasmids carrying all three cassettes after digestion with BamHI+MluI+SpeI and designated pMV200. An additional restriction site, NcoI, was eliminated from the M.rep cassette by digestion of pMV200 with NcoI, fill in with Klenow, and ligation and recircularization, resulting in the formation of pMV201. A schematic of the formation of pMV200 from pMV123 and pUC19, and of pMV201 from pMV200, is shown in FIG. 8. Plasmids pMV200 and pMV201 were transformed into *M. smegmatis* and BCG. Both plasmids yielded Kan$^R$ transformants, thus indicating their ability to replicate in mycobacteria.

A synthetic multiple cloning sequence (MCS) (SEQ ID NO:19) (FIG. 9) was then designed and synthesized to facilitate versatile molecular cloning and manipulations for foreign gene expressions in mycobacteria, and for integration into the mycobacterial chromosome. The synthetic MCS, shown in FIG. 9, contains 16 restriction sites unique to pMV201 and includes a region carrying translation stop codons in each of three reading frames, and a T1 transcription terminator derived from *E. coli* rrnAB ribosomal RNA operon.

Figure 10:
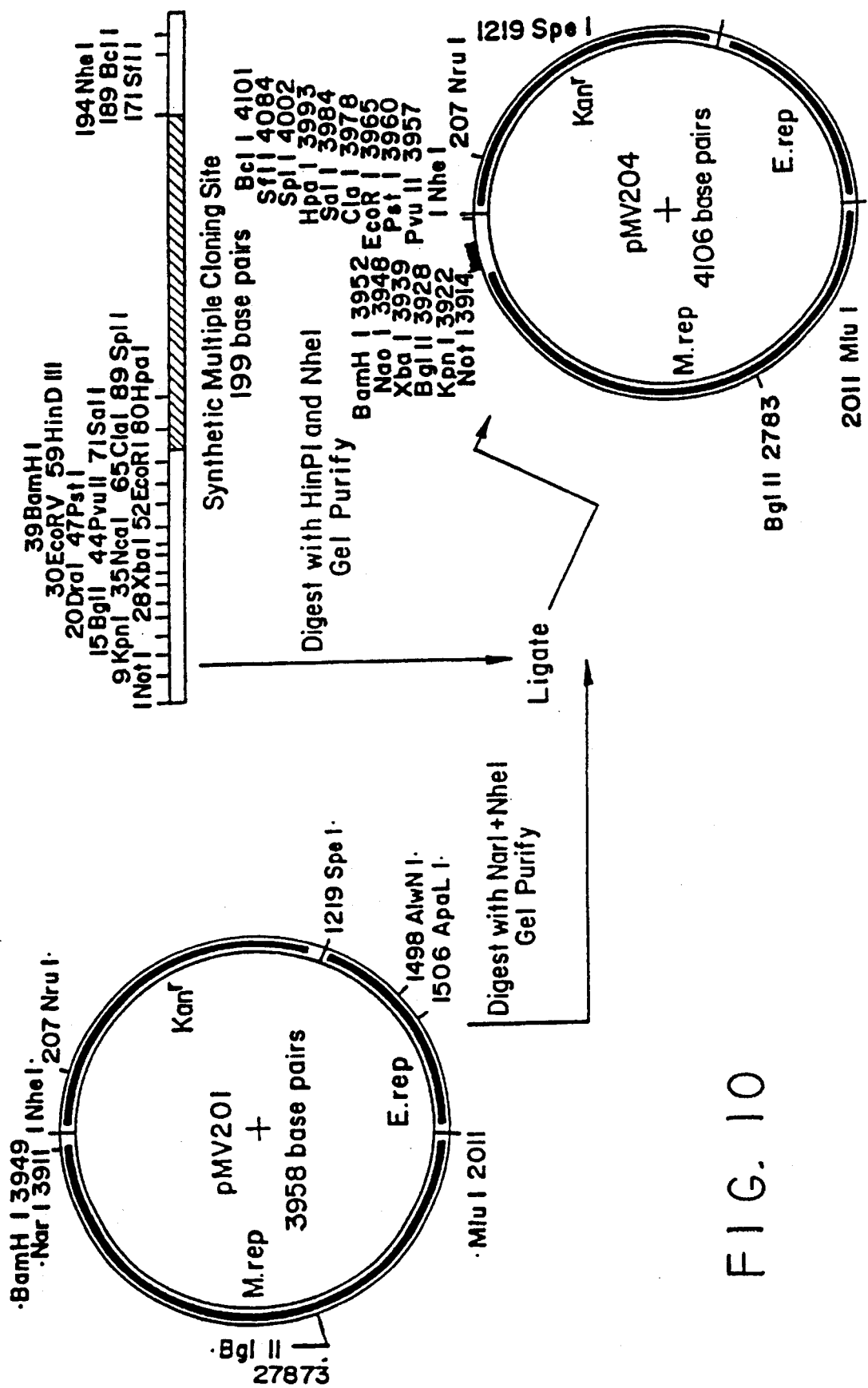

To insert the MCS cassette, pMV201 was digested with NarI and NheI, and the resulting fragment was gel purified. The MCS was digested with HinPI and NheI and, the resulting fragment was gel purified. The two fragments were then ligated to yield pMV204. A schematic of the construction of pMV204 is shown in FIG. 10.

Figure 11:
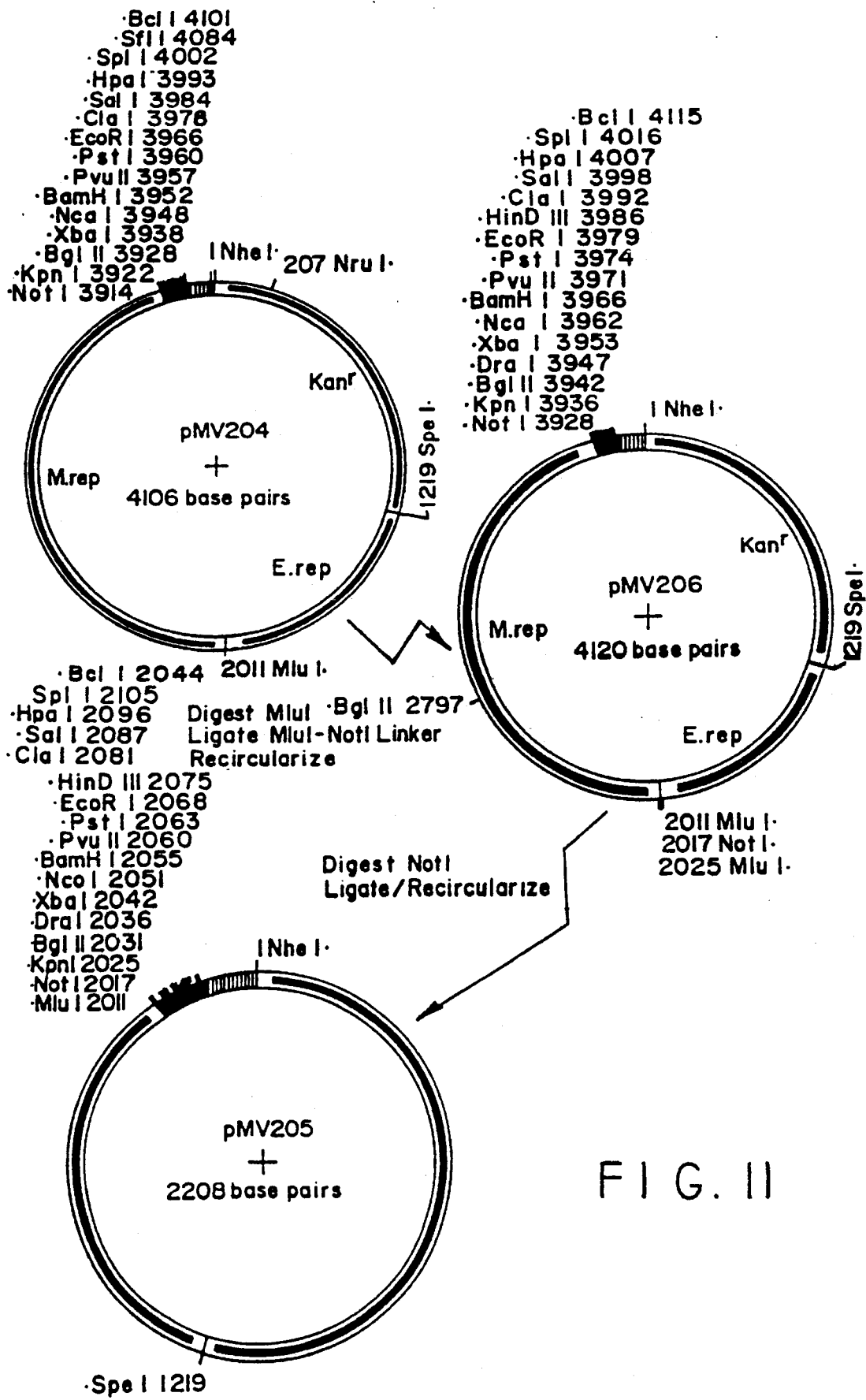
Figure 17:
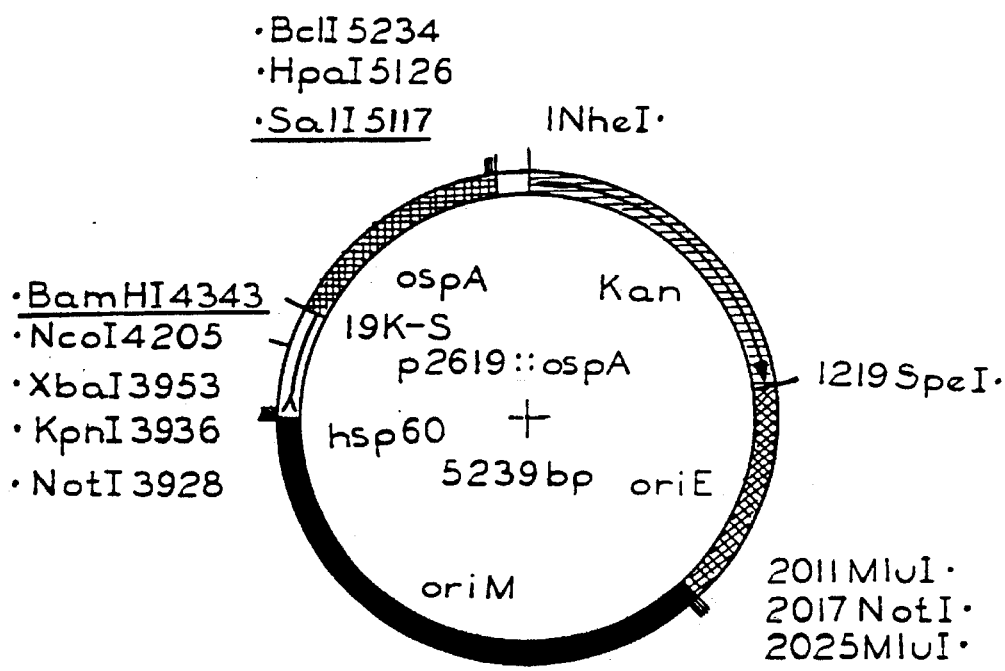
Figure 27:
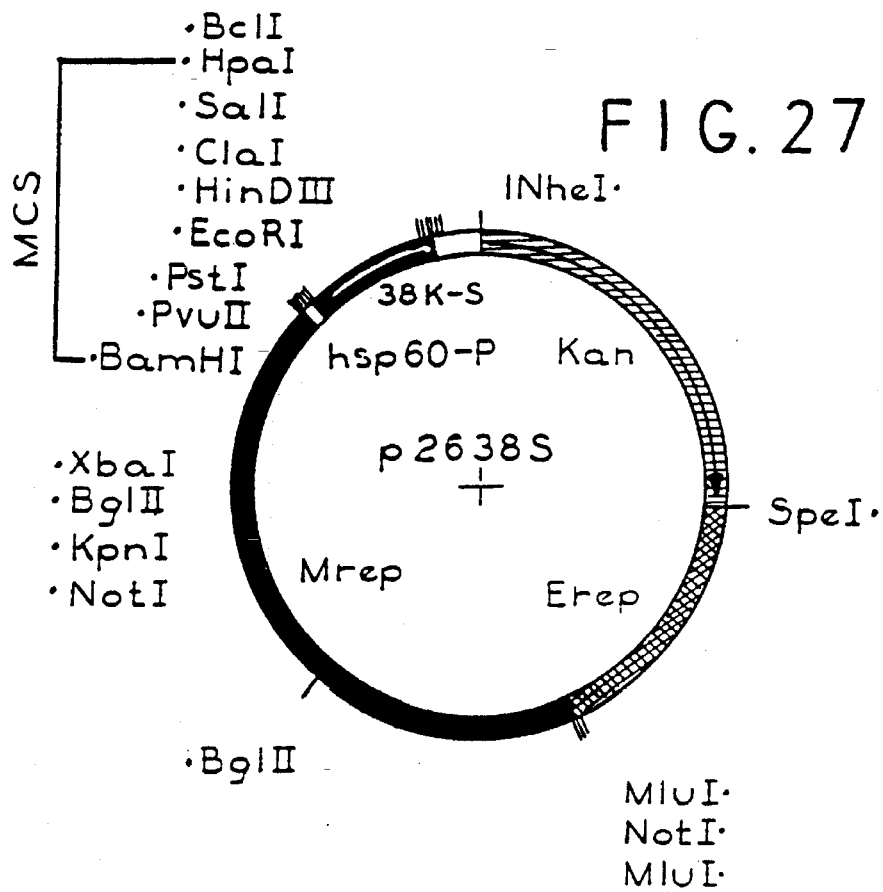
Figure 19:
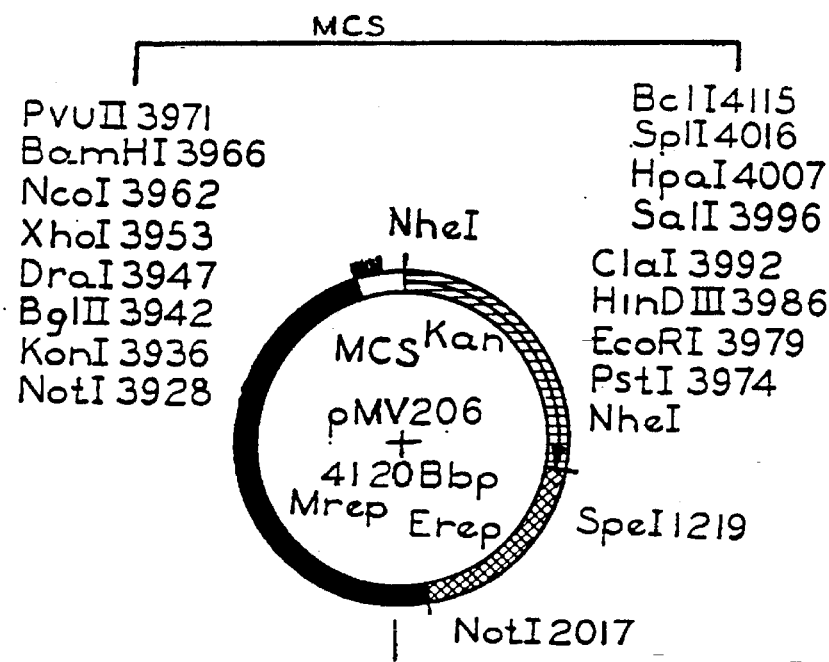
Figure 23:
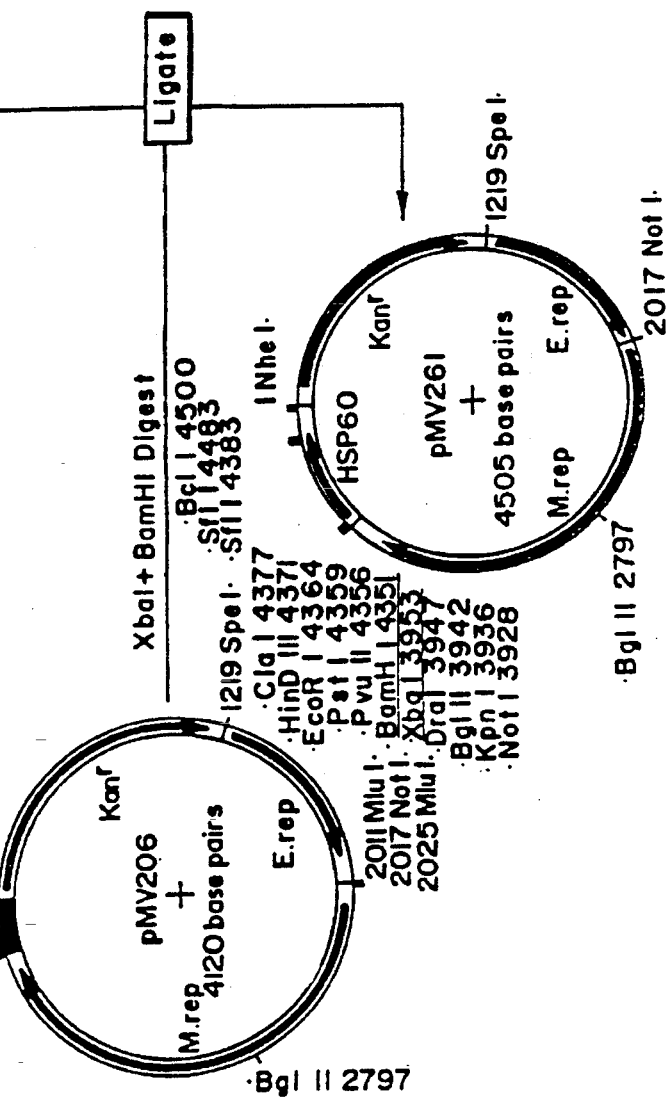
Figure 25:
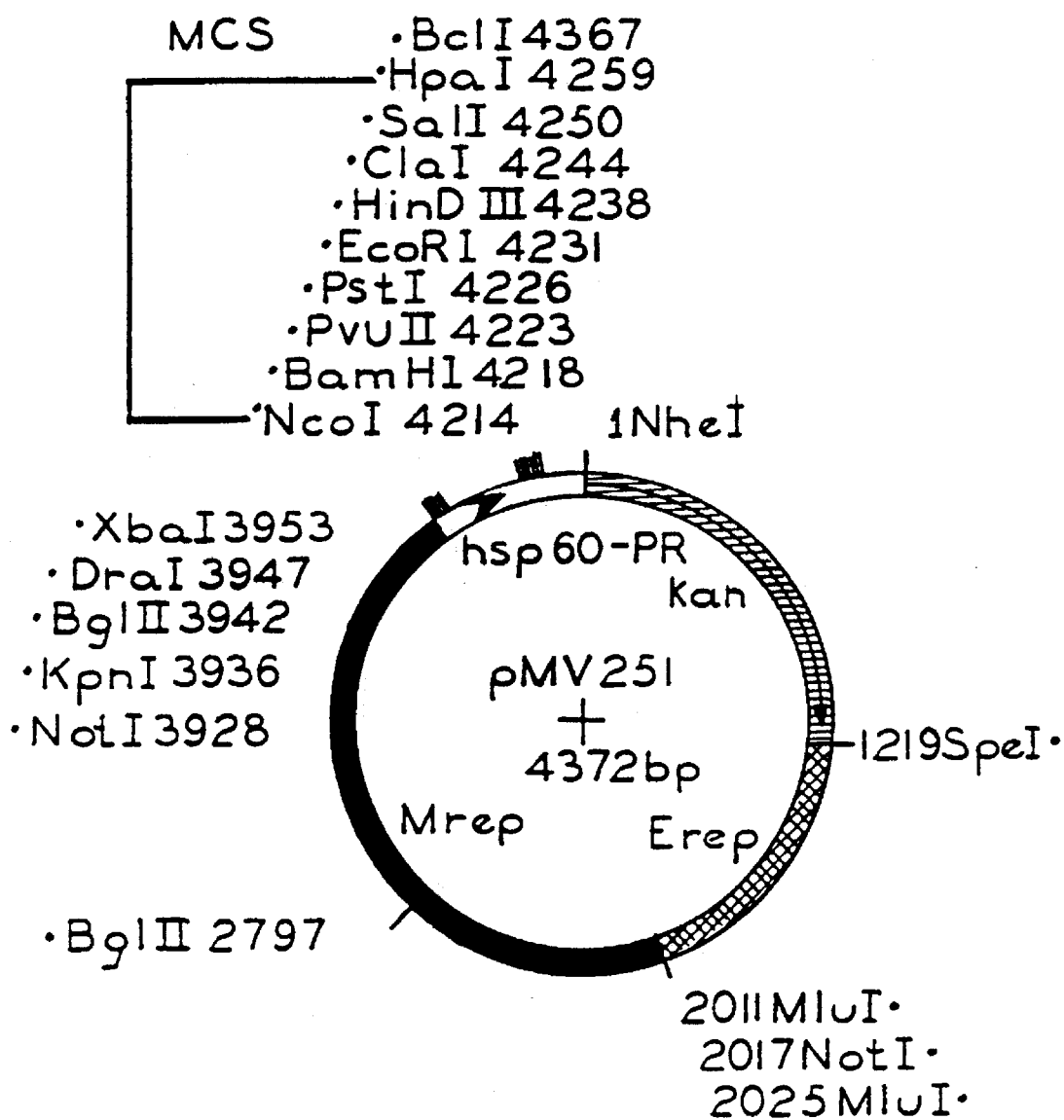

Plasmid pMV204 was then further manipulated to facilitate removal of the M.rep cassette in further constructions. pMV204 was digested with MluI, and an MluI-Not I linker was inserted into the MluI site between the M.rep and the E.rep to generate pMV206. A schematic of the construction of pMV206 from pMV204 is shown in FIG. 11, and the DNA sequence of pMV206 is given in FIG. 12 (SEQ ID NOS:20 and 21).

7. Insertion of BCG HSP60 promoter sequence

The published sequence of the BCG HSP60 gene (Thole, et al., *Infect. and Immun.*, Vol. 55, pgs. 1466–1475 (June 1987)), and surrounding sequence permitted the construction of an HSP60 promoter fragment by PCR. The 251 bp HSP60 promoter fragment (SEQ ID NO:22) (FIG. 13, and as published by Stover, et al. (1991)) was amplified by PCR with primers including added XbaI and NheI sites. The PCR HSP60 fragment is then digested with XbaI and NheI, and is ligated into XbaI digested pMV206 to form pRB26 (FIG. 14).

8. Insertion of DNA encoding the 19 kda *M. tuberculosis* signal sequence and OspA gene into mycobacterial expression vector The sequence of the 19 kda *M. tuberculosis* gene is given in Ashbridge, et al., *Nucleic Acids Research,* Vol. 17, pg. 1249 (1989). The 19 kda antigen gene ribosomal binding site, start codon, and signal sequence from *M. tuberculosis* chromosomal DNA were amplified by PCR with nucleotide primers. The resulting 153 bp fragment (SEQ ID NO:23) (FIG. 15) obtained by PCR includes added BglII (5') and BamHI: EcoRI sites (3'). This fragment contains the entire 5' region of the 19 kda gene up to the 27th codon with the exception of the promoter sequence. The PCR fragment is digested with BglII and EcoRI and ligated into BamHI-EcoRI digested pRB26 to form p2619S (FIG. 16).

The gene encoding the OspA antigen is described in Bergstrom, et al., *Molecular Microbiology,* Vol. 3, No. 4, pgs. 479–486 (1989). The OspA gene sequence, excluding only the N-terminal 18 codons (encoding the secretion signal) was derived by PCR with added BamHI (5') and SalI (3') sites to provide a 780 bp OspA fragment. p2619S was digested with BamHI and SalI, and the 780bp PCR OspA fragment was digested with BamHI and SalI to generate cohesive ends and ligated to BamHI and SalI digested p2619S to form p2619::OspA. (FIG. 17).

EXAMPLE 2

Construction of mycobacterial vector including promoter and DNA encoding signal sequence of 19 kda *M. tuberculosis* antigen Plasmid pMV206 was constructed as described in Example 1. The 19 kda *M. tuberculosis* antigen gene promoter, ribosomal binding site, start codon, and secretion signal was amplified by PCR with nucleotide primers. The PCR fragment includes added XbaI and BamHI sites. This sequence (SEQ ID NO:24), shown in FIG. 18, which is 286 bp in length, includes the entire published 5' region of the 19 kda gene up to the 27th codon. The PCR fragment was then digested with XbaI and BamHI, and ligated into XbaI and BamHI digested pMV206 to form p19PS (FIG. 19). The 780 bp OspA PCR cassette, as described in Example 1, was digested with BamHI and SalI, and ligated to BamHI and SalI digested p19PS to form p19PS::OspA.

EXAMPLE 3

Construction of mycobacterial expression vector with *M. tuberculosis* 38 kda antigen promoter and signal sequence and OspA gene The gene sequence for the *M. tuberculosis* 38 kda antigen is given in Andersen, et al., *Infection and Immunity*, Vol. 57, No. 8, pgs. 2481–2488 (August 1989). A DNA sequence encoding the 38 kda antigen promoter, ribosomal binding site, start codon, and secretion signal, obtained from *M. tuberculosis* chromosomal DNA, and containing the entire 5' sequence up to the 45th codon, was amplified by PCR with nucleotide primers. The resulting PCR fragment includes added XbaI and BamHI sites. The PCR fragment (SEQ ID NO:25), 297 bp in length, and shown in FIG. 20, was digested with XbaI and BamHI, and ligated into XbaI and BamHI digested pMV206 to form p38PS (FIG. 21). The 780 bp OspA PCR cassette, as hereinabove described in Examples 1 and 2, is digested with BamHI and SalI and ligated into BamHI and SalI digested p38PS to form p38PS::OspA.

EXAMPLE 4

Construction of mycobacterial expression vector with expression cassette based on BCG HSP60 and OspA gene pMV206 was constructed as hereinabove described in Example 1.

The published sequence of the BCG HSP60 gene (Thole, et al, *Infect. and Immunity*, Vol. 55, pgs. 1466–1475 (June 1987)), and surrounding sequence permitted the construction of a cassette carrying expression control sequences (i.e., promoter, ribosomal binding site, and translation initiation sequences as published in Stover, et al. (1991)) by PCR. The BCG HSP61 cassette (SEQ ID NOS:26 and 27) (FIG. 22) contains 375 bases 5' to the BCG HSP60 start codon, and 15 bases (5 codons) 3' to the start codon. FIG. 22 also shows the peptide sequence (SEQ ID NO: 28) coded for by basis 382–404. PCR oligonucleotide primers were then synthesized. Primer Xba-HSP60, of the following sequence:

CAG ATC TAG ACG GTG ACC ACA ACG CGC C (SEQ ID NO:29) was synthesized for the 5' end of the cassette, and primer Bam-HSP61, of the following sequence:

CTA GGG ATC CGC AAT TGT CTT GGC CAT TG (SEQ ID NO:30) was synthesized for the 3' end of the cassette. The primers were used to amplify the cassette by PCR from BCG strain Pasteur chromosomal DNA. The addition of the Bam HI site at the 3' end of the cassette adds one codon (Asp) to the first six codons of the HSF60 gene.

Each of pMV206 and the PCR cassette HSP61 was digested with XbaI and BamHI. The PCR cassette was then inserted between the XbaI and BamHI sites of pMV206, then ligated to form plasmid pMV261. The construction of this plasmid is shown schematically in FIG. 23.

The 780 bp OspA PCR cassette as hereinabove described, was digested with BamHI and SalI, and ligated to BamHI and SalI digested pMV261 to form p261::OspA.

EXAMPLE 5

A DNA cassette encoding the promoters and transcription start sites, as identified in Stover, et al. (1991), ribosome binding site, and start codon of the BCG HSP60 gene, was constructed by PCR. Such a cassette is the same as that of the BCG HSP61 cassette hereinabove described except that this cassette does not include the 15 bases (5 codons) 3' to the start codon. This cassette, which is 267 bp in length (SEQ ID NO:31), and shown in FIG. 24, includes added XbaI and NcoI sites, with a start codon included in the NcoI site. The cassette, after construction, was digested with XbaI and NcoI.

This cassette was placed into XbaI and NcoI digested pMV206 to form pMV251. (FIG. 25). A full length OspA gene (including the signal sequence and as published in Bergstrom, et al. (1989)) was then derived by PCR as an NcoI-SalI restriction fragment. This fragment was then digested with NcoI and SalI, and ligated to NcoI and SalI digested pMV251 to form p251::OspA.

EXAMPLE 6 pRB26 was constructed as described in Example 1. The 38 kda antigen gene ribosomal binding site, start codon, and secretion signal sequence was obtained from *M. tuberculosis* chromosomal DNA and amplified by PCR with nucleotide primers. The resulting fragment also includes added BglII-BamHI:EcoRI sites. The PCR fragment, 210 bp in length (SEQ ID NO:32) (FIG. 26), is digested with BglII and EcoRI and ligated into BamHI and EcoRI digested pRB26 to form p2638S (FIG. 27). p2638S is then digested with BamHI and SalI. The 780 bp OspA PCR fragment described in Example 1 is digested with BamHI and SalI and ligated to the BamHI and SalI digested p2638S to form p2638::OspA.

EXAMPLE 7

This example describes the formation of p3638::OspA, which includes sequences encoding bacteriophage integration into a mycobacterium chromosome, DNA encoding the secretion signal of the 38 kda *M. tuberculosis* antigen, as well as the OspA gene.

pMV206 was constructed as hereinabove described in Example 1.

Plasmid pMH9.4, which includes the mycobacteriophage L5 attP site, and the L5 integrase gene, was employed in providing the L5 integration sequences to a BCG expression vector. The construction of pMH9.4, as well as its integration into *M. smegmatis* and BCG, is described below in sections (i) through (vi).

(i) Identification of the DNA sequences of the attachment sites, attB, attL, and attR, of *M. smegmatis*

Figure 28:
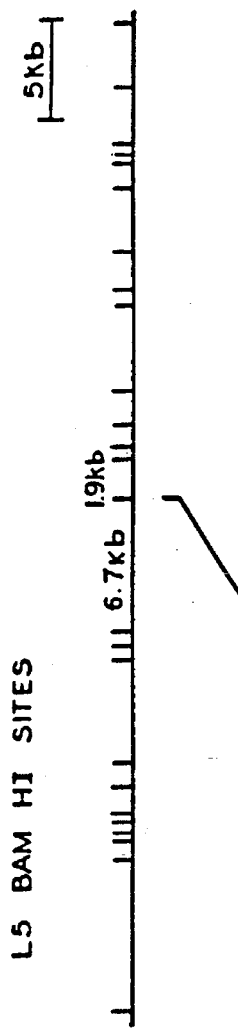

Using standard technologies, a lambda EMBL3 library was constructed using chromosomal DNA prepared from mc²61 (a strain of *M. smegmatis* which includes an *M. smegmatis* chromosome into which has been integrated the genome of mycobacterial phage L5) and digested with Bam HI. Phage L5 contains DNA having restriction sites identical to those of phage L1 (Snapper, et al. 1988), except that L5 is able to replicate at 42° C. and phage L1 is incapable of such growth. This library was then probed with a 6.7 kb DNA fragment isolated from the L5 genome that had been previously identified as carrying the attP sequence (Snapper, et al 1988). One of the positive clones was plaque purified, DNA prepared, and a 1.1 kb Sal I fragment (containing the AttL sequence) sub-cloned into sequencing vector pUC119. The DNA sequence of this fragment was determined using a shotgun approach coupled with Sanger sequencing. By isolating and sequencing the attL junction site and comparing this to the DNA sequence of L5 that was available, a region was determined where the two sequences aligned but with a specific discontinuity present. The discontinuity represents one side of a core sequence, which is identical in AttP, attB, and attL. The region containing the recombinational crossover point is shown in FIG. 28.

The attL DNA (1.1 kb Sal I fragment) was used as a probe to hybridize to a Southern blot of Bam HI digested mc²6 DNA, which is a strain of *M. smegmatis* which includes an *M. smegmatis* chromosome without any phage integration (Jacobs, et al, 1987, hereinabove cited.). A single band of approximately 6.4 kb was detected corresponding to the attB sequence of *M. smegmatis*. This same attL probe was used to screen a cosmid library of mc²6 (provided by Dr. Bill Jacobs of the Albert Einstein College of Medicine of Yeshiva University), and a number of positive cosmid clones were identified. DNA was prepared from these clones, and a 1.9 kb Sal I fragment (containing the attB site) that hybridizes to the attL probe was subcloned into pUC119 for sequencing and further analysis. The DNA sequence containing the core sequence was determined and is shown in FIG. 28 for attP (SEQ ID NO: 33), for attL (SEQ ID NO: 34) and for attB (SEQ ID NO: 35). The core sequence, which is identical in attP, attB and attL, has a length of 43 bp.

The mc²61 lambda EMBL3 library was then probed with the 1.9 kb SalI fragment containing the attB site. Positive plaques were identified, DNA was prepared, and analyzed by restriction analysis and Southern blots. Lambda clones were identified that contained a 3.2 kb Bam HI fragment containing the putative attR site. The 3.2 kb Bam HI fragment was purified and cloned into pUC119 for sequencing and further analysis.

(ii) Determination of attP-integrase region of L5 genome

Concurrent with the above procedures, a significant portion of the DNA sequence of L5 had been determined and represented in several "contigs" or islands of DNA sequence. Sequences of the 6.7 kb Bam HI fragment hereinabove described were determined by (a) analysis of the location of Bam HI sites in the contigs of the DNA of L5, and (b) by determining a short stretch of DNA sequence from around the Bam HI sites of plasmid pJR-1 (FIG. 33), which carries the 6.7 kb Bam HI fragment of L5.

A segment of DNA sequence was located that represented the 6.7 kb Bam HI fragment of phage L5. Studies of other phages have shown that the integrase genes are often located close to the attP site. It was thus determined that the L5 integrase (int) gene should lie either within the 6.7 kb Bam HI fragment or in a DNA sequence on either side of it. The DNA sequence in the regions was then analyzed by translating it into all six possible reading frames and searching these amino acid sequences for similarity to the family of integrase related proteins, and through computer-assisted analysis of the DNA sequence. As shown in FIG. 29, there are shown two domains of reasonably good conservation among L5 integrase and other integrases Domain 1—SEQ ID NOS: 36–56; Domain 2—SEQ ID NOS: 57–79, and three amine acid residues that are absolutely conserved in domain 2. (See Yagil, et al., *J. Mol. Biol.*, Vol. 207, pgs. 695–717 (1989), and Poyart-Salmeron, et al., *J. EMBO.*, Vol. 8, pgs. 2425–2433 (1989) ). A region was identified, and analysis of the corresponding DNA sequence showed a reading frame that could encode for a protein of approximately 333 amino acids (FIG. 31; SEQ ID NO:80). These observations identified the putative int gene.

Figure 34:
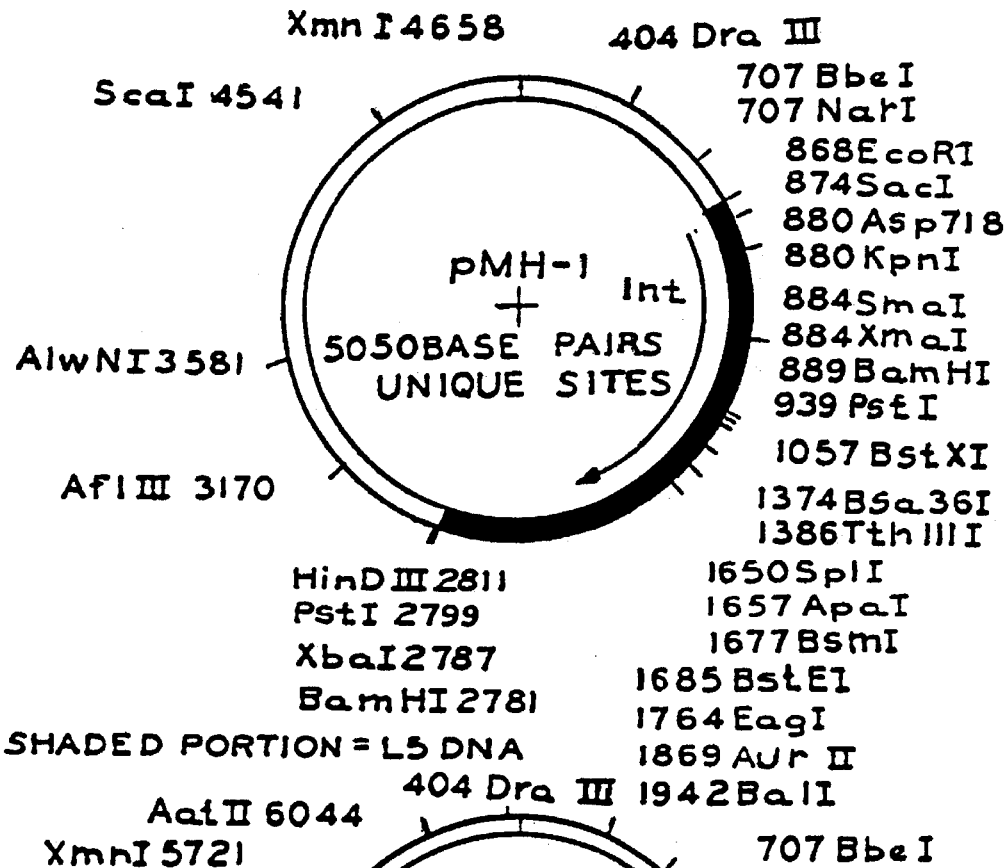

The location of the int gene was not within the 6.7 kb Bam HI fragment; however, it was very close to it with one of the Bam HI sites (that defines the 6.7 kb Bam HI fragment) less than 100 bp upstream of the start of the gene. Analysis of the Bam HI sites showed that the int gene lay within a 1.9 kb Bam HI fragment located adjacent to the 6.7 kb Bam HI fragment. This 1.9 kb Bam HI fragment was cloned by purification of the fragment from a Bam HI digest of L5 DNA and cloning into pUC 119, to generate pMH1 (FIG. 34).

Figure 30:
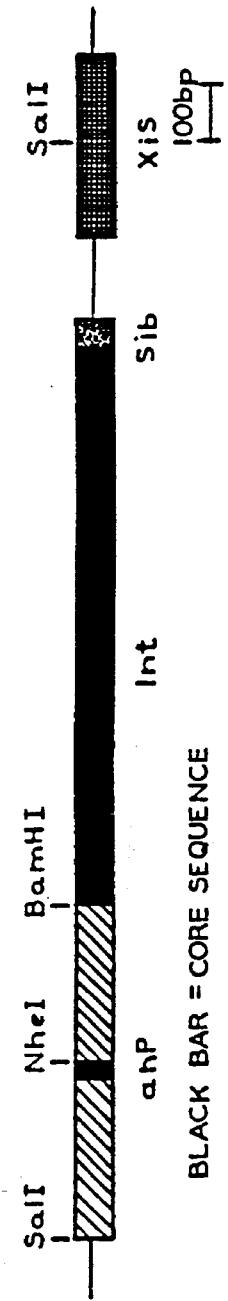

From a combination of the above approaches, a schematic of the organization of the attP-int region of L5 was constructed (FIG. 30), and the gene sequence of the attP-int region is given in FIG. 31. (SEQ ID NOS: 81–82)

(iii) Construction of PMH5

Figure 32:
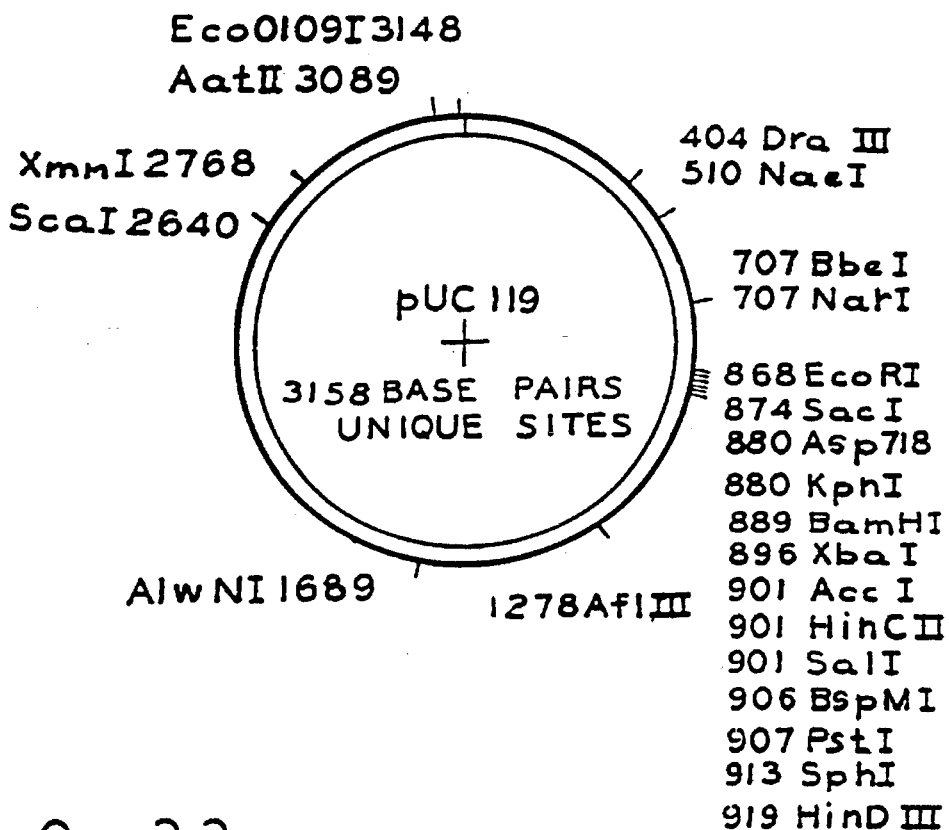
Figure 33:
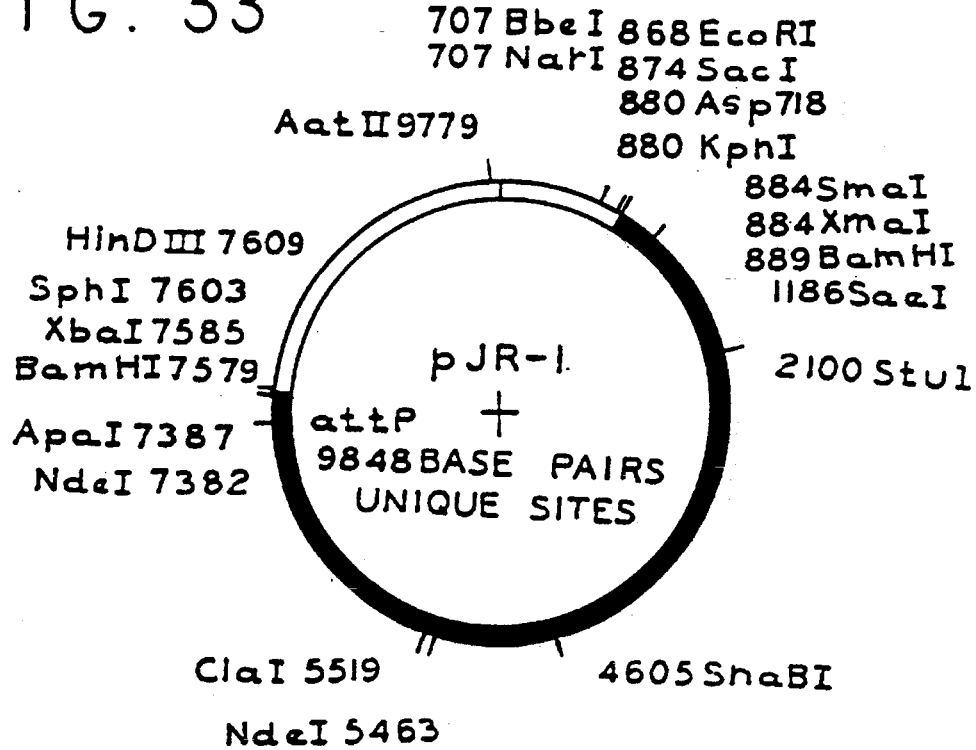

The 6.7 kb Bam HI fragment of mycobacteriophage L5, which contains the attP site, as hereinabove described, was cloned into the Bam HI site of pUC 119 (FIG. 32). This was achieved by purifying the 6.7 kb Bam HI fragment from a Bam HI digest of L5 DNA separated by agarose gel electrophoresis and ligating with Bam HI cut pUC 119. DNA was prepared from candidate recombinants and characterized by restriction enzyme analysis and gel electrophoresis. A recombinant was identified that contained the 6.7 kb Bam HI fragment of L5 cloned into pUC 119. This plasmid was named pJR-1, as shown in FIG. 33.

Analysis of DNA sequence data from a project to sequence L5 showed that a 1.9 kb Bam HI fragment adjacent to the 6.7 kb Bam HI fragment hereinabove described contained the integrase gene.

Figure 35:
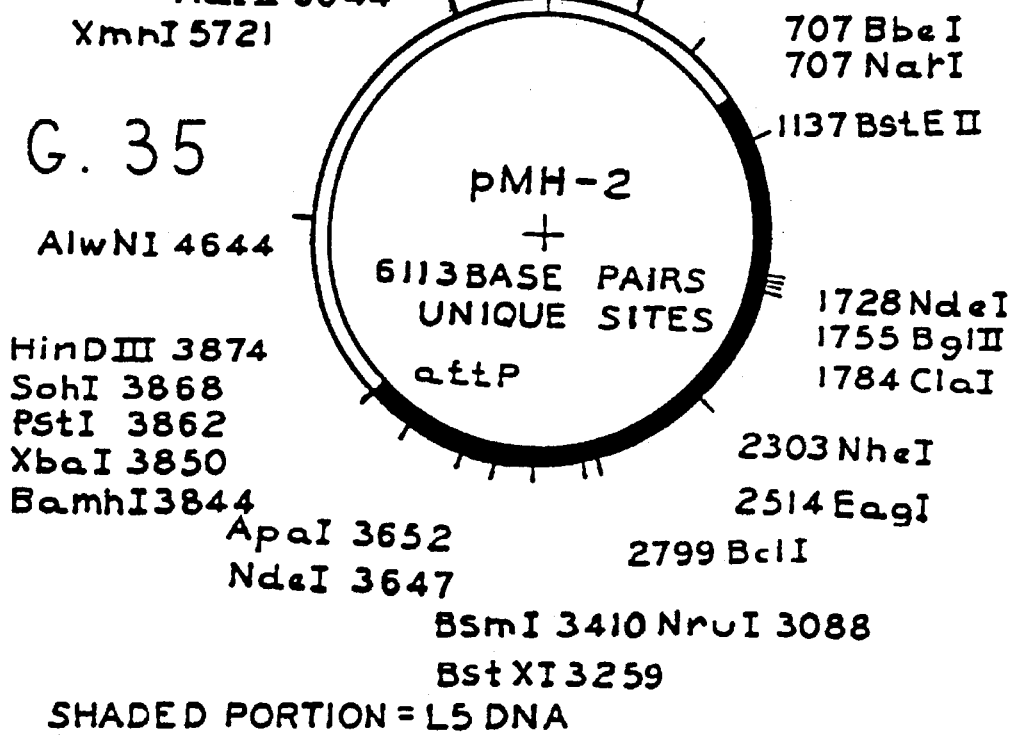

A plasmid containing a 1.9 kb Bam HI fragment containing the DNA encoding for the integrase cloned into the Bam HI site of pUC 119 was constructed. The 1.9 kb fragment was purified from a Bam HI digest of L5 DNA and cloned into the Bam HI site of pUC 119. Construction of the recombinant was determined by restriction analysis and gel electrophoresis. This plasmid was called pMH1, the construction of which is shown schematically in FIG. 34.

pJR-1 was then modified by digestion with EcoRI and SnaBI (both are unique cloning sites), between which is a Bam HI site. The Eco RI-Sna BI fragment, including the Bam HI site was excised, and the plasmid was religated to form plasmid of pMH2, which contains on Bam HI site compared to two Bam HI sites contained in pJR-1. A schematic of the construction of pMH2 is shown in FIG. 35.

Figure 36:
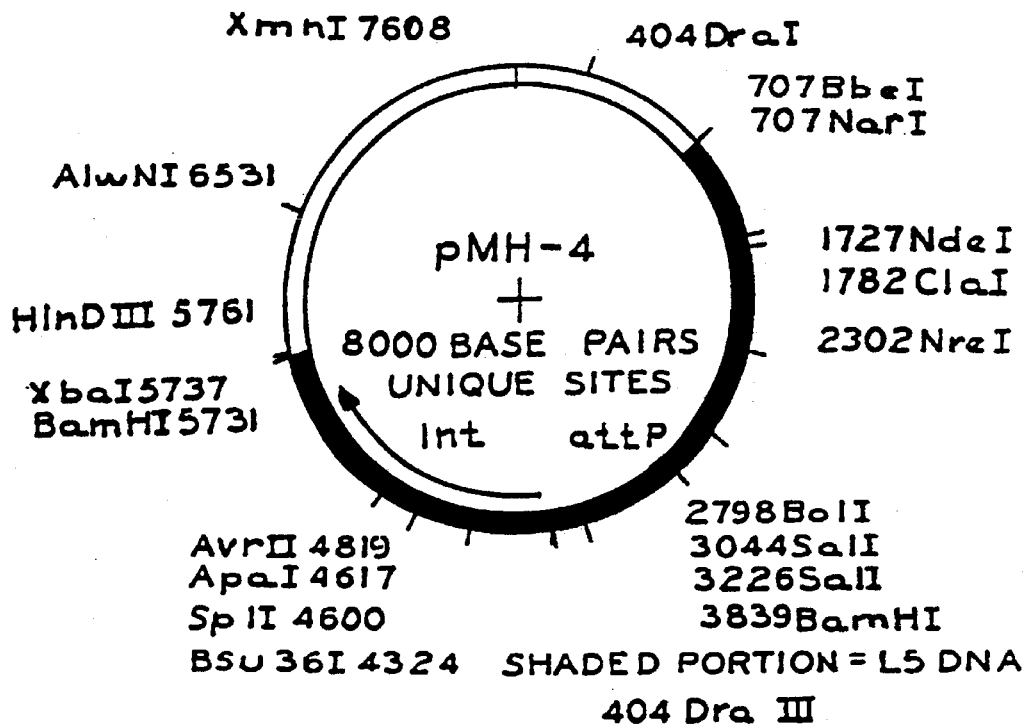
Figure 37:
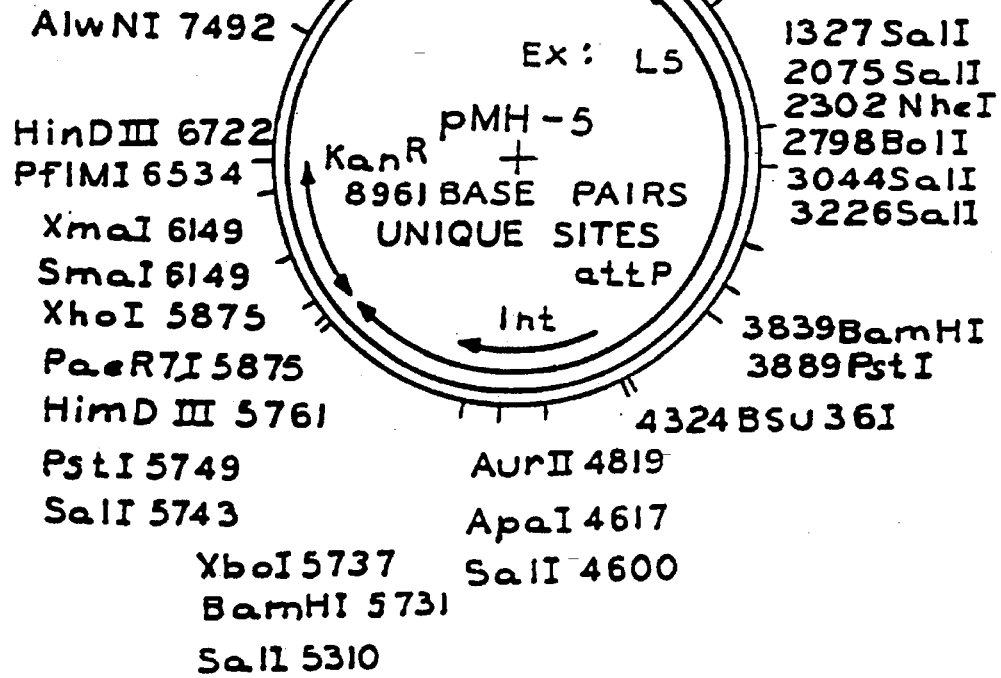

The 1.9 kb Bam HI fragment, which includes the integrase gene, was purified from a Bam HI digest of pMH1 and ligated to Bam HI digested pMH2. Recombinants were identified as above and the orientation of the 1.9 kb fragment determined. A plasmid called pMH4 was thus constructed (FIG. 36) in which the region from the Sna BI site (upstream of attP) through to the Bam HI site (downstream of the integrase gene) was identical to that in L5.

pMH4 was digested with HindIII (unique site) and was ligated to a 1 kb HindIII fragment purified from pKD43 (supplied by Keith Darbyshire of the Nigel Gindley Laboratory) that contains the gene determining resistance to kanamycin. Recombinants were identified and characterized as above. This plasmid is called pMH5. A schematic of the construction of pMH5 is shown in FIG. 37.

(iv) Integration of pMH5 into attB of *M. smegmatis*

Figure 38:
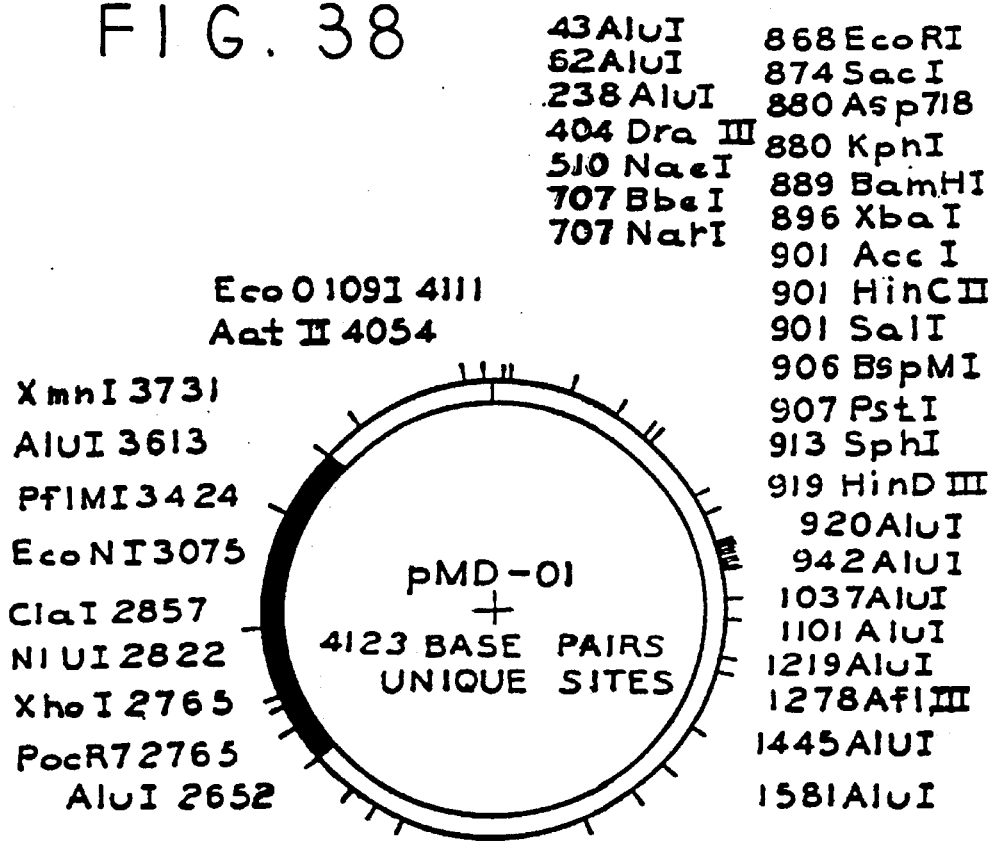

Plasmids pYUB12 (a gift from Dr. Bill Jacobs, a schematic of the formation of which is shown in FIG. 1), pMDO1 (FIG. 38), and pMH5 were electroporated, with four different concentrations of plasmid DNA over a 1,000-fold range, into *M. smegmatis* strain mc$^2$155, a strain which is able to support plasmid replication. In sections (iv) through (vi), all electroporation procedures of *M. smegmatis*, or of BCG, were carried out as follows:

Cultures of organism were grown in Middlebrook 7H9 media, as described by Snapper, et al. (1988), harvested by centrifugation, washed three times with cold 10% glycerol, and resuspended at approximately a 100×concentration of cells.

1 µl of DNA was added to 100 µl of cells in an ice-cold cuvette and pulsed in a Bio-Rad Gene Pulser, and given a single pulse at 1.25 kv at 25 µF. 1 ml of broth was added the cells incubated for 1 hr. at 37° C. for expression of the antibiotic-resistant marker. Cells were then concentrated and plated out on Middlebrook or tryptic soy media containing 15 µg/ml kanamycin. Colonies were observed after 3 to 5 days incubation at 37° C.

Each of pYUB12, pMDO1, and pMH5 carries kanamycin resistance. Plasmid pYUB12 carries an origin of DNA replication, while pMDO1 lacks a mycobacterial origin of replication. Plasmid pMH5 does not carry a mycobacterial origin of replication, but carries a 2 kb region of phage L5 which contains the attP site and the integrase gene (FIG. 31). The number of transformants were linear with DNA concentration. Plasmid pYUB12 gives a large number of transformants (2×10$^5$ per µg DNA) in mc$^2$ 155, while pMH5 gives 6×10$^4$ transformants per µg DNA, and pMDO1 gives no transformants.

The above experiment was then repeated by electroporating the plasmids pYUB12, pMDO1, and pMH5 into *M. smegmatis* strain mc$^2$6, which does not support plasmid replication. No transformants in mc$^2$6 were obtained from pYUB12 or pMDO1, while pMH5 gave approximately 10$^4$ kanamycin resistant transformants in mc$^2$6 per µg of DNA, thus indicating integration of pMH5 into the mc$^2$6 chromosome.

Figure 39:
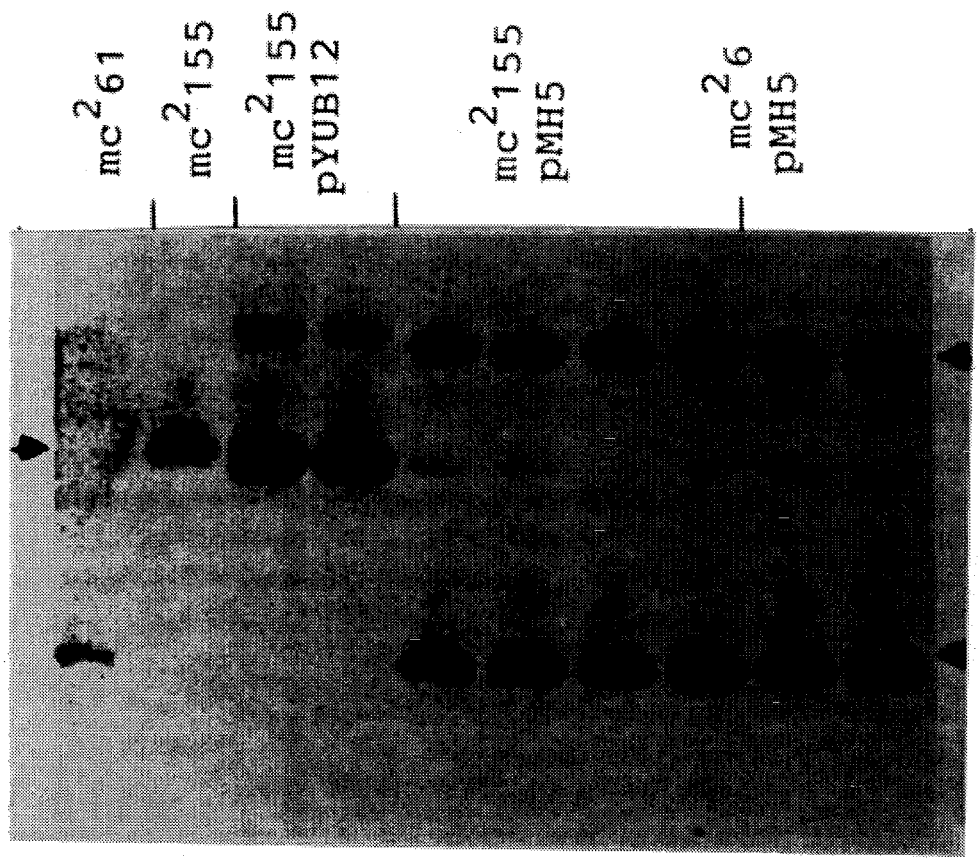

DNA from six independent pMH5 transformants (four in mc$^2$155 and two in mc$^2$6) was prepared. These DNA's (along with DNA from both mc$^2$155 itself, and mc$^{155}$ carrying the plasmid pYUB12) were digested with a restriction enzyme, and analyzed by Southern blot and hybridization with the *M. smegmatis* 1.9 kb attB probe hereinabove described. As shown in FIG. 39, all six transformants have integrated into the attB site, resulting in the production of two new DNA fragments with different mobilities. If pMH5 did not integrate into the attB site, it would be expected that a single band, corresponding to the attB site in the mc$^2$155 control, would be obtained.

Figure 40:
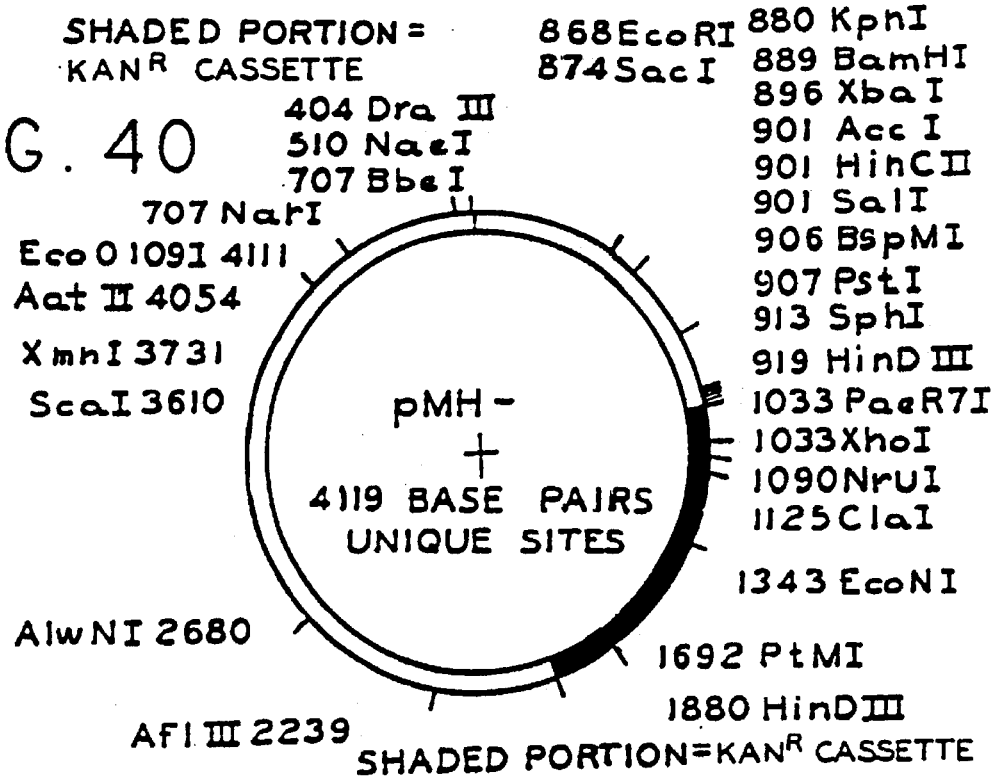
Figure 41:
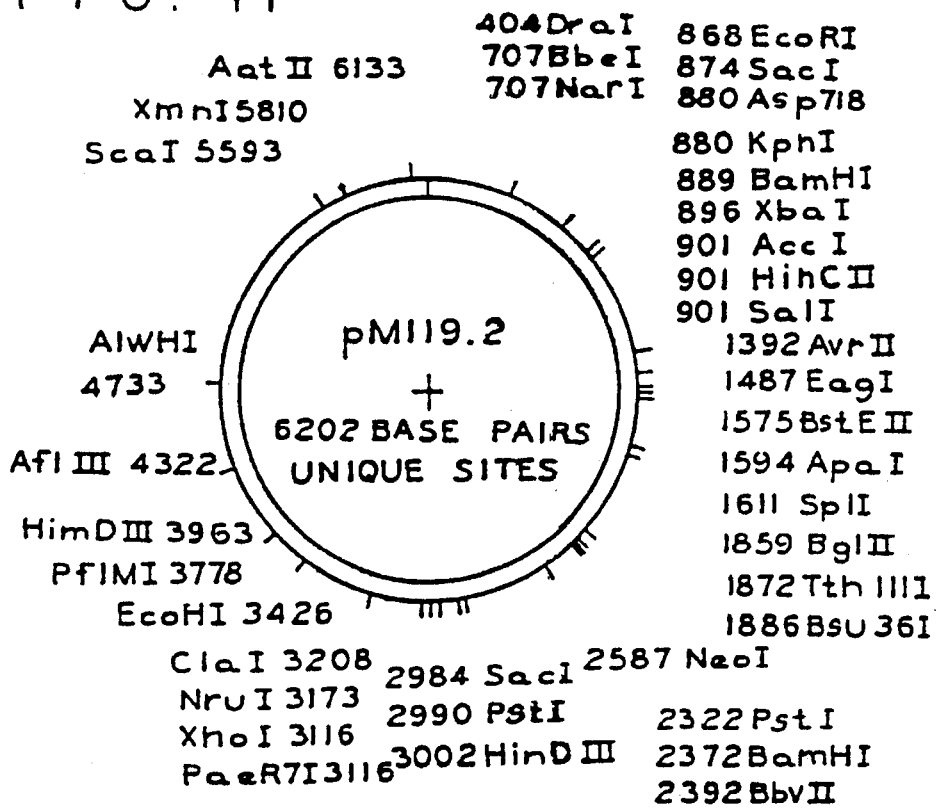
Figure 42:
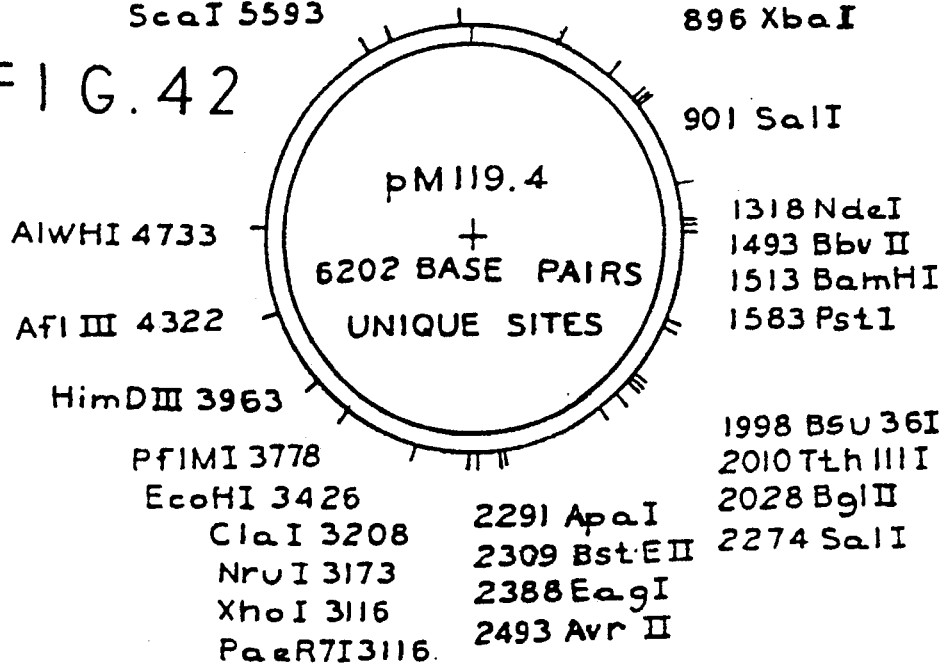

(v) Construction of pMH9.2 and pMH9.4 pUC119 was digested with HindIII, and a 1 kb HindIII fragment, containing a kanamycin resistance gene, purified from pKD43, was ligated to the HindIII digested pUC119 to form pMH8 (FIG. 40). A 2 kb SalI fragment (bp 3226–5310), which carries the attP and integrase gene from SalI digested pMH5, was purified and inserted in both orientations relative to the vector backbone of SalI digested pMH8 to form plasmids pMH9.2 and pMH9.4 (FIGS. 41 and 42).

*M. smegmatis* strain mc$^2$155 cells carrying, as a result of electroporation, plasmid pYUB12, pMH9.2 or pMH9.4, or strain mc$^2$6 cells carrying plasmid pMH5, as a result of electroporation as hereinabove described, were grown to saturation in broth with kanamycin. Cultures were then diluted 1:100 into broth without kanamycin and grown to saturation. Two further cycles of dilution and growth were done, corresponding to about 20 generations of bacterial growth. Cultures were plated out to single colonies on non-selective plates, and approximately 100 of these colonies were patch plated onto both non-selective and selective plates. The % of colonies that were sensitive to kanamycin, thus corresponding to the percentage of cells which lost the plasmid, is given below in Table I.

TABLE I

|  | % loss |
|---|---|
| pYUB12 (mc$^2$155) | 35 |
| pMH5 (mc$^2$6) | 17 |
| pMH9.2 (mc$^2$155) | 3 |
| pMH9.4 (mc$^2$155) | 0 |

(vi) Transformation of BCG with pMH9.4

Figure 43:
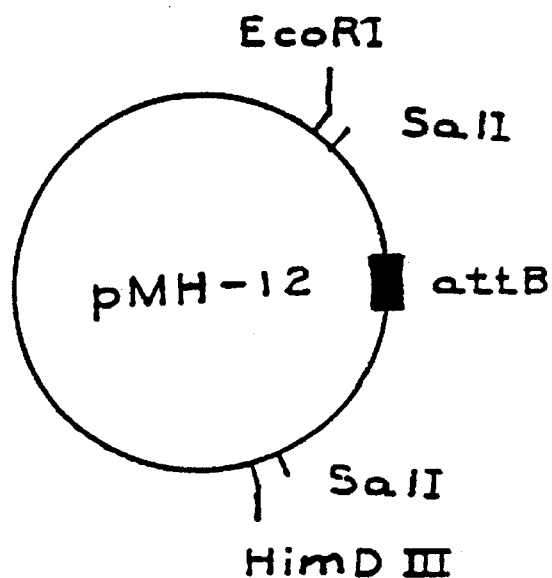

The 1.9 kb Sal I fragment, which includes the *M. smegmatis* attB site as hereinabove described was cloned into pUC119, and the plasmid generated was named pMH-12. (FIG. 43).

Figure 44:
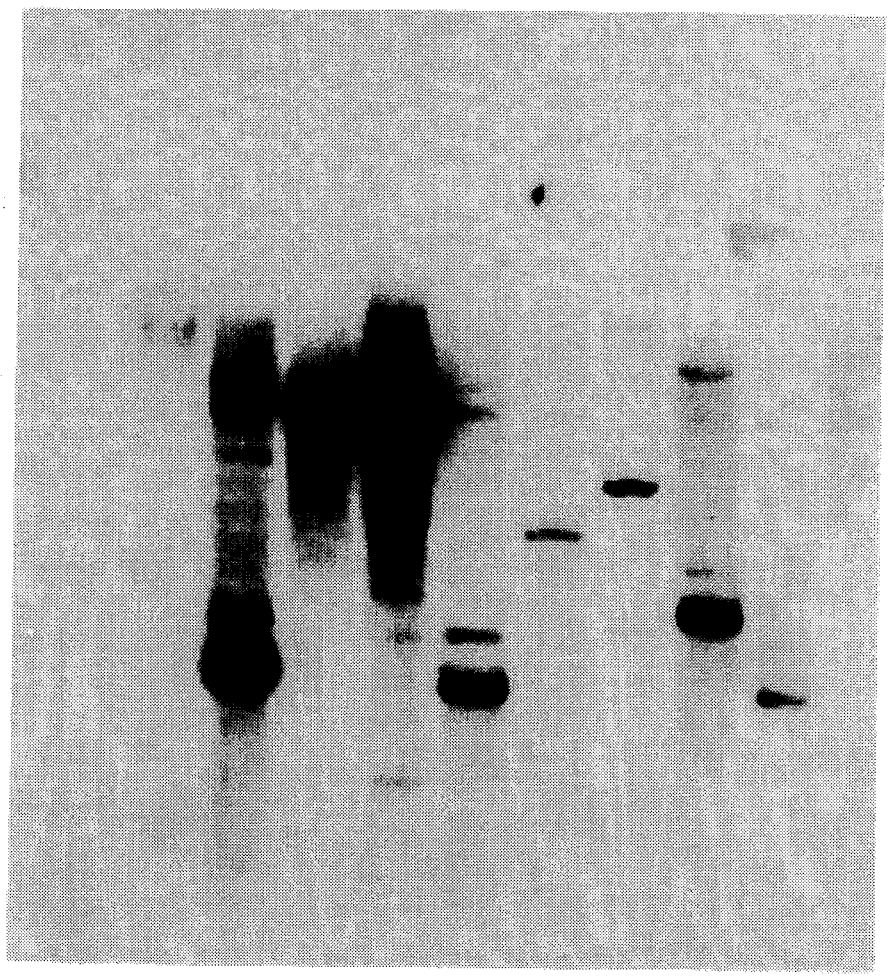

Gel purified Sal I 1.9 kb *M. smegmatis* fragment containing attB (isolated from pMH-12) was used to probe a Southern transfer of Bam HI digested mycobacterial DNA's, including BCG substrain Pasteur, shown in FIG. 44. This demonstrated that there is one Bam HI fragment of BCG that strongly hybridizes to the *M. smegmatis* attB probe and three hybridize weakly. The strongest hybridizing band is the fastest moving band (approximately 1.9 kb).

Figure 45:
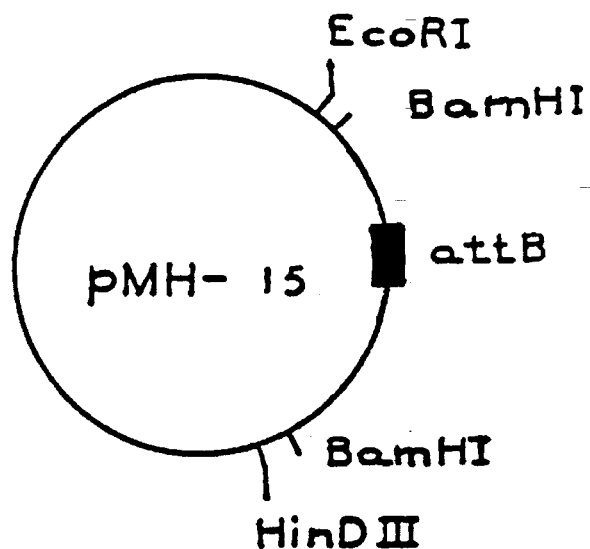
FIG. 45 is a map of pMH-15.

The same probe as above was used to probe a BCG cosmid library (provided by Dr. Bill Jacobs) and positive clones were identified. DNA was prepared from several positive clones and analyzed by restriction analysis and Southern blotting. The 1.9 kb Bam HI fragment (corresponding to the strongly hybridizing band in the Southern blot was identified, gel purified from the cosmid DNA and cloned into pUC119. The resulting plasmid was named pMH-15. (FIG. 45).

Figure 46:
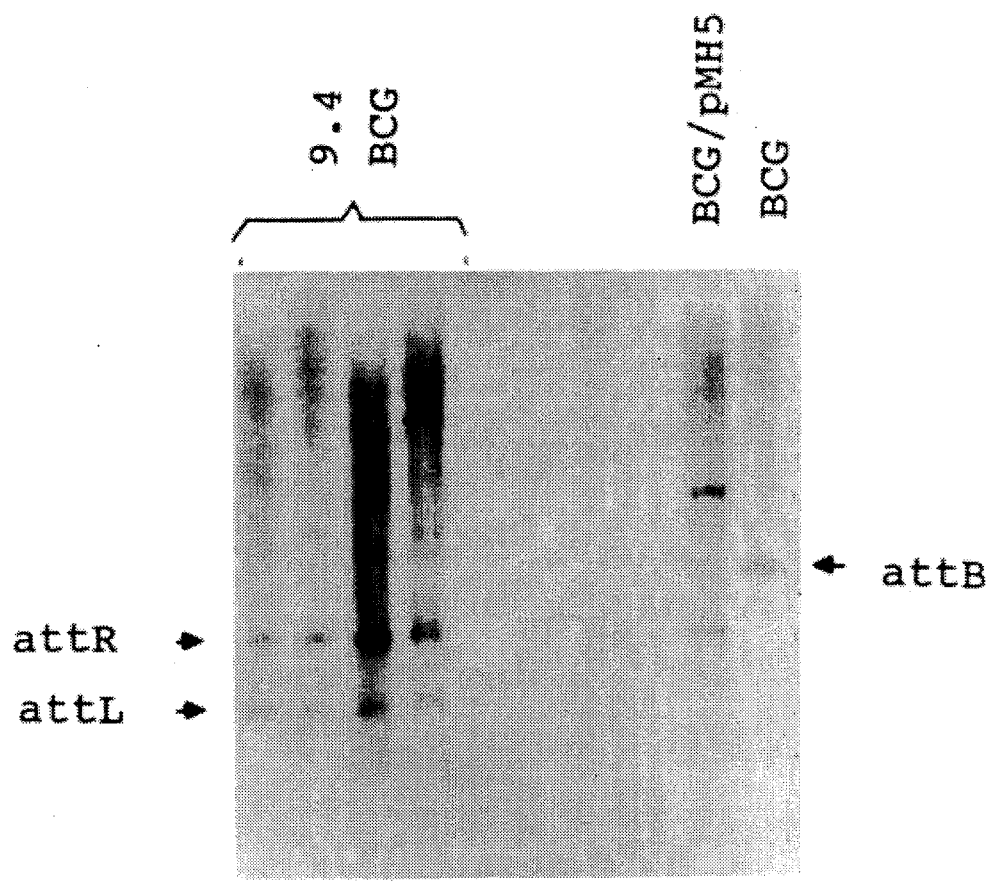
FIG. 46 is a Southern blot of DNA of a BCG organism transformed with pMH5, wherein such DNA was analyzed by BamHI restriction and probing with the 1.9 kb BamHI attB fragment from pMH-15.

Plasmid pMH-5 and pMH9.4 were electroporated into BCG Pasteur. It was observed that pMH9.4 transforms BCG with high efficiency (approximately 10$^4$ transformants/µg DNA), while pMH-5 transforms BCG at low efficiency (1–10 transformants/μg DNA). DNA was prepared from BCG transformants and analyzed by Bam HI restriction and Southern blot analysis, probing with gel purified 1.9 kb Bam HI BCG attB fragment from pMH-15. These data are shown in FIG. 41 and show that integration of both pMH5 and pMH9.4 is specific to the BCG attB site (ie. the strongly cross-hybridizing fragment in BCG). This is illustrated by the loss of the 1.9 kb Bam HI fragment from the transformants and the appearance of two new bands representing attL and attR junction fragments. FIG. 46 shows just one of the pMH5/BCG transformants, although all of the four that were analyzed show that one of the bands (the largest) is smaller than expected (and different in each of the transformants), indicating that the transformation effiency of pMH-5 is low in BCG. In contrast, the four pMH9.4 transformants are identical to each other (FIG. 46) and give attR and attL junction fragments of the predicted sizes.

Plasmid pMV206 was digested with NotI to remove the mycobacterial replicon. The resulting 2209 bp fragment, which includes the aph (Kan$^R$) gene, the $E.$ $coli$ replicon and the multiple cloning site, was ligated and recircularized to form pMV205, the construction of which is schematically depicted in FIG. 11.

PCR with primers XbaI-Att/Int and NheI-Att/Int was then performed on a Sal I fragment from pMH9.4, which contains the attP site and the L5 integrase gene. The resulting cassette was then digested with XbaI and NheI and a 1789 bp fragment was gel purified. pMV205 was then digested with NheI, and the resulting fragment was ligated to the 1989 bp fragment obtained from pMH9.4 to form pMV306. A schematic of the construction of pMV306 is shown in FIG. 47.

p2638::OspA (from Example 6) and pMV306 were each digested with XbaI and SalI. The XbaI-SalI fragment of p2638:OspA, which contains the HSP60 promoter, 38 kda secretion signal sequence, and OspA antigen sequence, was ligated into XbaI and SalI digested pMV306 to form p3638::OspA.

EXAMPLE 8 pRB26 was constructed as described in Example 1. The 32 kda α-antigen gene of $M.$ $Tuberculous$ or BCG (Matsuo, et al., $J.$ $Bacteriol,$ Vol. 170, No. 9, pgs 3847–3854 (September 1988); Borremans, et al., $Infect.$ $and$ $Immun.,$ Vol. 57, No. 10, pgs. 3123–3130 (October 1989)) was obtained from BCG chromosomal DNA and amplified by PCR using primers including added BglII-BamHI:EcoRI sites. The PCR fragment, 420 bp in length (FIG. 48 (SEQ ID NO:83)), was digested with BglII and EcoRI, and ligated into BamHI and EcoRI digested pRB26 to form pAB261 (FIG. 49), which contains the entire α-antigen gene. pAB261 was then digested with BamHI and SalI, and the 780bp PCR OspA cassette hereinabove described in Example 1, was also digested with BamHI and SalI, and was ligated to BamHI and SalI digested pAB261 to form pAB261::OspA.

EXAMPLE 9

Plasmid pMV206 was constructed as hereinabove described in Example 1.

A partial sequence of the 5' region of the BCG HSP70 gene (which encodes the BCG HSP70 heat shock protein, also known as the 70 kda antigen) obtained by Dr. Raju Lathigra (Medical Research Council, London) permitted the construction of a cassette carrying the promoter sequence. The HSP70 promoter was amplified by PCR with primers including Xba and NheI sites. The HSP70 promoter PCR fragment, 121 bp in length (FIG. 50), was digested with XbaI and NheI, and ligated to XbaI digested pMV206 to form pRB27. (FIG. 51.) The 32 kda α-antigen gene of BCG was obtained from BCG chromosomal DNA as described in Example 8, and amplified by PCR using primers including added BglII-BamHI:EcoRI sites. The PCR fragment was digested with BglII and EcoRI, and ligated into BamHI and EcoRI digested pRB27 to form pAB271 (FIG. 52), which contains the entire α-antigen gene. pAB271 was then digested with BamHI and SalI, and the 780 bp PCR OspA cassette hereinabove described in Example 1, was also digested with BamHI and SalI, and was ligated to BamHI and SalI digested pAB271 to form pAB271::OspA.

EXAMPLE 10

Figure 53:
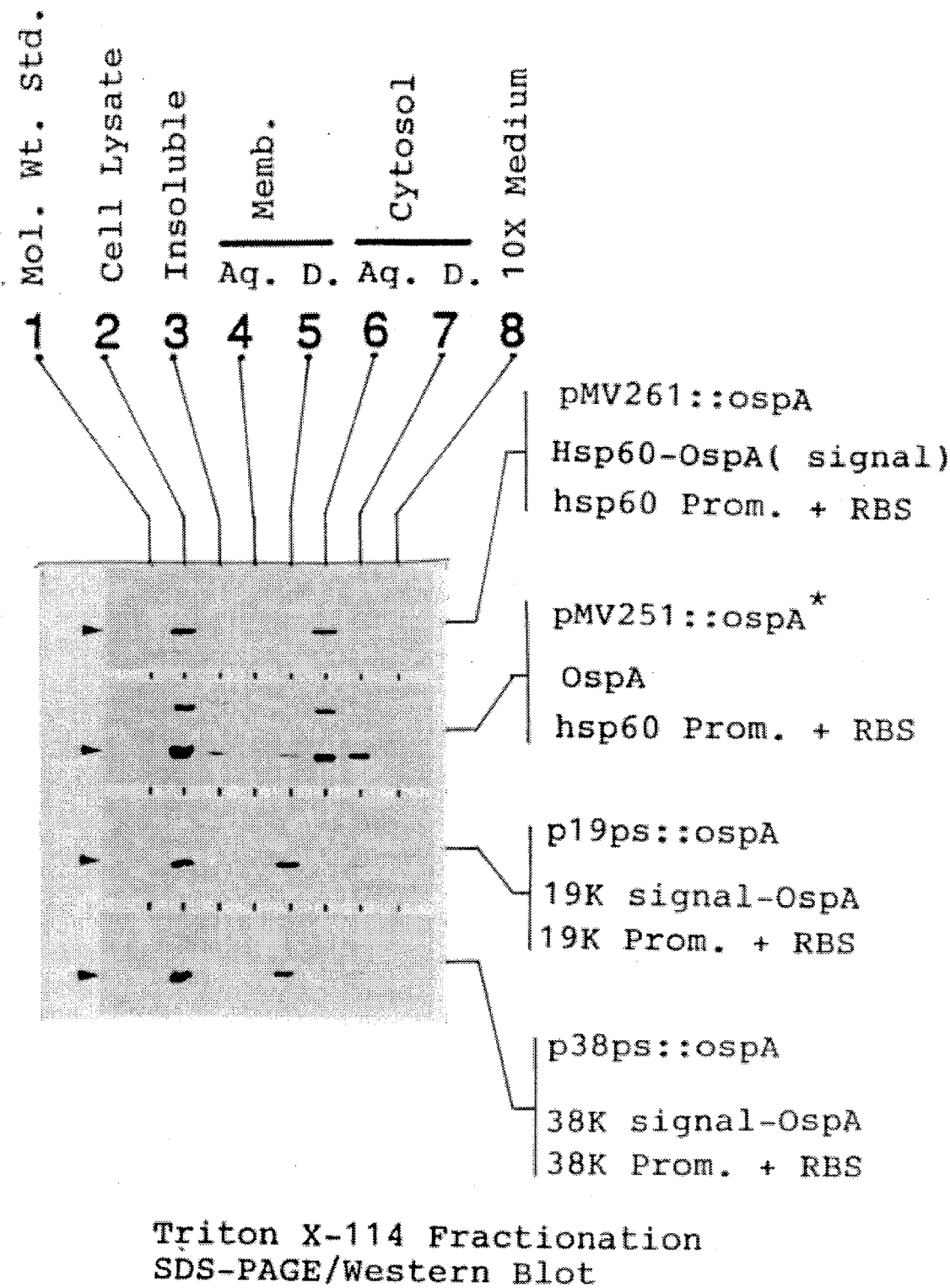
FIG. 53 is a Western blot of cell envelopes of BCG organisms transformed with p 19PS: :OspA, p38PS: :OspA, pMV261::OspA, and pMV251::OspA, wherein the Western blot was conducted with anti-OspA monoclonal antibody H5332.
Figure 54:
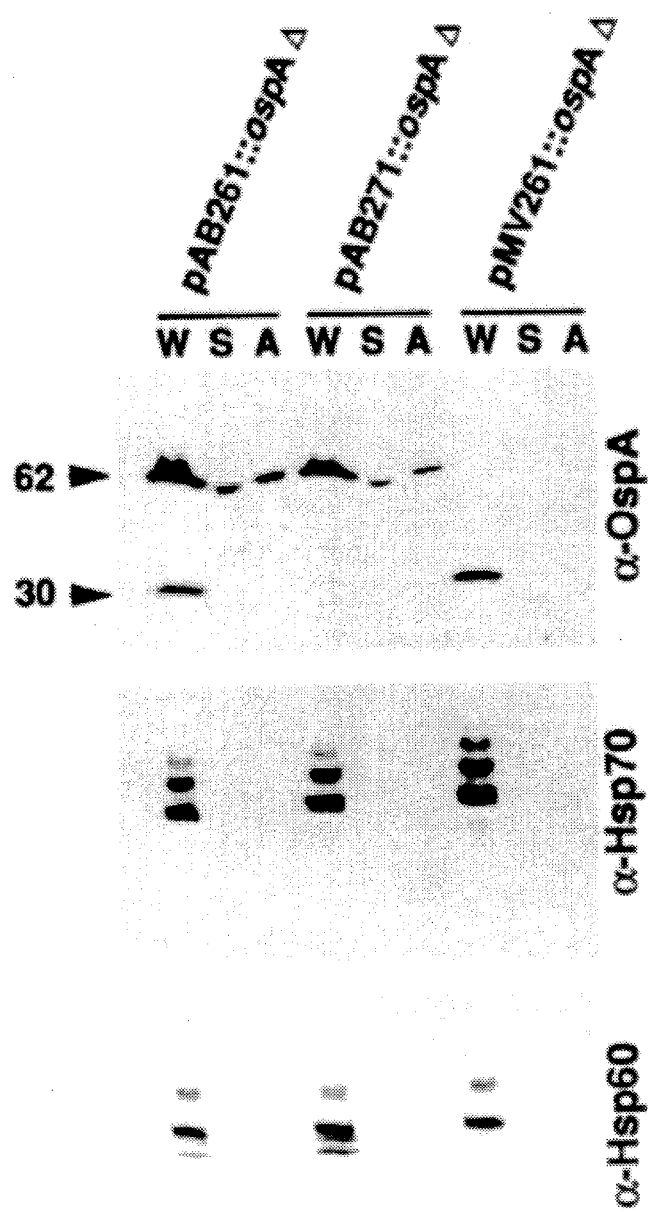
FIG. 54 is an immunoblot of cell supernatants from cell pellets of BCG cells transformed with pAB261::OspA, pAB271::OspA, or pMV261::OspA, wherein the immunoblotting was conducted with anti-OspA, anti-HSP70, or anti-HSP60.
Figure 55:
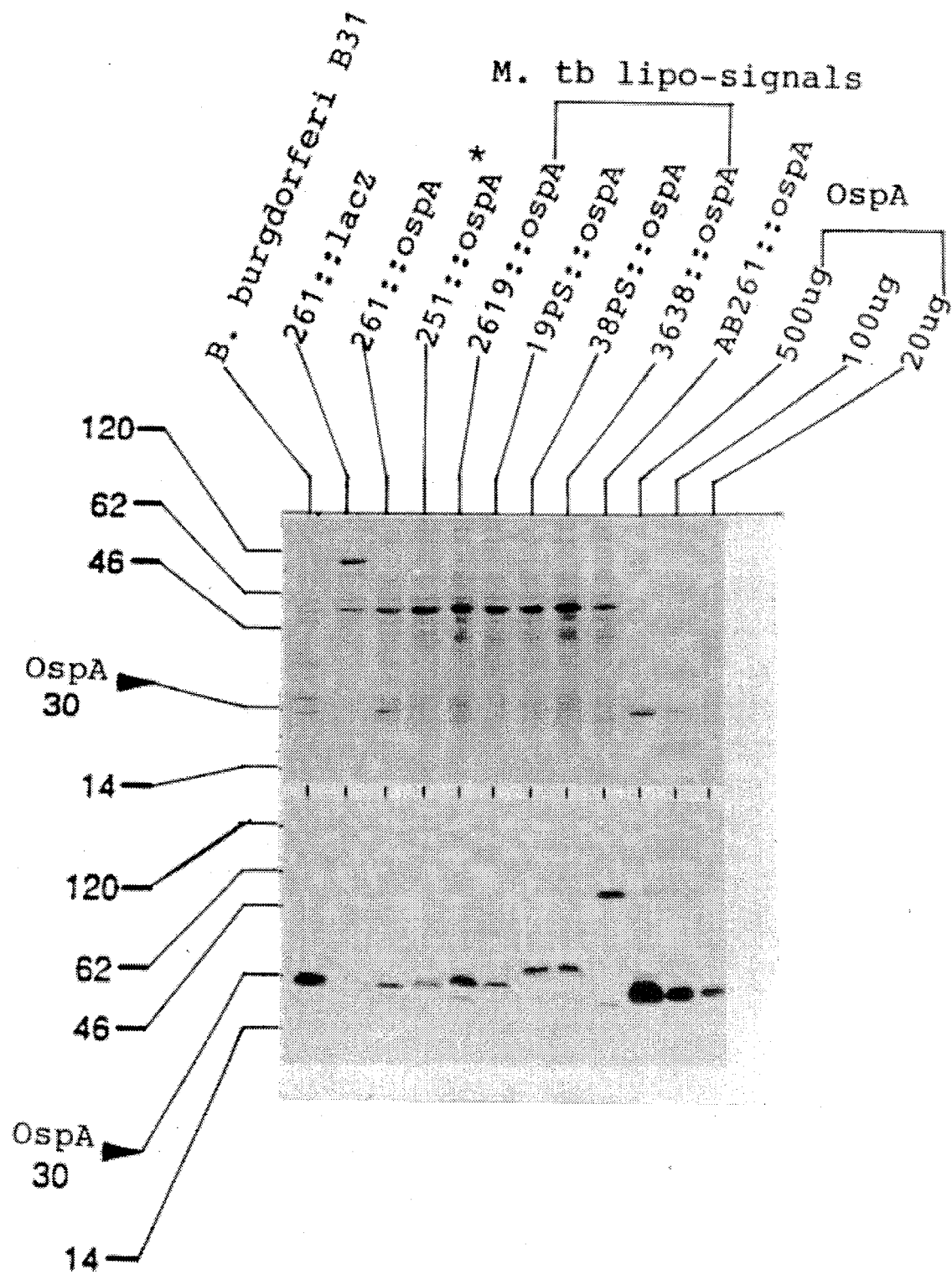
FIG. 55 is a Western blot of BCG culture volume equivalents, with anti-Osp monoclonal antibody H5332, from BCG organisms transformed with pMV261::OspA, pMV251::OspA, p2619::OspA, p19PS::OspA, p38PS::OspA, p3638::OspA, pAB261::OspA, or pMV261/LZ.
Figure 56:
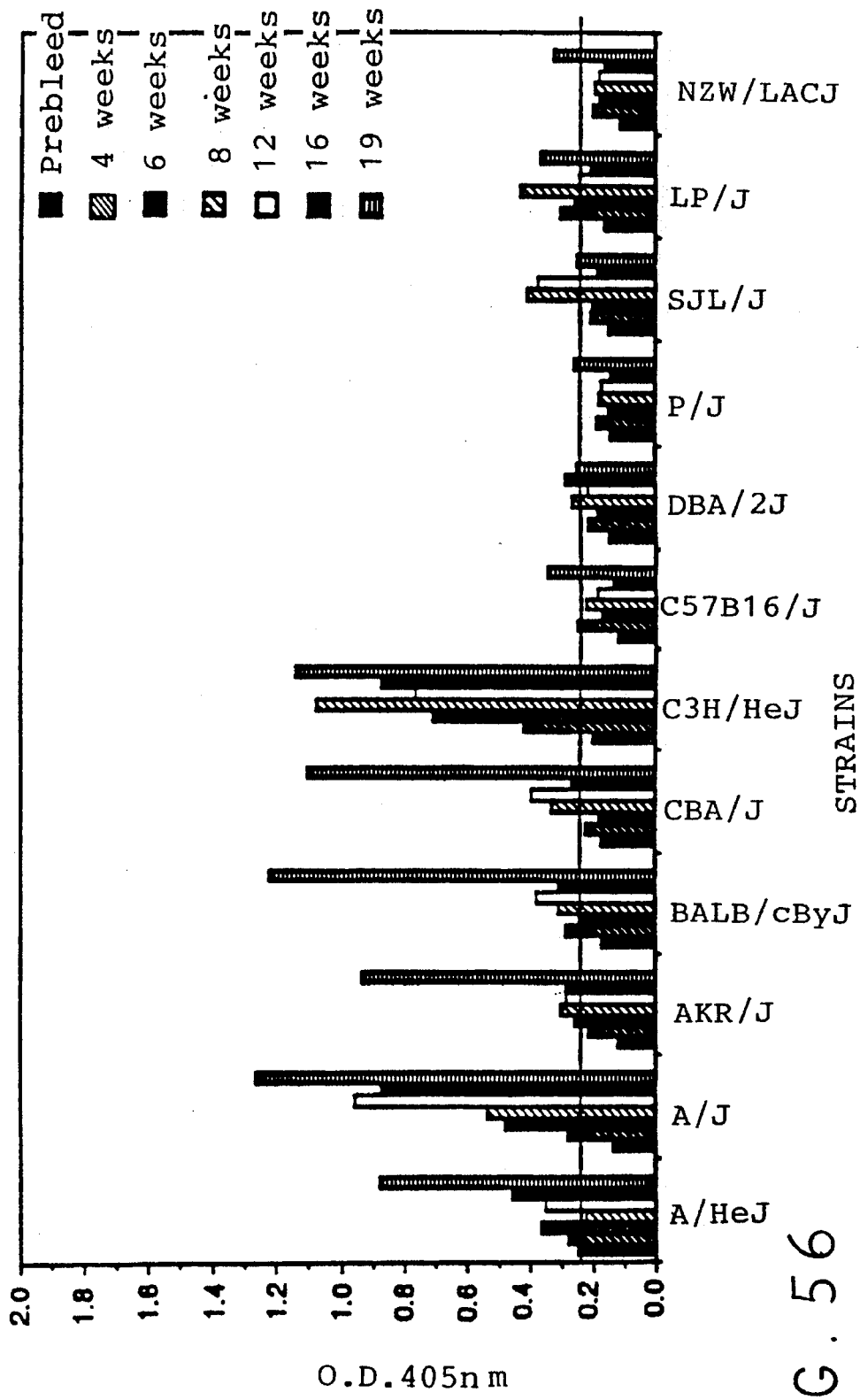
FIGS. 56 and 57 are graphs of the immune responses of various strains of mice immunized with 1×10⁶ CFU of BCG transformed with pMV261::OspA, followed by a booster intraperitoneal injection of 1×10⁶ CFU of BCG transformed with pMV261::OspA 17 weeks later.
Figure 57:
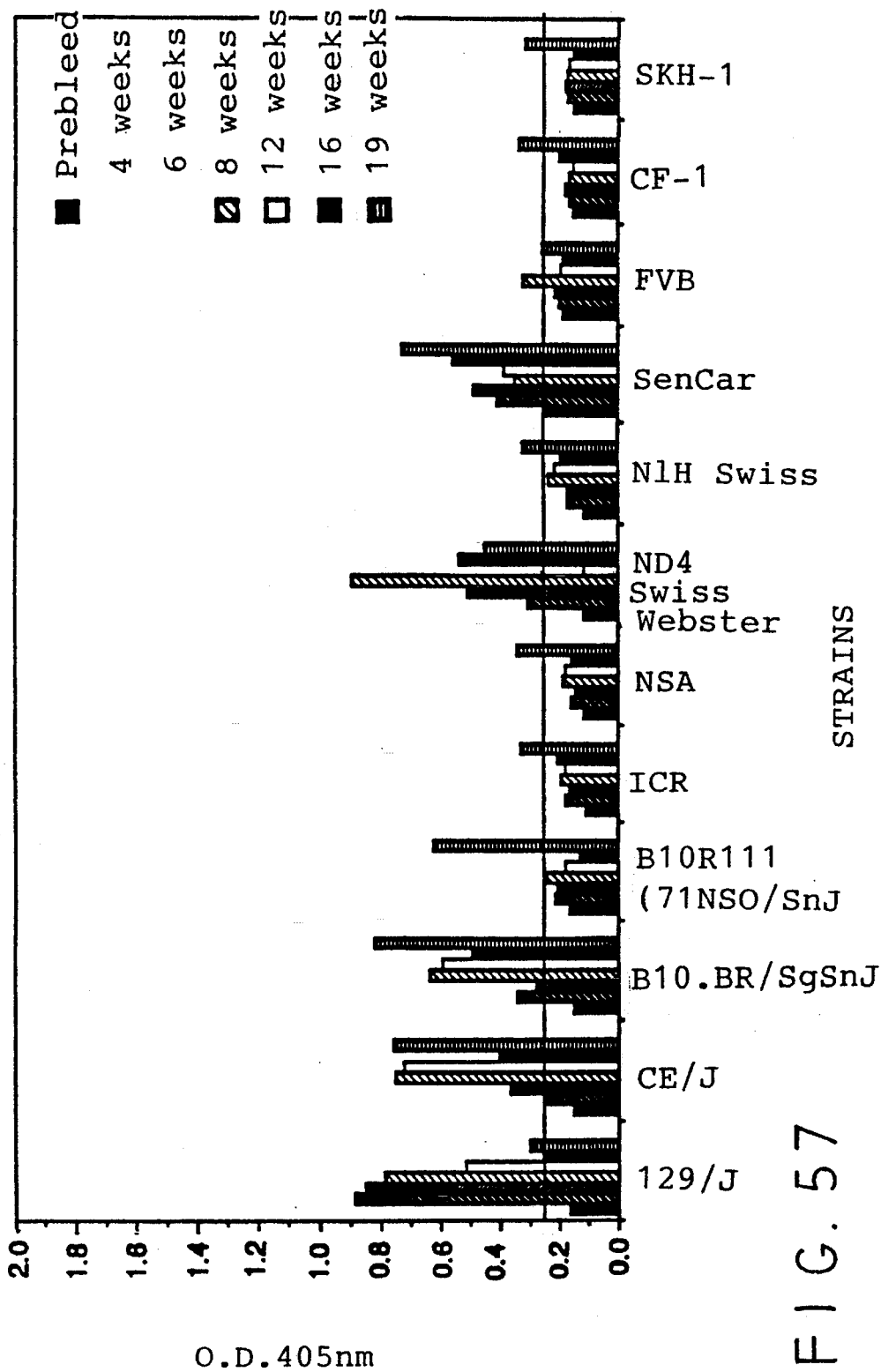

Vectors p19PS::OspA, p38PS::OspA, pMV261::OspA, and pMV251::OspA were transformed into BCG. The transformed BCG cells were cultured, and the cells were then sedimented from the cultures. The cells were then suspended in phosphate buffered saline (PBS), and cell suspensions were normalized to equivalent densities. The cells were disrupted by sonication, the cell envelopes were sedimented, and the supernatant (a Cytosol-enriched fraction) was saved. The cell envelopes were resuspended in PBS, and membranes were solubilized at 4° C. by the addition of Triton X-114 to 2% (vol./vol.). Insoluble material (a cell wall-enriched fraction) was sedimented, and the supernatant (membrane-enriched fraction) was removed. Triton X-114 was added to the Cytosol-enriched fraction. After brief warming of the Triton X-114 solutions at 37° C., separation of aqueous and detergent phases was achieved by a short centrifugation. These two phases were back-extracted three times, and proteins in representative samples were precipitated by the addition of acetone. A portion of each culture supernatant was concentrated by an ultrafiltration device (Centricon-30, Areicon). Samples representing culture volume equivalents were processed by SDS-PAGE, transferred to nitrecellulose, and Western blotted with anti-OspA monoclonal antibody (Mab) H5332. (Howe, et al., $Infect$ $and$ $Immun.,$ Vol. 54, No. 1, pgs. 207–212 (October 1986) ). Filter-bound antibody was visualized with an enhanced chemiluminescence system (Amersham). As shown in FIG. 53, Lane 1 is a molecular weight standard (Rainbow Markers, Amersham); lane 2 is a whole cell sonicate fraction; lane 3 is Triton X-114 insoluble material; lane 4 is the aqueous phase membrane fraction; lane 5 i s the detergent phase membrane fraction; lane 6 is the aqueous phase Cytosol fraction; lane 7 is the detergent phase Cytosol fraction; and lane 8 is a concentrated culture medium.

As can be seen from FIG. 53, recombinant chimeric OspA fusion proteins expressed from the expression vectors p19PS: :OspA and p38PS: :OspA were found to be localized predominantly in the Tritou X-114 phase from the membrane fractions, thus suggesting that these recombinant OspA proteins were fused to the micobacterial 19 kda and 38 kda secretion signals, which directed secretion and post-translational processing by fatty acylation at an M-terminal cysteine. OspA expressed with its native lipoprotein signal peptide by pMV251::OspA was found to be localized in detergent soluble BCG membrane fractions although additional OspA was also found in BCG cytoplasmic aqueous fractions, thus suggesting that the OspA signal was not as efficiently processed in BCG as were the 19 kda and 38 kda signal sequences. Recombinant OspA expressed by pMV261::OspA, wherein OspA was not fused to a lipoprotein signal, was found to be localized only in aqueous cytoplasmic fractions.

EXAMPLE 11

Figure 58:
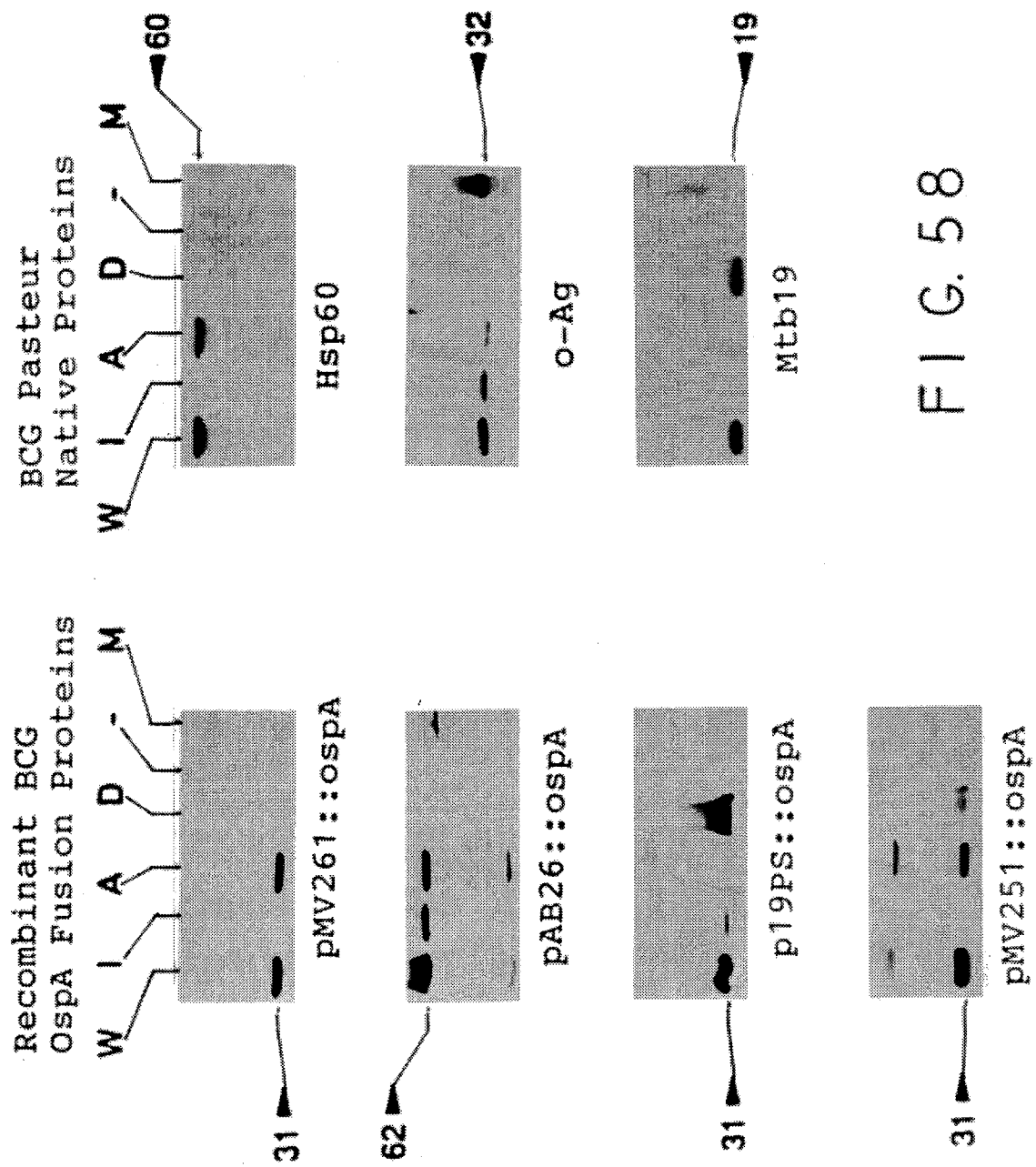
FIG. 58 is a blot of cell culture supernatant with anti-OspA monoclonal antibody H5332, from BCG organisms transformed with pMV261::OspA, pAB261::OspA, p19PS::OspA, or pMV251::OspA.

BCG cells were transformed with either pAB261::OspA, pAB271::OspA, or pMV261::OspA and cultured. Portions of BCG culture supernatants were depleted of bovine serum albumin (BSA), a component of the medium, by adsorption with Affi-gel Blue (Bio Rad). BCG cell pellets from the cultures were suspensed in PBS and sonicated. Adsorbed or unadsorbed supernatants were concentrated (Centricon 30) and then diluted to the same relative concentration, on a culture volume basis, as the lysed cells. Samples were used for SDS-PAGE and subsequent immunoblotting with anti-OspA (Mab H 5332), anti-Hsp70 (Mab IT-41, WHO mycobacterial monoclonal antibody bank), or anti-Hsp60 (Mab IT-13, WHO mycobacterial monoclonal antibody bank). As shown in FIG. 54, lane M.W. Std. is a molecular weight standard, lanes W are whole cell lysates, lanes S are culture supernatants (unadsorbed), and lanes A are adsorbed supernatants. As shown in FIG. 54, it was determined that fusion of the OspA gene, without the secretion signal, to the complete α-antigen gene resulted in high level expression, and a substantial fraction of the resulting recombinant α-antigen-OspA fusion protein was found to be excreted into the culture media. The absence of detectable quantities of cytoplasmic proteins (Hsp60 and Hap70) in the supernatant indicated that cell lysis was minimal, and that the recombinant α-antigen::OspA fusion protein was specifically targeted to be secreted and is not simply found in culture supernatants due to autolysis.

EXAMPLE 12

BCG organisms (Pasteur strain) were transformed with one of the following vectors:

pMV261::OspA
pMV251::OspA
p2619::OspA
p19PS::OspA
p38PS::OspA
p3638::OspA
pAB261::OspA

As a negative control, pMV261/LZ was used to transform a control group of organisms. pMV261/LZ was constructed by cloning a BamHI restriction fragment carrying the *E. coli* lacZ gene (which encodes β-galactosidase) into the BamHI site of Bam HI digested pMV261.

The transformed BCG colonies were isolated by selection for kamamycin resistance and expanded in liquid media culture for further analysis. Recombinant BCG samples representing culture volume equivalents were processed by SDS-PAGE, transferred to nitrocellulose, and Western blotted with anti-OspA Mab H5332. Positive controls employed were a processed sample of *B. burgdorferi* strain B31, and samples of OspA antigens in concentrations of 500 μg/ml, 100 μg/ml. and 20 μg/ml. The filter-bound antibody was visualized with an enhanced chemilumineseuce system (Amersham). As shown in FIG. 55, OspA was expressed by BCG transformed with vectors including the OspA gene. FIG. 55 also shows the expression of a fusion protein of OspA and a mycobacterial secretion signal by BCG transformed with p2619::OspA, p19PS::OspA, p38PS::OspA, or p3638::OspA.

EXAMPLE 13

BCG organisms were transformed with pMV261:: OspA, and the transformed organisms were cultured. Twenty-four different strains of mice, with five mice representing each strain, were immunized with a single dose of $1\times10^6$ CFU of BCG transformed with pMV261::OspA (post freeze titer of 42%) intraperitoneally. The mice were bled every four weeks for 16 weeks, and also at 19 weeks. Sera were analyzed by ELISA on whole cells of *Borrelia burgdorferi* and BCG lysate coated on wells. The reaction was developed with peroxidase conjugated anti-mouse immunoglobulin and substrate. Color development was read as absorbance at 405 nm. Positive sera had optical density (O.D.) values at three standard deviations above the mean of the prebleed sera. At 17 weeks, the mice were given a booster intraperitoneal injection of $1\times10^6$ CFU of BCG transformed with pMV261::OspA.

As shown in FIGS. 56 and 57, the following strains:

A/HeJ
A/J
AKR/J
BALB/cByJ
CBA/J
C3H/HeJ
SJL/J
LP/J
129/J
CE/J
B10.BR/SgSnJ
D4 Swiss Webster
SenCar
FVB showed an immune response after a single immunization, and the following strains:

A/HeJ
A/J
C3H/HeJ
129/J
CE/J
B10.BR/SgSnJ
D4 Swiss Webster had responded with significantly high levels of antibody against *Borrelia burgdorferi.*

EXAMPLE 14

BCG organisms transformed with either pMV261::OspA, pAB261::OspA, p19PS::OspA, or pMV251::OspA, plus non-recombinant BCG Pasteur organisms were subjected to cell fractionation and Triton X-114 detergent phase partitioning analysis (Bordier, et al; *J. Biol, Chem.*, Vol. 256, pg. 1604 (1981); Radolf, et al., *Infect and Immun.*, Vol. 56, pg. 490 (1988)) to determine if expression of OspA genes in the vectors hereinabove described resulted in export and lipid acylation of recombinant OspA protein.

Recombinant BCG cells wee sedimented from BCG cultures, suspended in phosphate buffered saline (PBS), and cell suspensions were adjusted to equivalent densities. Cells were disrupted by sonication and mebranes were solubilized at 4° C. by the addition of Triton X-114 to 2% (vol./vol.). Insoluble material (cell wall enriched fraction) was centrifuged, and the supernatant was subjected to detergent phase partitioning. After briefly warming (37° C.) the Triton X-114 solutions, separation of aqueous and detergent phases was achieved by a short centrifugation. The two phases were back-extracted three times, and proteins in representative samples were precipitated by the addition of acetone. A portion of each culture supernatant was concentrated by ultrafiltration. Samples representing 5-fold concentrated culture volume equivalents were processed by SDS-PAGE, transferred to nitrocellulose and blotted with anti-OspA MAb H5332. (FIG. 58). Similar fractions from non-recombinant BCG were blotted with appropriate monoclonal antibodies specific for the BCG or *M. tuberculosis* Hsp60 protein (IT13), α antigen (HYT27), or *M. tuberculosis* 19 kda antigen (HYT6) to determine the cellular location of the native fusion partners. As shown in FIG. 58, lane W is a whole cell sonicate fraction; lane I is a Triton X-114 insoluble cell wall enriched fraction; lane A is a cytosol-enriched aqueous fraction; lane D is a detergent phase (membrane-enriched) fraction and lane M is a 5-fold concentrated culture medium fraction.

As shown in FIG. 58, the OspA gene product encoded by pMV261:: OspA was found excessively in the aqueous cytosolic fraction (lane A) and correlated with the exclusive cytoplasmic location of HSP60. The α-antigen-OspA gene product expressed by pAB261::OspA and the native BCG α-antigen were found in the insoluble cell wall enriched fraction (lane I), aqueous cytosolic fraction (lane A), and media fraction (lane M), but not in the detergent soluble lipoprotein-enriched fraction (lane D). The presence of the α-antigen in the recombinant BCG culture media was not due to recombinant BCG autolysis, as HSP60 was not found in the culture media. Compared to the native BCG α-antigen, a substantially smaller fraction of the fusion protein expressed by pAB261::OspA was secreted into the media, while a larger portion was found in the cell wall enriched insoluble fraction. This suggests that fusion to the α-antigen could also direct foreign antigens to the cell wall. Substitution of the *M. tuberculosis* 19 kda antigen signal peptide for the OspA signal peptide resulted in expression of a chimeric OspA protein that was located almost exclusively in the detergent soluble fraction. This finding indicated that fusion of the *M. tuberculosis* 19 kda antigen signal peptide to OspA did direct efficient expression and export of the OspA protein to the membrane of BCG. This result was in contrast to the product expressed by organisms transformed with pMV251::OspA, where most of OspA was found in the aqueous fraction, which may have been due to inefficient processing of the native Borrelia signal peptide.

EXAMPLE 15

The recombinant BCG organisms of Example 14 were analyzed by flow cytometry to determine if the recombinant OspA gene products were accessible on the surface of recombinant BCG to anti-OspA antibody.

Approximately $2\times10^8$ recombinant BCG organisms grown in Dubos media supplemented with albumin-dextrose complex and 0.05% Tween 80 were harvested by centrifugation. The pelleted recombinant BCG organisms were washed with 10 ml. of phosphate buffered saline (pH 7.4) containing 0.05% Tween 80 (PBS-T80), resuspended in 5 ml. PBS-T80, and fixed for 10 minutes in 2% paraformaldehyde. Fixed recombinant BCG organisms were pelleted and washed twice with 5 ml. PBS-T80, and then resuspended in 1 ml. of PBS-T80. Polyclonal rabbit sera specific for OspA (BCG-adsorbed) was added to the fixed recombinant BCG cell suspension to a final dilution of 1:200 and incubated for 30 minutes at room temperature and 30 minutes on ice. The suspension was then pelleted by centrifugation, washed twice with 0.5 ml. PBS-T80 and resuspended in 1 ml. PBS-T80. Goat anti-rabbit FITC-conjugated secondary antibody was added to a final dilution of 1:50 and incubated for 30 minutes on ice. The recombinant BCG-secondary antibody suspension was pelleted by centrifugation, washed twice with 1 ml. PBS-T80 and resuspended in 2 ml. PBS-T80. Labeled recombinant BCG were mildly sonicated to disperse clumped cells and dilutions were analyzed by flow cytometry on an FACS scan (Becton-Dickinson). Recombinant BCG containing the designated plasmids and expressing the designated chimeric OspA gene products are compared to non-recombinant BCG. (FIG. 59).

As shown in FIG. 59, recombinant BCG organisms expressing OspA from plasmids p19PS:OspA, pMV251::OspA, and pAB261::OspA, all demonstrated increased surface fluorescence with anti-OspA sera when compared with non-recombinant BCG or recombinant BCG expressing OspA from plasmid pMV261::OspA. The relative surface fluorescence exhibited by expression of OspA from organisms transformed with pMV251::OspA was less than that observed for organisms transformed with p19PS::OspA, and was in agreement with the fractionation analysis of Example 14. The recombinant BCG expressing OspA from pAB261::OspA also exhibited surface flourescence, thus confirming that the α-antigen-OspA fusion protein found in the Triton insoluble fraction (Example 14) was cell wall associated and not derived from insoluble inclusion bodies. Therefore, it was possible to export OspA to the surface of BCG as a membrane-associated lipoprotein by fusion to the *M. tuberculosis* 19 kda antigen signal sequence, or as a secreted and cell wall associated protein by fusion to the α-antigen.

EXAMPLE 16

C3H/He, BALB/C, and Swiss Webster mice were immunized with $10^6$ colony forming units of BCG organisms transformed with pMV261::OspA, pMV251::OspA, p19PS::OspA, pAB261::OspA, or of non-recombinant BCG Pasteur. The mice were given a booster of the identical dose at 16 weeks. As shown in FIG. 60, all three mouse strains immunized with BCG transformed with pMV251::OspA or p19PS::OspA exhibited strong OspA-specific antibody responses within 4 to 8 weeks after a single immunization as measured by ELISA to whole Borrelia organisms or purified OspA. Particularly striking were the anti-OspA responses elicited by a single dose of BCG organisms transformed with either pMV251::OspA or p19Pg::OspA; in the low responder Swiss Webster strain; the same strain of mice immunized with BCG transformed with pMV261::OspA or pAB261::OspA did not mount anti-OspA responses even after boosting. Peak anti-OspA antibody titers exceeding $1:10^5$ in BALB/C and C3H/He mice, and $1:10^4$ in Swiss Webster mice were elicited by boosting with BCG transformed with pMV251: :OspA or p19PS: :OspA, and these responses were 100 to 1,000-fold higher than the responses induced with BCG transformed with pMV261::OspA or pAB261::OspA.

EXAMPLE 17

Immune sera from the immunized C3H/He and BALB/C mice of Example 16 were analyzed for their ability to inhibit growth of the non-pathogenic B31 laboratory strain of *B. burdorferi* in culture in two independent experiments. (Sadziene, et al., *J. Infect. Diseases,* in press (1992). Growth inhibition titers for each of the immune sera are given in Table I below:

TABLE I

| Mouse Strain | Vector | Titer | |
|---|---|---|---|
| | | Experiment 1 | Experiment 2 |
| BALB/C | pMV261::OspA | <8 | N/A |
| BALB/C | pMV251::OspA | 4096 | 8924 |
| BALB/C | p19PS::OspA | 1024 | 16384 |
| BALB/C | pAB261::OspA | N/A | N/A |
| BALB/C | none(Control) | <8 | <8 |
| C3H/He | pMV261::OspA | 32 | N/A |
| C3H/He | pMV251::OspA | 1024 | 32768 |
| C3H/He | p19PS::OspA | 2048 | 16384 |
| C3H/He | pAB261::OspA | 256 | N/A |
| C3H/He | none(Control) | <8 | <8 |

The above results show that antisera obtained from mice immunized with BCG transformed with pMV251::OspA or p19PS::OspA exhibited strong growth inhibition titers while sera derived from mice immunized with BCG transformed with pMV261::OspA showed lower or undetectable growth inhibition titers.

C3H/He and BALB/C mice immunized with the BCG organisms hereinabove described were then challenged with either $10^6$ *B. burgdorferi* strain Sh$^2$ organisms intraperitoneally (IP) or $10^4$ organisms intradermally (ID). The *B. burgdorferi* organisms were administered 5 weeks after a booster immunization of $10^6$ transformed BCG organisms. The mice were sacrificed 14 days after the *B. burgdorferi* challenge, and plasma, and bladder tissue were cultured in BSKI I media. (Schwan, et al., *J. Clin. Microbiol*, Vol. 20, pg. 155 (1984) ). Cultures were monitored through day 14 by phase contrast microscopy for the presence of spirochetes. The presence of one or more spirochetes per 20 high power fields in any one of the plasma or tissue cultures was scored as an infection. The fraction of the challenged mice exhibiting positive infections in the IP, and ID challenges are given in Table II below.

TABLE II

| Mouse | | No. of Infections | |
|---|---|---|---|
| Strain | Vector | IP | ID |
| BALB/C | pMV261::OspA | 5/5 | N/A |
| BALB/C | pMV251::OspA | 0/5 | 0/5 |
| BALB/C | p19PS::OspA | 0/5 | 0/5 |
| BALB/C | pAB261::OspA | 4/5 | N/A |
| BALB/C | none(Control) | 4/4 | 4/4 |
| C3H/He | pMV261::OspA | 3/4 | N/A |
| C3H/He | pMV251::OspA | 0/5 | 0/5 |
| C3H/He | p19PS::OspA | 3/5 | 0/5 |
| C3H/He | pAB261::OspA | 3/5 | N/A |
| C3H/He | none(Control) | 5/5 | 5/5 |

The above results show that all control mice were found to be infected, whereas the mice that were immunized with BCG transformed with pMV251::OspA or p19PS::OspA were protected from infection.

It is to be understood however, that the scope of the present invention is not to be limited to the specific embodiments described above. The invention may be practiced other than as particularly described and still be within the scope of the accompanying claims.

What is claimed is:

1. Recombinant mycobacteria transformed with DNA encoding a polypeptide, said polypeptide comprising a lipoprotein secretion signal sequence and an antigen heterologous to the mycobacteria wherein the lipoprotein secretion signal causes the antigen to be produced as a lipoprotein.

2. The mycobacteria of claim 1 wherein the mycobacteria is BCG.

3. The mycobacteria of claim 2 wherein said DNA further includes a mycobacterial origin of replication.

4. The mycobacteria of claim 2 wherein said DNA further comprises a sequence encoding mycobacteriophage integration into a mycobacterium chromosome.

5. The mycobacteria of claim 1 wherein the lipoprotein secretion signal sequence is a secretion signal sequence of a mycobacterial lipoprotein.

6. The mycobacteria of claim 5 wherein said mycobacterial lipoprotein is an *M. tuberculosis* lipoprotein.

7. The mycobacteria of claim 6 wherein said *M. tuberculosis* lipoprotein is selected from the group consisting of the 19 kda and 38 kda antigens.

8. The mycobacteria of claim 6 wherein the mycobacteria is BCG.

9. The mycobacteria of claim 5 wherein the mycobacteria is BCG.

10. Mycobacteria transformed with DNA encoding a polypeptide, said polypeptide comprising a lipoprotein secretion signal sequence and an antigen which elicits antibodies against *Borrelia burgdorferi*, wherein the lipoprotein secretion signal causes the antigen to be produced as a lipoprotein.

11. The mycobacteria of claim 10 wherein said DNA encodes an antigen derived from *Borrelia burgdorferi*.

12. The mycobacteria of claim 11 wherein said antigen is selected from the group consisting of Outer Surface Protein A antigen and an Outer Surface Protein B antigen.

13. The mycobacteria of claim 10 wherein said mycobacteria is BCG.

14. The mycobacteria of claim 13 wherein the antigen is an Outer Surface Protein A antigen.

15. The mycobacteria of claim 14 wherein said lipoprotein secretion signal sequence is the lipoprotein secretion signal sequence of Outer Surface Protein A.

16. The mycobacteria of claim 10 wherein the lipoprotein secretion signal sequence is a secretion signal sequence of a mycobacterial lipoprotein.

17. The mycobacteria of claim 16 wherein said mycobacterial lipoprotein is an *M. tuberculosis* lipoprotein.

18. The mycobacteria of claim 17 wherein said *M. tuberculosis* lipoprotein is selected from the group consisting of the 19 kda and 38 kda antigens.

19. The mycobacteria of claim 16 wherein the mycobacteria is BCG.

20. The mycobacteria of claim 10 wherein the antigen is an Outer Surface Protein A antigen.

21. A method of protecting an animal against Lyme disease, comprising:

administering to an animal the mycobacteria of claim 10 in an amount effective to protect an animal against Lyme disease.

22. The method of claim 21 wherein said DNA encodes an antigen derived from *Borrelia burgdorferi*.

23. The method of claim 22 wherein said antigen is selected from the group consisting of an Outer Surface Protein A antigen and Outer Surface Protein B antigen.

24. The method of claim 22 wherein the lipoprotein secretion signal sequence is a secretion signal sequence of a mycobacterial lipoprotein.

25. The method of claim 24 wherein said mycobacterial lipoprotein is an *M. tuberculosis* lipoprotein.

26. The method of claim 25 wherein said *M. tuberculosis* lipoprotein is selected from the group consisting of the 19 kda and 38 kda antigens.

27. The method of claim 22 wherein the antigen is an Outer Surface Protein A antigen.

28. The method of claim 27 wherein the mycobacteria is BCG.

29. The method of claim 21 wherein the mycobacteria is BCG.

30. The method of claim 29 wherein the antigen is an Outer Surface Protein A antigen.

31. The method of claim 30 wherein said lipoprotein secretion signal sequence is the lipoprotein secretion signal sequence of Outer Surface Protein A.

* * * * *

SEQUENCE LISTING ( 1 ) GENERAL INFORMATION:

( i i i ) NUMBER OF SEQUENCES: 84

( 2 ) INFORMATION FOR SEQ ID NO:1:

( i ) SEQUENCE CHARACTERISTICS:
( A ) LENGTH: 6407 nucleotides
( B ) TYPE: nucleic acid
( C ) STRANDEDNESS: double
( D ) TOPOLOGY: circular ( i i ) MOLECULE TYPE: nucleic acid ( x i ) SEQUENCE DESCRIPTION: SEQ ID NO: 1:

```
GCTAGCGCTA TATGCGTTGA TGCAATTTCT ATGCGCACCC GTTCTCGGAG CACTGTCCGA    60
CCGCTTTGGC CGCCGCCCAG TCCTGCTCGC TTCGCTACTT GGAGCCACTA TCGACTACGC   120
GATCATGGCG ACCACACCCG TCCTGTGGAT CCTCTACGCC GGACGCATCG TGGCCGGCAT   180
CACCGGCGCC GCCCTATACC TTGTCTGCCT CCCCGCGTTG CGTCGCGGTG CATGGAGCCG   240
GGCCACCTCG ACCTGAATGG AAGCCGGCGG CACCTCGCTA ACGGATTCAC CACTCCAAGA   300
ATTGGAGCCA ATCAATTCTT GCGGAGAACT GTGAATGCGC AAACCAACCC TTGGCAGAAC   360
ATATCCATCG CGTCCGCCAT CTCCAGCAGC CGCACGCGGC GCATCTCGGG CAGCGTTGGG   420
TCCTGGCCAC GGGTGCGCAT GATCGTGCTC CTGTCGTTGA GGACCCGGCT AGGCTGGCGG   480
GGTTGCCTTA CTGGTTAGCA GAATGAATCA CCGATACGCG AGCGAACGTG AAGCGACTGC   540
TGCTGCAAAA CGTCTGCGAC CTGAGCAACA ACATGAATGG TCTTCGGTTT CCGTGTTTCG   600
```

| | | | | | |
|---|---|---|---|---|---|
| TAAAGTCTGG | AAACGCGGAA | GTCAGCGCCC | TGCACCATTA | TGTTCCGGAT | CTGCATCGCA | 660 |
| GGATGCTGCT | GGCTACCCTG | TGGAACACCT | ACATCTGTAT | TAACGAAGCG | CTGGCATTGA | 720 |
| CCCTGAGTGA | TTTTTCTCTG | GTCCCGCCGC | ATCCATACCG | CCAGTTGTTT | ACCCTCACAA | 780 |
| CGTTCCAGTA | ACCGGGCATG | TTCATCATCA | GTAACCCGTA | TCGTGAGCAT | CCTCTCTCGT | 840 |
| TTCATCGGTA | TCATTACCCC | CATGAACAGA | AATTCCCCCT | TACACGGAGG | CATCAAGTGA | 900 |
| CCAAACAGGA | AAAACCGCC | CTTAACATGG | CCCGCTTTAT | CAGAAGCCAG | ACATTAACGC | 960 |
| TTCTGGAGAA | ACTCAACGAG | CTGGACGCGG | ATGAACAGGC | AGACATCTGT | GAATCGCTTC | 1020 |
| ACGACCACGC | TGATGAGCTT | TACCGCAGAA | CGAGGACAGT | CGCACGACGA | AGTTCTTCTG | 1080 |
| GATCGCGCCC | GTGCTGGAAG | CACTCAACCT | CGAAGCGTGT | GGTTGCGGAG | CCATCTAGCA | 1140 |
| ACCACACGAA | ACATGCGCAA | CGAACCGCGC | AACGAACAAC | GCCTAGAACT | GGCACTAGAT | 1200 |
| GAGCTGACTC | GTATCGTTGG | TAAACCTAGT | TTGACCAGCA | TGTTTAACT | ACGTTCGGTG | 1260 |
| AGCTGTCAAC | GGGGCCTGTA | ACGGCACAAC | GAACCGTGCA | ACGAGAGTGG | CCACGGATGC | 1320 |
| CACCACAAGC | ACTACAACGG | AGTTCGCCAC | GTACATCACC | ACAACCACCG | ATTCTGGCGG | 1380 |
| TGAGCTCCAC | GATATTCAGC | GGAAATGGCT | TGGTATCGAC | CAAGATTCGT | AGAACCCGT | 1440 |
| CTCGTCTGGC | TGGTATTCAA | AACGGACGCA | ACGAAACACG | CAACGAGACA | GGCATGGCCC | 1500 |
| AAACCAGAAA | ACTAGCGTCT | ACCAGGACTT | TTACCTGTCC | GACCCGTTGC | AACGGAACCC | 1560 |
| CCCACGGAAC | CCCCGCGACA | CCCGCTCCCC | AATTGCGTTA | GAACAGCGGT | GGATTGTCGG | 1620 |
| CTTCGTTGTG | GGCCTTTTGA | GCCGCTTCCT | GTTCTGCCGC | ACGCTCTTTC | CTCGCCCGAT | 1680 |
| AGCCGAGTCG | CTTAACGGTG | TCCAGATGCA | GCCCGAAATG | TTTGGCCGTT | TGCGGCCAAG | 1740 |
| AGTGGCCCTC | GTCGTCGTGA | TAGGCGCGGA | TGCGTTCGCG | GCGTGCAGCC | TGCTCGGCGA | 1800 |
| GCCACTCGCT | GCGTTCCTGC | GCCACGAGCC | GGACGACGTG | GCGTTCGGAT | AGTCCGGTGA | 1860 |
| TTCGAGCGCC | TTCGGCGGCG | GTCACGCGCC | GCTTTTGCG | GACAGTCGGC | TGCCGGTTGT | 1920 |
| AGCCGTCGCT | GTAGCCGTCG | CTGTAGCCGT | CGCTCATAGC | AATGCCTCCA | TGGCTGACGC | 1980 |
| GGACTTTGCG | CGCCGCGCAA | CTGTGCTCGC | CGCCGTGCGC | GCTGCTGCGC | CCTTCCGCGA | 2040 |
| GATGGCCGAC | TGGCGCGCAC | TGAGTGTGGC | CTCGTAGACC | ACGATCCCGT | CCGCCCAAAT | 2100 |
| GCGCGACTTG | GTTGTGATCC | AACGCCAAAT | GCTGTTGGCG | ATGGCGCGGA | CCTCGCTGTC | 2160 |
| CGGTAGCGGT | CCGGGACACA | CGTCGTTGCA | CGGGAATTCG | GCGTTTCGCG | CGTGGCACTC | 2220 |
| GGCATAGATC | GCGCGGCCGA | GTCCGTCCAC | GTTCCGGGTC | GGCAGGTAGA | TCCGCATGAG | 2280 |
| GGCGGGACGA | TAGGCCCACA | ACCTGACGGA | ATCGAACAGT | GCGCAATTCC | GCCCTAGCGG | 2340 |
| CGTCGGAGCC | GCTTTGTACG | TGGTCTGCTG | ACGCCAGCGC | GGCGGTGGCA | TGTTCGCGCC | 2400 |
| GAGCTCGGCC | TCGATGTGGC | TGAGTGTGTA | GAGATCTGAG | TGGAGCCATT | CCGTTTCCCA | 2460 |
| GGCGATGTGG | CCGGGGTTTT | TGGTCATGAG | GCCTGAGTAA | CTGCGGTCGC | CGTCGACGGC | 2520 |
| GCGCCGAAGG | CCTTCGGCGC | ACGCCGCCAT | GTATGCGAGC | GGCTTACGCC | GCGCGTATTC | 2580 |
| GGTGCGTGGA | ACAGGGGCGT | TGAGTGCCCA | CACTGCGTGT | GCGTGGCCGT | TGGCGCGATT | 2640 |
| GCCCACGATC | GCGTTGGGCA | GCGGATGGGA | CCCCGGGCG | CTGAGCGCTC | GGAGCGCTGC | 2700 |
| GTCTGGATGG | TCTACGTCCA | CGACCAGCAG | GTTTGCCAGC | GCTGTTGGGT | TCGCCTCGAT | 2760 |
| GTACCGGCGG | CCTAGGGCCG | ACGCGCGGCT | TTGGCGGTAG | ATCCCCTCGA | GCAGATCGTC | 2820 |
| GCTTGCCAGC | GGCCAGTACG | GCAGCCAGAG | CTGCTCAAAT | TCGTCGGCGA | CGTGGCTCAC | 2880 |
| GCTTGGTAGT | AGACCACGAT | TAATCACCGG | TGTATGGTCC | GACACGAGCT | CCAAGTCAGA | 2940 |
| TATTTCGCTG | AGGGGCCACC | CCACAACTGC | ACACTCCCCC | GCTCTCCCGT | CGAGCCCTGA | 3000 |

| | | | | | | |
|---|---|---|---|---|---|---|
| TGATGAAACA | CCAGCGACAG | CCGAGCACCC | CCAACCACCT | GTACCAACCA | GGAGGAACAC | 3060 |
| ATGCGTCGTT | TCGAGGACGT | TTCCGGGCCG | CTAAGAGCCG | CTGTGGCGGC | CGTACACGCC | 3120 |
| GCCTTAGACC | CGTTAGACCC | CCTGCCGCCT | GAATGCGCGG | GTACGAGCCA | CACAGCACCC | 3180 |
| GAACTTACGG | AGCTGGTGGG | CTCACCTGGC | TTTATGGCGT | ACGAATCGGC | TGTGTGCGAC | 3240 |
| CTGTTGGGCG | AGGTGAGATA | CGCGCTACTC | ACGCTGGCAA | GGGCGACACA | GCCGCCCAC | 3300 |
| CGAGCCCGCA | CGGCCGCGCG | CGGTGTCAAC | AACCGGGTGA | GTCGTGCACA | CCAGCAGGTG | 3360 |
| TTCGAGGCTT | GGCTCGAAGT | GCAGGACATC | GTGGCGAACG | CCGCCCGATG | AGCCGCGCCT | 3420 |
| TACGCTGGCT | GCCAGCCGTT | CGCGGGCTGG | TTGGTGCAGC | GCGTCGAGCG | GTTAGAGGCC | 3480 |
| CTGCGGTGTT | CCACCACCGC | AGGCCTCGCC | CTTTTAAGG | CTGAATTTGC | TTGTCTCCGA | 3540 |
| ATCCAACTGG | CTTGTCCAAG | GGTGTATCTA | CGCTTAGTCC | AAAGTTCAAA | CGAGGGGATT | 3600 |
| ACACATGACC | AACTTCGATA | ACGTTCTCGG | CTCGATCTGC | CTCGCGCGTT | TCGGTGATGA | 3660 |
| CGGTGAAAAC | CTCTGACACA | TGCAGCTCCC | GGAGACGGTC | ACAGCTTGTC | TGTAAGCGGA | 3720 |
| TGCCGGGAGC | AGACAAGCCC | GTCAGGGCGC | GTCAGCGGGT | GTTGGCGGGT | GTCGGGGCGC | 3780 |
| AGCCATGACC | CAGTCACGTA | GCGATAGCGG | AGTGTATACT | GGCTTAACTA | TGCGGCATCA | 3840 |
| GAGCAGATTG | TACTGAGAGT | GCACCATATG | CGGTGTGAAA | TACCGCACAG | ATGCGTAAGG | 3900 |
| AGAAAATACC | GCATCAGGCG | CTCTTCCGCT | TCCTCGCTCA | CTGACTCGCT | GCGCTCGGTC | 3960 |
| GTTCGGCTGC | GGCGAGCGGT | ATCAGCTCAC | TCAAAGGCGG | TAATACGGTT | ATCCACAGAA | 4020 |
| TCAGGGGATA | ACGCAGGAAA | GAACATGTGA | GCAAAAGGCC | AGCAAAAGGC | CAGGAACCGT | 4080 |
| AAAAAGGCCG | CGTTGCTGGC | GTTTTTCCAT | AGGCTCCGCC | CCCCTGACGA | GCATCACAAA | 4140 |
| AATCGACGCT | CAAGTCAGAG | GTGGCGAAAC | CCGACAGGAC | TATAAAGATA | CCAGGCGTTT | 4200 |
| CCCCCTGGAA | GCTCCCTCGT | GCGCTCTCCT | GTTCCGACCC | TGCCGCTTAC | CGGATACCTG | 4260 |
| TCCGCCTTTC | TCCCTTCGGG | AAGCGTGGCG | CTTTCTCAAT | GCTCACGCTG | TAGGTATCTC | 4320 |
| AGTTCGGTGT | AGGTCGTTCG | CTCCAAGCTG | GGCTGTGTGC | ACGAACCCCC | CGTTCAGCCC | 4380 |
| GACCGCTGCG | CCTTATCCGG | TAACTATCGT | CTTGAGTCCA | ACCCGGTAAG | ACACGACTTA | 4440 |
| TCGCCACTGG | CAGCAGCCAC | TGGTAACAGG | ATTAGCAGAG | CGAGGTATGT | AGGCGGTGCT | 4500 |
| ACAGAGTTCT | TGAAGTGGTG | GCCTAACTAC | GGCTACACTA | GAAGGACAGT | ATTTGGTATC | 4560 |
| TGCGCTCTGC | TGAAGCCAGT | TACCTTCGGA | AAAAGAGTTG | GTAGCTCTTG | ATCCGGCAAA | 4620 |
| CAAACCACCG | CTGGTAGCGG | TGGTTTTTTT | GTTTGCAAGC | AGCAGATTAC | GCGCAGAAAA | 4680 |
| AAAGGATCTC | AAGAAGATCC | TTTGATCTTT | TCTACGGGGT | CTGACGCTCA | GTGGAACGAA | 4740 |
| AACTCACGTT | AAGGGATTTT | GGTCATGAGA | TTATCAAAAA | GGATCTTCAC | CTAGATCCTT | 4800 |
| TTATTATTGA | AGCATTTATC | AGGGTTATTG | TCTCATGAGC | GGATACATAT | TTGAATGTAT | 4860 |
| TTAGAAAAAT | AAACAAATAG | GGGTTCCGCG | CACATTTCCC | CGAAAAGTGC | CACCTGACGT | 4920 |
| CGGGGGGCGC | TGAGGTCTGC | CTCGTGAAGA | AGGTGTTGCT | GACTCATACC | AGGCCTGAAT | 4980 |
| CGCCCCATCA | TCCAGCCAGA | AAGTGAGGGA | GCCACGGTTG | ATGAGAGCTT | TGTTGTAGGT | 5040 |
| GGACCAGTTG | GTGATTTTGA | ACTTTTGCTT | TGCCACGGAA | CGGTCTGCGT | TGTCGGGAAG | 5100 |
| ATGCGTGATC | TGATCCTTCA | ACTCAGCAAA | AGTTCGATTT | ATTCAACAAA | GCGACGTTGT | 5160 |
| GTCTCAAAAT | CTCTGATGTT | ACATTGCACA | AGATAAAAAT | ATATCATCAT | GAACAATAAA | 5220 |
| ACTGTCTGCT | TACATAAACA | GTAATACAAG | GGGTGTTATG | AGCCATATTC | AACGGGAAAC | 5280 |
| GTCTTGCTCG | AGGCCGCGAT | TAAATTCCAA | CATGGATGCT | GATTTATATG | GGTATAAATG | 5340 |
| GGCTCGCGAT | AATGTCGGGC | AATCAGGTGC | GACAATCTAT | CGATTGTATG | GGAAGCCCCA | 5400 |

| | | | | | |
|---|---|---|---|---|---|
| TGCGCCAGAG | TTGTTTCTGA | AACATGGCAA | AGGTAGCGTT | GCCAATGATG | TTACAGATGA | 5460 |
| GATGGTCAGA | CTAAACTGGC | TGACGGAATT | TATGCCTCTT | CCGACCATCA | AGCATTTTAT | 5520 |
| CCGTACTCCT | GATGATGCAT | GGTTACTCAC | CACTGCGATC | CCCGGGAAAA | CAGCATTCCA | 5580 |
| GGTATTAGAA | GAATATCCTG | ATTCAGGTGA | AAATATTGTT | GATGCGCTGG | CAGTGTTCCT | 5640 |
| GCGCCGGTTG | CATTCGATTC | CTGTTTGTAA | TTGTCCTTTT | AACAGCGATC | GCGTATTTCG | 5700 |
| TCTCGCTCAG | GCGCAATCAC | GAATGAATAA | CGGTTTGGTT | GATGCGAGTG | ATTTTGATGA | 5760 |
| CGAGCGTAAT | GGCTGGCCTG | TTGAACAAGT | CTGGAAAGAA | ATGCATAAGC | TTTTGCCATT | 5820 |
| CTCACCGGAT | TCAGTCGTCA | CTCATGGTGA | TTTCTCACTT | GATAACCTTA | TTTTTGACGA | 5880 |
| GGGGAAATTA | ATAGGTTGTA | TTGATGTTGG | ACGAGTCGGA | ATCGCAGACC | GATACCAGGA | 5940 |
| TCTTGCCATC | CTATGGAACT | GCCTCGGTGA | GTTTTCTCCT | TCATTACAGA | AACGGCTTTT | 6000 |
| TCAAAAATAT | GGTATTGATA | ATCCTGATAT | GAATAAATTG | CAGTTTCATT | TGATGCTCGA | 6060 |
| TGAGTTTTTC | TAATCAGAAT | TGGTTAATTG | GTTGTAACAC | TGGCAGAGCA | TTACGCTGAC | 6120 |
| TTGACGGGAC | GGCGGCTTTG | TTGAATAAAT | CGAACTTTTG | CTGAGTTGAA | GGATCAGATC | 6180 |
| ACGCATCTTC | CCGACAACGC | AGACCGTTCC | GTGGCAAAGC | AAAAGTTCAA | AATCACCAAC | 6240 |
| TGGTCCACCT | ACAACAAAGC | TCTCATCAAC | CGTGGCTCCC | TCACTTTCTG | GCTGGATGAT | 6300 |
| GGGGCGATTC | AGGCCTGGTA | TGAGTCAGCA | ACACCTTCTT | CACGAGGCAG | ACCTCAGCGC | 6360 |
| CCCCCCATCG | TCCATTCCGA | CAGCATCGCC | AGTCACTATG | GCGTGCT | | 6407 |

(2) INFORMATION FOR SEQ ID NO:2:

(i) SEQUENCE CHARACTERISTICS:
        (A) LENGTH: 6407 nucleotides
        (B) TYPE: nucleic acid
        (C) STRANDEDNESS: double
        (D) TOPOLOGY: circular (ii) MOLECULE TYPE: nucleic acid (xi) SEQUENCE DESCRIPTION: SEQ ID NO: 2:

| | | | | | |
|---|---|---|---|---|---|
| CAGCACGCCA | TAGTGACTGG | CGATGCTGTC | GGAATGGACG | ATGGGGGGGC | GCTGAGGTCT | 60 |
| GCCTCGTGAA | GAAGGTGTTG | CTGACTCATA | CCAGGCCTGA | ATCGCCCCAT | CATCCAGCCA | 120 |
| GAAAGTGAGG | GAGCCACGGT | TGATGAGAGC | TTTGTTGTAG | GTGGACCAGT | TGGTGATTTT | 180 |
| GAACTTTTGC | TTTGCCACGG | AACGGTCTGC | GTTGTCGGGA | AGATGCGTGA | TCTGATCCTT | 240 |
| CAACTCAGCA | AAAGTTCGAT | TTATTCAACA | AAGCCGCCGT | CCCGTCAAGT | CAGCGTAATG | 300 |
| CTCTGCCAGT | GTTACAACCA | ATTAACCAAT | TCTGATTAGA | AAAACTCATC | GAGCATCAAA | 360 |
| TGAAACTGCA | ATTTATTCAT | ATCAGGATTA | TCAATACCAT | ATTTTTGAAA | AAGCCGTTTC | 420 |
| TGTAATGAAG | GAGAAAACTC | ACCGAGGCAG | TTCCATAGGA | TGGCAAGATC | CTGGTATCGG | 480 |
| TCTGCGATTC | CGACTCGTCC | AACATCAATA | CAACCTATTA | ATTTCCCTC | GTCAAAAATA | 540 |
| AGGTTATCAA | GTGAGAAATC | ACCATGAGTG | ACGACTGAAT | CCGGTGAGAA | TGGCAAAAGC | 600 |
| TTATGCATTT | CTTTCCAGAC | TTGTTCAACA | GGCCAGCCAT | TACGCTCGTC | ATCAAAATCA | 660 |
| CTCGCATCAA | CCAAACCGTT | ATTCATTCGT | GATTGCGCCT | GAGCGAGACG | AAATACGCGA | 720 |
| TCGCTGTTAA | AAGGACAATT | ACAAACAGGA | ATCGAATGCA | ACCGGCGCAG | GAACACTGCC | 780 |
| AGCGCATCAA | CAATATTTTC | ACCTGAATCA | GGATATTCTT | CTAATACCTG | GAATGCTGTT | 840 |
| TTCCCGGGGA | TCGCAGTGGT | GAGTAACCAT | GCATCATCAG | GAGTACGGAT | AAAATGCTTG | 900 |
| ATGGTCGGAA | GAGGCATAAA | TTCCGTCAGC | CAGTTTAGTC | TGACCATCTC | ATCTGTAACA | 960 |
| TCATTGGCAA | CGCTACCTTT | GCCATGTTTC | AGAAACAACT | CTGGCGCATG | GGCTTCCCA | 1020 |

```
TACAATCGAT AGATTGTCGC ACCTGATTGC CCGACATTAT CGCGAGCCCA TTTATACCCA    1080
TATAAATCAG CATCCATGTT GGAATTTAAT CGCGGCCTCG AGCAAGACGT TCCCGTTGA    1140
ATATGGCTCA TAACACCCCT TGTATTACTG TTTATGTAAG CAGACAGTTT TATTGTTCAT    1200
GATGATATAT TTTTATCTTG TGCAATGTAA CATCAGAGAT TTGAGACAC AACGTCGCTT    1260
TGTTGAATAA ATCGAACTTT TGCTGAGTTG AAGGATCAGA TCACGCATCT TCCCGACAAC    1320
GCAGACCGTT CCGTGGCAAA GCAAAGTTC AAAATCACCA ACTGGTCCAC CTACAACAAA    1380
GCTCTCATCA ACCGTGGCTC CCTCACTTTC TGGCTGGATG ATGGGGCGAT TCAGGCCTGG    1440
TATGAGTCAG CAACACCTTC TTCACGAGGC AGACCTCAGC GCCCCCGAC GTCAGGTGGC     1500
ACTTTTCGGG GAAATGTGCG CGGAACCCCT ATTTGTTTAT TTTTCTAAAT ACATTCAAAT    1560
ATGTATCCGC TCATGAGACA ATAACCCTGA TAAATGCTTC AATAATAAAA GGATCTAGGT    1620
GAAGATCCTT TTTGATAATC TCATGACCAA AATCCCTTAA CGTGAGTTTT CGTTCCACTG    1680
AGCGTCAGAC CCCGTAGAAA AGATCAAAGG ATCTTCTTGA GATCCTTTTT TTCTGCGCGT    1740
AATCTGCTGC TTGCAAACAA AAAAACCACC GCTACCAGCG GTGGTTTGTT TGCCGGATCA    1800
AGAGCTACCA ACTCTTTTTC CGAAGGTAAC TGGCTTCAGC AGAGCGCAGA TACCAAATAC    1860
TGTCCTTCTA GTGTAGCCGT AGTTAGGCCA CCACTTCAAG AACTCTGTAG CACCGCCTAC    1920
ATACCTCGCT CTGCTAATCC TGTTACCAGT GGCTGCTGCC AGTGGCGATA AGTCGTGTCT    1980
TACCGGGTTG GACTCAAGAC GATAGTTACC GGATAAGGCG CAGCGGTCGG GCTGAACGGG    2040
GGGTTCGTGC ACACAGCCCA GCTTGGAGCG AACGACCTAC ACCGAACTGA GATACCTACA    2100
GCGTGAGCAT TGAGAAAGCG CCACGCTTCC CGAAGGGAGA AAGGCGGACA GGTATCCGGT    2160
AAGCGGCAGG GTCGGAACAG GAGAGCGCAC GAGGGAGCTT CCAGGGGGAA ACGCCTGGTA    2220
TCTTTATAGT CCTGTCGGGT TTCGCCACCT CTGACTTGAG CGTCGATTTT TGTGATGCTC    2280
GTCAGGGGGG CGGAGCCTAT GGAAAAACGC CAGCAACGCG GCCTTTTTAC GGTTCCTGGC    2340
CTTTTGCTGG CCTTTTGCTC ACATGTTCTT TCCTGCGTTA TCCCCTGATT CTGTGGATAA    2400
CCGTATTACC GCCTTTGAGT GAGCTGATAC CGCTCGCCGC AGCCGAACGA CCGAGCGCAG    2460
CGAGTCAGTG AGCGAGGAAG CGGAAGAGCG CCTGATGCGG TATTTTCTCC TTACGCATCT    2520
GTGCGGTATT TCACACCGCA TATGGTGCAC TCTCAGTACA ATCTGCTCTG ATGCCGCATA    2580
GTTAAGCCAG TATACACTCC GCTATCGCTA CGTGACTGGG TCATGGCTGC GCCCCGACAC    2640
CCGCCAACAC CCGCTGACGC GCCCTGACGG GCTTGTCTGC TCCCGGCATC CGCTTACAGA    2700
CAAGCTGTGA CCGTCTCCGG GAGCTGCATG TGTCAGAGGT TTTCACCGTC ATCACCGAAA    2760
CGCGCGAGGC AGATCGAGCC GAGAACGTTA TCGAAGTTGG TCATGTGTAA TCCCCTCGTT    2820
TGAACTTTGG ACTAAGCGTA GATACACCCT TGGACAAGCC AGTTGGATTC GGAGACAAGC    2880
AAATTCAGCC TTAAAAGGG CGAGGCCTGC GGTGGTGGAA CACCGCAGGG CCTCTAACCG    2940
CTCGACGCGC TGCACCAACC AGCCCGCGAA CGGCTGGCAG CCAGCGTAAG GCGCGGCTCA    3000
TCGGGCGGCG TTCGCCACGA TGTCCTGCAC TTCGAGCCAA GCCTCGAACA CCTGCTGGTG    3060
TGCACGACTC ACCCGGTTGT TGACACCGCG CGCGGCCGTG CGGGCTCGGT GGGGCGGCTG    3120
TGTCGCCCTT GCCAGCGTGA GTAGCGCGTA TCTCACCTCG CCCAACAGGT CGCACACAGC    3180
CGATTCGTAC GCCATAAAGC CAGGTGAGCC CACCAGCTCC GTAAGTTCGG GTGCTGTGTG    3240
GCTCGTACCC GCGCATTCAG GCGGCAGGGG GTCTAACGGG TCTAAGGCGG CGTGTACGGC    3300
CGCCACAGCG GCTCTTAGCG GCCCGGAAAC GTCCTCGAAA CGACGCATGT GTTCCTCCTG    3360
GTTGGTACAG GTGGTTGGGG GTGCTCGGCT GTCGCTGGTG TTTCATCATC AGGGCTCGAC    3420
```

-continued

```
GGGAGAGCGG GGGAGTGTGC AGTTGTGGGG TGGCCCCTCA GCGAAATATC TGACTTGGAG    3480
CTCGTGTCGG ACCATACACC GGTGATTAAT CGTGGTCTAC TACCAAGCGT GAGCCACGTC    3540
GCCGACGAAT TTGAGCAGCT CTGGCTGCCG TACTGGCCGC TGGCAAGCGA CGATCTGCTC    3600
GAGGGGATCT ACCGCCAAAG CCGCGCGTCG GCCCTAGGCC GCCGGTACAT CGAGGCGAAC    3660
CCAACAGCGC TGGCAAACCT GCTGGTCGTG GACGTAGACC ATCCAGACGC AGCGCTCCGA    3720
GCGCTCAGCG CCCGGGGGTC CCATCCGCTG CCCAACGCGA TCGTGGGCAA TCGCGCCAAC    3780
GGCCACGCAC ACGCAGTGTG GGCACTCAAC GCCCCTGTTC CACGCACCGA ATACGCGCGG    3840
CGTAAGCCGC TCGCATACAT GGCGGCGTGC GCCGAAGGCC TTCGGCGCGC CGTCGACGGC    3900
GACCGCAGTT ACTCAGGCCT CATGACCAAA AACCCCGGCC ACATCGCCTG GAAACGGAA    3960
TGGCTCCACT CAGATCTCTA CACACTCAGC CACATCGAGG CCGAGCTCGG CGCGAACATG    4020
CCACCGCCGC GCTGGCGTCA GCAGACCACG TACAAAGCGG CTCCGACGCC GCTAGGGCGG    4080
AATTGCGCAC TGTTCGATTC CGTCAGGTTG TGGGCCTATC GTCCCGCCCT CATGCGGATC    4140
TACCTGCCGA CCCGGAACGT GGACGGACTC GGCCGCGCGA TCTATGCCGA GTGCCACGCG    4200
CGAAACGCCG AATTCCCGTG CAACGACGTG TGTCCCGGAC CGCTACCGGA CAGCGAGGTC    4260
CGCGCCATCG CCAACAGCAT TTGGCGTTGG ATCACAACCA AGTCGCGCAT TTGGGCGGAC    4320
GGGATCGTGG TCTACGAGGC CACACTCAGT GCGCGCCAGT CGGCCATCTC GCGGAAGGGC    4380
GCAGCAGCGC GCACGGCGGC GAGCACAGTT GCGCGGCGCG CAAAGTCCGC GTCAGCCATG    4440
GAGGCATTGC TATGAGCGAC GGCTACAGCG ACGGCTACAG CGACGGCTAC AACCGGCAGC    4500
CGACTGTCCG CAAAAAGCGG CGCGTGACCG CCGCCGAAGG CGCTCGAATC ACCGGACTAT    4560
CCGAACGCCA CGTCGTCCGG CTCGTGGCGC AGGAACGCAG CGAGTGGCTC GCCGAGCAGG    4620
CTGCACGCCG CGAACGCATC CGCGCCTATC ACGACGACGA GGGCCACTCT TGGCCGCAAA    4680
CGGCCAAACA TTTCGGGCTG CATCTGGACA CCGTTAAGCG ACTCGGCTAT CGGGCGAGGA    4740
AAGAGCGTGC GGCAGAACAG GAAGCGGCTC AAAAGGCCCA CAACGAAGCC GACAATCCAC    4800
CGCTGTTCTA ACGCAATTGG GGAGCGGGTG TCGCGGGGGT TCCGTGGGGG GTTCCGTTGC    4860
AACGGGTCGG ACAGGTAAAA GTCCTGGTAG ACGCTAGTTT CTGGTTTGG GCCATGCCTG    4920
TCTCGTTGCG TGTTTCGTTG CGTCCGTTTT GAATACCAGC CAGACGAGAC GGGGTTCTAC    4980
GAATCTTGGT CGATACCAAG CCATTTCCGC TGAATATCGT GGAGCTCACC GCCAGAATCG    5040
GTGGTTGTGG TGATGTACGT GGCGAACTCC GTTGTAGTGC TTGTGGTGGC ATCCGTGGCC    5100
ACTCTCGTTG CACGGTTCGT TGTGCCGTTA CAGGCCCCGT TGACAGCTCA CCGAACGTAG    5160
TTAAAACATG CTGGTCAAAC TAGGTTTACC AACGATACGA GTCAGCTCAT CTAGTGCCAG    5220
TTCTAGGCGT TGTTCGTTGC GCGGTTCGTT GCGCATGTTT CGTGTGGTTG CTAGATGGCT    5280
CCGCAACCAC ACGCTTCGAG GTTGAGTGCT TCCAGCACGG GCGCGATCCA GAAGAACTTC    5340
GTCGTGCGAC TGTCCTCGTT CTGCGGTAAA GCTCATCAGC GTGGTCGTGA AGCGATTCAC    5400
AGATGTCTGC CTGTTCATCC GCGTCCAGCT CGTTGAGTTT CTCCAGAAGC GTTAATGTCT    5460
GGCTTCTGAT AAAGCGGGCC ATGTTAAGGG CGGTTTTTTC CTGTTTGGTC ACTTGATGCC    5520
TCCGTGTAAG GGGGAATTTC TGTTCATGGG GGTAATGATA CCGATGAAAC GAGAGAGGAT    5580
GCTCACGATA CGGGTTACTG ATGATGAACA TGCCCGGTTA CTGGAACGTT GTGAGGGTAA    5640
ACAACTGGCG GTATGGATGC GGCGGGACCA GAGAAAAATC ACTCAGGGTC AATGCCAGCG    5700
CTTCGTTAAT ACAGATGTAG GTGTTCCACA GGGTAGCCAG CAGCATCCTG CGATGCAGAT    5760
CCGGAACATA ATGGTGCAGG GCGCTGACTT CCGCGTTTCC AGACTTTACG AAACACGGAA    5820
```

```
ACCGAAGACC ATTCATGTTG TTGCTCAGGT CGCAGACGTT TTGCAGCAGC AGTCGCTTCA    5880
CGTTCGCTCG CGTATCGGTG ATTCATTCTG CTAACCAGTA AGGCAACCCC GCCAGCCTAG    5940
CCGGGTCCTC AACGACAGGA GCACGATCAT GCGCACCCGT GGCCAGGACC CAACGCTGCC    6000
CGAGATGCGC CGCGTGCGGC TGCTGGAGAT GGCGGACGCG ATGGATATGT CTGCCAAGG     6060
GTTGGTTTGC GCATTCACAG TTCTCCGCAA GAATTGATTG GCTCCAATTC TTGGAGTGGT    6120
GAATCCGTTA GCGAGGTGCC GCCGGCTTCC ATTCAGGTCG AGGTGGCCCG GCTCCATGCA    6180
CCGCGACGCA ACGCGGGGAG GCAGACAAGG TATAGGGCGG CGCCGGTGAT GCCGGCCACG    6240
ATGCGTCCGG CGTAGAGGAT CCACAGGACG GGTGTGGTCG CCATGATCGC GTAGTCGATA    6300
GTGGCTCCAA GTAGCGAAGC GAGCAGGACT GGGCGGCGGC CAAAGCGGTC GGACAGTGCT    6360
CCGAGAACGG GTGCGCATAG AAATTGCATC AACGCATATA GCGCTAG               6407
```

( 2 ) INFORMATION FOR SEQ ID NO:3:

( i ) SEQUENCE CHARACTERISTICS:
        ( A ) LENGTH: 314 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 3:

```
Phe Leu Pro Pro Asn Asp Ala Glu Asn His Ala Lys Gln Ala Ala Glu
 1               5                  10                  15
Gln Glu Ala Ala Arg Glu Lys Arg Ala Arg Tyr Gly Leu Arg Lys Val
            20                  25                  30
Thr Asp Leu His Leu Gly Phe His Lys Ala Thr Gln Pro Trp Ser His
        35                  40                  45
Gly Glu Asp Asp His Tyr Ala Arg Ile Arg Glu Arg Arg Ala Ala Gln
    50                  55                  60
Glu Ala Leu Trp Glu Ser Arg Glu Gln Ala Val Leu Arg Val Val His
65                  70                  75                  80
Arg Glu Ser Leu Gly Thr Ile Arg Ala Gly Glu Ala Ala Thr Val Arg
                85                  90                  95
Arg Lys Lys Arg Val Thr Pro Gln Arg Asn Tyr Gly Asp Ser Tyr Gly
            100                 105                 110
Asp Ser Tyr Gly Asp Ser Met Ala Ile Gly Gly His Ser Val Arg Val
        115                 120                 125
Lys Arg Ala Ala Cys Ser His Glu Gly Gly His Ala Ser Ser Arg Gly
    130                 135                 140
Glu Ala Leu His Gly Val Pro Ala Cys Gln Thr His Gly Arg Leu Gly
145                 150                 155                 160
Arg Asp Arg Gly Gly Leu His Ala Val Gln Asn His Asp Leu Ala Leu
                165                 170                 175
His Gln Gln Arg His Arg Pro Gly Arg Gln Gly Thr Ala Thr Arg Ser
            180                 185                 190
Val Arg Arg Gln Val Pro Ile Arg Arg Lys Ala Arg Pro Val Arg Cys
        195                 200                 205
Leu Asp Arg Pro Arg Thr Arg Gly Arg Glu Pro Asp Ala Pro Leu Asp
    210                 215                 220
Ala His Pro Arg Ser Ser Leu Gly Val Val Gln Arg Phe Arg Val Thr
225                 230                 235                 240
Arg Leu Glu Ala Arg Ala Ala Asp Ser Gly Ser Gln Val His Asp Ala
                245                 250                 255
```

```
Ser  Ala  Leu  Ala  Ala  Thr  Ala  His  Glu  Arg  Arg  Ala  Arg  Gly  Arg  His
               260                      265                      270

Pro  Gln  Thr  His  Leu  Ser  Arg  Leu  Pro  Ala  Met  Gly  Asn  Gly  Leu  Arg
          275                      280                      285

His  Pro  Arg  Pro  Lys  Gln  Asp  His  Pro  Arg  Leu  Leu  Gln  Pro  Arg  Arg
     290                      295                      300

Arg  Arg  Arg  Ala  Ser  Pro  Arg  Arg  Val
305                      310
```

( 2 ) INFORMATION FOR SEQ ID NO:4:

( i ) SEQUENCE CHARACTERISTICS:
        ( A ) LENGTH: 368 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 4:

```
Leu  Leu  Ala  Glu  Met  Ala  Ser  Ala  Ser  Lys  Ala  Arg  Arg  Ala  Val  Thr
 1                  5                      10                      15

Ser  Ala  Ala  Thr  Arg  Ala  Ala  Ala  Gly  Lys  Arg  Ser  Ile  Ala  Ser  Gln
               20                      25                      30

Arg  Ala  Ser  Leu  Thr  Ala  Glu  Tyr  Val  Val  Ile  Gly  Asp  Ala  Trp  Ile
          35                      40                      45

Arg  Ser  Lys  Thr  Thr  Ile  Trp  Arg  Trp  Ile  Ser  Asn  Ala  Ile  Ala  Arg
     50                      55                      60

Val  Glu  Ser  Asp  Pro  Leu  Pro  Gly  Pro  Cys  Val  Asp  Asn  Cys  Pro  Phe
65                      70                      75                      80

Glu  Ala  Asn  Arg  Ala  His  Cys  Glu  Ala  Tyr  Ile  Ala  Arg  Gly  Leu  Gly
               85                      90                      95

Asp  Val  Asn  Arg  Thr  Pro  Leu  Tyr  Ile  Arg  Met  Leu  Ala  Pro  Arg  Tyr
               100                     105                     110

Ala  Trp  Leu  Arg  Val  Ser  Asp  Phe  Leu  Ala  Cys  Asn  Arg  Gly  Leu  Pro
          115                     120                     125

Thr  Pro  Ala  Ala  Lys  Tyr  Thr  Gln  Gln  Arg  Trp  Arg  Pro  Pro  Pro
     130                     135                     140

Met  Asn  Ala  Gly  Leu  Glu  Ala  Glu  Ile  His  Ser  Leu  Thr  Tyr  Leu  Asp
145                     150                     155                     160

Ser  His  Leu  Trp  Glu  Thr  Glu  Trp  Ala  Ile  His  Gly  Pro  Asn  Lys  Thr
               165                     170                     175

Met  Leu  Gly  Ser  Tyr  Ser  Arg  Asp  Gly  Asp  Val  Ala  Arg  Arg  Leu  Gly
               180                     185                     190

Glu  Ala  Cys  Ala  Ala  Met  Tyr  Ala  Leu  Pro  Lys  Arg  Arg  Ala  Tyr  Glu
          195                     200                     205

Thr  Arg  Pro  Val  Pro  Ala  Asn  Leu  Ala  Trp  Val  Ala  His  Ala  His  Gly
     210                     215                     220

Asn  Ala  Arg  Asn  Gly  Val  Ile  Ala  Asn  Pro  Leu  Pro  His  Ser  Gly  Arg
225                     230                     235                     240

Ala  Ser  Leu  Ala  Arg  Leu  Ala  Ala  Asp  Pro  His  Asp  Val  Asp  Val  Val
               245                     250                     255

Leu  Leu  Asn  Ala  Leu  Ala  Thr  Pro  Asn  Ala  Glu  Ile  Tyr  Arg  Arg  Gly
               260                     265                     270

Leu  Ala  Ser  Ala  Arg  Ser  Gln  Arg  Tyr  Ile  Gly  Glu  Leu  Leu  Asp  Asp
          275                     280                     285

Ser  Ala  Leu  Pro  Trp  Tyr  Pro  Leu  Trp  Leu  Gln  Glu  Phe  Glu  Asp  Ala
```

|   |   |   |   |   | 290 |   |   |   |   | 295 |   |   |   |   | 300 |   |   |
|---|---|---|---|---|---|---|---|---|---|---|---|---|---|---|---|---|---|

Val His Ser Val Ser Pro Leu Leu Gly Arg Asn Ile Val Pro Thr His
305                     310                 315                 320

Asp Ser Val Leu Glu Leu Asp Ser Ile Glu Ser Leu Pro Trp Gly Val
                    325                 330                 335

Val Ala Cys Glu Gly Ala Arg Gly Asp Leu Gly Ser Ser Ser Val Gly
            340                 345                 350

Ala Val Ala Ser Cys Gly Trp Gly Gly Thr Gly Val Leu Leu Phe Val
            355                 360                 365

(2) INFORMATION FOR SEQ ID NO:5:

(i) SEQUENCE CHARACTERISTICS:
        (A) LENGTH: 271 amino acids
        (B) TYPE: amino acid
        (D) TOPOLOGY: linear (ii) MOLECULE TYPE: peptide (xi) SEQUENCE DESCRIPTION: SEQ ID NO: 5:

Met Ser His Ile Gln Arg Glu Thr Ser Cys Ser Arg Pro Arg Leu Asn
1               5               10                  15

Ser Asn Met Asp Ala Asp Leu Tyr Gly Tyr Lys Trp Ala Arg Asp Asn
            20                  25                  30

Val Gly Gln Ser Gly Ala Thr Ile Tyr Arg Leu Tyr Gly Lys Pro His
        35                  40                  45

Ala Pro Glu Leu Phe Leu Lys His Gly Lys Gly Ser Val Ala Asn Asp
    50                  55                  60

Val Thr Asp Glu Met Val Arg Leu Asn Trp Leu Thr Glu Phe Met Pro
65              70                  75                  80

Leu Pro Thr Ile Lys His Phe Ile Arg Thr Pro Asp Asp Ala Trp Leu
                85                  90                  95

Leu Thr Thr Ala Ile Pro Gly Lys Thr Ala Phe Gln Val Leu Glu Glu
            100                 105                 110

Tyr Pro Asp Ser Gly Glu Asn Ile Val Asp Ala Leu Ala Val Phe Leu
        115                 120                 125

Arg Arg Leu His Ser Pro Ile Val Cys Asn Cys Pro Phe Asn Ser Asp
130                 135                 140

Arg Val Phe Arg Leu Ala Gln Ala Gln Ser Arg Met Asn Asn Gly Leu
145                 150                 155                 160

Val Asp Ala Ser Asp Phe Asp Asp Glu Arg Asn Gly Trp Pro Val Glu
                165                 170                 175

Gln Val Trp Lys Glu Met His Lys Leu Leu Pro Phe Ser Pro Asp Ser
            180                 185                 190

Val Val Thr His Gly Asp Phe Ser Leu Asp Asn Leu Ile Phe Asp Glu
            195                 200                 205

Gly Lys Leu Ile Gly Cys Ile Asp Val Gly Arg Val Gly Ile Ala Asp
        210                 215                 220

Arg Tyr Gln Asp Leu Ala Ile Leu Trp Asn Cys Leu Gly Glu Phe Ser
225                 230                 235                 240

Pro Ser Leu Gln Lys Arg Leu Phe Gln Lys Tyr Gly Ile Asp Asn Pro
                245                 250                 255

Asp Met Asn Lys Leu Gln Phe His Leu Met Leu Asp Glu Phe Phe
            260                 265                 270

(2) INFORMATION FOR SEQ ID NO:6:

( i ) SEQUENCE CHARACTERISTICS:
    ( A ) LENGTH: 17 nucleotides
    ( B ) TYPE: nucleic acid
    ( C ) STRANDEDNESS: single
    ( D ) TOPOLOGY: linear ( i i ) MOLECULE TYPE: nucleic acid ( x i ) SEQUENCE DESCRIPTION: SEQ ID NO: 6:

CTTGTATGGG AAGCCCC                        17

( 2 ) INFORMATION FOR SEQ ID NO:7:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 7:

GTGAGAATGG CAAAAGATTA TGCATTTCTT TCCAG            35

( 2 ) INFORMATION FOR SEQ ID NO:8:

( i ) SEQUENCE CHARACTERISTICS:
        ( A ) LENGTH: 40 nucleotides
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 8:

GTCTGGAAAG AAATGCATAA TCTTTTGCCA TTCTCACCGG      40

( 2 ) INFORMATION FOR SEQ ID NO:9:

( i ) SEQUENCE CHARACTERISTICS:
        ( A ) LENGTH: 20 nucleotides
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 9:

CGTAGAGGAT CCACAGGACG                    20

( 2 ) INFORMATION FOR SEQ ID NO:10:

( i ) SEQUENCE CHARACTERISTICS:
        ( A ) LENGTH: 22 nucleotides
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 10:

TCCGTGCAAC GAGTGTCCCG GA                  22

( 2 ) INFORMATION FOR SEQ ID NO:11:

( i ) SEQUENCE CHARACTERISTICS:
        ( A ) LENGTH: 23 nucleotides
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 11:

CACCCGTCCT GTGGATCCTC TAC    23

( 2 ) INFORMATION FOR SEQ ID NO:12:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 12:

TGGCGACCGC AGTTACTCAG GCCT    24

( 2 ) INFORMATION FOR SEQ ID NO:13:

( i ) SEQUENCE CHARACTERISTICS:
        ( A ) LENGTH: 28 nucleotides
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 13:

CTCGACTAGT GAGGTCTGCC TCGTGAAG    28

( 2 ) INFORMATION FOR SEQ ID NO:14:

( i ) SEQUENCE CHARACTERISTICS:
        ( A ) LENGTH: 33 nucleotides
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 14:

CAGAGGATCC TTAGCTAGCC ACTGACGTCG GGG    33

( 2 ) INFORMATION FOR SEQ ID NO:15:

( i ) SEQUENCE CHARACTERISTICS:
        ( A ) LENGTH: 27 nucleotides
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 15:

CCACTAGTTC CACTGAGCGT CAGACCC    27

( 2 ) INFORMATION FOR SEQ ID NO:16:

( i ) SEQUENCE CHARACTERISTICS:
        ( A ) LENGTH: 30 nucleotides
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 16:

```
GACAACGCGT TGCGCTCGGT CGTTCGGCTG                                                    30
```

( 2 ) INFORMATION FOR SEQ ID NO:17:

( i ) SEQUENCE CHARACTERISTICS:
        ( A ) LENGTH: 26 nucleotides
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 17:

```
CCATACGCGT GAGCCCACCA GCTCCG                                                        26
```

( 2 ) INFORMATION FOR SEQ ID NO:18:

( i ) SEQUENCE CHARACTERISTICS:
        ( A ) LENGTH: 23 nucleotides
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 18:

```
CACCGGTCCT GTGGATCCTC TAC                                                           23
```

( 2 ) INFORMATION FOR SEQ ID NO:19:

( i ) SEQUENCE CHARACTERISTICS:
        ( A ) LENGTH: 208 nucleotides
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 19:

```
GAAGGCGCGG CCGCGGTACC AGATCTTTAA ATCTAGATAT CCATGGATCC AGCTGCAGAA                   60
TTCGAAGCTT ATCGATGTCG ACGTAGTTAA CTAGCGTACG ATCGACTGCC AGGCATCAAA                  120
TAAAACGAAA GGCTCAGTCG AAAGACTGGG CCTTTCGTTT TATCTGTTGT TTGTCCGGCC                  180
ATCATGGCCG CGGTGATCAG CTAGTACG                                                    208
```

( 2 ) INFORMATION FOR SEQ ID NO:20:

( i ) SEQUENCE CHARACTERISTICS:
        ( A ) LENGTH: 4120 nucleotides
        ( B ) TYPE: nucleic acid
        ( C ) STRANDEDNESS: double
        ( D ) TOPOLOGY: circular ( i i ) MOLECULE TYPE: nucleic acid ( x i ) SEQUENCE DESCRIPTION: SEQ ID NO: 20:

```
GCTAGCCAAC AAAGCGACGT TGTGTCTCAA AATCTCTGAT GTTACATTGC ACAAGATAAA                   60
AATATATCAT CATGAACAAT AAAACTGTCT GCTTACATAA ACAGTAATAC AAGGGGTGTT                  120
ATGAGCCATA TTCAACGGGA AACGTCTTGC TCGAGGCCGC GATTAAATTC CAACATGGAT                  180
GCTGATTTAT ATGGGTATAA ATGGGCTCGC GATAATGTCG GCAATCAGG TGCGACAATC                   240
TATCGCTTGT ATGGAAGCC CCATGCGCCA GAGTTGTTTC TGAAACATGG CAAAGGTAGC                   300
GTTGCCAATG ATGTTACAGA TGAGATGGTC AGACTAAACT GGCTGACGGA ATTTATGCCT                  360
CTTCCGACCA TCAAGCATTT TATCCGTACT CCTGATGATG CATGGTTACT CACCACTGCG                  420
```

| | | | | | | |
|---|---|---|---|---|---|---|
| ATCCCCGGGA | AAACAGCATT | CCAGGTATTA | GAAGAATATC | CTGATTCAGG | TGAAAATATT | 480 |
| GTTGATGCGC | TGGCAGTGTT | CCTGCGCCGG | TTGCATTCGA | TTCCTGTTTG | TAATTGTCCT | 540 |
| TTTAACAGCG | ATCGCGTATT | TCGTCTCGCT | CAGGCGCAAT | CACGAATGAA | TAACGGTTTG | 600 |
| GTTGATGCGA | GTGATTTTGA | TGACGAGCGT | AATGGCTGGC | CTGTTGAACA | AGTCTGGAAA | 660 |
| GAAATGCATA | ATCTTTTGCC | ATTCTCACCG | GATTCAGTCG | TCACTCATGG | TGATTTCTCA | 720 |
| CTTGATAACC | TTATTTTTGA | CGAGGGAAA | TTAATAGGTT | GTATTGATGT | TGGACGAGTC | 780 |
| GGAATCGCAG | ACCGATACCA | GGATCTTGCC | ATCCTATGGA | ACTGCCTCGG | TGAGTTTTCT | 840 |
| CCTTCATTAC | AGAAACGGCT | TTTTCAAAAA | TATGGTATTG | ATAATCCTGA | TATGAATAAA | 900 |
| TTGCAGTTTC | ATTTGATGCT | CGATGAGTTT | TTCTAATCAG | AATTGGTTAA | TTGGTTGTAA | 960 |
| CACTGGCAGA | GCATTACGCT | GACTTGACGG | GACGGCGGCT | TTGTTGAATA | AATCGAACTT | 1020 |
| TTGCTGAGTT | GAAGGATCAG | ATCACGCATC | TTCCCGACAA | CGCAGACCGT | TCCGTGGCAA | 1080 |
| AGCAAAAGTT | CAAAATCACC | AACTGGTCCA | CCTACAACAA | AGCTCTCATC | AACCGTGGCT | 1140 |
| CCCTCACTTT | CTGGCTGGAT | GATGGGGCGA | TTCAGGCCTG | GTATGAGTCA | GCAACACCTT | 1200 |
| CTTCACGAGG | CAGACCTCAC | TAGTTCCACT | GAGCGTCAGA | CCCCGTAGAA | AAGATCAAAG | 1260 |
| GATCTTCTTG | AGATCCTTTT | TTTCTGCGCG | TAATCTGCTG | CTTGCAAACA | AAAAAACCAC | 1320 |
| CGCTACCAGC | GGTGGTTTGT | TTGCCGGATC | AAGAGCTACC | AACTCTTTTT | CCGAAGGTAA | 1380 |
| CTGGCTTCAG | CAGAGCGCAG | ATACCAAATA | CTGTCCTTCT | AGTGTAGCCG | TAGTTAGGCC | 1440 |
| ACCACTTCAA | GAACTCTGTA | GCACCGCCTA | CATACCTCGC | TCTGCTAATC | CTGTTACCAG | 1500 |
| TGGCTGCTGC | CAGTGGCGAT | AAGTCGTGTC | TTACCGGGTT | GGACTCAAGA | CGATAGTTAC | 1560 |
| CGGATAAGGC | GCAGCGGTCG | GGCTGAACGG | GGGGTTCGTG | CACACAGCCC | AGCTTGGAGC | 1620 |
| GAACGACCTA | CACCGAACTG | AGATACCTAC | AGCGTGAGCA | TTGAGAAAGC | GCCACGCTTC | 1680 |
| CCGAAGGGAG | AAAGGCGGAC | AGGTATCCGG | TAAGCGGCAG | GGTCGGAACA | GGAGAGCGCA | 1740 |
| CGAGGGAGCT | TCCAGGGGGA | AACGCCTGGT | ATCTTTATAG | TCCTGTCGGG | TTTCGCCACC | 1800 |
| TCTGACTTGA | GCGTCGATTT | TTGTGATGCT | CGTCAGGGGG | GCGGAGCCTA | TGGAAAAACG | 1860 |
| CCAGCAACGC | GGCCTTTTTA | CGGTTCCTGG | CCTTTTGCTG | GCCTTTTGCT | CACATGTTCT | 1920 |
| TTCCTGCGTT | ATCCCCTGAT | TCTGTGGATA | ACCGTATTAC | CGCCTTTGAG | TGAGCTGATA | 1980 |
| CCGCTCGCCG | CAGCCGAACG | ACCGAGCGCA | ACGCGTGCGG | CCGCACGCGT | GAGCCCACCA | 2040 |
| GCTCCGTAAG | TTCGGGCGCT | GTGTGGCTCG | TACCCGCGCA | TTCAGGCGGC | AGGGGGTCTA | 2100 |
| ACGGGTCTAA | GGCGGCGTGT | ACGGCCGCCA | CAGCGGCTCT | CAGCGGCCCG | GAAACGTCCT | 2160 |
| CGAAACGACG | CATGTGTTCC | TCCTGGTTGG | TACAGGTGGT | TGGGGTGCT | CGGCTGTCGC | 2220 |
| TGGTGTTCCA | CCACCAGGGC | TCGACGGGAG | AGCGGGGAG | TGTGCAGTTG | TGGGGTGGCC | 2280 |
| CCTCAGCGAA | ATATCTGACT | TGGAGCTCGT | GTCGGACCAT | ACACCGGTGA | TTAATCGTGG | 2340 |
| TCTACTACCA | AGCGTGAGCC | ACGTCGCCGA | CGAATTTGAG | CAGCTCTGGC | TGCCGTACTG | 2400 |
| GCCGCTGGCA | AGCGACGATC | TGCTCGAGGG | GATCTACCGC | CAAAGCCGCG | CGTCGGCCCT | 2460 |
| AGGCCGCCGG | TACATCGAGG | CGAACCCAAC | AGCGCTGGCA | AACCTGCTGG | TCGTGGACGT | 2520 |
| AGACCATCCA | GACGCAGCGC | TCCGAGCGCT | CAGCGCCCGG | GGGTCCCATC | CGCTGCCCAA | 2580 |
| CGCGATCGTG | GGCAATCGCG | CCAACGGCCA | CGCACACGCA | GTGTGGGCAC | TCAACGCCCC | 2640 |
| TGTTCCACGC | ACCGAATACG | CGCGGCGTAA | GCCGCTCGCA | TACATGGCGG | CGTGCGCCGA | 2700 |
| AGGCCTTCGG | CGCGCCGTCG | ATGGCGACCG | CAGTTACTCA | GGCCTCATGA | CCAAAAACCC | 2760 |
| CGGCCACATC | GCCTGGGAAA | CGGAATGGCT | CCACTCAGAT | CTCTACACAC | TCAGCCACAT | 2820 |

-continued

```
CGAGGCCGAG  CTCGGCGCGA  ACATGCCACC  GCCGCGCTGG  CGTCAGCAGA  CCACGTACAA    2880
AGCGGCTCCG  ACGCCGCTAG  GGCGGAATTG  CGCACTGTTC  GATTCCGTCA  GGTTGTGGGC    2940
CTATCGTCCC  GCCCTCATGC  GGATCTACCT  GCCGACCCGG  AACGTGGACG  GACTCGGCCG    3000
CGCGATCTAT  GCCGAGTGCC  ACGCGCGAAA  CGCCGAATTT  CCGTGCAACG  ACGTGTGTCC    3060
CGGACCGCTA  CCGGACAGCG  AGGTCCGCGC  CATCGCCAAC  AGCATTTGGC  GTTGGATCAC    3120
AACCAAGTCG  CGCATTTGGG  CGGACGGGAT  CGTGGTCTAC  GAGGCCACAC  TCAGTGCGCG    3180
CCAGTCGGCC  ATCTCGCGGA  AGGGCGCAGC  AGCGCGCACG  GCGGCGAGCA  CAGTTGCGCG    3240
GCGCGCAAAG  TCCGCGTCAG  CCATGCATGG  AGGCATTGCT  ATGAGCGACG  GCTACAGCGA    3300
CGGCTACAGC  GACGGCTACA  ACCGGCAGCC  GACTGTCCGC  AAAAAGCGGC  GCGTGACCGC    3360
CGCCGAAGGC  GCTCGAATCA  CCGGACTATC  CGAACGCCAC  GTCGTCCGGC  TCGTGGCGCA    3420
GGAACGCAGC  GAGTGGCTCG  CCGAGCAGGC  TGCACGCCGC  GAACGCATCC  GCGCCTATCA    3480
CGACGACGAG  GGCCACTCTT  GGCCGCAAAC  GGCCAAACAT  TTCGGGCTGC  ATCTGGACAC    3540
CGTTAAGCGA  CTCGGCTATC  GGGCGAGGAA  AGAGCGTGCG  GCAGAACAGG  AAGCGGCTCA    3600
AAAGGCCCAC  AACGAAGCCG  ACAATCCACC  GCTGTTCTAA  CGCAATTGGG  GAGCGGGTGT    3660
CGCGGGGGTT  CCGTGGGGGG  TTCCGTTGCA  ACGGGTCGGA  CAGGTAAAAG  TCCTGGTAGA    3720
CGCTAGTTTT  CTGGTTTGGG  CCATGCCTGT  CTCGTTGCGT  GTTTCGTTGC  GCCCGTTTTG    3780
AATACCAGCC  AGACGAGACG  GGGTTCTACG  AATCTTGGTC  GATACCAAGC  CATTTCCGCT    3840
GAATATCGGG  GAGCTCACCG  CCAGAATCGG  TGGTTGTGGT  GATGTACGTG  GCGAACTCCG    3900
TTGTAGTGTT  GTGGTGGCAT  CCGTGGCGCG  GCCGCGGTAC  CAGATCTTTA  AATCTAGATA    3960
TCCATGGATC  CAGCTGCAGA  ATTCGAAGCT  TATCGATGTC  GACGTAGTTA  ACTAGCGTAC    4020
GATCGACTGC  CAGGCATCAA  ATAAAACGAA  AGGCTCAGTC  GAAAGACTGG  GCCTTTCGTT    4080
TTATCTGTTG  TTTGTCCGGC  CATCATGGCC  GCGGTGATCA                            4120
```

(2) INFORMATION FOR SEQ ID NO:21:

(i) SEQUENCE CHARACTERISTICS:
        (A) LENGTH: 4120 nucleotides
        (B) TYPE: nucleic acid
        (C) STRANDEDNESS: double
        (D) TOPOLOGY: circular (ii) MOLECULE TYPE: nucleic acid (xi) SEQUENCE DESCRIPTION: SEQ ID NO: 21:

```
TGATCACCGC  GGCCATGATG  GCCGGACAAA  CAACAGATAA  AACGAAAGGC  CCAGTCTTTC     60
GACTGAGCCT  TTCGTTTTAT  TTGATGCCTG  GCAGTCGATC  GTACGCTAGT  TAACTACGTC    120
GACATCGATA  AGCTTCGAAT  TCTGCAGCTG  GATCCATGGA  TATCTAGATT  TAAAGATCTG    180
GTACCGCGGC  CGCGCCACGG  ATGCCACCAC  AACACTACAA  CGGAGTTCGC  CACGTACATC    240
ACCACAACCA  CCGATTCTGG  CGGTGAGCTC  CCCGATATTC  AGCGGAAATG  GCTTGGTATC    300
GACCAAGATT  CGTAGAACCC  CGTCTCGTCT  GGCTGGTATT  CAAAACGGGC  GCAACGAAAC    360
ACGCAACGAG  ACAGGCATGG  CCCAAACCAG  AAAACTAGCG  TCTACCAGGA  CTTTTACCTG    420
TCCGACCCGT  TGCAACGGAA  CCCCCCACGG  AACCCCGCGC  ACACCCGCTC  CCCAATTGCG    480
TTAGAACAGC  GGTGGATTGT  CGGCTTCGTT  GTGGGCCTTT  TGAGCCGCTT  CCTGTTCTGC    540
CGCACGCTCT  TTCCTCGCCC  GATAGCCGAG  TCGCTTAACG  GTGTCCAGAT  GCAGCCCGAA    600
ATGTTTGGCC  GTTTGCGGCC  AAGAGTGGCC  CTCGTCGTCG  TGATAGGCGC  GGATGCGTTC    660
GCGGCGTGCA  GCCTGCTCGG  CGAGCCACTC  GCTGCGTTCC  TGCGCCACGA  GCCGGACGAC    720
```

| | | | | | |
|---|---|---|---|---|---|
| GTGGCGTTCG | GATAGTCCGG | TGATTCGAGC | GCCTTCGGCG | GCGGTCACGC | GCCGCTTTTT | 780
| GCGGACAGTC | GGCTGCCGGT | TGTAGCCGTC | GCTGTAGCCG | TCGCTGTAGC | CGTCGCTCAT | 840
| AGCAATGCCT | CCATGCATGG | CTGACGCGGA | CTTTGCGCGC | CGCGCAACTG | TGCTCGCCGC | 900
| CGTGCGCGCT | GCTGCGCCCT | TCCGCGAGAT | GGCCGACTGG | CGCGCACTGA | GTGTGGCCTC | 960
| GTAGACCACG | ATCCCGTCCG | CCCAAATGCG | CGACTTGGTT | GTGATCCAAC | GCCAAATGCT | 1020
| GTTGGCGATG | GCGCGGACCT | CGCTGTCCGG | TAGCGGTCCG | GGACACACGT | CGTTGCACGG | 1080
| AAATTCGGCG | TTTCGCGCGT | GGCACTCGGC | ATAGATCGCG | CGGCCGAGTC | CGTCCACGTT | 1140
| CCGGGTCGGC | AGGTAGATCC | GCATGAGGGC | GGGACGATAG | GCCCACAACC | TGACGGAATC | 1200
| GAACAGTGCG | CAATTCCGCC | CTAGCGGCGT | CGGAGCCGCT | TTGTACGTGG | TCTGCTGACG | 1260
| CCAGCGCGGC | GGTGGCATGT | TCGCGCCGAG | CTCGGCCTCG | ATGTGGCTGA | GTGTGTAGAG | 1320
| ATCTGAGTGG | AGCCATTCCG | TTTCCCAGGC | GATGTGGCCG | GGGTTTTTGG | TCATGAGGCC | 1380
| TGAGTAACTG | CGGTCGCCAT | CGACGGCGCG | CCGAAGGCCT | TCGGCGCACG | CCGCCATGTA | 1440
| TGCGAGCGGC | TTACGCCGCG | CGTATTCGGT | GCGTGGAACA | GGGGCGTTGA | GTGCCCACAC | 1500
| TGCGTGTGCG | TGGCCGTTGG | CGCGATTGCC | CACGATCGCG | TTGGGCAGCG | GATGGGACCC | 1560
| CCGGGCGCTG | AGCGCTCGGA | GCGCTGCGTC | TGGATGGTCT | ACGTCCACGA | CCAGCAGGTT | 1620
| TGCCAGCGCT | GTTGGGTTCG | CCTCGATGTA | CCGGCGGCCT | AGGGCCGACG | CGCGGCTTTG | 1680
| GCGGTAGATC | CCCTCGAGCA | GATCGTCGCT | TGCCAGCGGC | CAGTACGGCA | GCCAGAGCTG | 1740
| CTCAAATTCG | TCGGCGACGT | GGCTCACGCT | TGGTAGTAGA | CCACGATTAA | TCACCGGTGT | 1800
| ATGGTCCGAC | ACGAGCTCCA | AGTCAGATAT | TTCGCTGAGG | GGCCACCCCA | CAACTGCACA | 1860
| CTCCCCCGCT | CTCCCGTCGA | GCCCTGGTGG | TGGAACACCA | GCGACAGCCG | AGCACCCCCA | 1920
| ACCACCTGTA | CCAACCAGGA | GGAACACATG | CGTCGTTTCG | AGGACGTTTC | CGGGCCGCTG | 1980
| AGAGCCGCTG | TGGCGGCCGT | ACACGCCGCC | TTAGACCCGT | TAGACCCCCT | GCCGCCTGAA | 2040
| TGCGCGGGTA | CGAGCCACAC | AGCGCCCGAA | CTTACGGAGC | TGGTGGGCTC | ACGCGTGCGG | 2100
| CCGCACGCGT | TGCGCTCGGT | CGTTCGGCTG | CGGCGAGCGG | TATCAGCTCA | CTCAAAGGCG | 2160
| GTAATACGGT | TATCCACAGA | ATCAGGGGAT | AACGCAGGAA | AGAACATGTG | AGCAAAAGGC | 2220
| CAGCAAAAGG | CCAGGAACCG | TAAAAAGGCC | GCGTTGCTGG | CGTTTTTCCA | TAGGCTCCGC | 2280
| CCCCCTGACG | AGCATCACAA | AAATCGACGC | TCAAGTCAGA | GGTGGCGAAA | CCCGACAGGA | 2340
| CTATAAAGAT | ACCAGGCGTT | TCCCCCTGGA | AGCTCCCTCG | TGCGCTCTCC | TGTTCCGACC | 2400
| CTGCCGCTTA | CCGGATACCT | GTCCGCCTTT | CTCCCTTCGG | GAAGCGTGGC | GCTTTCTCAA | 2460
| TGCTCACGCT | GTAGGTATCT | CAGTTCGGTG | TAGGTCGTTC | GCTCCAAGCT | GGGCTGTGTG | 2520
| CACGAACCCC | CCGTTCAGCC | CGACCGCTGC | GCCTTATCCG | GTAACTATCG | TCTTGAGTCC | 2580
| AACCCGGTAA | GACACGACTT | ATCGCCACTG | GCAGCAGCCA | CTGGTAACAG | GATTAGCAGA | 2640
| GCGAGGTATG | TAGGCGGTGC | TACAGAGTTC | TTGAAGTGGT | GGCCTAACTA | CGGCTACACT | 2700
| AGAAGGACAG | TATTTGGTAT | CTGCGCTCTG | CTGAAGCCAG | TTACCTTCGG | AAAAAGAGTT | 2760
| GGTAGCTCTT | GATCCGGCAA | ACAAACCACC | GCTGGTAGCG | GTGGTTTTTT | TGTTTGCAAG | 2820
| CAGCAGATTA | CGCGCAGAAA | AAAAGGATCT | CAAGAAGATC | CTTTGATCTT | TTCTACGGGG | 2880
| TCTGACGCTC | AGTGGAACTA | GTGAGGTCTG | CCTCGTGAAG | AAGGTGTTGC | TGACTCATAC | 2940
| CAGGCCTGAA | TCGCCCCATC | ATCCAGCCAG | AAAGTGAGGG | AGCCACGGTT | GATGAGAGCT | 3000
| TTGTTGTAGG | TGGACCAGTT | GGTGATTTTG | AACTTTTGCT | TTGCCACGGA | ACGGTCTGCG | 3060
| TTGTCGGGAA | GATGCGTGAT | CTGATCCTTC | AACTCAGCAA | AAGTTCGATT | TATTCAACAA | 3120

| | | | | | |
|---|---|---|---|---|---|
| AGCCGCCGTC | CCGTCAAGTC | AGCGTAATGC | TCTGCCAGTG | TTACAACCAA | TTAACCAATT | 3180
| CTGATTAGAA | AAACTCATCG | AGCATCAAAT | GAAACTGCAA | TTTATTCATA | TCAGGATTAT | 3240
| CAATACCATA | TTTTTGAAAA | AGCCGTTTCT | GTAATGAAGG | AGAAAACTCA | CCGAGGCAGT | 3300
| TCCATAGGAT | GGCAAGATCC | TGGTATCGGT | CTGCGATTCC | GACTCGTCCA | ACATCAATAC | 3360
| AACCTATTAA | TTTCCCCTCG | TCAAAATAA | GGTTATCAAG | TGAGAAATCA | CCATGAGTGA | 3420
| CGACTGAATC | CGGTGAGAAT | GGCAAAAGAT | TATGCATTTC | TTTCCAGACT | TGTTCAACAG | 3480
| GCCAGCCATT | ACGCTCGTCA | TCAAAATCAC | TCGCATCAAC | CAAACCGTTA | TTCATTCGTG | 3540
| ATTGCGCCTG | AGCGAGACGA | AATACGCGAT | CGCTGTTAAA | AGGACAATTA | CAAACAGGAA | 3600
| TCGAATGCAA | CCGGCGCAGG | AACACTGCCA | GCGCATCAAC | AATATTTTCA | CCTGAATCAG | 3660
| GATATTCTTC | TAATACCTGG | AATGCTGTTT | TCCCGGGGAT | CGCAGTGGTG | AGTAACCATG | 3720
| CATCATCAGG | AGTACGGATA | AAATGCTTGA | TGGTCGGAAG | AGGCATAAAT | TCCGTCAGCC | 3780
| AGTTTAGTCT | GACCATCTCA | TCTGTAACAT | CATTGGCAAC | GCTACCTTTG | CCATGTTTCA | 3840
| GAAACAACTC | TGGCGCATGG | GGCTTCCCAT | ACAAGCGATA | GATTGTCGCA | CCTGATTGCC | 3900
| CGACATTATC | GCGAGCCCAT | TTATACCCAT | ATAAATCAGC | ATCCATGTTG | GAATTTAATC | 3960
| GCGGCCTCGA | GCAAGACGTT | TCCCGTTGAA | TATGGCTCAT | AACACCCCTT | GTATTACTGT | 4020
| TTATGTAAGC | AGACAGTTTT | ATTGTTCATG | ATGATATATT | TTTATCTTGT | GCAATGTAAC | 4080
| ATCAGAGATT | TTGAGACACA | ACGTCGCTTT | GTTGGCTAGC | | | 4120

( 2 ) INFORMATION FOR SEQ ID NO:22:

( i ) SEQUENCE CHARACTERISTICS:
        ( A ) LENGTH: 251 nucleotides
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 22:

| | | | | | |
|---|---|---|---|---|---|
| TCTAGACAAG | GTCGAACGAG | GGGCATGACC | CGGTGCGGGG | CTTCTTGCAC | TCGGCATAGG | 60
| CGAGTGCTAA | GAATAACGTT | GGCACTCGCG | ACCGGTGAGT | CGTAGGTCGG | GACGGTGAGG | 120
| CCAGGCCCGT | CGTCGCAGCG | AGTGGCAGCG | AGGACAACTT | GAGCCGTCCG | TCGCGGGCAC | 180
| TGCGCCCGGC | CAGCGTAAGT | AGCGGGGTTG | CCGTCACCCG | GTGACCCCCG | GTTTCATCCC | 240
| CGATCGCTAG | C | | | | | 251

( 2 ) INFORMATION FOR SEQ ID NO:23:

( i ) SEQUENCE CHARACTERISTICS:
        ( A ) LENGTH: 153 nucleotides
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 23:

| | | | | | |
|---|---|---|---|---|---|
| AGATCTGTCC | TCAATGCCGA | TGGACCGCTA | CGACAGGCAA | AGGAGCACAG | GGTGAACCGT | 60
| GGACTGACGG | TCGCGGTAGC | CGGAGCCGCC | ATTCTGGTCG | CAGGTCTTTC | CGGATGTTCA | 120
| AGCAACAAGT | CCACGGATCC | AGCTGCAGAA | TTC | | | 153

( 2 ) INFORMATION FOR SEQ ID NO:24:

( i ) SEQUENCE CHARACTERISTICS:
  ( A ) LENGTH: 286 nucleotides
  ( B ) TYPE: nucleic acid
  ( C ) STRANDEDNESS: single
  ( D ) TOPOLOGY: linear ( i i ) MOLECULE TYPE: nucleic acid ( x i ) SEQUENCE DESCRIPTION: SEQ ID NO: 24:

```
TCTAGACGGT TTGTGTTCCA TCGGCACTAC ATTGCCACTA CTACGGTGCA CGCCGGTAGA      60
TGCCGTTGGC GAACCACGCT ACCGACCAGA AAGAGAGAAT TTTCCGCCGC ACCTAGACCT     120
CGGGCCCTGC TAACGCGCAT ACTGCCGAAG CGGTCCTCAA TGCCGATGGA CCGCTACGAC     180
AGGCAAAGGA GCACAGGGTG AAGCGTGGAC TGACGGTCGC GGTAGCCGGA GCCGCCATTC     240
TGGTCGCAGG TCTTTCCGGA TGTTCAAGCA ACAAGTCCAG GGATCC                    286
```

( 2 ) INFORMATION FOR SEQ ID NO:25:

( i ) SEQUENCE CHARACTERISTICS:
    ( A ) LENGTH: 297 nucleotides
    ( B ) TYPE: nucleic acid
    ( C ) STRANDEDNESS: single
    ( D ) TOPOLOGY: linear ( i i ) MOLECULE TYPE: nucleic acid ( x i ) SEQUENCE DESCRIPTION: SEQ ID NO: 25:

```
TCTAGATGTT CTTCGACGGC AGGCTGGTGG AGGAAGGGCC CACCGAACAG CTATTCTCCT      60
CGCCGAAGCA TGCGGAAACC GCCCGATACG TCGCCGGACT GTCGGGGAC GTCAAGGACG      120
CCAAGCGCGG AAATTGAAGA GCACAGAAAG GTATGGCGTG AAAATTCGTT TGCATACGCT     180
GTTGGCCGTG TTGACCGCTG CGCCGCTGCT GCTAGCAGCG GCGGGCTGTG GCTCGAAACC     240
ACCGAGCGGT TCGCCTGAAA CGGGCGCCGG CGCCGGTACT GTCGCGACTA CGGATCC       297
```

( 2 ) INFORMATION FOR SEQ ID NO:26:

( i ) SEQUENCE CHARACTERISTICS:
    ( A ) LENGTH: 404 nucleotides
    ( B ) TYPE: nucleic acid
    ( C ) STRANDEDNESS: single
    ( D ) TOPOLOGY: linear ( i i ) MOLECULE TYPE: nucleic acid ( x i ) SEQUENCE DESCRIPTION: SEQ ID NO: 26:

```
TCTAGAGGTG ACCACAACGA CGCGCCCGCT TTGATCGGGG ACGTCTGCGG CCGACCATTT      60
ACGGGTCTTG TTGTCGTTGG CGGTCATGGG CCGAACATAC TCACCCGGAT CGGAGGGCCG    120
AGGACAAGGT CGAACGAGGG GCATGACCCG GTGCGGGGCT TCTTGCACTC GGCATAGGCG    180
AGTGCTAAGA ATAACGTTGG CACTCGCGAC CGGTGAGTCG TAGGTCGGGA CGGTGAGGCC    240
AGGCCCGTCG TCGCAGCGAG TGGCAGCGAG GACAACTTGA GCCGTCCTGC GCGGGCACTG    300
CGCCCGGCCA GCGTAAGTAG CGGGGTTGCC GTCACCCGGT GACCCCGGT TTCATCCCCG     360
ATCCGGAGGA ATCACTTCGC AATGGCCAAG ACAATTGCGG ATCC                     404
```

( 2 ) INFORMATION FOR SEQ ID NO:27:

( i ) SEQUENCE CHARACTERISTICS:
    ( A ) LENGTH: 404 nucleotides
    ( B ) TYPE: nucleic acid
    ( C ) STRANDEDNESS: single
    ( D ) TOPOLOGY: linear ( i i ) MOLECULE TYPE: nucleic acid ( x i ) SEQUENCE DESCRIPTION: SEQ ID NO: 27:

| | | | | | |
|---|---|---|---|---|---|
| GGATCCGCAA | TTGTCTTGGC | CATTGCGAAG | TGATTCCTCC | GGATCGGGGA | TGAAACCGGG | 60 |
| GGTCACCGGG | TGACGGCAAC | CCCGCTACTT | ACGCTGGCCG | GGCGCAGTGC | CCGCGACGGA | 120 |
| CGGCTCAAGT | TGTCCTCGCT | GCCACTCGCT | GCGACGACGG | GCCTGGCCTC | ACCGTCCCGA | 180 |
| CCTACGACTC | ACCGGTCGCG | AGTGCCAACG | TTATTCTTAG | CACTCGCCTA | TGCCGAGTGC | 240 |
| AAGAAGCCCC | GCACCGGGTC | ATGCCCCTCG | TTCGACCTTG | TCCTCGGCCC | TCCGATCCGG | 300 |
| GTGAGTATGT | TCGGCCCATG | ACCGCCAACG | ACAACAAGAC | CCGTAAATGG | TCGGCCGCAG | 360 |
| ACGTCCCCGA | TCAAAGCGGG | CGCGTCGTTG | TGGTCACCTC | TAGA | | 404 |

( 2 ) INFORMATION FOR SEQ ID NO:28:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: polypeptide ( x i ) SEQUENCE DESCRIPTION: SEQ ID NO: 28:

Met  Ala  Lys  Thr  Ile  Ala  Asp  Pro
 1                    5

( 2 ) INFORMATION FOR SEQ ID NO:29:

( i ) SEQUENCE CHARACTERISTICS:
        ( A ) LENGTH: 28 nucleotides
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 29:

CAGATCTAGA CGGTGACCAC AACGCGCC        28

( 2 ) INFORMATION FOR SEQ ID NO:30:

( i ) SEQUENCE CHARACTERISTICS:
        ( A ) LENGTH: 29 nucleotides
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 30:

CTAGGGATCC GCAATTGTCT TGGCCATTG        29

( 2 ) INFORMATION FOR SEQ ID NO:31:

( i ) SEQUENCE CHARACTERISTICS:
        ( A ) LENGTH: 267 nucleotides
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 31:

| | | | | | |
|---|---|---|---|---|---|
| TCTAGACAAG | GTCGAACGAG | GGGCATGACC | CGGTGCGGGG | CTTCTTGCAC | TCGGCATAGG | 60 |
| CGAGTGCTAA | GAATAACGTT | GGCACTCGCG | ACCGGTGAGT | CGTAGGTCGG | GACGGTGAGG | 120 |
| CCAGGCCCGT | CGTCGCAGCG | AGTGGCAGCG | AGGACAACTT | GAGCCGTCCG | TCGCGGGCAC | 180 |

| TGCGCCCGGC | CAGCGTAAGT | AGCGGGGTTG | CCGTCACCCG | GTGACCCCCG | GTTTCATCCC | 240 |
| CGATCCGGAG | GAATCACTTC | GCCATGG | | | | 267 |

(2) INFORMATION FOR SEQ ID NO:32:

(i) SEQUENCE CHARACTERISTICS:
        (A) LENGTH: 210 nucleotides
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 32:

| AGATCTGGAC | GTCAAGGACG | CCAAGCGCGG | AAATTGAAGA | GCACAGAAAG | GTATGGCGTG | 60 |
| AAAATTCGTT | TGCATACGCT | GTTGGCCGTG | TTGACCGCTG | CGCCGCTGCT | GCTAGCAGCG | 120 |
| GCGGGCTGTG | GCTCGAAACC | ACCGAGCGGT | TCGCCTGAAA | CGGGCGCCGG | CGCCGGTACT | 180 |
| GTCGCGACTA | CGGATCCAGC | TGCAGAATTC | | | | 210 |

(2) INFORMATION FOR SEQ ID NO:33:

(i) SEQUENCE CHARACTERISTICS:
        (A) LENGTH: 83 nucleotides
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 33:

| AAAACACCCT | CTGACCAGCC | GAGCGGGCGA | CGGGAATCGA | ACCCGCGTAG | CTAGTTTGGA | 60 |
| AGAATGGGTG | TCTGCCGACC | ACA | | | | 83 |

(2) INFORMATION FOR SEQ ID NO:34:

(i) SEQUENCE CHARACTERISTICS:
        (A) LENGTH: 83 nucleotides
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 34:

| AAAACACCCT | CTGACCAGCC | GAGCGGGCGA | CGGGAATCGA | ACCCGCGTAG | CTAGTTTGGA | 60 |
| AGACTAGGGC | TCTACCATTG | AGC | | | | 83 |

(2) INFORMATION FOR SEQ ID NO:35:

(i) SEQUENCE CHARACTERISTICS:
        (A) LENGTH: 83 nucleotides
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 35:

| CGCACGTGGC | GGTCCCTACC | GAGCGGGCGA | CGGGAATCGA | ACCCGCGTAG | CTAGTTTGGA | 60 |
| AGACTAGGGC | TCTACCATTG | AGC | | | | 83 |

(2) INFORMATION FOR SEQ ID NO:36:

(i) SEQUENCE CHARACTERISTICS:
    (A) LENGTH: 28 amino acids
    (B) TYPE: amino acid
    (D) TOPOLOGY: linear (ii) MOLECULE TYPE: peptide (xi) SEQUENCE DESCRIPTION: SEQ ID NO: 36:

Arg Leu Ala Met Glu Leu Ala Val Val Thr Gly Gln Arg Val Gly Asp
 1               5                   10                  15
Leu Cys Glu Met Lys Trp Ser Asp Ile Val Asp Gly
                20                  25

(2) INFORMATION FOR SEQ ID NO:37:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO: 37:

Arg Leu Ala Met Asp Leu Ala Val Val Thr Gly Gln Arg Val Gly Asp
 1               5                   10                  15
Leu Cys Arg Met Lys Trp Ser Asp Ile Asn Asp Asn
                20                  25

(2) INFORMATION FOR SEQ ID NO:38:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO: 38:

Val Phe Leu Val Arg Phe Ile Met Leu Thr Gly Cys Arg Thr Ala Glu
 1               5                   10                  15
Ile Arg Leu Ser Glu Arg Ser Trp Phe Arg Leu Asp
                20                  25

(2) INFORMATION FOR SEQ ID NO:39:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO: 39:

Lys Lys Ile Ala Ile Leu Cys Leu Ser Thr Gly Ala Arg Trp Gly Glu
 1               5                   10                  15
Ala Ala Arg Leu Lys Ala Glu Asn Ile Ile His Asn
                20                  25

(2) INFORMATION FOR SEQ ID NO:40:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO: 40:

```
Met  Ile  Ala  Val  Lys  Leu  Ser  Leu  Leu  Thr  Phe  Val  Arg  Ser  Ser  Glu
 1              5                        10                       15

Leu  Arg  Phe  Ala  Arg  Trp  Asp  Glu  Phe  Asp  Phe  Asp
              20                        25
```

( 2 ) INFORMATION FOR SEQ ID NO:41:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 41:

```
Lys  Ser  Val  Val  Glu  Phe  Ala  Leu  Ser  Thr  Gly  Leu  Arg  Arg  Ser  Asn
 1              5                        10                       15

Ile  Ile  Met  Leu  Glu  Trp  Gln  Gln  Ile  Asp  Met  Gln
              20                        25
```

( 2 ) INFORMATION FOR SEQ ID NO:42:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 42:

```
Glu  Thr  Val  Val  Arg  Ile  Cys  Leu  Ala  Thr  Gly  Ala  Arg  Met  Ser  Glu
 1              5                        10                       15

Ala  Glu  Ser  Leu  Arg  Lys  Ser  Gln  Leu  Ala  Lys  Tyr
              20                        25
```

( 2 ) INFORMATION FOR SEQ ID NO:43:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 43:

```
Gly  Leu  Ile  Val  Arg  Ile  Cys  Leu  Ala  Thr  Gly  Ala  Arg  Trp  Ser  Glu
 1              5                        10                       15

Ala  Glu  Thr  Leu  Thr  Gln  Ser  Gln  Val  Met  Pro  Tyr
              20                        25
```

( 2 ) INFORMATION FOR SEQ ID NO:44:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 44:

```
Ala  Gly  Ala  Val  Glu  Val  Gln  Ala  Leu  Thr  Gly  Met  Arg  Ile  Gly  Glu
 1              5                        10                       15

Leu  Leu  Ala  Leu  Gln  Val  Arg  Asp  Val  Asp  Leu  Lys
              20                        25
```

( 2 ) INFORMATION FOR SEQ ID NO:45:

( i ) SEQUENCE CHARACTERISTICS:
    ( A ) LENGTH: 28 amino acids
    ( B ) TYPE: amino acid
    ( D ) TOPOLOGY: linear ( i i ) MOLECULE TYPE: peptide ( x i ) SEQUENCE DESCRIPTION: SEQ ID NO: 45:

```
Thr Ala Gly Val Glu Lys Ala Leu Ser Leu Gly Val Thr Lys Leu Val
 1               5                  10                  15

Glu Arg Met Ile Ser Val Ser Gly Val Ala Asp Asp
                20                  25
```

( 2 ) INFORMATION FOR SEQ ID NO:46:

( i ) SEQUENCE CHARACTERISTICS:
    ( A ) LENGTH: 28 amino acids
    ( B ) TYPE: amino acid
    ( D ) TOPOLOGY: linear ( i i ) MOLECULE TYPE: peptide ( x i ) SEQUENCE DESCRIPTION: SEQ ID NO: 46:

```
Lys Met Leu Leu Ala Thr Leu Trp Asn Thr Gly Ala Arg Ile Asp Glu
 1               5                  10                  15

Ala Leu Ala Leu Thr Arg Gly Asp Phe Ser Leu Ala
                20                  25
```

( 2 ) INFORMATION FOR SEQ ID NO:47:

( i ) SEQUENCE CHARACTERISTICS:
    ( A ) LENGTH: 28 amino acids
    ( B ) TYPE: amino acid
    ( D ) TOPOLOGY: linear ( i i ) MOLECULE TYPE: peptide ( x i ) SEQUENCE DESCRIPTION: SEQ ID NO: 47:

```
Tyr Cys Leu Thr Leu Leu Cys Phe Ile His Gly Phe Arg Ala Ser Glu
 1               5                  10                  15

Ile Cys Arg Leu Arg Ile Ser Asp Ile Asp Leu Lys
                20                  25
```

( 2 ) INFORMATION FOR SEQ ID NO:48:

( i ) SEQUENCE CHARACTERISTICS:
    ( A ) LENGTH: 28 amino acids
    ( B ) TYPE: amino acid
    ( D ) TOPOLOGY: linear ( i i ) MOLECULE TYPE: peptide ( x i ) SEQUENCE DESCRIPTION: SEQ ID NO: 48:

```
Tyr Cys Leu Ile Leu Leu Ala Tyr Arg Met Gly Met Arg Ile Ser Glu
 1               5                  10                  15

Leu Leu Asp Leu His Tyr Gln Asp Leu Asp Leu Asn
                20                  25
```

( 2 ) INFORMATION FOR SEQ ID NO:49:

( i ) SEQUENCE CHARACTERISTICS:
    ( A ) LENGTH: 28 amino acids
    ( B ) TYPE: amino acid
    ( D ) TOPOLOGY: linear ( i i ) MOLECULE TYPE: peptide (xi) SEQUENCE DESCRIPTION: SEQ ID NO: 49:

Arg Leu Phe Ala Gln Leu Leu Tyr Gly Thr Gly Met Arg Ile Ser Glu
 1               5                  10                  15

Gly Leu Gln Leu Arg Val Lys Asp Leu Asp Phe Asp
            20                  25

(2) INFORMATION FOR SEQ ID NO:50:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO: 50:

Lys Leu Ile Leu Met Leu Met Tyr Glu Gly Leu Arg Ile Gly Glu
 1               5                  10                  15

Val Leu Ser Leu Arg Leu Glu Asp Ile Val Thr Trp
            20                  25

(2) INFORMATION FOR SEQ ID NO:51:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO: 51:

Ala Thr Met Thr Met Ile Val Gln Glu Cys Gly Met Arg Ile Ser Glu
 1               5                  10                  15

Leu Cys Thr Leu Lys Lys Gly Cys Leu Leu Glu Asp
            20                  25

(2) INFORMATION FOR SEQ ID NO:52:

(i) SEQUENCE CHARACTERISTICS:
        (A) LENGTH: 28 amino acids
        (B) TYPE: amino acid
        (C) TOPOLOGY: linear (ii) MOLECULE TYPE: peptide (xi) SEQUENCE DESCRIPTION: SEQ ID NO: 52:

Tyr Ala Ile Ala Thr Leu Leu Ala Tyr Thr Gly Val Arg Ile Ser Glu
 1               5                  10                  15

Ala Leu Ser Ile Lys Met Asn Asp Phe Asn Leu Gln
            20                  25

(2) INFORMATION FOR SEQ ID NO:53:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO: 53:

Tyr Val Ile Phe His Leu Ala Leu Glu Thr Ala Met Arg Gln Gln Glu
 1               5                  10                  15

Ile Leu Ala Leu Arg Trp Glu His Ile Asp Leu Arg
            20                  25

( 2 ) INFORMATION FOR SEQ ID NO:54:

( i ) SEQUENCE CHARACTERISTICS:
      ( A ) LENGTH: 28 amino acids
      ( B ) TYPE: amino acid
      ( D ) TOPOLOGY: linear ( i i ) MOLECULE TYPE: peptide ( x i ) SEQUENCE DESCRIPTION: SEQ ID NO: 54:

Tyr Asp Glu Ile Leu Ile Leu Leu Lys Thr Gly Leu Arg Ile Ser Glu
 1               5                  10                  15

Phe Gly Gly Leu Thr Leu Pro Asp Leu Asp Phe Glu
            20                  25

( 2 ) INFORMATION FOR SEQ ID NO:55:

( i ) SEQUENCE CHARACTERISTICS:
      ( A ) LENGTH: 4 amino acids
      ( B ) TYPE: amino acid
      ( D ) TOPOLOGY: linear ( i i ) MOLECULE TYPE: peptide ( x i ) SEQUENCE DESCRIPTION: SEQ ID NO: 55:

Thr Gly Met Arg
 1

( 2 ) INFORMATION FOR SEQ ID NO:56:

( i ) SEQUENCE CHARACTERISTICS:
      ( A ) LENGTH: 28 amino acids
      ( B ) TYPE: amino acid
      ( D ) TOPOLOGY: linear ( i i ) MOLECULE TYPE: peptide ( x i ) SEQUENCE DESCRIPTION: SEQ ID NO: 56:

Arg Ile Ala Ala Tyr Ile Leu Ala Trp Thr Ser Leu Arg Phe Gly Glu
 1               5                  10                  15

Leu Ile Glu Leu Arg Arg Lys Asp Ile Val Asp Asp
            20                  25

( 2 ) INFORMATION FOR SEQ ID NO:57:

( i ) SEQUENCE CHARACTERISTICS:
      ( A ) LENGTH: 36 amino acids
      ( B ) TYPE: amino acid
      ( D ) TOPOLOGY: linear ( i i ) MOLECULE TYPE: peptide ( x i ) SEQUENCE DESCRIPTION: SEQ ID NO: 57:

His Glu Leu Arg Ser Leu Ser Ala Arg Leu Tyr Glu Lys Gln Ile Ser
 1               5                  10                  15

Asp Lys Phe Ala Gln His Leu Leu Gly His Lys Ser Asp Thr Met
            20                  25                  30

Ala Ser Gln Tyr Arg
            35

( 2 ) INFORMATION FOR SEQ ID NO:58:

( i ) SEQUENCE CHARACTERISTICS:
      ( A ) LENGTH: 37 amino acids
      ( B ) TYPE: amino acid
      ( D ) TOPOLOGY: linear ( i i ) MOLECULE TYPE: peptide ( x i ) SEQUENCE DESCRIPTION: SEQ ID NO: 58:

His Glu Leu Arg Ser Leu Ser Ala Arg Leu Tyr Arg Asn Gln Ile Gly
1               5                   10                  15

Asp Lys Phe Ala Gln Arg Leu Leu Gly His Lys Ser Asp Ser Met Ala
            20                  25                  30

Ala Arg Tyr Arg Asp
        35

( 2 ) INFORMATION FOR SEQ ID NO:59:

( i ) SEQUENCE CHARACTERISTICS:
    ( A ) LENGTH: 37 amino acids
    ( B ) TYPE: amino acid
    ( D ) TOPOLOGY: linear ( i i ) MOLECULE TYPE: peptide ( x i ) SEQUENCE DESCRIPTION: SEQ ID NO: 59:

His Asp Met Arg Arg Thr Ile Ala Thr Asn Leu Ser Glu Leu Gly Cys
1               5                   10                  15

Pro Pro His Val Ile Glu Lys Leu Leu Gly His Gln Met Val Gly Val
            20                  25                  30

Met Ala His Tyr Asn
        35

( 2 ) INFORMATION FOR SEQ ID NO:60:

( i ) SEQUENCE CHARACTERISTICS:
    ( A ) LENGTH: 38 amino acid residues
    ( B ) TYPE: amino acid
    ( D ) TOPOLOGY: linear ( i i ) MOLECULE TYPE: peptide ( x i ) SEQUENCE DESCRIPTION: SEQ ID NO: 60:

His Ala Leu Arg His Ser Phe Ala Thr His Phe Met Ile Asn Gly Gly
1               5                   10                  15

Ser Ile Ile Thr Leu Gln Arg Ile Leu Gly His Thr Arg Ile Glu Gln
            20                  25                  30

Thr Met Val Tyr Ala His
        35

( 2 ) INFORMATION FOR SEQ ID NO:61:

( i ) SEQUENCE CHARACTERISTICS:
    ( A ) LENGTH: 40 amino acids
    ( B ) TYPE: amino acid
    ( D ) TOPOLOGY: linear ( i i ) MOLECULE TYPE: peptide ( x i ) SEQUENCE DESCRIPTION: SEQ ID NO: 61:

His Gly Phe Arg Thr Met Ala Arg Gly Ala Leu Gly Glu Ser Gly Leu
1               5                   10                  15

Trp Ser Asp Asp Ala Ile Glu Arg Gln Ser Leu His Ser Glu Arg Asn
            20                  25                  30

Asn Val Arg Ala Ala Tyr Ile His
        35                  40

( 2 ) INFORMATION FOR SEQ ID NO:62:

( i ) SEQUENCE CHARACTERISTICS:

(A) LENGTH: 38 amino acids
(B) TYPE: amino acid
(D) TOPOLOGY: linear (ii) MOLECULE TYPE: peptide (xi) SEQUENCE DESCRIPTION: SEQ ID NO: 62:

| His | Asp | Leu | Arg | His | Thr | Trp | Ala | Ser | Trp | Leu | Val | Gln | Ala | Gly | Val |
|---|---|---|---|---|---|---|---|---|---|---|---|---|---|---|---|
| 1 | | | | 5 | | | | | 10 | | | | | 15 | |
| Pro | Ile | Ser | Val | Leu | Gln | Glu | Met | Gly | Gly | Trp | Glu | Ser | Ile | Glu | Met |
| | | | 20 | | | | | 25 | | | | | 30 | | |
| Val | Arg | Arg | Tyr | Ala | His | | | | | | | | | | |
| | | | 35 | | | | | | | | | | | | |

(2) INFORMATION FOR SEQ ID NO:63:

(i) SEQUENCE CHARACTERISTICS:
(A) LENGTH: 38 amino acids
(B) TYPE: amino acid
(D) TOPOLOGY: linear (ii) MOLECULE TYPE: peptide (xi) SEQUENCE DESCRIPTION: SEQ ID NO: 63:

| His | Val | Leu | Arg | His | Thr | Phe | Ala | Ser | His | Phe | Met | Met | Asn | Gly | Gly |
|---|---|---|---|---|---|---|---|---|---|---|---|---|---|---|---|
| 1 | | | | 5 | | | | | 10 | | | | | 15 | |
| Asn | Ile | Leu | Val | Leu | Gln | Arg | Val | Leu | Gly | His | Thr | Asp | Ile | Lys | Met |
| | | | 20 | | | | | 25 | | | | | 30 | | |
| Thr | Met | Arg | Tyr | Ala | His | | | | | | | | | | |
| | | | 35 | | | | | | | | | | | | |

(2) INFORMATION FOR SEQ ID NO:64:

(i) SEQUENCE CHARACTERISTICS:
(A) LENGTH: 38 amino acids
(B) TYPE: amino acid
(D) TOPOLOGY: linear (ii) MOLECULE TYPE: peptide (xi) SEQUENCE DESCRIPTION: SEQ ID NO: 64:

| His | Val | Leu | Arg | His | Thr | Phe | Ala | Ser | His | Phe | Met | Met | Asn | Gly | Gly |
|---|---|---|---|---|---|---|---|---|---|---|---|---|---|---|---|
| 1 | | | | 5 | | | | | 10 | | | | | 15 | |
| Asn | Ile | Leu | Val | Leu | Lys | Glu | Ile | Leu | Gly | His | Ser | Thr | Ile | Glu | Met |
| | | | 20 | | | | | 25 | | | | | 30 | | |
| Thr | Met | Arg | Tyr | Ala | His | | | | | | | | | | |
| | | | 35 | | | | | | | | | | | | |

(2) INFORMATION FOR SEQ ID NO:65:

(i) SEQUENCE CHARACTERISTICS:
(A) LENGTH: 39 amino acids
(B) TYPE: amino acid
(D) TOPOLOGY: linear (ii) MOLECULE TYPE: peptide (xi) SEQUENCE DESCRIPTION: SEQ ID NO: 65:

| His | Thr | Leu | Arg | His | Thr | His | Ile | Ser | Leu | Leu | Ala | Glu | Met | Asn | Ile |
|---|---|---|---|---|---|---|---|---|---|---|---|---|---|---|---|
| 1 | | | | 5 | | | | | 10 | | | | | 15 | |
| Ser | Leu | Lys | Ala | Ile | Met | Lys | Arg | Val | Gly | His | Arg | Asp | Glu | Lys | Thr |
| | | | 20 | | | | | 25 | | | | | 30 | | |
| Thr | Ile | Lys | Val | Tyr | Thr | His | | | | | | | | | |
| | | | 35 | | | | | | | | | | | | |

( 2 ) INFORMATION FOR SEQ ID NO:66:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 66:

```
His Ser Ala Arg Val Gly Ala Ala Arg Asp Met Ala Arg Ala Gly Val
 1               5                  10                  15
Ser Ile Pro Glu Ile Met Gln Ala Gly Gly Trp Thr Asn Val Asn Ile
            20                  25                  30
Val Met Asn Tyr Ile Arg
            35
```

( 2 ) INFORMATION FOR SEQ ID NO:67:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 67:

```
His Thr Phe Arg His Ser Tyr Ala Met His Met Leu Tyr Ala Gly Ile
 1               5                  10                  15
Pro Leu Lys Val Leu Gln Ser Leu Met Gly His Lys Ser Ile Ser Ser
            20                  25                  30
Thr Glu Val Tyr Thr Lys
            35
```

( 2 ) INFORMATION FOR SEQ ID NO:68:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 68:

```
His Met Leu Arg His Ser Cys Gly Phe Ala Leu Ala Asn Met Gly Ile
 1               5                  10                  15
Asp Thr Arg Leu Ile Gln Asp Tyr Leu Gly His Arg Asn Ile Arg His
            20                  25                  30
Thr Val Arg Tyr Thr Ala
            35
```

( 2 ) INFORMATION FOR SEQ ID NO:69:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 69:

```
His Met Leu Arg His Ala Cys Gly Tyr Glu Leu Ala Glu Arg Gly Ala
 1               5                  10                  15
Asp Thr Arg Leu Ile Gln Asp Tyr Leu Gly His Arg Asn Ile Arg His
            20                  25                  30
```

Thr Val Arg Tyr Thr Ala
                35

( 2 ) INFORMATION FOR SEQ ID NO:70:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 70:

His Thr Leu Arg His Ser Phe Ala Thr Ala Leu Leu Arg Ser Gly Tyr
1                   5                  10                  15

Asp Ile Arg Thr Val Gln Asp Leu Leu Gly His Ser Asp Val Ser Thr
                20                  25                  30

Thr Met Ile Tyr Thr His
                35

( 2 ) INFORMATION FOR SEQ ID NO:71:

( i ) SEQUENCE CHARACTERISTICS:
        ( A ) LENGTH: 39 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 71:

His Met Leu Arg His Thr His Ala Thr Gln Leu Ile Arg Glu Gly Trp
1                   5                  10                  15

Asp Val Ala Phe Val Gln Lys Arg Leu Gly His Ala His Val Gln Thr
                20                  25                  30

Thr Leu Asn Thr Tyr Val His
                35

( 2 ) INFORMATION FOR SEQ ID NO:72:

( i ) SEQUENCE CHARACTERISTICS:
        ( A ) LENGTH: 38 amino acid residues
        ( B ) TYPE: amino acid
        ( D ) TOPOLOGY: linear ( i i ) MOLECULE TYPE: peptide ( x i ) SEQUENCE DESCRIPTION: SEQ ID NO: 72:

His Ala Phe Arg His Thr Val Gly Thr Arg Met Ile Asn Asn Gly Met
1                   5                  10                  15

Pro Gln His Ile Val Gln Lys Phe Leu Gly His Glu Ser Pro Glu Met
                20                  25                  30

Thr Ser Arg Tyr Ala His
                35

( 2 ) INFORMATION FOR SEQ ID NO:73:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 73:

His Gln Leu Arg His Phe Phe Cys Thr Asn Ala Ile Glu Lys Gly Phe

```
     1               5                    10                   15
Ser  Ile  His  Glu  Val  Ala  Asn  Gln  Ala  Gly  Asn  Ser  Asn  Ile  Asn  Thr
                    20                       25                  30

Thr  Leu  Leu  Tyr  Thr
               35
```

( 2 ) INFORMATION FOR SEQ ID NO:74:

( i ) SEQUENCE CHARACTERISTICS:
        ( A ) LENGTH: 39 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 74:

```
His  Asp  Leu  Arg  His  Glu  Ala  Ile  Ser  Arg  Phe  Phe  Glu  Leu  Gly  Ser
 1               5                    10                   15

Leu  Asn  Val  Met  Glu  Ile  Ala  Ala  Ile  Ser  Gly  His  Arg  Ser  Met  Asn
                    20                       25                  30

Met  Leu  Lys  Arg  Tyr  Thr  His
               35
```

( 2 ) INFORMATION FOR SEQ ID NO:75:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 75:

```
His  Ser  Leu  Arg  Asn  Thr  Phe  Cys  Thr  Asn  Tyr  Ala  Asn  Ala  Gly  Met
 1               5                    10                   15

Asn  Pro  Lys  Ala  Leu  Gln  Tyr  Ile  Met  Gly  His  Ala  Asn  Ile  Ala  Met
                    20                       25                  30

Thr  Leu  Asn  Tyr  Tyr  Ala
               35
```

( 2 ) INFORMATION FOR SEQ ID NO:76:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 76:

```
His  Ile  Gly  Arg  His  Leu  Met  Thr  Ser  Phe  Leu  Ser  Met  Lys  Gly  Leu
 1               5                    10                   15

Thr  Glu  Leu  Thr  Asn  Val  Val  Gly  Asn  Trp  Ser  Asp  Lys  Arg  Ala  Ser
                    20                       25                  30

Ala  Val  Ala  Thr  Thr  Tyr  Thr  His
               35                    40
```

( 2 ) INFORMATION FOR SEQ ID NO:77:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 77:

Leu  Arg  His  Thr
 1

( 2 ) INFORMATION FOR SEQ ID NO:78:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 78:

Leu  Leu  Gly  His
 1

( 2 ) INFORMATION FOR SEQ ID NO:79:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 79:

His  Asp  Leu  Arg  Ala  Val  Gly  Ala  Thr  Phe  Ala  Ala  Gln  Ala  Gly  Ala
 1                    5                        10                           15

Thr  Thr  Lys  Glu  Leu  Met  Ala  Arg  Leu  Gly  His  Thr  Thr  Pro  Arg  Met
                20                       25                      30

Ala  Met  Lys  Tyr  Gln  Met
                35

( 2 ) INFORMATION FOR SEQ ID NO:80:

( i ) SEQUENCE CHARACTERISTICS:
        ( A ) LENGTH: 327 amino acids
        ( B ) TYPE: amino acid
        ( D ) TOPOLOGY: linear ( i i ) MOLECULE TYPE: polypeptide ( x i ) SEQUENCE DESCRIPTION: SEQ ID NO: 80:

Leu  Ala  Gly  Glu  Lys  Arg  Leu  Ile  Glu  Met  Glu  Thr  Trp  Thr  Pro  Pro
 1                    5                        10                           15

Gln  Asp  Arg  Ala  Lys  Lys  Ala  Ala  Ala  Ser  Ala  Ile  Thr  Leu  Glu  Glu
                20                       25                      30

Tyr  Thr  Arg  Lys  Trp  Leu  Val  Glu  Arg  Asp  Leu  Ala  Asp  Gly  Thr  Arg
           35                       40                      45

Asp  Leu  Tyr  Ser  Gly  Met  Ala  Glu  Arg  Arg  Ile  Tyr  Pro  Val  Leu  Gly
      50                       55                      60

Glu  Val  Ala  Val  Thr  Glu  Asn  Thr  Pro  Ala  Leu  Val  Arg  Ala  Trp  Trp
 65                       70                      75                           80

Ala  Gly  Met  Gly  Arg  Glu  Asn  Pro  Thr  Ala  Arg  Arg  His  Ala  Tyr  Asn
                85                       90                      95

Val  Leu  Arg  Ala  Val  Met  Asn  Thr  Ala  Val  Glu  Asp  Glu  Leu  Ile  Ala
               100                      105                     110

Glu  Met  Pro  Cys  Arg  Ile  Glu  Gln  Lys  Ala  Ala  Asp  Glu  Arg  Asp  Val
               115                      120                     125

Glu  Ala  Leu  Thr  Pro  Glu  Glu  Leu  Asp  Ile  Val  Ala  Ala  Glu  Ile  Phe
           130                      135                     140

Glu  Asn  Tyr  Arg  Ile  Ala  Ala  Tyr  Ile  Leu  Ala  Met  Thr  Ser  Leu  Arg

| 145 | | | | 150 | | | | 155 | | | | 160 | | | |
|---|---|---|---|---|---|---|---|---|---|---|---|---|---|---|---|
| Phe | Gly | Glu | Leu | Ile | Glu | Leu | Glu | Arg | Arg | Asp | Ile | Val | Asp | Asp | Gly |
| | | | | 165 | | | | | 170 | | | | 175 | | |
| Met | Thr | Met | Glu | Leu | Arg | Val | Arg | Arg | Gly | Ala | Ser | Arg | Val | Gly | Asn |
| | | | 180 | | | | | 185 | | | | | 190 | | |
| Lys | Ile | Val | Val | Gly | Asn | Ala | Lys | Thr | Val | Arg | Ser | Lys | Arg | Pro | Val |
| | | | 195 | | | | | 200 | | | | | 205 | | |
| Thr | Val | Pro | Pro | Asn | Val | Ala | Glu | Met | Ile | Arg | Ala | Trp | Met | Lys | Asp |
| | 210 | | | | | 215 | | | | | 220 | | | | |
| Arg | Thr | Lys | Met | Asn | Arg | Gly | Pro | Glu | Ala | Phe | Leu | Val | Thr | Thr | Thr |
| 225 | | | | | 230 | | | | | 235 | | | | | 240 |
| Gln | Gly | Met | Arg | Leu | Ser | Lys | Ser | Ala | Phe | Thr | Lys | Ser | Leu | Lys | Arg |
| | | | | 245 | | | | | 250 | | | | | 255 | |
| Gly | Tyr | Ala | Lys | Ile | Gly | Arg | Pro | Glu | Leu | Arg | Ile | His | Asp | Leu | Arg |
| | | | 260 | | | | | 265 | | | | | 270 | | |
| Ala | Val | Gly | Ala | Thr | Phe | Ala | Ala | Gln | Ala | Cys | Ala | Thr | Thr | Lys | Glu |
| | | | 275 | | | | 280 | | | | | 285 | | | |
| Leu | Asn | Ala | Arg | Leu | Gly | His | Thr | Thr | Pro | Arg | Met | Ala | Met | Lys | Tyr |
| | 290 | | | | | 295 | | | | | 300 | | | | |
| Gln | Met | Ala | Ser | Glu | Ala | Arg | Asp | Glu | Ala | Ile | Ala | Glu | Ala | Met | Ser |
| 305 | | | | | 310 | | | | | 315 | | | | | 320 |
| Glu | Lys | Ala | Lys | Thr | Ser | Ile | | | | | | | | | |
| | | | | 325 | | | | | | | | | | | |

( 2 ) INFORMATION FOR SEQ ID NO:81:

( i ) SEQUENCE CHARACTERISTICS:
        ( A ) LENGTH: 2089 nucleotides
        ( B ) TYPE: nucleic acid
        ( C ) STRANDEDNESS: double
        ( D ) TOPOLOGY: linear ( i i ) MOLECULE TYPE: nucleic acid ( x i ) SEQUENCE DESCRIPTION: SEQ ID NO: 81:

```
GTCGACCACC AAGGGCACCA TCTCTGCTTG GGCCACCCCG TTGGCCGCAG CCAGCTCGCT      60
GAGAGCCGTG AACGACAGGG CGAACGCCAG CCCGCCGACG GCGAGGGTTC CGACCGCTGC     120
AACTCCCGGT GCAACCTTGT CCCGGTCTAT TCTCTTCACT GCACCAGCTC CAATCTGGTG     180
TGAATGCCCC TCGTCTGTTC GCGCAGGCGG GGGGCTCTAT TCGTTTGTCA GCATCGAAAG     240
TAGCCAGATC AGGGATGCGT TGCAACCGCG TATGCCCAGG TCAGAAGAGT CGCACAAGAG     300
TTGCAGACCC CTGGAAAGAA AAATGGCCAG AGGGCGAAAA CACCCTCTGA CCAGCGGAGC     360
GGGCGACGGG AATCGAACCC GCGTAGCTAG TTTGGAAGAA TGGGTGTCTG CCGACCACAT     420
ATGGGCCGGT CAAGATAGGT TTTTACCCCC TCTCGGCTGC ATCCTCTAAG TGGAAAGAAA     480
TTGCAGGTCG TAGAAGCGCG TTGAAGCCTG AGAGTTGCAC AGGAGTTGCA ACCCGGTAGC     540
CTTGTTCACG ACGAGAGGAG ACCTAGTTGG CACGTCGCGG ATGGGGATCG CTGAAGACTC     600
AGCGCAGCGG GAGGATCCAA GCCTCATACG TCAACCCGCA GGACGGTGTG AGGTACTACG     660
CGCTGCAGAC CTACGACAAC AAGATGGACG CCGAAGCCTG GCTCGCGGGC GAGAAGCGGC     720
TCATCGAGAT GGAGACCTGG ACCCCTCCAC AGGACCGGGC GAAGAAGGCA GCCGCCAGCG     780
CCATCACGCT GGAGGAGTAC ACCCGGAAGT GGCTCGTGGA GCGCGACCTC GCAGACGGCA     840
CCAGGGATCT GTACAGCGGG CACGCGGAGC GCCGCATCTA CCCGGTGCTA GGTGAAGTGG     900
CGGTCACAGA GATGACGCCA GCTCTGGTGC GTGCGTGGTG GGCCGGGATG GGTAGGAAGC     960
```

```
ACCCGACTGC CCGCCGGCAT GCCTACAACG TCCTCCGGGC GGTGATGAAC ACAGCGGTCG    1020
AGGACAAGCT GATCGCAGAG AACCCGTGCC GGATCGAGCA GAAGGCAGCC GATGAGCGCG    1080
ACGTAGAGGC GCTGACGCCT GAGGAGCTGG ACATCGTCGC CGCTGAGATC TTCGAGCACT    1140
ACCGGATCGC GGCATACATC CTGGCGTGGA CGAGCCTCCG GTTCGGAGAG CTGATCGAGC    1200
TTCGCCGCAA GGACATCGTG GACGACGGCA TGACGATGAA GCTCCGGGTG CGCCGTGGCG    1260
CTTCCCGCGT GGGGAACAAG ATCGTCGTTG GCAACGCCAA GACCGTCCGG TCGAAGCGTC    1320
CTGTGACGGT TCCGCCTCAC GTCGCGGAGA TGATCCGAGC GCACATGAAG GACCGTACGA    1380
AGATGAACAA GGGCCCCGAG GCATTCCTGG TGACCACGAC GCAGGGCAAC CGGCTGTCGA    1440
AGTCCGCGTT CACCAAGTCG CTGAAGCGTG GCTACGCCAA GATCGGTCGG CCGGAACTCC    1500
GCATCCACGA CCTCCGCGCT GTCGGCGCTA CGTTCGCCGC TCAGGCAGGT GCGACGACCA    1560
AGGAGCTGAT GGCCCGTCTC GGTCACACGA CTCCTAGGAT GGCGATGAAG TACCAGATGG    1620
CGTCTGAGGC CCGCGACGAG GCTATCGCTG AGGCGATGTC CAAGCTGGCC AAGACCTCCT    1680
GAAACGCAAA AAGCCCCCCT CCCAAGGACA CTGAGTCCTA AGAGGGGGG TTTCTTGTCA    1740
GTACGCGAAG AACCACGCCT GGCCGCGAGC GCCAGCACCG CCGCTCTGTG CGGAGACCTG    1800
GGCACCAGCC CCGCCGCCGC CAGGAGCATT GCCGTTCCCG CCAGCTGAGT TCTGTTGTGC    1860
GCCGCCTATG TAGAGCTGGT CGTTGTAGGT CCGATCTCCA GGCGACTTTC CGGCGACGCT    1920
GAGGATGTCG ATCACAGAGC CTCCGGGACC GCCGGTTGCG GTCAAACCTG ACCATCCGAC    1980
AGCGGACGCC GTGGTGTTTC CTCCAGGGCC TCCGGCCTTG CCTGAGAATA CAGAGCCAGC    2040
TCCCGCTGCG CCTCCAGCTC CGACGAGCCC GGTGATCGTC TTGGTCGAC              2089
```

(2) INFORMATION FOR SEQ ID NO:82:

(i) SEQUENCE CHARACTERISTICS:
        (A) LENGTH: 2089 nucleotides
        (B) TYPE: nucleic acid
        (C) STRANDEDNESS: double
        (D) TOPOLOGY: linear (ii) MOLECULE TYPE: nucleic acid (xi) SEQUENCE DESCRIPTION: SEQ ID NO: 82:

```
GTCGACCAAG ACGATCACCG GGCTCGTCGG AGCTGGAGGC GCAGCGGGAG CTGGCTCTGT     60
ATTCTCAGGC AAGGCCGGAG GCCCTGGAGG AAACACCACG GCGTCCGCTG TCGGATGGTC    120
AGGTTTGACC GCAACCGGCG GTCCCGGAGG CTCTGTGATC GACATCCTCA GCGTCGCCGG    180
AAAGTCGCCT GGAGATCGGA CCTACAACGA CCAGCTCTAC ATAGGCGGCG CACAACAGAA    240
CTCAGCTGGC GGGAACGGCA ATGCTCCTGG CGGCGGCGGG GCTGGTGCCC AGGTCTCCGC    300
ACAGAGCGGC GGTGCTGGCG CTCGCGGCCA GGCGTGGTTC TTCGCGTACT GACAAGAAAC    360
CCCCCTCTTT AGGACTCAGT GTCCTTGGGA GGGGGGCTTT TTGCGTTTCA GGAGGTCTTG    420
GCCAGCTTGG ACATCGCCTC AGCGATAGCC TCGTCGCGGG CCTCAGACGC CATCTGGTAC    480
TTCATCGCCA TCCTAGGAGT CGTGTGACCG AGACGGGCCA TCAGCTCCTT GGTCGTCGCA    540
CCTGCCTGAG CGGCGAACGT AGCGCCGACA GCGCGGAGGT CGTGGATGCG GAGTTCCGGC    600
CGACCGATCT TGGCGTAGCC ACGCTTCAGC GACTTGGTGA ACGCGGACTT CGACAGCCGG    660
TTGCCCTGCG TCGTGGTCAC CAGGAATGCC TCGGGGCCCT TGTTCATCTT CGTACGGTCC    720
TTCATGTGCG CTCGGATCAT CTCCGCGACG TGAGGCGGAA CCGTCACAGG ACGCTTCGAC    780
CGGACGGTCT TGGCGTTGCC AACGACGATC TTGTTCCCCA CGCGGGAAGC GCCACGGCGC    840
ACCCGGAGCT TCATCGTCAT GCCGTCGTCC ACGATGTCCT TGCGGCGAAG CTCGATCAGC    900
```

| | | | | | |
|---|---|---|---|---|---|
| TCTCCGAACC | GGAGGCTCGT | CCACGCCAGG | ATGTATGCCG | CGATCCGGTA | GTGCTCGAAG | 960 |
| ATCTCAGCGG | CGACGATGTC | CAGCTCCTCA | GGCGTCAGCG | CCTCTACGTC | GCGCTCATCG | 1020 |
| GCTGCCTTCT | GCTCGATCCG | GCACGGGTTC | TCTGCGATCA | GCTTGTCCTC | GACCGCTGTG | 1080 |
| TTCATCACCG | CCCGGAGGAC | GTTGTAGGCA | TGCCGGCGGG | CAGTCGGGTG | CTTCCTACCC | 1140 |
| ATCCCGGCCC | ACCACGCACG | CACCAGAGCT | GGCGTCATCT | CTGTGACCGC | CACTTCACCT | 1200 |
| AGCACCGGGT | AGATGCGGCG | CTCCGCGTGC | CCGCTGTACA | GATCCCTGGT | GCCGTCTGCG | 1260 |
| AGGTCGCGCT | CCACGAGCCA | CTTCCGGGTG | TACTCCTCCA | GCGTGATGGC | GCTGGCGGCT | 1320 |
| GCCTTCTTCG | CCCGGTCCTG | TGGAGGGGTC | CAGGTCTCCA | TCTCGATGAG | CCGCTTCTCG | 1380 |
| CCCGCGAGCC | AGGCTTCGGC | GTCCATCTTG | TTGTCGTAGG | TCTGCAGCGC | GTAGTACCTC | 1440 |
| ACACCGTCCT | GCGGGTTGAC | GTATGAGGCT | TGGATCCTCC | CGCTGCGCTG | AGTCTTCAGC | 1500 |
| GATCCCCATC | CGCGACGTGC | CAACTAGGTC | TCCTCTCGTC | GTGAACAAGG | CTACCGGGTT | 1560 |
| GCAACTCCTG | TGCAACTCTC | AGGCTTCAAC | GCGCTTCTAC | GACCTGCAAT | TTCTTTCCAC | 1620 |
| TTAGAGGATG | CAGCCGAGAG | GGGGTAAAAA | CCTATCTTGA | CCGGCCCATA | TGTGGTCGGC | 1680 |
| AGACACCCAT | TCTTCCAAAC | TAGCTACGCG | GGTTCGATTC | CCGTCGCCCG | CTCCGCTGGT | 1740 |
| CAGAGGGTGT | TTTCGCCCTC | TGGCCATTTT | TCTTTCCAGG | GGTCTGCAAC | TCTTGTGCGA | 1800 |
| CTCTTCTGAC | CTGGGCATAC | GCGGTTGCAA | CGCATCCCTG | ATCTGGCTAC | TTTCGATGCT | 1860 |
| GACAAACGAA | TAGAGCCCCC | CGCCTGCGCG | AACAGACGAG | GGGCATTCAC | ACCAGATTGG | 1920 |
| AGCTGGTGCA | GTGAAGAGAA | TAGACCGGGA | CAAGGTTGCA | CCGGGAGTTG | CAGCGGTCGG | 1980 |
| AACCCTCGCC | GTCGGCGGGC | TGGCGTTCGC | CCTGTCGTTC | ACGGCTCTCA | GCGAGCTGGC | 2040 |
| TGCGGCCAAC | GGGGTGGCCC | AAGCAGAGAT | GGTGCCCTTG | GTGGTCGAC | | 2089 |

( 2 ) INFORMATION FOR SEQ ID NO:83:

( i ) SEQUENCE CHARACTERISTICS:
        ( A ) LENGTH: 420 nucleotides
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 83:

| | | | | | |
|---|---|---|---|---|---|
| AGATCTGAGC | ACACGACGAC | ATACAGGACA | AAGGGGCACA | GGTATGACAG | ACGTGAGCCG | 60 |
| AAAGATTCGA | GCTTGGGGAC | GCCGATTGAT | GATCGGCACG | GCAGCGGCTG | TAGTCCTTCC | 120 |
| GGGCCTGGTG | GGGCTTGCCG | GCGGAGCGGC | AACCGCGGGC | GCGTTCTCCC | GGCCGGGGCT | 180 |
| GCCGGTCGAG | TACCTGCAGG | TGCCGTCGCC | GTCGATGGGC | CGCGACATCA | AGGTTCAGTT | 240 |
| CCAGAGCGGT | GGGAACAACT | CACCTGCGGT | TTATCTGCTC | GACGGCCTGC | GCGCCCAAGA | 300 |
| CGACTACAAC | GGCTGGGATA | TCAACACCCC | GGCGTTCGAG | TGGTACTACC | AGTCGGGACT | 360 |
| GTCGATAGTC | ATGCCGGTCG | GCGGGCAGTC | CAGCTTCTAC | AGCGACTGGT | ACAGCCCGGC | 420 |

( 2 ) INFORMATION FOR SEQ ID NO:84:

( i ) SEQUENCE CHARACTERISTICS:
        ( A ) LENGTH: 121 nucleotides
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 84:

```
TCTAGACCCG  CACGACCAGC  GTTAGCATGC  TCAGTAAGTT  GAGTGCATCA  GGCTCAGCTC         60

TGAATTGACA  GCACACCGCC  GTCGAGGCAA  GCTTGAGCGG  GGTGCACTCA  TCATAGCTAG        120

C                                                                            121
```